United States Patent [19]

Nakamura et al.

[11] Patent Number: 4,891,363

[45] Date of Patent: Jan. 2, 1990

[54] CYCLIC ETHER DERIVATIVES AND THEIR USE

[75] Inventors: Norio Nakamura; Nobuyuki Ookawa; Hiroyuki Koike; Toshio Sada; Takeshi Oshmia; Yoshio Iizuka; Hideki Miyazaki, all of Hiromachi, Japan

[73] Assignee: Sankyo Company Limited, Tokyo, Japan

[21] Appl. No.: 152,068

[22] Filed: Feb. 4, 1988

Related U.S. Application Data

[63] Continuation-in-part of Ser. No. 69,041, Jul. 1, 1987, abandoned, and Ser. No. 147,081, Jan. 20, 1988, abandoned, which is a continuation of Ser. No. 888,155, Jul. 18, 1986, abandoned.

[30] Foreign Application Priority Data

Jul. 26, 1985 [JP] Japan .................................. 60-163965
Jul. 4, 1986 [JP] Japan .................................. 61-157319
Jan. 26, 1987 [JP] Japan .................................. 62-15484

[51] Int. Cl.$^4$ ...................... A61K 31/665; C07F 9/58; C07F 9/65; C07F 9/142
[52] U.S. Cl. ......................................... 514/94; 514/89; 514/91; 514/101; 514/450; 514/459; 514/471; 546/22; 548/112; 548/413; 549/222; 549/346; 549/419; 549/474
[58] Field of Search .................. 546/22; 548/112, 413; 549/222; 514/89, 91, 94, 101

[56] References Cited

U.S. PATENT DOCUMENTS 4,794,183 12/1988 Nakamura et al. .................... 546/22

Primary Examiner—Richard L. Raymond
Attorney, Agent, or Firm—Frishauf, Holtz, Goodman & Woodward

[57] ABSTRACT

Compounds of formula (I):

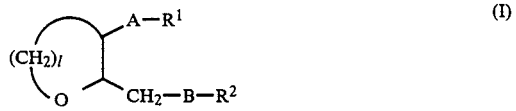

(wherein: l is 2–4; A and B are oxygen or sulfur; one of $R^1$ and $R^2$ represents a long chain alkyl, alkylcarbamoyl or aliphatic acyl group and the other of $R^1$ and $R^2$ represents a group of formula (III) or (II/):

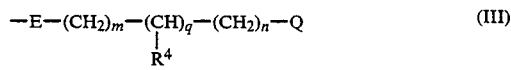

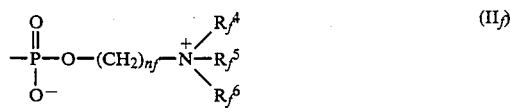

in which

E represents a single bond, a bivalent heterocyclic group or a group of formula —CO—, —COO— or —CONR$^6$—, where R$^6$ is hydrogen or an imino-protecting group; m is 0–3; n is 0–10; q is 0 or 1; $R^4$ is optionally protected hydroxy, mercapto group or carboxy; Q is an amino or nitrogen-containing heterocyclic group;

$R_f^4$, $R_f^5$ and $R_f^6$ are independently selected from the group consisting of hydrogen atoms and $C_1$–$C_6$ alkyl groups, or $R_f^4$ and $R_f^5$ or $R_f^4$, $R_f^5$ and $R_f^6$, together with the nitrogen atom to which they are attached, form a heterocyclic ring) are PAF antagonists which may be used to treat asthma, hypotension, inflammation and shock. They may be prepared by reacting the corresponding compound having a haloalkyl phosphate ester or alkylenephosphate ester group in place of the ammonioalkyl phosphate ester group with an appropriate amine.

51 Claims, No Drawings

CYCLIC ETHER DERIVATIVES AND THEIR USE

This application is a continuation-in-part of (i) application Ser. No. 69,041 filed July 1, 1987 (now abandoned) and of (ii) application Ser. No. 147,081 filed Jan. 20, 1988 (now abandoned) which was a continuation application of Ser. No. 888,155 filed July 18, 1986 (now abandoned).

BACKGROUND TO THE INVENTION

The present invention relates to a new class of cyclic ether derivatives and inner salts and pharmaceutically acceptable salts thereof which have excellent antagonism against platelet activating factor (hereafter abbreviated, as is conventional, to "PAF").

Natural PAF, at least as isolated from mammalian tissues, is a mixture of from 2 to 5 phospholipids, the number depending upon the nature of the original tissue. The major constituents of PAF may be represented by the formula (A):

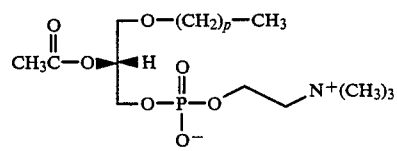

in which p is the integer 15 or 17. Natural PAF is levorotatory and the various components of natural PAF may be identified, for example as: $l$-$C_{16:0}$=formula (A) where p is 15; and $l$-$C_{18:0}$=formula (A) where p is 17.

PAF exhibits a strong platelet activating and aggregating effect. It also has a hypotensive effect and increases vasopermeability; it is believed to be an active agent in the induction of anaphylactic shock (for example endotoxin-induced shock), to act as a mediator of inflammatory disease and to act as an activator of neutrophiles. Accordingly, PAF antagonists have been investigated with a view to developing new types of anti-shock agent and of anti-inflammatory agent. In particular, analogs of natural PAF's have been investigated in an attempt to find such PAF antagonists. Currently, several compounds are known as PAF antagonists. For example, the compound of formula (B):

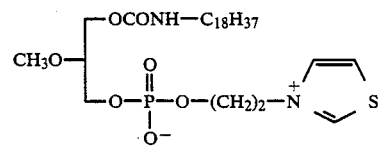

(also known as CV-3988) is disclosed in U.S. Pat. No. 4,408,052, whilst the compound of formula (C):

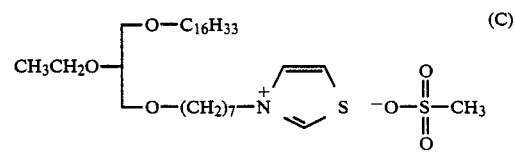

(known as ONO-6240) is disclosed in European Patent Publication No. 146258. These compounds however, are unsatisfactory for one or more of the following reasons: they lack sufficient intensity of antagonism towards PAF; the duration of their effect is insufficient; biological utilization is inadequate.

The closest prior art, from the structural point of view, to the compounds of the present invention is believed to be the compounds disclosed in U.S. patent application Ser. No. 818 876 filed 14th Jan. 1986. However, these prior compounds are useful as anti-tumor agents, and appear to be substantially free from PAF-like activity and from PAF antagonistic activity. On the contrary, the compounds of the present invention have been found to be excellent PAF antagonists, resulting in anti-asthmatic, anti-inflammatory and anti-shock activities which have excellent duration, biological utilization and level of activity. Other PAF antagonists are described in U.S. patent application Ser. No. 014 936 filed 13 Feb. 1987, but those compounds, unlike those of the present invention, lack a cyclic ether structure.

Other glycerol derivatives known to have PAF inhibitory activity are disclosed in EP Patent Publication No. 157 609.

BRIEF SUMMARY OF INVENTION

It is an object of the present invention to provide a series of novel compounds having excellent PAF antagonist activity.

It is a further object of the invention to provide methods and compositions for using such compounds in the treatment and prophylaxis of asthma, inflammation and the shock state.

It is a still further object of the invention to provide processes for producing such compounds.

The compounds of the invention are those cyclic ethers of formula (I):

in which:

l is an integer of from 2 to 4;

A and B are independently selected from the group consisting of oxygen atoms and sulfur atoms;

one of $R^1$ and $R^2$ represents an alkyl group containing from 8 to 22 carbon atoms, an aliphatic carboxylic acyl group containing from 8 to 22 carbon atoms or a group of formula (II):

in which $R^3$ represents an alkyl group containing from 8 to 22 carbon atoms, and $R^5$ represents a hydrogen atom, a $C_1$-$C_4$ alkyl group, a $C_1$-$C_4$ alkanoyl group or a $C_7$-$C_9$ aralkyl group, and the other of $R^1$ and $R^2$ represents a group of formula (III) or (II$f$):

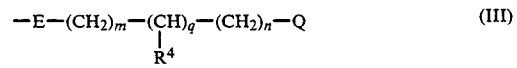

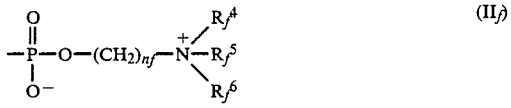 (II/)

in which E represents a single bond, a bivalent heterocyclic group or a group of formula

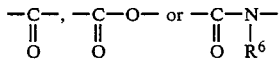

in which, $R^6$ represents a hydrogen atom or an imino-protecting group;

m is the cypher O or an integer from 1 to 3;
n is the cypher O or an integer from 1 to 10;
q is the cypher O or the integer 1;
$n_f$ is an integer of from 2 to 10;
$R^4$ represents a hydroxy group, a $C_1-C_4$ alkanoyloxy group, a $C_1-C_4$ alkoxy group, a $C_7-C_9$ aralkyloxy group, a carbamoyloxy group, an alkylcarbamoyloxy group in which the alkyl part is $C_1-C_4$, a dialkylcarbamoyloxy group in which each alkyl part is $C_1-C_4$, a mercapto group, a $C_1-C_4$ alkylthio group, a $C_7-C_9$ aralkylthio group, a $C_1-C_4$ alkanoylthio group, a carbamoylthio group, an alkylcarbamoylthio group in which the alkyl part is $C_1-C_4$, a dialkylcarbamoylthio group in which each alkyl part is $C_1-C_4$ or a carboxy group;

Q represents a group of formula (IV):

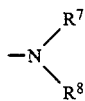 (IV)

in which $R^7$ and $R^8$ are independently selected from the group consisting of hydrogen atoms and $C_1-C_6$ alkyl groups,
or a monovalent heterocyclic group;

$R_f^4$, $R_f^5$ and $R_f^6$ are independently selected from the group consisting of hydrogen atoms and $C_1-C_6$ alkyl groups, or $R_f^4$ and $R_f^5$ or $R_f^4$, $R_f^5$ and $R_f^6$, together with the nitrogen atom to which they are attached, form a heterocyclic ring which may be aromatic or partly or wholly saturated;

said heterocyclic groups in formula (III) having from 5 to 14 ring atoms, of which 1 to 4 atoms are hetero-atoms selected from the group consisting of nitrogen, oxygen and sulfur atoms, at least one of these being a nitrogen atom, and said heterocyclic group being unsubstituted or having at least one substituent selected from the group consisting of substituents (a) and substituents (b);

substituents (a):
oxygen atoms and $C_6-C_{14}$ aryl groups;
substituents (b):
halogen atoms, hydroxy groups, $C_1-C_4$ alkyl groups, $C_1-C_4$ haloalkyl groups, $C_1-C_4$ hydroxyalkyl groups, $C_1-C_4$ alkoxy groups, $C_1-C_6$ alkanoyl groups, $C_3-C_6$ alkenoyl groups, $C_7-C_{15}$ aromatic carboxylic acyl groups, carbamoyl groups, $C_7-C_{15}$ aralkyl groups, $C_2-C_5$ alkoxycarbonyl groups, cyano groups, amino groups, alkylamino groups in which the alkyl part is $C_1-C_4$, dialkylcarbamoyloxy groups in which each alkyl part is $C_1-C_4$ and nitro groups;
said aryl groups and the aryl parts of aralkyl groups and aromatic acyl groups being unsubstituted or having at least one substituent selected from the group consisting of substituents (b);

said heterocyclic groups in formula (II/) having from 3 to 10 ring atoms, of which from 1 to 4 atoms are hetero-atoms selected from the group consisting of nitrogen, oxygen and sulfur atoms, at least one of these being a nitrogen atom, and said heterocyclic group being unsubstituted or having at least one substituent selected from the group consisting of substituents (c);

substituent (c):
$C_1-C_6$ alkyl groups, $C_1-C_5$ hydroxyalkyl groups, $C_1-C_6$ alkoxy groups, carbamoyl groups, mono- and di-alkylcarbamoyl groups in which the alkyl or each alkyl part is $C_1-C_5$ and halogen atoms;
provided that when one of $R^1$ and $R^2$ is a group of formula (II/), then the other of $R^1$ and $R^2$ is a group of formula (II) where $R^5$ is a hydrogen atom and $R^3$ is an alkyl group containing from 10 to 22 carbon atoms ($R_f^3$);

and pharmaceutically acceptable salts (including quaternary and inner salts) and esters thereof.

The invention also provides a pharmaceutical composition for the treatment of inflammation or shock, comprising a PAF antagonist in combination with a pharmaceutically acceptable carrier or diluent, wherein the PAF antagonist is selected from the group consisting of compounds of formula (I) and pharmaceutically acceptable salts and esters thereof.

The invention still further provides a method for the treatment of prophylaxis of asthma, inflammation or shock comprising administering an amount of a PAF antagonist to an animal (which may be a mammal, e.g. human) sufficient to effect treatment or prophylaxis of inflammation or shock, wherein said PAF antagonist is selected from the group consisting of compounds of formula (I) and pharmaceutically acceptable salts and esters thereof.

The invention also provides methods of preparing the compounds of the invention, which are described in more detail below and hereafter.

The one kind of compounds of the invention may be prepared by reacting a compound of formula (III/):

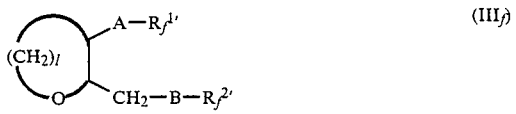 (III/)

in which
l, A and B are as defined above; and
one of $R_f^{1'}$ and $R_f^{2'}$ represents a group of formula $-CONH-R_f^3$ (in which $R_f^3$ represents an alkyl group containing from 10 to 22 carbon atoms) and the other represents a group of formula (IV/):

 (IV/)

(in which $n_f$ is as defined and $Y_f$ represents a halogen atom) or a group of formula (V/):

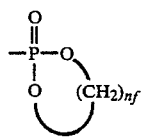 (V*f*)

(in which n*f* is as defined above) with an amine compound of formula (VI*f*):

$$R_f^4 NR_f^5 R_f^6 \quad (VI_f)$$

(in which $R_f^4$, $R_f^5$ and $R_f^6$ are as defined above).

DETAILED DESCRIPTION OF INVENTION

The compounds of the invention exhibit a number of possibilities for salt formation. For example, the compounds may, depending on their exact nature, form acid addition salts (because of the presence of a nitrogen atom in the heterocyclic group represented by E or Q or in the group of formula $-NR^7R^8$ represented by Q), carboxylate salts (where $R^4$ represents a carboxy group), inner salts (where $R^4$ represents a carboxy group and there is a basic nitrogen atom in the molecule, e.g. from E or Q) and quaternary ammonium salts (where there is a basic nitrogen atom in the molecule, e.g. from E or Q), by the addition of a suitable compound, e.g. an alkyl halide. It is also possible for one compound to exist as a combination of two or more of these different forms of salt, for example, where the compound contains both a carboxy group (from $R^4$) and a basic nitrogen atom (from E and/or Q), the compound may be both a carboxylate salt (e.g. with an alkali metal atom such as sodium or potassium) and an acid addition salt of that nitrogen atom (e.g. with an acid such as hydrochloric acid). All of these possibilities form part of the present invention, as explained in more detail below.

Thus, the compounds of the invention where one of $R^1$ and $R^2$ is a group of formula (III) can exist in the form of an inner salt, i.e. a compound of formula (I) as shown above in which one of $R^1$ and $R^2$ represents a group of formula (III'):

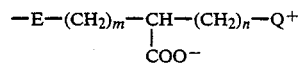 (III')

in which, E, m and n are as defined above and $Q^+$ represents a quaternised form of any of the groups defined above for Q, e.g. a quaternised heterocyclic group or a group of formula (IV'):

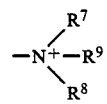 (IV')

in which $R^7$, $R^8$ and $R^9$ are independently selected from the group consisting of hydrogen atoms and $C_1-C_6$ alkyl groups.

Alternatively, the compounds may exist in the form of a quaternary ammonium salt or an acid addition salt, in which Q represents a group of formula (IV''):

$$-\overset{R^7}{\underset{R^8}{N^+}}-R^9 \quad Z^- \quad (IV'')$$

in which $R^7$, $R^8$ and $R^9$ are as defined above and $Z^-$ represents a complementary pharmaceutically acceptable anion (preferably a halogen atom, an anionic residue of another mineral acid, a $C_1-C_6$ alkylsulfonyloxy group, an arylsulfonyloxy group or an anion derived from an organic carboxylic acid or an amino acid), or a quaternised heterocyclic group together with a complementary pharmaceutically acceptable anion.

Also, where $R^4$ represents a carboxy group, the resulting compounds may form salts with cations, particularly with metals (e.g. alkali metals such as sodium or potassium, alkaline earth metals such as calcium or magnesium or other metals such as tin), but also with ammonia and organic amines and amino acids, as is, of course, well known.

In addition, it is possible to have some combination of the above. In particular, it is possible under specific circumstances, e.g. during certain chromatographic procedures, to form a compound in which the carboxy group represented by $R^4$ has formed a salt with a cation and the nitrogen atom or atoms of Q and/or E has or have formed a quaternary ammonium salt.

The compounds of the invention where one of $R^1$ and $R^2$ is a group of formula (II*f*) can exist in the form of an inner salt, i.e. as shown above in which one of $R^1$ and $R^2$ represents a group of formula (II*f*):

$$\underset{O^-}{\overset{O}{\underset{\|}{-P}}-O-(CH_2)_{n_f}-\overset{+}{N}\begin{array}{c}R_f^4\\R_f^5\\R_f^6\end{array}} \quad (II_f)$$

(in which n*f*, $R_f^4$, $R_f^5$ and $R_f^6$ are as defined above) or it may exist in the form of a salt, in which one of $R^1$ and $R^2$ represents a group of formula (II*f'*):

$$\underset{OH}{\overset{O}{\underset{\|}{-P}}-O-(CH_2)_{n_f}-\overset{+}{N}\begin{array}{c}R_f^4\\R_f^5\\R_f^6\end{array}} Z_f^- \quad (II_{f'})$$

(in which n*f* $R_f^4$, $R_f^5$ and $R_f^6$ are as defined above, and $Z_f$ represents a pharmaceutically acceptable anion, preferably a hydroxy group, a halogen atom, a $C_1-C_6$ alkylsulfonyloxy group or an arylsulfonyloxy group).

Salts in which one of $R^1$ and $R^2$ represents the aforementioned group of formula (II*f'*) can also form salts with cations, particularly metals (e.g. alkali metals such as sodium or potassium or alkaline earth metals such as calcium or magnesium), in which the cation replaces the hydrogen atom of the hydroxy group attached to the phosphorus atom in the group of formula (II*f'*).

Where $Z^-$ in the above formula (IV'') represents a halide ion, this may be, for example, a fluoride, chloride, bromide or iodide ion. Where $Z^-$ represents a residue of another mineral acid, this may be any pharmaceutically acceptable acid, and the anion may be, for example, a sulfate or phosphate anion. Where $Z^-$ represents an alkylsulfonyloxy group, the alkyl part is $C_1-C_6$ and may be a straight or branched chain group, which may be substituted or unsubstituted; examples include the methanesulfonyloxy and ethanesulfonyloxy groups; substituents are preferably halogen atoms and a preferred substituted group is the trifluoromethanesulfonyloxy group. Where $Z^-$ represents an arylsulfonyloxy group, the aryl part is a $C_6$–$C_{10}$ carbocyclic aryl group, which may be substituted or unsubstituted and, if substituted, may have from 1 to 3 substituents preferably selected from the group consisting of $C_1$–$C_4$ alkyl (preferably methyl) groups, halogen atoms, $C_1$–$C_4$ alkoxy groups and nitro groups. Examples of such arylsulfonyloxy groups include the benzenesulfonyloxy and p-toluenesulfonyloxy groups. Where $Z^-$ represents an anion derived from an organic carboxylic acid, this may be any pharmaceutically acceptable acid, preferably a lower alkanoic aci, and examples include oxalic acid and maleic acid. Where $Z^-$ represents an anion derived from an amino acid, this may be any known pharmaceutically acceptable amino acid, and examples include glutamic acid and aspartic acid.

Where $Z_f$ in the above formula (II$f$) represents a halogen atom, this may be, for example, a chlorine, bromine or iodine atom. Where $Z_f$ represents an alkylsulfonyloxy group, the alkyl part is $C_1$–$C_6$ and may be a straight or branched chain group; examples include the methanesulfonyloxy and ethanesulfonyloxy groups. Where $Z_f$ represents an arylsulfonyloxy group, the aryl part is a $C_6$–$C_{10}$ carbocyclic aryl group, which may be substituted or unsubstituted and, if substituted, may have from 1 to 3 substituents preferably selected from the group consisting of $C_1$–$C_4$ alkyl (preferably methyl) groups, halogen atoms, $C_1$–$C_4$ alkoxy groups and nitro groups.

Examples of such arylsulfonyloxy groups include the benzenesulfonyloxy and p-toluenesulfonyloxy groups.

In the compounds of the invention, one of $R^1$ and $R^2$ represents the above defined group of formula (III) [or (III')], whilst the other represents a $C_8$–$C_{22}$, preferably $C_{10}$–$C_{22}$, alkyl or aliphatic acyl group, which may be a straight or branched chain group, or a group of formula (II):

in which $R^3$ represents an alkyl group containing from 8 to 22, preferably from 10 to 22, carbon atoms, which also may be a straight or branched chain group, and $R^5$ represents a hydrogen atom, a $C_1$–$C_4$ alkyl group, a $C_1$–$C_4$ alkanoyl group or a $C_7$–$C_9$ aralkyl group.

Examples of such $C_8$–$C_{22}$ alkyl groups which may be represented by $R^1$, $R^2$ and $R^3$ include the octyl, 3-methylheptyl, 4-methylheptyl, 2-ethylhexyl, nonyl, 1-methyloctyl, 2-methyloctyl, 3-ethylheptyl, decyl, 3-methylnonyl, 8-methylnonyl, 3-ethyloctyl, 3,7-dimethyloctyl, undecyl, dodecyl, tridecyl, tetradecyl, pentadecyl, hexadecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl, henicosyl and docosyl groups. Straight and branched chain alkyl groups having from 13 to 20 carbon atoms, for example the hexadecyl, 1-methylpentadecyl, 14-methylpentadecyl, 13,13-dimethyltetradecyl, heptadecyl, 15-methylhexadecyl, octadecyl and 1-methylheptadecyl groups are preferred.

Examples of such $C_8$–$C_{22}$ alkanoyl groups which may be represented by $R^1$ and $R^2$ include the heptylcarbonyl, octylcarbonyl, 3-methylheptylcarbonyl, 4-methylheptylcarbonyl, 2-ethylhexylcarbonyl, nonylcarbonyl, decylcarbonyl, 3-methylnonylcarbonyl, 8-methylnonylcarbonyl, 3-ethyloctylcarbonyl, 3,7-dimethyloctylcarbonyl, undecylcarbonyl, dodecylcarbonyl, tridecylcarbonyl, tetradecylcarbonyl, pentadecylcarbonyl, hexadecylcarbonyl, 1-methylpentadecylcarbonyl, 14-methylpentadecylcarbonyl, 13,13-dimethyltetradecylcarbonyl, heptadecylcarbonyl, 15-methylhexadecylcarbonyl, octadecylcarbonyl, 1-methylheptadecylcarbonyl, nonadecylcarbonyl, icosylcarbonyl and henicosylcarbonyl; preferably a straight or branched chain aliphatic acyl group containing from 13 to 20 carbon atoms.

Where $R^5$ represents an alkyl group, this is a lower alkyl group having from 1 to 4 carbon atoms and it may be a straight or branched chain group. The group more preferably has from 1 to 3 carbon atoms, and examples of such groups include the methyl, ethyl, propyl, isopropyl, butyl, isobutyl, sec-butyl and t-butyl groups, of which the methyl and ethyl groups are preferred.

Where $R^5$ represents an alkanoyl group, this is a lower carboxylic alkanoyl group having from 1 to 4 carbon atoms and it may be a straight or branched chain group. The group more preferably has from 2 to 4 carbon atoms and examples of such groups include the formyl, acetyl, propionyl, butyryl, and isobutyryl groups, of which the acetyl and propionyl groups are preferred.

Where $R^5$ represents an aralkyl group, the aryl part may be as defined above and may be substituted or unsubstituted. Where it is substituted, the substituents are preferably selected from the group consisting of substituents (b), defined above, more preferably halogen atoms and $C_1$ to $C_4$ alkyl, $C_1$ to $C_4$ haloalkyl, $C_1$ to $C_4$ alkoxy, $C_2$ to $C_5$ alkoxycarbonyl, aryl and nitro groups. The alkyl part is preferably a $C_1$ to $C_4$ alkyl group, for example selected from those alkyl groups defined above in relation to $R^5$, more preferably a methyl, ethyl or propyl group. Examples of such aralkyl groups include aralkyl groups having, in total, from 7 to 9 carbon atoms, for example the benzyl, phenethyl, phenylpropyl and 1- or 2-, preferably 1-, naphthylmethyl, of which the benzyl group is preferred. Such preferred groups may, if desired, be substituted as defined above.

Where E represents said group of formula

and $R^6$ represents an imino-protecting group, there is no particular limitation on the nature of such a group, and any group which is conventionally employed as an imino-protecting group may equally be employed in the present invention. In general, we prefer that $R^6$ should be a hydrogen atom, a $C_1$–$C_4$ alkyl group, a $C_1$–$C_4$ alkanoyl group or a $C_7$–$C_9$ aralkyl group, example of which have been given in relation to the corresponding groups which may be represented by $R^5$. Examples of other imino-protecting groups include: haloalkanoyl groups and aromatic acyl groups, such as the chloroacetyl and benzoyl groups; alkoxycarbonyl groups, such as the t-butoxycarbonyl, 2,2,2-tribromoethoxycarbonyl and 2-trimethylsilylethoxycarbonyl groups; and alkenyloxycarbonyl groups, such as the allyloxycarbonyl group.

Where E represents a bivalent heterocyclic group, this may have from 5 to 14, preferably from 5 to 7, ring atoms, of which from 1 to 4, preferably from 1 to 3, are hetero-atoms selected from the group consisting of sulfur and/or oxygen and/or nitrogen atoms, at least one being a nitrogen atom. Such groups may be fully unsaturated or partly or completely hydrogenated. Also included are analogs of such groups in which a phenyl or substituted phenyl group is fused to the heterocyclic ring. Examples of these heterocyclic groups include the furanediyl, thiophenediyl, pyrrolediyl, azepinediyl, morpholinediyl, thiomorpholinediyl, pyrazolediyl, imidazolediyl, oxazolediyl, isoxazolediyl, thiazolediyl, isothiazolediyl, oxadiazolediyl (e.g. 1,2,3-oxadiazolediyl), triazolediyl, tetrazolediyl, thiadiazolediyl (e.g. 1,2,3-thiadiazolediyl), pyranediyl, pyridinediyl, pyridazinediyl, pyrimidinediyl and pyrazinediyl groups, and partly or completely hydrogenated analogs thereof, of which those heterocyclic groups having 5 or 6, more preferably 5, ring atoms are preferred and the imidazolediyl, oxazolediyl, isoxazolediyl and thiazolediyl groups and partly or completely hydrogenated analogs thereof are more preferred.

The heterocyclic groups represented by E may be substituted or unsubstituted, and, if substituted, the substituents may be selected from the group consisting of substituents (a) and (b) defined above, more preferably those substituents exemplified hereafter in relation to the substituted heterocyclic groups which may be represented by Q. However, the heterocyclic groups represented by E are preferably unsubstituted.

Q may represent a group of formula (IV):

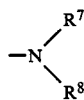

(IV)

in which $R^7$ and $R^8$ are independently selected from the group consisting of hydrogen atoms and $C_1$–$C_6$ alkyl groups, or a monovalent heterocyclic group having from 5 to 14, preferably from 5 to 10 and more preferably from 5 to 7, ring atoms; alternatively, of course, it may represent the corresponding quaternised group $Q^+$, which may be a heterocyclic group or a group of formula (IV'):

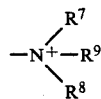

(IV')

or (IV''):

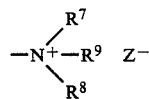

(IV'')

in which $R^7$, $R^8$, $R^9$ and $Z^-$ are as defined above.

Where Q represents a nitrogen-containing heterocyclic group, this has from 5 to 14, preferably from 5 to 10, ring atoms, of which from 1 to 4, preferably from 1 to 3, are hetero-atoms selected from the group consisting of sulfur and/or oxygen and/or nitrogen atoms, at least one being a nitrogen atom. Such groups may be fully unsaturated or partly or completely hydrogenated. Also included are analogs of such groups in which a phenyl or substituted phenyl group is fused to the heterocyclic ring. Examples of these heterocyclic groups include the pyrrolyl, pyrrolidinyl, piperidinyl, piperazinyl, azepinyl, morpholinyl (e.g. morpholino), thiomorpholinyl (e.g. thiomorpholino), pyridyl, thiazolyl, oxazolyl, oxadiazolyl, isoxazolyl, imidazolinyl, pyridazinyl, pyrimidinyl, pyrazinyl, quinolyl, isoquinolyl, imidazolyl, triazolyl and tetrazolyl groups, of which aromatic heterocyclic groups having 5 or 6 ring atoms and optionally having a phenyl group fused thereto are preferred and the pyridyl, imidazolyl, thiazolyl, quinolyl and isoquinolyl groups are more preferred. Such groups may be quaternized, in which case the positive charge of the quaternary nitrogen atom is balanced by a negative charge from an anion $Z^-$, as defined above.

These hetrocylic groups may be substituted or unsubstituted. Where they are substituted, the substituents are defined above as substituents (a) and (b), and preferred examples include: $C_1$ to $C_4$ alkyl groups, such as the alkyl groups exemplified above in relation to the alkyl groups which may be represented by $R^5$; $C_1$ to $C_4$ hydroxyalkyl groups, such as the hydroxymethyl, hydroxyethyl and hydroxypropyl groups; $C_1$ to $C_4$ alkoxy groups, such as the methoxy and ethoxy groups; and halogen atoms, such as the fluorine, chlorine and bromine atoms.

Where $R^7$, $R^8$ or $R^9$ represents a lower alkyl group, this may be a straight or branched chain alkyl group containing from 1 to 6 carbon atoms, and examples include the $C_1$–$C_4$ alkyl groups exemplified above in relation to $R^5$ as well as the pentyl, isopentyl, 2-methylbutyl, neopentyl, hexyl, 4-methylpentyl, 3-methylpentyl, 2-methylpentyl, 3,3-dimethylbutyl, 2,2-dimethylbutyl, 1,1-dimethylbutyl, 1,2-dimethylbutyl, 1,3-dimethylbutyl or 2,3-dimethylbutyl; of these, we particularly prefer those alkyl groups containing from 1 to 4 carbon atoms such as those exemplified above in relation to $R^5$.

$R^4$ may represent a hydroxy group, a $C_1$–$C_4$ alkanoyloxy group, a $C_1$–$C_4$ alkoxy group, a $C_7$–$C_9$ aralkyloxy group, a carbamyloxy group, a mono or di alkylcarbamoyloxy group in which the or each alkyl part is $C_1$–$C_4$, a mercapto group, a $C_1$–$C_4$ alkylthio group, a $C_7$–$C_9$ aralkylthio group, a $C_1$–$C_4$ alkanoylthio group, a carbamoylthio group, a mono or di alkylcarbamoylthio group in which the or each alkyl part is $C_1$–$C_4$ or a carboxy group;

Where $R^4$ represents an alkoxy group, this may be a straight or branched chain group. The group more preferably has from 1 to 3 carbon atoms and examples of such groups include the methoxy, ethoxy, propoxy, isopropoxy, butoxy, isobutoxy, sec-butoxy and t-butoxy groups, of which the methoxy and ethoxy groups are preferred.

Where $R^4$ represents an aralkyloxy group, this may be the aralkyloxy group corresponding to any one of the aralkyl groups exemplified above in relation to the aralkyl groups which may be represented by $R^5$.

Where $R^4$ represents an alkanoyloxy group, this may be the alkanoyloxy group corresponding to any one of the alkanoyl groups exemplified above in relation to the alkanoyl groups which may be represented by $R^5$.

Where $R^4$ represents a mono or di alkylcarbamoyloxy group, the or each alkyl part may be any one of the alkyl groups exemplified above in relation to the alkyl groups whic may be represented by $R^5$. Specific examples of such alkylcarbamoyloxy groups include the methylcarbamoyloxy, ethylcarbamoyloxy, propylcarbamoyloxy, isopropylcarbamoyloxy, butylcarbamoyloxy, isobutylcarbamoyloxy, sec-butylcarbamoyloxy, t-butylcarbamoyloxy, dimethylcarbamoyloxy, diethylcarbamoyloxy, dipropylcarbamoyloxy, dibutylcarbamoyloxy, methylethylcarbamoyloxy and methylpropylcarbamoyloxy groups.

Where $R^4$ represents an alkanoylthio group, this may be the alkanoylthio group corresponding to any one of the alkanoyl groups exemplified above in relation to the alkanoyl groups which may be represented by $R^5$.

Where $R^4$ represents a mono or di alkylcarbamoylthio group, the or each alkyl part may be any one of the alkyl groups exemplified above in relation to the alkyl groups which may be represented by $R^5$. Specific examples of such alkylcarbamoylthio groups include the methylcarbamoylthio, ethylcarbamoylthio, propylcarbamoylthio, isopropylcarbamoylthio, butylcarbamoylthio, isobutylcarbamoylthio, sec-butylcarbamoylthio, t-butylcarbamoylthio, dimethylcarbamoylthio, diethylcarbamoylthio, dipropylcarbamoylthio, dibutylcarbamoylthio, methylethylcarbamoylthio and methylpropylcarbamoylthio groups.

Where $R^4$ represents an alkylthio group, this may be a straight or branched chain group. The group more preferably has from 1 to 3 carbon atoms and examples of such groups include the methylthio, ethylthio, propylthio, isopropylthio, butylthio, isobutylthio, sec-butylthio and t-butylthio groups, of which the methylthio and ethylthio groups are preferred.

Where $R^4$ represents an aralkylthio group, this may be the aralkylthio group corresponding to any one of the aralkyl groups exemplified above in relation to the aralkyl groups which may be represened by $R^5$.

Where $R^4$ represents a carboxy group, this may, if desired, be esterified to form the corresponding ester of the carboxylic acid of formula (I). There is no particular limitation on the nature of the ester to be formed, provided that, where the resulting compound is to be used for pharmaceutical purposes, it is pharmaceutically acceptable; where the compound is to be used for other purposes, e.g. as an intermediate, even this restriction does not apply. Examples of esters which may be formed include: esters with any one of the lower alkyl groups defined above in relation to the alkyl groups which may be represented by $R^5$; aralkyl esters, such as the benzyl, p-nitrobenzyl, o-nitrobenzyl, triphenylmethyl, diphenylmethyl, bis(o-nitrophenyl)methyl, 9-anthrylmethyl, 2,4,6-trimethylbenzyl, p-bromobenzyl, p-methoxybenzyl and piperonyl esters; aliphatic acyloxymethyl esters, such as the acetoxymethyl, propionyloxymethyl, butyryloxymethyl, isobutyryloxymethyl and pivaloyloxymethyl esters; 1-(alkoxycarbonyloxy)ethyl esters, in which the alkoxy part is $C_1$-$C_6$, preferably $C_1$-$C_4$, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl and 1-isobutoxycarbonyloxyethyl esters; esters capable of being hydrolyzed in vivo, such as the phthalidyl, (2-oxo-5-methyl-1,3-dioxolen-4-yl)methyl and (2-oxo-5-phenyl-1,3-dioxolen-4-yl)methyl esters; alkoxymethyl esters, in which the alkoxy part is $C_1$-$C_6$, preferably $C_1$-$C_4$, such as the methoxymethyl, ethoxymethyl, propoxymethyl, isopropoxymethyl, butoxymethyl and methoxyethoxymethyl esters; and halogenated $C_1$-$C_6$, preferably $C_1$-$C_4$, alkyl esters, such as the 2,2,2-trichloroethyl 2-haloethyl (e.g. 2-chloroethyl, 2-fluoroethyl, 2-bromoethyl or 2-iodoethyl) and 2,2-dibromoethyl esters. Of these, the alkyl esters, the aralkyl esters and esters capable of being hydrolyzed in vivo are preferred and the $C_1$-$C_4$ alkyl esters are most preferred.

In the compounds of the invention where one of $R^1$ and $R^2$ is a group of formula (II$f$), one of $R^1$ and $R^2$ represents the above defined group of formula (II$f$) [or (II$f'$)], whilst the other represents an alkylcarbamoyl group of formula —CONH—$R_f^3$ where $R_f^3$ represents a $C_{10}$-$C_{22}$ alkyl group, which may be a straight or branched chain group. Examples of such alkyl groups include the decyl, 3-methylnonyl, 8-methylnonyl, 3-ethyloctyl, 3,7-dimethyloctyl, undecyl, dodecyl, tridecyl, tetradecyl, pentadecyl, hexadecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl, henicosyl and docosyl groups. Straight and branched chain alkyl groups having from 16 to 18 carbon atoms, for example as the hexadecyl, 1-methylpentadecyl, 14-methylpentadecyl, 13,13-dimethyltetradecyl, heptadecyl, 15-methylhexadecyl, octadecyl and 1-methylheptadecyl groups are preferred.

Where $R_f^4$, $R_f^5$ or $R_f^6$ represents an alkyl group, this is a lower alkyl group having from 1 to 6 carbon atoms and it may be a straight or branched chain group. The group more preferably has from 1 to 5 carbon atoms and examples of such groups include the methyl, ethyl, propyl, isopropyl, butyl, isobutyl, sec-butyl, t-butyl and pentyl groups, of which the methyl and ethyl groups are preferred.

Where one of $R_f^4$, $R_f^5$ and $R_f^6$ (for example $R_f^6$) represents a hydrogen atom, the group of formula (II$f$) which is represented by one of $R^1$ and $R^2$, may be represented by the following formula (II$f''$):

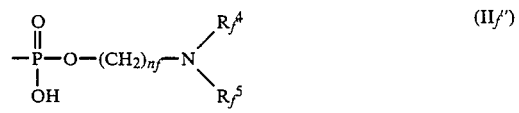

(in which $R_f^4$, $R_f^5$ and $n_f$ are as defined above) which is tautomeric with the group of formula (II$f'''$):

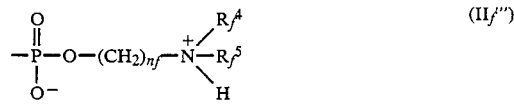

(in which $R_f^4$, $R_f^5$ and $n_f$ are as defined above).

Where $R_f^4$ and $R_f^5$ or $R_f^4$, $R_f^5$ and $R_f^6$ represents a heterocyclic group this will generally contain from 3 to 10 ring atoms and, in general, of these, at least one, preferably from 1 to 4 and more preferably 1 or 2, atoms (including the nitrogen atom to which $R_f^4$, $R_f^5$ and $R_f^6$ are attached) are hetero-atoms selected from the group consisting of nitrogen, oxygen and sulfur atoms. Specific examples of such groups are given below. Such groups may be unsubstituted or may have at least one substituent, the maximum number of substituents being dictated by the number of substitutable positions and other factors, such as steric constraints. However, in general, where the groups are substituted, from 1 to 3 substituents are preferred. Examples of such substituents include: $C_1$-$C_6$, preferably $C_1$-$C_5$, alkyl groups (such as those exemplified above in relation to $R_f^4$, $R_f^5$ and $R_f^6$), $C_1$-$C_6$, preferably $C_1$-$C_5$, alkoxy groups (such as the methoxy, ethoxy, propoxy, isopropoxy, butoxy and isobutoxy groups, prefereably the methoxy or ethoxy groups), $C_1$-$C_5$ hydroxyalkyl groups (such as the hydroxymethyl, 1-hydroxyethyl, 2-hydroxyethyl, 1-hydroxypropyl, 3-hydroxypropyl, 4-hydroxybutyl and 5-hydroxypentyl groups), carbamoyl groups, mono- and di-alkylcarbamoyl groups in which the or each alkyl part is $C_1$-$C_5$ (such as the methylcarbamoyl, ethylcarbamoyl, propylcarbamoyl, isopropylcarbamoyl, butylcarbamoyl, isobutylcarbamoyl, sec-butylcarbamoyl, t-butylcarbamoyl, penthylcarbamoyl, t-pentylcarbamoyl, dimethylcarbamoyl, diethylcarbamoyl, dipropylcarbamoyl, dibutylcarbamoyl, methylethylcarbamoyl and methylpropylcarbamoyl (groups) and halogen atoms (such as the fluorine, chlorine or bromine atoms).

Where $R_f^4$ and $R_f^5$, together with the nitrogen atom to which they are attached form a heterocyclic ring system, this is necessarily a non-aromatic ring system and should contain from 3 to 10, preferably from 3 to 7 and more preferably from 5 to 7, ring atoms (including the aforementioned nitrogen atom) and have at least one hetero-atom (the aforementioned nitrogen atom). It may have additionally from 0 to 3 hetero-atoms selected from the group consisting of nitrogen, oxygen and sulfur atoms. Examples of such non-aromatic heterocyclic groups include the 1-pyrrolidinyl, piperidino, 1-azepinyl, 1-aziridinyl, 1-azetidinyl, morpholino and thiomorpholino (=perhydro-1,4-thiazin-4-yl) groups. Of these, the 1-pyrrolidinyl and piperidino groups are preferred. These non-aromatic heterocyclic groups may be substituted or unsubstituted and, if substituted, the substituents may be selected from those defined above in relation to heterocyclic groups generally.

Where $R_f^4$, $R_f^5$ and $R_f^6$, together with the nitrogen atom to which they are attached, form a heterocyclic ring, this may be an aromatic heterocyclic group or may be a non-aromatic heterocyclic group in which the aforementioned nitrogen atom is doubly bonded, but it is preferably an aromatic heterocyclic ring, and preferably has from 5 to 10 ring atoms, of which at least the aforementioned nitrogen atom is a hetero-atom; it may contain from 0 to 3 additional hetero-atoms selected from the group consisting of nitrogen, oxygen and sulfur atoms. Examples of such aromatic heterocyclic rings include the 1-pyridyl, 3-thiazolyl, 3-oxazolyl, 1-pyridazinyl, 1-quinolyl, 2-isoquinolyl, 1-imidazolyl and N-triazolyl groups. Such groups may be substituted or unsubstituted and, if substituted, may have at least one (and preferably from 1 to 3) substituents selected from the group consisting of those substituents identified generally above. Of these, 5- and 6-membered aromatic heterocyclic groups, such as the unsubstituted 1-pyridyl and 3-thiazolyl groups, are preferred.

The value $n_f$ is an integer from 2 to 10, preferably from 2 to 6, e.g. 2 or 3.

Since the carbon atoms at the $\alpha$- and $\beta$-positions (relative to the ether oxygen atom) of the ether ring are asymmetric, a total of four stereoisomers of each compound is possible, in which each asymmetric carbon atom is in the R-configuration or the S-configuration, i.e. R,R, R,S, S,S and S,R isomers. The chiral synthesis of the compounds of the invention can be possible. The present invention envisages both the individual isolated isomers, as well as mixtures of these isomers. Where the process of the invention produces the compounds of the invention in the form of mixtures of isomers, these may, if desired, be employed as the mixtures, or the mixtures may be separated into individual isomers by conventional separation or resolution techniques.

More preferably, the compounds of the invention where one of $R^1$ and $R^2$ is a group of formula (III) are represented by the formula (Ia):

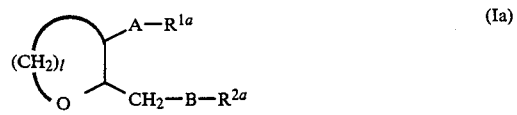

(Ia)

in which:
l, A and B are as defined above, and
one of $R^{1a}$ and $R^{2a}$ represents an alkyl group containing from 8 to 22 carbon atoms, an aliphatic carboxylic acyl group containing from 8 to 22 carbon atoms or a group of formula (II), as defined above, and the other of $R^{1a}$ and $R^{2a}$ represents a group of formula (IIIa):

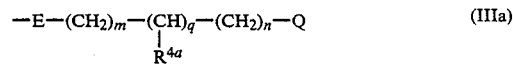

(IIIa)

in which
m, n, q and Q are as defined above, and
E represents a single bond, a bivalent heterocyclic group or a group of formula

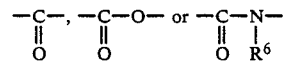

in which, $R^6$ is as defined above;
$R^{4a}$ represents a hydroxy group, a $C_1$-$C_4$ alkanoyloxy group, a $C_1$-$C_4$ alkoxy group, a $C_7$-$C_9$ aralkyloxy group, a carbamoyloxy group, an alkylcarbamoyloxy group in which the alkyl part is $C_1$-$C_4$, a dialkylcarbamoyloxy group in which each alkyl part is $C_1$-$C_4$, a mercapto group, a $C_1$-$C_4$ alkylthio group, a $C_7$-$C_9$ aralkylthio group, a $C_1$-$C_4$ alkanoylthio group, a carbamoylthio group, an alkylcarbamoylthio group in which the alkyl part is $C_1$-$C_4$, a dialkylcarbamoylthio group in which each alkyl part is $C_1$-$C_4$, a carboxy group or an alkoxycarbonyl group in which the alkoxy part is $C_1$-$C_4$;
said heterocyclic groups having from 5 to 10 ring atoms, of which from 1 to 4 are hetero-atoms selected from the group consisting of nitrogen, oxygen and sulfur atoms, the heterocyclic groups represented by E being unsubstituted and the heterocyclic groups represented by Q being unsubstituted or having at least one substituent selected from the group consisting of $C_1$-$C_4$ alkyl groups.

Where $R^{4a}$ represents an alkanoyloxy group, an alkoxy group, an aralkyloxy group, an alkylcarbamoyloxy group, a dialkylcarbamoyloxy group, an alkylthio group, an aralkylthio group, an alkanoylthio group, an alkylcarbamoylthio group or a dialkylcarbamoylthio group, these may be as exemplified above in relation to the corresponding groups which may be represented by $R^4$. Specific examples of alkoxycarbonyl groups which may be represented by $R^{4a}$ include the methoxycarbonyl, ethoxycarbonyl, propoxycarbonyl, isopropoxycarbonyl, butoxycarbonyl, isobutoxycarbonyl, sec-butoxycarbonyl and t-butoxycarbonyl groups, of which the methoxycarbonyl and ethoxycarbonyl groups are preferred.

Since the compounds of the present invention contain at least two asymmetric carbons at the α- and β-positions relative to the ethereal oxygen atom in the ether ring, and may, depending on the nature of the substituents, contain more asymmetric carbon atoms, there exist at least four stereoisomers due to the R and S configurations of each α- and β- carbon atom. The present invention covers both the individual isolated stereoisomers and mixtures of any two or more thereof. In tests, it has been found that the 3S isomers surprisingly have even better activity than do the 3R isomers; thus, the (3S, 2R) isomers are better than the (3R, 2S) isomers and the (3S, 2S) isomers are better than the (3R, 3R) isomers.

One class of compounds of the present invention are those compounds of formula (I), defined above, in which:

l is an integer of from 2 to 4;

A and B are independently selected from the group consisting of oxygen atoms and sulfur atoms;

one of $R^1$ or $R^2$ represents an alkyl group containing from 10 to 22 carbon atoms, an aliphatic carboxylic acyl group containing from 10 to 22 carbon atoms or a group of formula (IIa):

  (IIa)

in which $R^3$ represents an alkyl group containing from 10 to 22 carbon atoms, and the other represents a group of formula (IIIb):

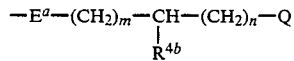  (IIIb)

in which, $E^a$ represents a single bond or a group of formula

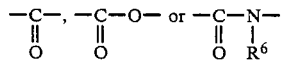

in which, $R^6$ represents a hydrogen atom or an imino-protecting group;

m is the cypher 0 or an integer from 1 to 3;

n is the cypher 0 or an integer from 1 to 10;

$R^{4b}$ represents a hydrogen atom, a carboxy group or an alkoxycarbonyl group in which the alkoxy part is $C_1$-$C_4$;

Q represents a group of formula (IV):

  (IV)

in which $R^7$ and $R^8$ are independently selected from the group consisting of hydrogen atoms and $C_1$-$C_6$ alkyl groups, or a monovalent heterocyclic group having from 5 to 7 ring atoms, of which from 1 to 4 atoms are hetero-atoms selected from the group consisting of nitrogen, oxygen and sulfur atoms at least one of these being a nitrogen atom, and the heterocyclic groups represented by Q being unsubstituted or having at least one substituent selected from the group consisting of $C_1$-$C_4$ alkyl groups, $C_1$-$C_4$ hydroxyalkyl groups, $C_1$-$C_4$ alkoxy groups and halogen atoms or such a heterocyclic group having another ring fused thereto;

and pharmaceutically acceptable salts thereof (including quaternary and inner salts).

Another class of compounds of the present invention are those compounds of formula (I), defined above, in which:

l is an integer of from 2 to 4;

A and B are independently selected from the group consisting of oxygen atoms and sulfur atoms;

one of $R^1$ or $R^2$ represents an alkyl group containing from 10 to 22 carbon atoms, an aliphatic carboxylic acyl group containing from 10 to 22 carbon atoms or a group of formula (IIa):

  (IIa)

in which $R^3$ represents an alkyl group containing from 10 to 22 carbon atoms and the other represents a group of formula (IIIc):

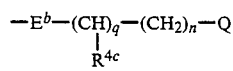  (IIIc)

in which, $E^b$ represents a group of formula $-(CH_2)_{m'}-$ or a bivalent heterocyclic group;

m' is an integer from 1 to 3;

n is the cypher 0 or an integer from 1 to 10;

q is the cypher 0 or the integer 1;

$R^{4c}$ represents a hydroxy group, a $C_1$-$C_4$ alkanoyloxy group, a $C_1$-$C_4$ alkoxy group, a $C_7$-$C_9$ aralkyloxy group, a carbamoyloxy group, an alkylcarbamoyloxy group in which the alkyl part is $C_1$-$C_4$, a dialkylcarbamoyloxy group in which each alkyl part is $C_1$-$C_4$, a mercapto group, a $C_1$-$C_4$ alkanoylthio group, a $C_1$-$C_4$ alkylthio group, a $C_7$-$C_9$ aralkylthio group, a carbamoylthio group, an alkylcarbamoylthio group in which the alkyl part is $C_1$-$C_4$ or a dialkylcarbamoylthio group in which each alkyl part is $C_1$-$C_4$;

Q represents a group of formula (IV):

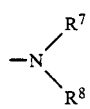  (IV)

in which $R^7$ and $R^8$ are independently selected from the group consisting of hydrogen atoms and $C_1$-$C_6$ alkyl groups, or a monovalent heterocyclic group having from 5 to 7 ring atoms, of which from 1 to 4 atoms are hetero-atoms selected from the group consisting of nitrogen, oxygen and sulfur atoms at least one of these being a nitrogen atom, and the heterocyclic groups represented by Q being unsubstituted or having at least one substituent selected from the group consisting of $C_1$-$C_4$ alkyl groups, $C_1$-$C_4$ hydroxyalkyl groups, $C_1$-$C_4$ alkoxy groups, carbamoyl groups and halogen atoms or such a heterocyclic group having another ring fused thereto;

and pharmaceutically acceptable salts thereof (including quaternary and inner salts).

Preferred compounds of the invention are:

(1) Those compounds of formula (I), defined above, in which:

l is the integer 2 or 3, preferably 3.

(2) Those compounds of formula (I), defined above, in which:
A represents an oxygen or sulfur atom and B represents an oxygen atom.
(3) Those compounds of formula (I), defined above, in which:
$R^1$ represents $C_8$–$C_{22}$ alkyl group or a group of formula (II):

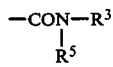 (II)

(in which $R^3$ and $R^5$ are as defined above), preferably said group of formula (II).
(4) Those compounds defined in (3) above in which $R^5$ represents a hydrogen atom or a $C_2$–$C_4$ alkanoyl group.
(5) Those compounds defined in (3) above in which $R^3$ represents a $C_{13}$–$C_{20}$ alkyl group.
(6) Those compounds of formula (I), defined above, in which:
n is an integer from 1 to 7.
(7) Those compounds of formula (I), defined above, in which:
Q represents a thiazolyl, pyridyl, quinolyl, isoquinolyl or imidazolyl group or a thiazolyl, pyridyl, quinolyl, isoquinolyl or imidazolyl group containing at least one substituent selected from the group consisting of $C_1$–$C_4$ alkyl groups.
(8) Those compounds of formula (I), defined above, in which:
Q represents a thiazolyl or pyridyl group.
(9) Those compounds of formula (I), defined above, in which:
E represents an isoxazolediyl or thiazolediyl group.
(10) Those compounds defined in (9) above, in which E represents a 3,5-isoxazolediyl group.
(11) Those compounds of formula (I), defined above, in which:
$R^2$ represents a group of formula (III):

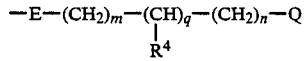 (III)

in which, E, Q, $R^4$, m, n and q are as defined above.
(12) Those compounds of formula (I), defined above, in which:
in the group represented by $R^2$, the group of formula

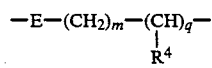

is a group of formula:

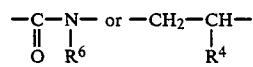

[in which $R^4$ is as defined above and $R^6$ is as defined above, but is more preferably a hydrogen atom or an acetyl group]
or an isoxazolediyl group.
(13) Those compounds of formula (I), defined above, in which:

$R^1$ represents a group of formula (II):

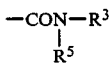 (II)

in which $R^3$ and $R^5$ are as defined above, and $R^2$ represents a group of formula (III):

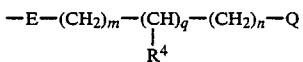 (III)

in which, E, m, n, q, $R^4$ and Q are as defined above.
(14) Those compounds defined in (13) above in which $R^5$ represents a hydrogen atom or a $C_2$–$C_4$ alkanoyl group.
(15) Those compounds defined in (13) above, in which:
the group of formula

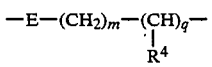

in the group represented by $R^2$ is a group of formula:

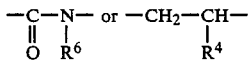

[in which $R^6$ is as defined in (12) above, but is more preferably a hydrogen atom or an acetyl group]
or an isoxazolediyl group.
Of the compounds of the invention where one of $R^1$ and $R^2$ is a group of formula (II$f$), we prefer those compounds in which:
(1) l is 2 or 3.
(2) $n_f$ is an integer from 2 to 6.
(3a) $R_f^4$, $R_f^5$ and $R_f^6$ are independently selected from the group consisting of hydrogen atoms and $C_1$–$C_6$ alkyl groups.
(3) $R_f^4$ and $R_f^5$, together with the nitrogen atom to which they are attached, represent a non-aromatic heterocyclic group having from 5 to 7 ring atoms, and
$R_f^6$ represents a hydrogen atom or a $C_1$–$C_6$ alkyl group.
(3c) $R_f^4$, $R_f^5$ and $R_f^6$, together with the nitrogen atom to which they are attached, represent an aromatic heterocyclic group having from 5 to 10 ring atoms, said heterocyclic group being unsubstituted or having at least one substituent selected from the group consisting of $C_1$–$C_5$ alkyl groups, $C_1$–$C_5$ alkoxy groups, $C_1$–$C_5$ hydroxyalkyl groups, carbamoyl groups and halogen atoms.
(4) $R^1$ represents said group of formula —CONHR$_f^3$ and $R^2$ represents said group of formula (II$f$).
(5) $R_f^3$ represents an alkyl group having from 16 to 18 carbon atoms.
In particular, preferred compounds are compounds of formula (I) where one of $R^1$ and $R^2$ is a group of formula (II$f$) in which:
$R^1$ represents said group of formula —CONHR$_f^3$;
$R^2$ represents said group of formula (II$f$):

$R_f^4$, $R_f^5$ and $R_f^6$ are independently selected from the group consisting of hydrogen atoms and $C_1$-$C_6$ alkyl groups;

or $R_f^4$ and $R_f^5$, together with the nitrogen atom to which they are attached, represent a non-aromatic heterocyclic group having from 5 to 7 ring atoms, and $R_f^6$ represents a hydrogen atom or a $C_1$-$C_6$ alkyl group;

or $R_f^4$, $R_f^5$ and $R_f^6$, together with the nitrogen atom to which they are attached, represent an aromatic heterocyclic group having from 5 to 10 ring atoms, said group being unsubstituted or having at least one substituent selected from the group consisting of $C_1$-$C_5$ alkyl groups, $C_1$-$C_5$ alkoxy groups, $C_1$-$C_5$ hydroxyalkyl groups, carbamoyl groups and halogen atoms;

$n_f$ is an integer from 2 to 6; and $l$ is 2 or 3.

More preferred compounds are compounds of formula (I) where one of $R^1$ and $R^2$ is a group of formula ($II_f$) in which:

$R^1$ represents a group of formula —CONHR$_f^3$, where $R_f^3$ represents a $C_{16}$-$C_{18}$ alkyl group;

$R^2$ represents said group of formula ($II_f$):

$R_f^4$, $R_f^5$ and $R_f^6$ are independently selected from the group consisting of $C_1$-$C_6$ alkyl groups;

or $R_f^4$ and $R_f^5$, together with the nitrogen atom to which they are attached, represent a non-aromatic heterocyclic group having from 5 to 7 ring atoms, and $R_f^6$ represents a hydrogen atom or a $C_1$-$C_6$ alkyl group;

or $R_f^4$, $R_f^5$ and $R_f^6$, together with the nitrogen atom to which they are attached, represent an aromatic heterocyclic group having 5 to 7 ring atoms, said group being unsubstituted or having at least one substituent selected from the group consisting of $C_1$-$C_5$ alkyl groups and $C_1$-$C_5$ hydroxyalkyl groups;

$n_f$ is an integer from 2 to 6; and $l$ is 2 or 3.

The most preferred compounds are compounds of formula (I) where one of $R^1$ and $R^2$ is a group of formula ($II_f$), in which:

$R^1$ represents a group of formula —CONHR$_f^3$, where $R_f^3$ represents a $C_{16}$-$C_{18}$ alkyl group;

$R^2$ represents said group of formula ($II_f$):

$R_f^4$, $R_f^5$ and $R_f^6$ are independently selected from the group consisting of $C_1$-$C_6$ alkyl groups;

or $R_f^4$ and $R_f^5$, together with the nitrogen atom to which they are attached represent a piperidino or 1-pyrrolidinyl group, and $R_f^6$ represents a hydrogen atom or a $C_1$-$C_6$ alkyl group;

or $R_f^4$, $R_f^5$ and $R_f^6$, together with the nitrogen atom to which they are attached, represent a 1-pyridyl or 1-thiazolyl group which is unsubstituted or has at least one substituent selected from the group consisting of $C_1$-$C_5$ alkyl groups and $C_1$-$C_5$ hydroxyalkyl groups;

$n_f$ is an integer from 2 to 6; and $l$ is 2 or 3.

Examples of specific compounds of the invention where one of $R^1$ and $R^2$ is a group of formula (III) are given in the following formulae (I-1) to (I-10), in which the substituents are as defined in the corresponding one of Tables 1 to 10 [i.e. Table 1 relates to formula (I-1), Table 2 relates to formula (I-2) and so on]. The compounds of the invention are hereinafter, where appropriate, identified by the numbers appended to them in these Tables. In the Tables, the following abbreviations are used:

| Ac | acetyl |
| All | allyl |
| Boz | benzoyl |
| Bz | benzyl |
| Bzc | benzyloxycarbonyl |
| Car | carbamoyl |
| Dc | decyl |
| Dco | decanoyl |
| Ddc | dodecyl |
| Doc | docosyl |
| Doco | docosanoyl |
| Ei | icosyl |
| Eio | icosanoyl |
| Et | ethyl |
| Etc | ethoxycarbonyl |
| Hdc | hexadecyl |
| Hen | henicosyl |
| Heno | henicosanoyl |
| Hpdc | heptadecyl |
| Hpdo | heptadecanoyl |
| Imd | imidazolediyl, e.g. |

2,4-Imd is:

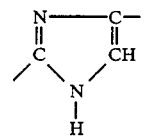

| Imid+ | imidazolyl 3-cation |
| Imin+ | imidazolinyl 1-cation |
| Isoxd | isoxazolediyl, e.g. |

3,5-Isoxd is:

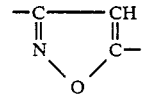

| Lau | lauroyl |
| Me | methyl |
| Mec | methoxycarbonyl |
| Mor | morpholino |
| Mor+ | morpholino 4-cation |
| Myr | myristyl |
| Ndc | nonadecyl |
| Ndco | nonadecanoyl |
| Odc | octadecyl |
| Oxa+ | oxazolyl 1-cation |
| Oxad | oxazolediyl, e.g. |

2,4-Oxad is:

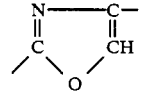

| Pal | palmitoyl |
| Pdc | pentadecyl |
| Pdco | pentadecanoyl |
| Pip | piperidyl |
| Pip+ | piperidyl 1-cation |
| Pym+ | pyrimidinyl 1-cation |
| Pyr | pyridyl |
| Pyr+ | pyridyl 1-cation |
| Pyrd | pyrrolidinyl |
| Pyrd+ | pyrrolidine 1-cation |
| Pyz+ | pyrazinyl 1-cation |
| Pyzn+ | pyridazinyl 1-cation |

-continued

| | |
|---|---|
| Quin+ | quinolyl 1-cation |
| iQuin+ | isoquinolyl 2-cation |
| Ste | stearoyl |
| Tco | tricosanoyl |
| Tdc | tridecyl |
| Tdco | tridecanoyl |
| Tedc | tetradecyl |
| Tez₂ | 2H—tetrazolyl |
| Thd | thiazolediyl, e.g. |

2,4-Thd is:

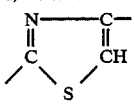

| | |
|---|---|
| Thi | thienyl |
| Thi+ | thiazolyl 3-cation |
| Thp | tetrahydropyranyl |
| Thz | perhydro-1,4-thiazin-4-yl (= thiomorpholino) |
| Tms | trimethylsilyl |
| Udc | undecyl |
| Udco | undecanoyl |

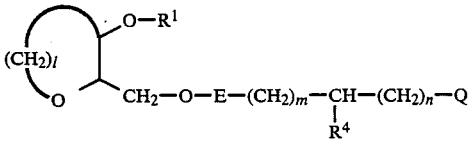 (I-1)

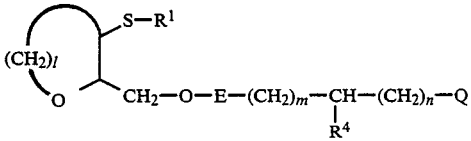 (I-2)

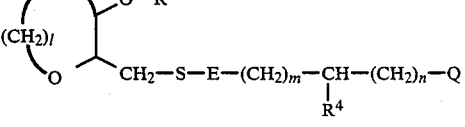 (I-3)

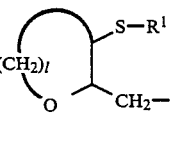 (I-4)

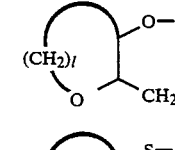 (I-5)

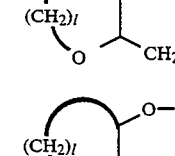 (I-6)

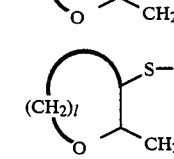 (I-7)

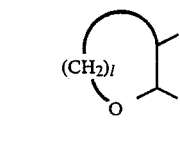 (I-8)

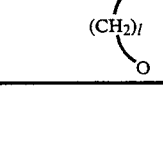 (I-9)

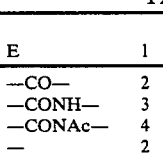 (I-10)

TABLE 1

| Cpd. No. | R¹ | E | l | m | n | R⁴ | Q |
|---|---|---|---|---|---|---|---|
| 1-1 | Dc | —CO— | 2 | 0 | 0 | H | 3-Thi+ |
| 1-2 | Udc | —CONH— | 3 | 1 | 1 | Etc | 1-Me-3-Imid+ |
| 1-3 | Ddc | —CONAc— | 4 | 2 | 2 | COOH | —N+Me₃ |
| 1-4 | Tdc | — | 2 | 3 | 3 | Mec | —NMe₂ |
| 1-5 | Tedc | —CO— | 3 | 0 | 4 | H | 1-Pip |
| 1-6 | Pdc | —CONH— | 4 | 1 | 5 | Etc | 1-Me-1-Pip+ |
| 1-7 | Hdc | —CONAc— | 2 | 2 | 6 | COOH | Mor |
| 1-8 | Hpdc | —COO— | 3 | 3 | 7 | Mec | 4-Me-4-Mor+ |
| 1-9 | Odc | —CO— | 4 | 0 | 8 | H | 1-Me-2-Pyr+ |
| 1-10 | Ndc | —CONH— | 2 | 1 | 9 | H | 1-Et-2-Pyr+ |
| 1-11 | Ei | —CONAc— | 3 | 2 | 10 | Etc | 3-Pyr |
| 1-12 | Hen | —COO— | 4 | 3 | 0 | COOH | 1-Me-3-Pyr+ |
| 1-13 | Doc | —CO— | 2 | 0 | 1 | Mec | 2-Pyr |
| 1-14 | Dco | —CONH— | 3 | 1 | 2 | H | 3-Me-4-Thi+ |
| 1-15 | Udco | —CONAc— | 4 | 2 | 3 | Etc | 3-Et-4-Me-5-Thi+ |
| 1-16 | Lau | — | 2 | 3 | 4 | COOH | 1-Et-2-Pyrd |
| 1-17 | Tdco | —CO— | 3 | 0 | 5 | Mec | 1,1-diEt-2-Pyrd+ |
| 1-18 | Myr | —CONH— | 4 | 1 | 6 | H | 1-Me-1-Imid+ |
| 1-19 | Pdco | —CONAc— | 2 | 2 | 7 | Etc | 1-Me-1-Pyrd+ |
| 1-20 | Pal | —COO— | 3 | 3 | 8 | COOH | 1-Me-1-Pip+ |
| 1-21 | Hpdo | —CO— | 4 | 0 | 9 | Mec | 3,4-diMe-5-Thi+ |
| 1-22 | Ste | —CONH— | 2 | 1 | 10 | H | I-Imin+ |
| 1-23 | Ndco | —CONAc— | 3 | 2 | 0 | Etc | Thz |
| 1-24 | Eio | —COO— | 4 | 3 | 1 | COOH | 3-Thi+ |
| 1-25 | Heno | —CO— | 2 | 0 | 2 | Mec | 1-Me-3-Imid+ |
| 1-26 | Doco | —CONH— | 3 | 1 | 3 | H | —N+Me₃ |
| 1-27 | —CONH— —Dc | —CONAc— | 4 | 2 | 4 | Etc | 5-Tez₂ |
| 1-28 | —CONH— | | | | | | |

TABLE 1-continued

| Cpd. No. | R¹ | E | l | m | n | R⁴ | Q |
|---|---|---|---|---|---|---|---|
|  | —Udc | — | 2 | 3 | 5 | COOH | 1-Pyz⁺ |
| 1-29 | —CONH— —Ddc | —CO— | 3 | 0 | 6 | Mec | 1-Pym⁺ |
| 1-30 | —CONH— —Tdc | —CONH— | 4 | 1 | 7 | H | 1-Quin⁺ |
| 1-31 | —CONH— —Tedc | —CONAc— | 2 | 2 | 8 | Etc | 2-iQuin⁺ |
| 1-32 | —CONH— —Pdc | —COO— | 3 | 3 | 9 | COOH | 1-Me-2-Pyr⁺ |
| 1-33 | —CONH— —Hdc | —CO— | 4 | 0 | 10 | Mec | 1-Et-2-Pyr⁺ |
| 1-34 | —CONH— —Hpdc | —CONH— | 3 | 0 | 5 | Etc | 3-Thi⁺ |
| 1-35 | —CONH— —Odc | —CONAc— | 3 | 2 | 1 | Etc | 1-Me-3-Pyr⁺ |
| 1-36 | —CONH— —Ndc | —COO— | 4 | 3 | 2 | COOH | 1-Pyzn⁺ |
| 1-37 | —CONH— —Ei | —CO— | 2 | 0 | 3 | Mec | 3-Me-5-Thi⁺ |
| 1-38 | —CONH— —Hen | —CONH— | 3 | 1 | 4 | H | 4-Me-5-Thi |
| *1-39 | —CONH— —Doc | —CONAc— | 4 | 2 | 5 | Etc | 3-Et-4-Oxa⁺ |
| 1-40 | Dc | —CO— | 2 | 3 | 6 | COOH | 1,1-diEt-2-Pyrd⁺ |
| 1-41 | Ddc | —CONH— | 3 | 0 | 7 | Mec | 1-Me-1-Imid⁺ |
| 1-42 | Tedc | —CONAc— | 4 | 1 | 8 | H | 1-Me-1-Pyrd⁺ |
| 1-43 | Hdc | —CO— | 2 | 2 | 9 | Etc | 1-Me-1-Pip⁺ |
| 1-44 | Hdc | —CONH— | 3 | 0 | 4 | H | 3-Thi⁺ |
| 1-45 | Hdc | —CONAc— | 3 | 1 | 3 | H | 3-Me-2-Thi⁺ |
| 1-46 | Hdc | — | 3 | 2 | 4 | H | 3-Thi⁺ |
| 1-47 | Odc | —CONH— | 4 | 0 | 10 | COOH | 3,4-diMe-5-Thi⁺ |
| 1-48 | Ei | —CONAc— | 2 | 1 | 0 | Mec | 1-Imin⁺ |
| 1-49 | Doc | —CO— | 3 | 2 | 1 | H | 1-Me-3-Imid⁺ |
| 1-50 | —CONH— —Udc | —CONH— | 4 | 3 | 2 | Etc | —N⁺Me₃ |
| 1-51 | —CONH— —Tdc | —CONAc— | 2 | 0 | 3 | COOH | 4-Me-4-Mor⁺ |
| 1-52 | —CONH— —Hdc | —CONH— | 3 | 0 | 4 | H | 3-Thi⁺ |
| 1-53 | —CONH— —Hpdc | —CONH— | 3 | 0 | 4 | H | 3-Thi⁺ |
| 1-54 | —CONH— —Odc | —CONH— | 3 | 0 | 4 | H | 3-Thi⁺ |
| 1-55 | —CONH— —HPdc | —CONAc— | 3 | 0 | 4 | H | 3-Thi⁺ |
| 1-56 | —CONH— —Hpdc | —CONH— | 3 | 0 | 0 | H | 1-Me-2-Pyr⁺ |
| 1-57 | —CONH— —Hpdc | —CONAc— | 3 | 0 | 0 | H | 1-Et-2-Pyr⁺ |
| 1-58 | Dc | — | 3 | 2 | 4 | —SAc | 3-Thi⁺ |
| 1-59 | Tedc | 3,5--Isoxd | 3 | 0 | 4 | —SAc | 1-Pip |
| 1-60 | Pdc | 2,4-Thd | 4 | 0 | 5 | OH | 1-Me-1-Pip⁺ |
| 1-61 | Hdc | — | 3 | 1 | 3 | —OAc | 3-Thi⁺ |
| 1-62 | Hpdc | — | 2 | 1 | 7 | SH | 4-Me-4-Mor⁺ |
| 1-63 | Odc | — | 3 | 1 | 8 | SH | 1-Me-2-Pyr⁺ |
| 1-64 | Ndc | — | 4 | 2 | 9 | MeCarO— | 1-Et-2-Pyr⁺ |
| 1-65 | Ei | — | 2 | 3 | 10 | 2-ThpO— | 3-Pyr |
| 1-66 | Hen | — | 3 | 1 | 0 | TmsO— | 1-Me-3-Pyr⁺ |
| 1-67 | Doc | — | 4 | 2 | 1 | MeOMeO— | 2-Pyr |
| 1-68 | Tdco | — | 2 | 1 | 5 | MecO | 1,1-diEt-2-Pyrd⁺ |
| 1-69 | Hpdo | — | 3 | 1 | 9 | —SAc | Thz |
| 1-70 | Ndco | — | 2 | 1 | 0 | —SMe | 1-Pyz⁺ |
| 1-71 | Eio | — | 3 | 2 | 1 | —SBz | 1-Pym⁺ |
| 1-72 | Doco | — | 2 | 2 | 3 | SH | 2-iQuin⁺ |
| 1-73 | —CONH— —Dc | — | 4 | 2 | 5 | OH | 1-Pyzn⁺ |
| 1-74 | —CONH— —Udc | — | 2 | 1 | 6 | —OAc | 3-Et-4-Oxa⁺ |
| 1-75 | —CONH— —Ddc | — | 3 | 2 | 7 | OH | 3-Me-2-Thi⁺ |
| 1-76 | —CONH— —Tedc | — | 2 | 2 | 9 | diMe— CarO | 4-Mor |
| 1-77 | —CONH— —Hdc | — | 3 | 2 | 4 | —SAc | 3-Thi⁺ |
| 1-78 | —CONH— —Hpdc | — | 2 | 2 | 1 | —OAc | 3-Thi⁺ |
| 1-79 | —CONH— —Odc | — | 3 | 1 | 2 | —OAc | 3-Thi⁺ |
| 1-80 | —CONH— | | | | | | |

TABLE 1-continued

| Cpd. No. | R¹ | E | l | m | n | R⁴ | Q |
|---|---|---|---|---|---|---|---|
| 1-81 | —Doc —CONH— | — | 3 | 2 | 6 | SH | 3-Thi⁺ |
| 1-82 | —Hdc —CONH— | — | 2 | 1 | 1 | —OBz | 3-Thi⁺ |
| 1-83 | —Hdc —CONH— | — | 2 | 1 | 2 | OH | 1-Quin⁺ |
| 1-84 | —Hdc —CONH— | — | 4 | 1 | 3 | —OAc | 3-Thi⁺ |
| 1-85 | —Hdc —CONH— | — | 3 | 1 | 4 | OH | 3-Thi⁺ |
| 1-86 | —Hdc —CONH— | — | 3 | 1 | 5 | OH | 3-Thi⁺ |
| 1-87 | —Hdc —CONH— | — | 3 | 1 | 6 | OH | 3-Thi⁺ |
| 1-88 | —Hdc —CONH— | — | 3 | 1 | 6 | —OAc | 3-Thi⁺ |
| 1-89 | —Hpdc —CONH— | — | 2 | 1 | 2 | —OAc | 3-Thi⁺ |
| 1-90 | —Hpdc —CONH— | — | 4 | 1 | 3 | OH | 3-Thi⁺ |
| 1-91 | —Hpdc —CONH— | — | 3 | 1 | 5 | —OAc | 1-Me-2-Quin⁺ |
| 1-92 | —Hpdc —CONH— | — | 3 | 1 | 6 | OH | 3-Thi⁺ |
| 1-93 | —Hpdc —CONH— | — | 3 | 1 | 6 | —OAc | 3-Thi⁺ |
| 1-94 | —Hpdc —CONH— | — | 3 | 1 | 5 | —OAc | 1-Pyr⁺ |
| 1-95 | —Hpdc —CONH— | — | 3 | 1 | 6 | —SAc | 1-Quin⁺ |
| 1-96 | —Odc —CONH— | — | 2 | 1 | 1 | MeO | —N⁻Me₃ |
| 1-97 | —Odc —CONH— | — | 4 | 1 | 3 | —OAc | 2-iQuin⁺ |
| 1-98 | —Odc —CONH— | — | 4 | 1 | 4 | CarO | 1-Quin⁺ |
| 1-99 | —Odc —CONH— | — | 3 | 1 | 5 | CarO | 2-Pyr |
| 1-100 | —Odc —CONH— | — | 3 | 1 | 6 | OH | 3-Thi⁺ |
| 1-101 | —Odc —CONH— | — | 3 | 1 | 6 | —OAc | 3-Thi⁺ |
| 1-102 | —Hpdc —CONH— | — | 3 | 2 | 4 | —OAc | 3-Thi⁺ |
| 1-103 | —Hpdc —CONH— | — | 3 | 2 | 5 | OH | 1-Quin⁺ |
| 1-104 | —Hpdc —CONH— | — | 3 | 2 | 4 | OH | 3-Thi⁺ |
| 1-105 | —Hpdc —CONH— | — | 3 | 2 | 5 | —OAc | 1-Quin⁺ |
| 1-106 | —Hpdc —CONH— | — | 3 | 1 | 2 | —OAc | 1-Me-2-Pyr⁺ |
| 1-107 | —Hpdc —CONH— | — | 3 | 1 | 2 | —OAc | 1-Et-2-Pyr⁺ |
| 1-108 | —Hpdc —CONH— | — | 3 | 1 | 2 | —OAc | 2-Pyr |
| 1-109 | —Hpdc —CONH— | — | 3 | 1 | 2 | —OAc | 1-Me-2-Quin⁺ |
| 1-110 | —CONH— Hpdc | —CONAc— | 3 | 0 | 0 | H | 1-Me-2-Pyr³⁰ |
| 1-111 | —CONH— Hpdc | —CONAc— | 3 | 0 | 0 | H | 1-Et-2-Quin⁺ |
| | —CONH— Hpdc | —CONH— | 3 | 0 | 0 | H | 2-Et-1-iQuin⁺ |

TABLE 2

| Cpd. No. | R¹ | E | l | m | n | R⁴ | Q |
|---|---|---|---|---|---|---|---|
| 2-1 | Dc | —CO— | 2 | 3 | 6 | COOH | 1,1-diEt-2-Pyrd⁺ |
| 2-2 | Ddc | —CONH— | 3 | 0 | 7 | Mec | 1-Me-1-Imid⁺ |
| 2-3 | Tedc | —CONAc— | 4 | 1 | 8 | H | 1-Me-1-Pyrd⁺ |
| 2-4 | Hdc | —CO— | 2 | 2 | 9 | Etc | 1-Me-1-Pip⁺ |
| 2-5 | Hdc | —CONH— | 3 | 0 | 4 | H | 3-Thi⁺ |
| 2-6 | Hdc | —CONAc— | 3 | 1 | 3 | H | 3-Thi⁺ |
| 2-7 | Hdc | — | 3 | 2 | 2 | H | 3-Thi⁺ |
| 2-8 | Odc | —CONH— | 4 | 0 | 10 | COOH | 3,4-diMe-5-Thi⁺ |
| 2-9 | Ei | —CONAc— | 2 | 1 | 0 | Mec | 1-Imin⁺ |
| 2-10 | Doc | —CO— | 3 | 2 | 1 | H | 1-Me-3-Imid⁺ |

TABLE 2-continued

| Cpd. No. | R¹ | E | l | m | n | R⁴ | Q |
|---|---|---|---|---|---|---|---|
| 2-11 | —CONH—Udc | —CONH— | 4 | 3 | 2 | Etc | —N⁺Me₃ |
| 2-12 | —CONH—Tdc | —CONAc— | 2 | 0 | 3 | COOH | 4-Me-4-Mor⁺ |
| 2-13 | —CONH—Pdc | —CO— | 3 | 1 | 5 | Mec | 1-Me-2-Pyr⁺ |
| 2-14 | —CONH—Hpdc | —CONH— | 3 | 0 | 4 | H | 3-Thi⁺ |
| 2-15 | —CONH—Hpdc | —CONAc— | 4 | 2 | 6 | COOH | 1-Et-2-Pyr⁺ |
| 2-16 | —CONH—Hpdc | —CO— | 3 | 3 | 7 | Etc | 1-Me-3-Pyr⁺ |
| 2-17 | —CONH—Ndc | —CONH— | 2 | 0 | 8 | Mec | 1,1-diMe-2-Pyrd⁺ |
| 2-18 | —CONH—Hen | —CONAc— | 3 | 1 | 9 | H | 1-Me-1-Imid⁺ |
| 2-19 | Ddc | — | 4 | 2 | 2 | OH | —N⁺Me₃ |
| 2-20 | Dco | — | 2 | 1 | 2 | 2-EtOEtO | 3-Me-4-Thi⁺ |
| 2-21 | Pdco | — | 4 | 1 | 7 | —OBzc | 1-Me-1-Pyrd⁺ |
| 2-22 | Ste | — | 4 | 2 | 10 | —SBoz | 5-Tez₂ |
| 2-23 | Heno | — | 4 | 1 | 2 | —SAc | 1-Quin⁺ |
| 2-24 | Tco | — | 3 | 1 | 4 | —OAc | 3-Thi⁺ |
| 2-25 | Myr | — | 2 | 1 | 8 | SH | 5-(2-HOEt)-4-Me-3-Thi⁺ |
| 2-26 | Pal | — | 3 | 1 | 10 | OH | 1-Me-2-Quin⁺ |
| 2-27 | —CONH—Ei | — | 3 | 1 | 4 | MeO | 3-Thi⁺ |
| 2-28 | —CONH—Hpdc | — | 3 | 1 | 4 | —OAc | 3-Thi⁺ |
| 2-29 | —CONH—Hpdc | —CONH— | 3 | 0 | 0 | H | 2-Pyr |
| 2-30 | —CONAc—Hpdc | —CONAc— | 3 | 0 | 0 | H | 2-Pyr |
| 2-31 | —CONAc—Hpdc | —CONAc— | 3 | 0 | 0 | H | 1-Et-2-Pyr⁺ |
| 2-32 | —CONAc—Hpdc | —CONH— | 3 | 0 | 0 | H | 1-Et-2-Pyr⁺ |

TABLE 3

| Cpd. No. | R¹ | E | l | m | n | R⁴ | Q |
|---|---|---|---|---|---|---|---|
| 3-1 | Dc | —CO— | 2 | 3 | 6 | COOH | 1,1-diEt-2-Pyrd⁺ |
| 3-2 | Ddc | —CONH— | 3 | 0 | 7 | Mec | 1-Me-1-Imid⁺ |
| 3-3 | Tedc | —CONAc— | 4 | 1 | 8 | H | 1-Me-1-Pyrd⁺ |
| 3-4 | Hdc | —CO— | 2 | 2 | 9 | Etc | 1-Me-1-Pip⁺ |
| 3-5 | Hdc | —CONH— | 3 | 0 | 4 | H | 5-(2-HOEt)-4-Me-3-Thi⁺ |
| 3-6 | Hdc | —CONAc— | 3 | 1 | 3 | H | 5-(2-HOEt)-4-Me-3-Thi⁺ |
| 3-7 | Hdc | — | 3 | 2 | 2 | H | 5-(2-HOEt)-4-Me-3-Thi⁺ |
| 3-8 | Odc | —CONH— | 4 | 0 | 10 | COOH | 3 4-diMe-5-Thi⁺ |
| 3-9 | Ei | —CONAc— | 2 | 1 | 0 | Mec | 1-Imin⁺ |
| 3-10 | Doc | —CO— | 3 | 2 | 1 | H | 1-Me-3-Imid⁺ |
| 3-11 | —CONH—Udc | —CONH— | 4 | 3 | 2 | Etc | —N⁺Me₃ |
| 3-12 | —CONH—Tdc | —CONAc— | 2 | 0 | 3 | COOH | 4-Me-4-Mor⁺ |
| 3-13 | —CONH—Pdc | —CO— | 3 | 1 | 5 | Mec | 1-Me-2-Pyr⁺ |
| 3-14 | —CONH—HPdc | —CONH— | 3 | 0 | 4 | H | 3-Thi⁺ |
| 3-15 | —CONH—Hpdc | —CONAc— | 4 | 2 | 6 | COOH | 1-Et-2-Pyr⁺ |
| 3-16 | —CONH—HPdc | —CO— | 3 | 3 | 7 | Etc | 1-Me-3-Pyr⁺ |
| 3-17 | —CONH—Ndc | —CONH— | 2 | 0 | 8 | Mec | 1,1-diMe-2-Pyrd⁺ |
| 3-18 | —CONH—Hen | —CONAc— | 3 | 1 | 9 | H | 1-Me-1-Imid⁺ |
| 3-19 | Udc | — | 3 | 1 | 1 | SH | 1-Me-3-Imid⁺ |
| 3-20 | Udco | — | 3 | 1 | 3 | —OBz | 3-Et-4-Me-5-Thi⁺ |
| 3-21 | Pal | — | 2 | 2 | 8 | MeO | 1-Me-1-Imin⁺ |
| 3-22 | Eio | — | 2 | 2 | 3 | OH | 1-Et-2-Quin⁺ |
| 3-23 | —CONH—Hdc | — | 2 | 1 | 4 | SH | 1-Me-3-Imid⁺ |

TABLE 4

| Cpd. No. | R¹ | E | l | m | n | R⁴ | Q |
|---|---|---|---|---|---|---|---|
| 4-1 | Dc | —CO— | 2 | 3 | 6 | COOH | 1,1-diEt-2-Pyrd⁺ |
| 4-2 | Ddc | —CONH— | 3 | 0 | 7 | Mec | 1-Me-1-Imid⁺ |
| 4-3 | Tedc | —CONAc— | 4 | 1 | 8 | H | 1-Me-1-Pyrd⁺ |
| 4-4 | Hdc | —CO— | 2 | 2 | 9 | Etc | 1-Me-1-Pip⁺ |

TABLE 4-continued

| Cpd. No. | R¹ | E | l | m | n | R⁴ | Q |
|---|---|---|---|---|---|---|---|
| 4-5 | Hdc | —CONH— | 3 | 0 | 4 | H | 3-Thi⁺ |
| 4-6 | Hdc | —CONAc— | 3 | 1 | 3 | H | 3-Thi⁺ |
| 4-7 | Hdc | — | 3 | 2 | 2 | H | 3-Thi⁺ |
| 4-8 | Odc | —CONH— | 4 | 0 | 10 | COOH | 3,4-diMe-5-Thi⁺ |
| 4-9 | Ei | —CONAc— | 2 | 1 | 0 | Mec | 1-Imin⁺ |
| 4-10 | Doc | —CO— | 3 | 2 | 1 | H | 1-Me-3-Imid⁺ |
| 4-11 | —CONH—Udc | —CONH— | 4 | 3 | 2 | Etc | —N⁺Me₃ |
| 4-12 | —CONH—Tdc | —CONAc— | 2 | 0 | 3 | COOH | 4-Me-4-Mor⁺ |
| 4-13 | —CONH—Pdc | —CO— | 3 | 1 | 5 | Mec | 1-Me-2-Pyr⁺ |
| 4-14 | —CONH—Hpdc | —CONH— | 3 | 0 | 4 | H | 3-Thi⁺ |
| 4-15 | —CONH—Hpdc | —CONAc— | 4 | 2 | 6 | H | 1-Et-2-Pyr⁺ |
| 4-16 | —CONH—Hpdc | —CO— | 3 | 3 | 7 | Etc | 1-Me-3-Pyr⁺ |
| 4-17 | —CONH—Ndc | —CONH— | 2 | 0 | 8 | Mec | 1,1-diMe-2-Pyrd⁺ |
| 4-18 | Tdc | — | 2 | 3 | 3 | SH | —NMe₂ |
| 4-19 | Lau | — | 4 | 2 | 4 | —OBoz | 1-Et-2-Pyrd |
| 4-20 | Myr | — | 3 | 2 | 6 | AllO— —COO— | 1-Me-1-Imid⁺ |
| 4-21 | —CONH—Hen | — | 2 | 2 | 5 | —OAc | 1-Pyr⁺ |

TABLE 5

| Cpd. No. | R2 | E | l | m | n | R4 | Q |
|---|---|---|---|---|---|---|---|
| 5-1 | Dc | —CO— | 2 | 0 | 0 | H | 3-Thi+ |
| 5-2 | Udc | —CONH— | 3 | 1 | 1 | Etc | 1-Me-3-Imid+ |
| 5-3 | Ddc | —CONAc— | 4 | 2 | 2 | COOH | —N+Me3 |
| 5-4 | Tdc | — | 2 | 3 | 3 | Mec | —NMe2 |
| 5-5 | Tedc | —CO— | 3 | 0 | 4 | H | 1-Pip |
| 5-6 | Pdc | —CONH— | 4 | 1 | 5 | Etc | 1-Me-1-Pip+ |
| 5-7 | Hdc | —CONAc— | 2 | 2 | 6 | COOH | Mor |
| 5-8 | Hpdc | —COO— | 3 | 3 | 7 | Mec | 4-Me-4-Mor+ |
| 5-9 | Odc | —CO— | 4 | 0 | 8 | H | 1-Me-2-Pyr+ |
| 5-10 | Ndc | —CONH— | 2 | 1 | 9 | H | 1-Et-2-Pyr+ |
| 5-11 | Ei | —CONAc— | 3 | 2 | 10 | Etc | 3-Pyr |
| 5-12 | Hen | —COO— | 4 | 3 | 0 | COOH | 1-Me-3-Pyr+ |
| 5-13 | Doc | —CO— | 2 | 0 | 1 | Mec | 2-Pyr |
| 5-14 | Dco | —CONH— | 3 | 1 | 2 | H | 4-Thi |
| 5-15 | Udco | —CONAc— | 4 | 2 | 3 | Etc | 4-Me-5-Thi |
| 5-16 | Lau | — | 2 | 3 | 4 | COOH | 1-Et-2-Pyrd |
| 5-17 | Tdco | —CO— | 3 | 0 | 5 | Mec | 1,1-diEt-2-Pyrd+ |
| 5-18 | Myr | —CONH— | 4 | 1 | 6 | H | 1-Me-1-Imid+ |
| 5-19 | Pdco | —CONAc— | 2 | 2 | 7 | Etc | 1-Me-1-Pyrd+ |
| 5-20 | Pal | —COO— | 3 | 3 | 8 | COOH | 1-Me-1-Pip+ |
| 5-21 | Hpdo | —CO— | 4 | 0 | 9 | Mec | 3,4-diMe-5-Thi+ |
| 5-22 | Ste | —CONH— | 2 | 1 | 10 | H | 1-Imin+ |
| 5-23 | Ndco | —CONAc— | 3 | 2 | 0 | Etc | Thz |
| 5-24 | Eio | —COO— | 4 | 3 | 1 | COOH | 5-(2-HOEt)-4-Me-3-Thi+ |
| 5-25 | Heno | —CO— | 2 | 0 | 2 | Mec | 1-Me-3-Imid+ |
| 5-26 | Doco | —CONH— | 3 | 1 | 3 | H | —N+Me3 |
| 5-27 | -CONH-Dc | —CONAc— | 4 | 2 | 4 | Etc | —NMe2 |
| 5-28 | -CONH-Udc | — | 2 | 3 | 5 | COOH | 1-Pip |
| 5-29 | -CONH-Ddc | —CO— | 3 | 0 | 6 | Mec | 1-Me-1-Pip+ |
| 5-30 | —CONH—Tdc | —CONH— | 4 | 1 | 7 | H | Mor |
| 5-31 | —CONH—Tedc | —CONAc— | 2 | 2 | 8 | Etc | 4-Me-4-Mor+ |
| 5-32 | —CONH—Pdc | —COO— | 3 | 3 | 9 | COOH | 1-Me-2-Pyr+ |
| 5-33 | —CONH—Hdc | —CO— | 4 | 0 | 10 | Mec | 1-Et-2-Pyr+ |
| 5-34 | —CONH—Hpdc | —CONH— | 2 | 1 | 0 | H | 3-Pyr |
| 5-35 | —CONH—Odc | —CONAc— | 3 | 2 | 1 | Etc | 1-Me-3-Pyr+ |
| 5-36 | —CONH—Ndc | —COO— | 4 | 3 | 2 | COOH | 2-Pyr |
| 5-37 | —CONH—Ei | —CO— | 2 | 0 | 3 | Mec | 4-Thi |
| 5-38 | —CONH—Hen | —CONH— | 3 | 1 | 4 | H | 4-Me-5-Thi |
| 5-39 | —CONH—Doc | —CONAc— | 4 | 2 | 5 | Etc | 1-Et-2-Pyrd |
| 5-40 | Dc | —CO— | 2 | 3 | 6 | COOH | 1,1-diEt-2-Pyrd+ |
| 5-41 | Ddc | —CONH— | 3 | 0 | 7 | Mec | 1-Me-1-Imid+ |
| 5-42 | Tedc | —CONAc— | 4 | 1 | 8 | H | 1-Me-1-Pyrd+ |
| 5-43 | Hdc | —CO— | 2 | 2 | 9 | Etc | 1-Me-1-Pip+ |
| 5-44 | Hdc | —CONH— | 3 | 0 | 4 | H | 3-Thi+ |
| 5-45 | Hdc | —CONAc— | 3 | 1 | 3 | H | 3-Thi+ |
| 5-46 | Hdc | — | 3 | 2 | 2 | H | 3-Thi+ |
| 5-47 | Odc | —CONH— | 4 | 0 | 10 | COOH | 3,4-diMe-5-Thi+ |
| 5-48 | Ei | —CONAc— | 2 | 1 | 0 | Mec | 1-Imin+ |
| 5-49 | Doc | —CO— | 3 | 2 | 1 | H | 1-Me-3-Imid+ |
| 5-50 | —CONH—Udc | —CONH— | 4 | 3 | 2 | Etc | —N+Me3 |
| 5-51 | —CONH—Tdc | —CONAc— | 2 | 0 | 3 | COOH | 4-Me-4-Mor+ |
| 5-52 | —CONH—Pdc | —CO— | 3 | 1 | 5 | Mec | 1-Me-2-Pyr+ |
| 5-53 | —CONH—Hpdc | —CONH— | 3 | 0 | 4 | H | 3-Thi+ |
| 5-54 | —CONH—Hpdc | —CONAc— | 4 | 2 | 6 | H | 1-Et-2-Pyr+ |

TABLE 5-continued

| Cpd. No. | R2 | E | l | m | n | R4 | Q |
|---|---|---|---|---|---|---|---|
| 5-55 | —CONH—Hpdc | —CO— | 3 | 3 | 7 | Etc | 1-Me-3-Pyr+ |
| 5-56 | —CONH—Ndc | —CONH— | 2 | 0 | 8 | Mec | 1,1-diMe-2-Pyrd+ |
| 5-57 | —CONH—Hen | —CONAc— | 3 | 1 | 9 | H | 1-Me-1-Imid+ |
| 5-58 | Dc | — | 2 | 1 | 2 | OH | 3-Thi+ |
| 5-59 | Tedc | 3,5-Isoxd | 3 | 0 | 4 | —SAc | 1-Pip |
| 5-60 | Pdc | 2,4-Thd | 4 | 0 | 5 | OH | 1-Me-1-Pip+ |
| 5-61 | Hdc | — | 3 | 1 | 3 | —OAc | 3-Thi+ |
| 5-62 | Hpdc | — | 2 | 2 | 7 | OH | 4-Me-4-Mor+ |
| 5-63 | Odc | — | 3 | 1 | 8 | SH | 1-Me-2-Pyr+ |
| 5-64 | Ndc | — | 4 | 2 | 9 | —OAc | 1-Et-2-Pyr+ |
| 5-65 | Ei | — | 2 | 3 | 10 | 2—ThpO | 3-Pyr |
| 5-66 | Hen | — | 3 | 1 | 0 | —O—Tms | 1-Me-3-Pyr+ |
| 5-67 | Doc | — | 4 | 2 | 1 | MeOMeO— | 2-Pyr |
| 5-68 | Tdco | — | 2 | 1 | 5 | MecO— | 1,1-diEt-2-—Pyrd+ |
| 5-69 | Hpdo | — | 3 | 1 | 9 | —SAc | 4-Mor |
| 5-70 | Ndco | — | 2 | 1 | 3 | —SMe | 1-Pyz+ |
| 5-71 | Eio | — | 3 | 2 | 1 | —SBz | 1-Pym+ |
| 5-72 | Doco | — | 2 | 2 | 3 | SH | 2-iQuin+ |
| 5-73 | —CONH—Dc | — | 4 | 2 | 5 | SH | 1-Pyzn+ |
| 5-74 | —CONH—Udc | — | 2 | 1 | 6 | —OAc | 3-Et-4-Oxa+ |
| 5-75 | —CONH—Ddc | — | 3 | 2 | 7 | OH | 3-Me-2-Thi+ |
| 5-76 | —CONH—Tedc | — | 3 | 2 | 9 | —OCar | 4-Mor |
| 5-77 | —CONH—Hdc | — | 3 | 1 | 4 | —SAc | 3-Thi+ |
| 5-78 | —CONH—Hpdc | — | 2 | 2 | 1 | —OAc | 3-Thi+ |
| 5-79 | —CONH—Odc | — | 3 | 1 | 2 | —OAc | 3-Thi+ |
| 5-80 | —CONH—Doc | — | 3 | 2 | 6 | SH | 3-Thi+ |
| 5-81 | —CONH—Hdc | — | 2 | 1 | 1 | —OBz | 3-Thi+ |
| 5-82 | —CONH—Hdc | — | 2 | 1 | 2 | OH | 1-Quin+ |
| 5-83 | —CONH—Hdc | — | 4 | 1 | 3 | —OAc | 3-Thi+ |
| 5-84 | —CONH—Hdc | — | 3 | 1 | 4 | OH | 3-Thi+ |
| 5-85 | —CONH—Hdc | — | 3 | 1 | 5 | OH | 3-Thi+ |
| 5-86 | —CONH—Hdc | — | 3 | 1 | 6 | OH | 3-Thi+ |
| 5-87 | —CONH—Hdc | — | 3 | 1 | 6 | —OAc | 3-Thi+ |
| 5-88 | —CONH—Hpdc | — | 2 | 1 | 2 | —OAc | 3-Thi+ |
| 5-89 | —CONH—Hpdc | — | 4 | 1 | 3 | OH | 3-Thi+ |
| 5-90 | —CONH—Hpdc | — | 3 | 1 | 5 | —OAc | 1-Me-2-Quin+ |
| 5-91 | —CONH—Hpdc | — | 3 | 1 | 6 | OH | 3-Thi+ |
| 5-92 | —CONH—Hpdc | — | 3 | 1 | 5 | —OAc | 1-Pyr+ |
| 5-93 | —CONH—Hpdc | — | 3 | 1 | 6 | —OAc | 1-Quin+ |
| 5-94 | —CONH—Odc | — | 2 | 1 | 1 | MeO | —N+Me3 |
| 5-95 | —CONH—Odc | — | 4 | 1 | 3 | —OAc | 2-iQuin+ |
| 5-96 | —CONH—Odc | — | 4 | 1 | 4 | —OAc | 3-Thi+ |
| 5-97 | —CONH—Odc | — | 3 | 1 | 5 | —OAc | 2-Pyr |
| 5-98 | —CONH—Odc | — | 3 | 1 | 6 | OH | 3-Thi+ |
| 5-99 | —CONH—Odc | — | 3 | 1 | 6 | —OAc | 3-Thi+ |
| 5-100 | —CONH—Hpdc | — | 3 | 2 | 4 | —OAc | 3-Thi+ |
| 5-101 | —CONH—Hpdc | — | 3 | 2 | 5 | OH | 1-Quin+ |
| 5-102 | —CONH—Hpdc | — | 3 | 2 | 4 | OH | 3-Thi+ |
| 5-103 | —CONH—Hpdc | — | 3 | 2 | 5 | —OAc | 1-Quin+ |
| 5-104 | —CONH—Hpdc | — | 3 | 1 | 2 | —OAc | 1-Me-2-Pyr+ |
| 5-105 | —CONH—Hpdc | — | 3 | 1 | 2 | —OAc | 1-Et-2-Pyr+ |
| 5-106 | —CONH—Hpdc | — | 3 | 1 | 2 | —OAc | 2-Pyr |
| 5-107 | —CONH—Hpdc | — | 3 | 1 | 2 | —OAc | 1-Me-2-Quin+ |

TABLE 6

| Cpd. No. | R2 | E | l | m | n | R4 | Q |
|---|---|---|---|---|---|---|---|
| 6-1 | Dc | —CO— | 2 | 3 | 6 | COOH | 1,1-diEt-2-Pyrd+ |
| 6-2 | Ddc | —CONH— | 3 | 0 | 7 | Mec | 1-Me-1-Imid+ |
| 6-3 | Tedc | —CONAc— | 4 | 1 | 8 | H | 1-Me-1-Pyrd+ |
| 6-4 | Hdc | —CO— | 2 | 2 | 9 | Etc | 1-Me-1-Pip+ |
| 6-5 | Hdc | —CONH— | 3 | 0 | 4 | H | 3-Thi+ |
| 6-6 | Hdc | —CONAc— | 3 | 1 | 3 | H | 3-Thi+ |
| 6-7 | Hdc | — | 3 | 2 | 2 | H | 3-Thi+ |
| 6-8 | Odc | —CONH— | 4 | 0 | 10 | COOH | 3,4-diMe-5-Thi+ |
| 6-9 | Ei | —CONAc— | 2 | 1 | 0 | Mec | 1-Imin+ |
| 6-10 | Doc | —CO— | 3 | 2 | 1 | H | 1-Me-3-Imid+ |
| 6-11 | —CONH—Udc | — | 4 | 3 | 2 | Etc | —N+Me3 |
| 6-12 | —CONH—Tdc | —CONAc— | 2 | 0 | 3 | COOH | 4-Me-4-Mor+ |
| 6-13 | —CONH—Pdc | —CO— | 3 | 1 | 5 | Mec | 1-Me-2-Pyr+ |
| 6-14 | —CONH—Hpdc | —CONH— | 3 | 0 | 4 | H | 3-Thi+ |
| 6-15 | —CONH—Hpdc | —CONAc— | 4 | 2 | 6 | COOH | 1-Et-2-Pyr+ |
| 6-16 | —CONH—Hpdc | —CO— | 3 | 3 | 7 | Etc | 1-Me-3-Pyr+ |
| 6-17 | —CONH—Ndc | —CONH— | 2 | 0 | 8 | Mec | 1,1-diMe-2-Pyrd+ |
| 6-18 | —CONH—Hen | —CONAc— | 3 | 1 | 9 | H | 1-Me-1-Imid+ |
| 6-19 | Ddc | — | 4 | 2 | 2 | OH | —N+Me3 |
| 6-20 | Dco | — | 2 | 1 | 2 | 2-EtO-EtO— | 3-Me-4-Thi+ |

TABLE 6-continued

| Cpd. No. | R² | E | l | m | n | R⁴ | Q |
|---|---|---|---|---|---|---|---|
| 6-21 | Pdco | — | 4 | 1 | 7 | —OBzc | 1-Me-1-Pyrd⁺ |
| 6-22 | Ste | — | 4 | 2 | 10 | —SBz | 5-Tez₂ |
| 6-23 | Heno | — | 4 | 1 | 2 | —SAc | 197 I-Quin⁺ |
| 6-24 | Tco | — | 3 | 1 | 4 | MeCar-O— | 3-Thi⁺ |
| 6-25 | —CONH—Tdc | — | 2 | 1 | 8 | SH | 5-(2-HOEt)-4-Me-3-Thi⁺ |
| 6-26 | —CONH—Pdc | — | 3 | 1 | 10 | OH | 1-Me-2-Quin⁺ |
| 6-27 | —CONH—Ei | — | 3 | 1 | 4 | MeO | 3-Thi⁺ |
| 6-28 | —CONH—Hpdc | — | 3 | 1 | 4 | —OAc | 3-Thi⁺ |
| 6-29 | —CONH—Hpdc | — | 3 | 1 | 6 | —OAc | 3-Thi⁺ |

TABLE 7

| Cpd. No. | R² | E | l | m | n | R⁴ | Q |
|---|---|---|---|---|---|---|---|
| 7-1 | Dc | —CO— | 2 | 3 | 6 | COOH | 1,1-diEt-2-Pyrd⁺ |
| 7-2 | Ddc | —CONH— | 3 | 0 | 7 | Mec | 1-Me-1-Imid⁺ |
| 7-3 | Tedc | —CONAc— | 4 | 1 | 8 | H | 1-Me-1-Pyrd⁺ |
| 7-4 | Hdc | —CO— | 2 | 2 | 9 | Etc | 1-Me-1-Pip⁺ |
| 7-5 | Hdc | —CONH— | 3 | 0 | 4 | H | 3-Thi⁺ |
| 7-6 | Hdc | —CONAc— | 3 | 1 | 3 | H | 3-Thi⁺ |
| 7-7 | Hdc | — | 3 | 2 | 2 | H | 3-Thi⁺ |
| 7-8 | Odc | —CONH— | 4 | 0 | 10 | COOH | 3,4-diMe-5-Thi⁺ |
| 7-9 | Ei | —CONAc— | 2 | 1 | 0 | Mec | 1-Imin⁺ |
| 7-10 | Doc | —CO— | 3 | 2 | 1 | H | 1-Me-3-Imid⁺ |
| 7-11 | —CONH—Udc | —CONH— | 4 | 3 | 2 | Etc | —N⁺Me₃ |
| 7-12 | —CONH—Tdc | —CONAc— | 2 | 0 | 3 | COOH | 4-Me-4-Mor⁺ |
| 7-13 | —CONH—Pdc | —CO— | 3 | 1 | 5 | Mec | 1-Me-2-Pyr⁺ |
| 7-14 | —CONH—Hpdc | —CONH— | 3 | 0 | 4 | H | 3-Thi⁺ |
| 7-15 | —CONH—Hpdc | —CONAc— | 4 | 2 | 6 | COOH | 1-Et-2-Pyr⁺ |
| 7-16 | —CONH—Hpdc | —CO— | 3 | 3 | 7 | Etc | 1-Me-3-Pyr⁺ |
| 7-17 | —CONH—Ndc | —CONH— | 2 | 0 | 8 | Mec | 1,1-diMe-2-Pyrd⁺ |
| 7-18 | —CONH—Hen | —CONAc— | 3 | 1 | 9 | H | 1-Me-1-Imid⁺ |
| 7-19 | Udc | — | 3 | 1 | 1 | SH | 1-Me-3-Imid⁺ |
| 7-20 | Udco | — | 3 | 1 | 3 | —OBz | 3-Et-4-Me-5-Thi⁺ |
| 7-21 | Pal | — | 2 | 2 | 8 | MeO | 1-Me-1-Imid⁺ |
| 7-22 | —CONH—Ndc | — | 2 | 2 | 3 | OH | 1-Et-2-Quin⁺ |
| 7-23 | —CONH—Odc | — | 2 | 1 | 3 | OH | 1-Me-3-Imid⁺ |

TABLE 8

| Cpd. No. | R² | E | l | m | n | R⁴ | Q |
|---|---|---|---|---|---|---|---|
| 8-1 | Dc | —CO— | 2 | 3 | 6 | COOH | 1,1-diEt-2-Pyrd⁺ |
| 8-2 | Ddc | —CONH— | 3 | 0 | 7 | Mec | 1-Me-1-Imid⁺ |
| 8-3 | Tedc | —CONAc— | 4 | 1 | 8 | H | 1-Me-1-Pyrd⁺ |
| 8-4 | Hdc | —CO— | 2 | 2 | 9 | Etc | 1-Me-1-Pip⁺ |
| 8-5 | Hdc | —CONH— | 3 | 0 | 4 | H | 3-Thi⁺ |
| 8-6 | Hdc | —CONAc— | 3 | 1 | 3 | H | 3-Thi⁺ |
| 8-7 | Hdc | — | 3 | 2 | 2 | H | 3-Thi⁺ |
| 8-8 | Odc | —CONH— | 4 | 0 | 10 | COOH | 3,4-diMe-5-Thi⁺ |
| 8-9 | Ei | —CONAc— | 2 | 1 | 0 | Mec | 1-Imin⁺ |
| 8-10 | Doc | —CO— | 3 | 2 | 1 | H | 1-Me-3-Imid⁺ |
| 8-11 | —CONH—Udc | —CONH— | 4 | 3 | 2 | Etc | —N⁺Me₃ |
| 8-12 | —CONH—Tdc | —CONAc— | 2 | 0 | 3 | COOH | 4-Me-4-Mor⁺ |
| 8-13 | —CONH—Pdc | —CO— | 3 | 1 | 5 | Mec | 1-Me-2-Pyr⁺ |
| 8-14 | —CONH—Hpdc | —CONH— | 3 | 0 | 4 | H | 3-Thi⁺ |
| 8-15 | —CONH—Hpdc | —CONAc— | 4 | 2 | 6 | COOH | 1-Et-2-Pyr⁺ |
| 8-16 | —CONH—Hpdc | —CO— | 3 | 3 | 7 | Etc | 1-Me-3-Pyr⁺ |
| 8-17 | —CONH—Ndc | —CONH— | 2 | 0 | 8 | Mec | 1,1-diMe-2-Pyrd⁺ |
| 8-18 | Tdc | — | 2 | 3 | 3 | SH | —NMe₂ |
| 8-19 | Lau | — | 4 | 2 | 4 | —OBz | 1-Et-2-Pyrd |
| 8-20 | Myr | — | 3 | 2 | 6 | AllO-COO— | 1-Me-1-Imid⁺ |
| 8-21 | —CONH—Hen | — | 2 | 2 | 5 | —OAc | 1-Pyr⁺ |

TABLE 9

| Cpd. No. | R¹ | E | A | B | l | n | Q |
|---|---|---|---|---|---|---|---|
| 9-1 | Dc | 3,5-Isoxd | O | O | 2 | 1 | 3-Thi⁺ |
| 9-2 | Udc | 2,4-Thd | O | S | 3 | 1 | 1-Me-3-Imid⁺ |
| 9-3 | Ddc | 2,4-Oxad | S | O | 4 | 2 | —N⁺Me₃ |
| 9-4 | Tdc | 2,4-Imd | S | S | 2 | 3 | —NMe₂ |
| 9-5 | Tedc | 3,5-Isoxd | O | O | 3 | 4 | 1-Pip |
| 9-6 | Pdc | 2,4-Thd | O | O | 4 | 5 | 1-Me-1-Pip⁺ |
| 9-7 | Hdc | 2,4-Oxad | O | O | 3 | 3 | 3-Thi⁺ |
| 9-8 | Hpdc | 2,4-Imd | O | O | 2 | 7 | 4-Me-4-Mor⁺ |
| 9-9 | Odc | 3,5-Isoxd | O | O | 3 | 8 | 1-Me-2-Pyr⁺ |

TABLE 9-continued

| Cpd. No. | R¹ | E | A | B | l | n | Q |
|---|---|---|---|---|---|---|---|
| 9-10 | Ndc | 2,4-Thd | O | O | 4 | 9 | 1-Et-2-Pyr+ |
| 9-11 | Ei | 2,4-Oxad | O | O | 2 | 10 | 3-Pyr |
| 9-12 | Hen | 2,4-Imd | O | O | 3 | 0 | 1-Me-3-Pyr+ |
| 9-13 | Doc | 3,5-Isoxd | O | O | 4 | 1 | 2-Pyr |
| 9-14 | Dco | 2,4-Thd | S | O | 2 | 2 | 3-Me-4-Thi+ |
| 9-15 | Udco | 2,4-Oxad | O | S | 3 | 3 | 3-Et-4-Me-5-Thi+ |
| 9-16 | Lau | 2,4-Imd | S | S | 4 | 4 | 1-Et-2-Pyrd |
| 9-17 | Tdco | 3,5-Isoxd | O | O | 2 | 5 | 1,1-diEt-2-Pyrd+ |
| 9-18 | Myr | 2,4-Thd | S | S | 3 | 6 | 1-Me-1-Imid+ |
| 9-19 | Pdco | 2,4-Oxad | S | O | 4 | 7 | 1-Me-1-Pyrd+ |
| 9-20 | Pal | 2,4-Imd | O | S | 2 | 8 | 1-Me-1-Imin+ |
| 9-21 | Hpdo | 3,5-Isoxd | O | O | 3 | 9 | 4-Thz |
| 9-22 | Ste | 2,4-Thd | S | O | 4 | 10 | 5-Tez₂ |
| 9-23 | Ndco | 2,4-Oxad | O | O | 2 | 1 | 1-Pyr+ |
| 9-24 | Eio | 2,4-Imd | O | O | 3 | 1 | 1-Pym+ |
| 9-25 | Heno | 3,5-Isoxd | S | O | 4 | 2 | 1-Quin+ |
| 9-26 | Doco | 2,4-Thd | O | O | 2 | 3 | 2-iQuin+ |
| 9-27 | Tco | 2,4-Oxad | S | O | 3 | 4 | 3-Thi+ |
| 9-28 | —CONH—Dc | 3,5-Isoxd | O | O | 4 | 5 | 1-Pyzn+ |
| 9-29 | —CONH—Udc | 3,5-Isoxd | O | O | 2 | 6 | 3-Et-4-Oxa+ |
| 9-30 | —CONH—Ddc | 3,5-Isoxd | O | O | 3 | 7 | 3-Me-2-Thi+ |
| 9-31 | —CONH—Tdc | 3,5-Isoxd | S | O | 2 | 8 | 5-(2-HOEt)-4-Me-3-Thi+ |
| 9-32 | —CONH—Tedc | 3,5-Isoxd | O | O | 2 | 9 | 4-Mor |
| 9-33 | —CONH—Pdc | 3,5-Isoxd | S | O | 3 | 10 | 1-Me-2-Quin+ |
| 9-34 | —CONH—Hdc | 3,5-Isoxd | O | O | 3 | 0 | 3-Pyr |
| 9-35 | —CONH—Hpdc | 3,5-Isoxd | O | O | 3 | 3 | 3-Pyr |
| 9-36 | —CONH—Odc | 3,5-Isoxd | O | O | 3 | 2 | 3-Pyr |
| 9-37 | —CONCH—Ndc | 3,5-Isoxd | O | S | 2 | 3 | 1-Et-2-Quin+ |
| 9-38 | —CONH—Ei | 3,5-Isoxd | S | O | 3 | 4 | 3-Thi+ |
| 9-39 | —CONH—Hen | 3,5-Isoxd | S | S | 2 | 5 | 1-Pyr+ |
| 9-40 | —CONH—Doc | 3,5-Isoxd | O | O | 3 | 6 | 3-Thi+ |
| 9-41 | —CONH—Hdc | 3,5-Isoxd | O | O | 3 | 0 | 3-Pyr |
| 9-42 | —CONH—Hdc | 3,5-Isoxd | O | O | 2 | 2 | 1-Quin+ |
| 9-43 | —CONH—Hdc | 3,5-Isoxd | O | O | 4 | 3 | 3-Thi+ |
| 9-44 | —CONH—Hdc | 3,5-Isoxd | O | O | 3 | 4 | 3-Thi+ |
| 9-45 | —CONH—Hdc | 3,5-Isoxd | O | O | 3 | 4 | 1-Quin+ |
| 9-46 | —CONH—Hdc | 3,5-Isoxd | O | O | 3 | 1 | 3-Thi+ |
| 9-47 | —CONH—Hdc | 3,5-Isoxd | O | O | 3 | 4 | 2-iQuin+ |
| 9-48 | —CONH—Hpdc | 3,5-Isoxd | O | O | 2 | 2 | 3-Thi+ |
| 9-49 | —CONH—Hpdc | 3,5-Isoxd | O | O | 4 | 3 | 3-Thi+ |
| 9-50 | —CONH—Hpdc | 3,4-Isoxd | O | O | 3 | 1 | 1-Et-2-Pyr+ |
| 9-51 | —CONH—Hpdc | 3,4-Isoxd | O | O | 3 | 2 | 1-Et-2-Pyr+ |
| 9-52 | —CONH—Hpdc | 3,4-Isoxd | O | O | 3 | 1 | 1-Et-2-Quin+ |
| 9-53 | —CONH—Hpdc | 3,4-Isoxd | O | O | 3 | 2 | 1-Et-2-Quin+ |
| 9-54 | —CONH—Hpdc | 3,4-Isoxd | O | O | 3 | 2 | 2-Et-3-iQuin+ |
| 9-55 | —CONH—Hpdc | 3,4-Isoxd | O | O | 3 | 1 | 2-Et-1-iQuin+ |
| 9-56 | —CONH—Hpdc | 3,4-Isoxd | O | O | 3 | 2 | 3-Thi+ |
| 9-57 | —CONH—Hpdc | 3,4-Isoxd | O | O | 3 | 3 | 3-Thi+ |
| 9-58 | —CONH—Hpdc | 3,4-Isoxd | O | O | 3 | 4 | 3-Thi+ |
| 9-59 | —CONH—Odc | 3,4-Isoxd | O | S | 3 | 2 | 3-Thi+ |
| 9-60 | —CONH—Hpdc | 3,5-Isoxd | O | O | 3 | 0 | 1-Me-3-Pyr+ |
| 9-61 | —CONH—Hpdc | 3,5-Isoxd | O | O | 3 | 1 | 1-Me-2-Quin+ |
| 9-62 | —CONH—Hpdc | 3,5-Isoxd | O | O | 3 | 4 | 3-Thi+ |
| 9-63 | —CONH—Hpdc | 3,5-Isoxd | O | O | 3 | 1 | 3-Thi+ |
| 9-64 | —CONH—Hpdc | 3,5-Isoxd | O | O | 3 | 4 | 1-Pyr+ |
| 9-65 | —CONH—Hpdc | 3,5-Isoxd | O | O | 3 | 4 | 1-Quin+ |
| 9-66 | —CONH—Odc | 3,5-Isoxd | O | S | 2 | 2 | 1-Me-3-Imid+ |
| 9-67 | —CONH—Odc | 3,5-Isoxd | O | O | 2 | 1 | —N+Me₃ |
| 9-68 | —CONH—Odc | 3,5-Isoxd | O | O | 3 | 1 | 2-iQuin+ |
| 9-69 | —CONH—Odc | 3,5-Isoxd | O | O | 4 | 4 | 1-Quin+ |
| 9-70 | —CONH—Odc | 3,5-Isoxd | O | O | 3 | 1 | 1-Me-2-Pyr+ |
| 9-71 | —CONH—Odc | 3,5-Isoxd | O | O | 3 | 1 | 3-Thi+ |
| 9-72 | —CONH—Odc | 3,5-Isoxd | O | O | 3 | 4 | 3-Thi+ |
| 9-73 | —CONH—Hpdc | 2,4-Thd | O | O | 3 | 4 | 3-Thi+ |
| 9-74 | —CONH—Hpdc | 2,4-Thd | O | O | 3 | 2 | 1-Quin+ |
| 9-75 | —CONH—Hpdc | 2,4-Thd | O | O | 3 | 1 | 3-Thi+ |
| 9-76 | —CONH—Hpdc | 2,4-Thd | O | O | 3 | 2 | 3-Thi+ |
| 9-77 | —CONH—Hpdc | 2,4-Oxad | O | O | 3 | 3 | 1-Me-2-Pyr+ |
| 9-78 | —CONH—Hpdc | 2,4-Oxad | O | O | 3 | 3 | 1-Quin+ |
| 9-79 | —CONH—HPDC | 2,4-Imd | O | O | 3 | 3 | 3-Thi+ |
| 9-80 | —CONH—Hpdc | 2,4-Imd | O | O | 3 | 3 | 1-Me-2-Quin+ |
| 9-81 | —CONAc—Hdc | 3,4-Isoxd | S | O | 3 | 0 | 2-Pyr |
| 9-82 | —CONAc—Hdc | 3,4-Isoxd | S | O | 3 | 2 | 1-Et-2-Pyr+ |
| 9-83 | —CONAc—Hpdc | 3,4-Isoxd | S | O | 3 | 1 | 2-Pyr |
| 9-84 | —CONAc—Hpdc | 3,4-Isoxd | S | O | 3 | 2 | 2-Pyr |
| 9-85 | —CONAc—Hpdc | 3,4-Isoxd | S | O | 3 | 1 | 1-Et-2-Pyr+ |
| 9-86 | —CONAc—Hpdc | 3,4-Isoxd | S | O | 3 | 2 | 1-Et-2-Pyr+ |
| 9-87 | —CONAc—Odc | 3,4-Isoxd | S | O | 3 | 1 | 1-Et-2-Pyr+ |
| 9-88 | —CONAc—Odc | 3,4-Isoxd | S | O | 3 | 2 | 2-Pyr |
| 9-89 | —CONAc—Hdc | 3,5-Isoxd | S | O | 3 | 1 | 1-Et-2-Pyr+ |
| 9-90 | —CONAc—Hdc | 3,5-Isoxd | S | O | 3 | 2 | 2-Pyr |
| 9-91 | —CONAc—Hpdc | 3,5-Isoxd | S | O | 3 | 1 | 1-Et-2-Pyr+ |
| 9-92 | —CONAc—Hpdc | 3,5-Isoxd | S | O | 3 | 2 | 1-Et-2-Pyr+ |
| 9-93 | —CONAc—Hpdc | 3,5-Isoxd | S | O | 3 | 1 | 2-Pyr |
| 9-94 | —CONAc—Hpdc | 3,5-Isoxd | S | O | 3 | 2 | 2-Pyr |
| 9-95 | —CONAc—Odc | 3,5-Isoxd | S | O | 3 | 1 | 2-Pyr |

TABLE 9-continued

| Cpd. No. | R¹ | E | A | B | $l$ | $n$ | Q |
|---|---|---|---|---|---|---|---|
| 9-96 | —CONAc—Odc | 3,5-Isoxd | S | O | 3 | 2 | 1-Et-2-Pyr+ |
| 9-97 | —CONAc—Hdc | 3,5-Isoxd | O | O | 3 | 1 | 2-Pyr |
| 9-98 | —CONAc—Hdc | 3,5-Isoxd | O | O | 3 | 2 | 1-Et-2-Pyr+ |
| 9-99 | —CONAc—Hpdc | 3,5-Isoxd | O | O | 3 | 1 | 2-Pyr |
| 9-100 | —CONAc—Hpdc | 3,5-Isoxd | O | O | 3 | 1 | 1-Et-2-Pyr+ |
| 9-101 | —CONAc—Hpdc | 3,5-Isoxd | O | O | 3 | 2 | 2-Pyr |
| 9-102 | —CONAc—Hpdc | 3,5-Isoxd | O | O | 3 | 2 | 1-Et-2-Pyr+ |
| 9-103 | —CONAc—Odc | 3,5-Isoxd | O | O | 3 | 1 | 1-Et-2-Pyr+ |
| 9-104 | —CONAc—Odc | 3,5-Isoxd | O | O | 3 | 2 | 2-Pyr |

TABLE 10

| Cpd. No. | R¹ | E | A | B | $l$ | $n$ | Q |
|---|---|---|---|---|---|---|---|
| 10-1 | Dc | 3,5-Isoxd | O | O | 2 | 3 | 3-Thi+ |
| 10-2 | Udc | 2,4-Thd | O | S | 3 | 1 | 1-Me-3-Imid+ |
| 10-3 | Ddc | 2,4-Oxad | S | O | 4 | 2 | —N+Me3 |
| 10-4 | Tdc | 2,4-Imd | S | S | 2 | 3 | —NMe2 |
| 10-5 | Tedc | 3,5-Isoxd | O | O | 3 | 4 | 1-Pip |
| 10-6 | Pdc | 2,4-Thd | O | O | 4 | 5 | 1-Me-1-Pip+ |
| 10-7 | Hdc | 2,4-Oxad | O | O | 3 | 3 | 3-Thi+ |
| 10-8 | Hpdc | 2,4-Imd | O | O | 2 | 7 | 4-Me-4-Mor+ |
| 10-9 | Odc | 3,5-Isoxd | O | O | 3 | 8 | 1-Me-2-Pyr+ |
| 10-10 | Ndc | 2,4-Thd | O | O | 4 | 9 | 1-Et-2-Pyr+ |
| 10-11 | Ei | 2,4-Oxad | O | O | 2 | 10 | 3-Pyr |
| 10-12 | Hen | 2,4-Imd | O | O | 3 | 0 | 1-Me-3-Pyr+ |
| 10-13 | Doc | 3,5-Isoxd | O | O | 4 | 1 | 2-Pyr |
| 10-14 | Dco | 2,4-Thd | S | O | 2 | 2 | 3-Me-4-Thi+ |
| 10-15 | Udco | 2,4-Oxad | O | S | 3 | 3 | 3-Et-4-Me-5-Thi+ |
| 10-16 | Lau | 2,4-Imd | S | S | 4 | 4 | 1-Et-2-Pyrd |
| 10-17 | Tdco | 3,5-Isoxd | O | O | 2 | 5 | 1,1-diEt-2-Pyrd+ |
| 10-18 | Myr | 2,4-Thd | S | S | 3 | 6 | 1-Me-1-Imid+ |
| 10-19 | Pdco | 2,4-Oxad | S | O | 4 | 7 | 1-Me-1-Pyrd+ |
| 10-20 | Pal | 2,4-Imd | O | S | 2 | 8 | 1-Me-1-Imin+ |
| 10-21 | Hpdo | 3,5-Isoxd | O | O | 3 | 9 | 4-Thz |
| 10-22 | Ste | 2,4-Thd | S | O | 4 | 10 | 5-Tez2 |
| 10-23 | Ndco | 2,4-Oxad | O | O | 2 | 3 | 1-Pyz+ |
| 10-24 | Eio | 2,4-Imd | O | O | 3 | 1 | 1-Pym+ |
| 10-25 | Heno | 3,5-Isoxd | S | O | 4 | 2 | 1-Quin+ |
| 10-26 | Doco | 2,4-Thd | O | O | 2 | 3 | 2-iQuin+ |
| 10-27 | Tco | 2,4-Oxad | S | O | 3 | 4 | 3-Thi+ |
| 10-28 | —CONH—Dc | 3,5-Isoxd | O | O | 4 | 5 | 1-Pyzn+ |
| 10-29 | —CONH—Udc | 3,5-Isoxd | O | O | 2 | 6 | 2-Pyr |
| 10-30 | —CONH—Ddc | 3,5-Isoxd | O | O | 3 | 7 | 3-Me-2-Thi+ |
| 10-31 | —CONH—Tdc | 3,5-Isoxd | S | O | 2 | 8 | 5-(2-HOEt)—4-Me-3-Thi+ |
| 10-32 | —CONH—Tedc | 3,5-Isoxd | O | O | 2 | 9 | 4-Mor |
| 10-33 | —CONH—Pdc | 3,5-Isoxd | S | O | 3 | 10 | 1-Me-2-Quin+ |
| 10-34 | —CONH—Hdc | 3,5-Isoxd | O | O | 3 | 3 | 3-Thi+ |
| 10-35 | —CONH—Hpdc | 3,5-Isoxd | O | O | 3 | 3 | 3-Thi+ |
| 10-36 | —CONH—Odc | 3,5-Isoxd | O | O | 3 | 2 | 3-Thi+ |
| 10-37 | —CONH—Ndc | 3,5-Isoxd | O | S | 2 | 3 | 1-Et-2-Quin+ |
| 10-38 | —CONH—Ei | 3,5-Isoxd | S | O | 3 | 4 | 3-Thi+ |
| 10-39 | —CONH—Hen | 3,5-Isoxd | S | S | 2 | 5 | 1-Pyr+ |
| 10-40 | —CONH—Doc | 3,5-Isoxd | O | O | 3 | 6 | 3-Thi+ |
| 10-41 | —CONH—Hdc | 3,5-Isoxd | O | O | 3 | 0 | 3-Pyr |
| 10-42 | —CONH—Hdc | 3,5-Isoxd | O | O | 2 | 2 | 1-Quin+ |
| 10-43 | —CONH—Hdc | 3,5-Isoxd | O | O | 4 | 3 | 3-Thi+ |
| 10-44 | —CONH—Hdc | 3,5-Isoxd | O | O | 3 | 4 | 3-Thi+ |
| 10-45 | —CONH—Hdc | 3,5-Isoxd | O | O | 3 | 4 | 1-Quin+ |
| 10-46 | —CONH—Hdc | 3,5-Isoxd | O | O | 3 | 1 | 3-Thi+ |
| 10-47 | —CONH—Hdc | 3,5-Isoxd | O | O | 3 | 4 | 2-iQuin+ |
| 10-48 | —CONH—Hpdc | 3,5-Isoxd | O | O | 2 | 2 | 3-Thi+ |
| 10-49 | —CONH—Hpdc | 3,5-Isoxd | O | O | 4 | 3 | 3-Thi+ |
| 10-50 | —CONH—Hpdc | 3,4-Isoxd | O | O | 3 | 0 | 1-Me-3-Pyr+ |
| 10-51 | —CONH—Hpdc | 3,4-Isoxd | O | O | 3 | 1 | 1-Me-3-Quin+ |
| 10-52 | —CONH—Hpdc | 3,4-Isoxd | O | O | 3 | 4 | 3-Thi+ |
| 10-53 | —CONH—Hpdc | 3,4-Isoxd | O | O | 3 | 1 | 3-Thi+ |
| 10-54 | —CONH—Hpdc | 3,4-Isoxd | O | O | 3 | 4 | 1-Pyr+ |
| 10-55 | —CONH—Hpdc | 3,4-Isoxd | O | O | 3 | 4 | 1-Quin+ |
| 10-56 | —CONH—Odc | 3,4-Isoxd | O | S | 2 | 1 | 1-Me-3-Imid+ |
| 10-57 | —CONH—Odc | 3,4-Isoxd | O | O | 2 | 1 | —N+Me3 |
| 10-58 | —CONH—Odc | 3,4-Isoxd | O | O | 3 | 2 | 2-iQuin+ |
| 10-59 | —CONH—Odc | 3,4-Isoxd | O | O | 4 | 4 | —N+Me3 |
| 10-60 | —CONH—Odc | 3,5-Isoxd | O | O | 3 | 1 | 1-Me-2-Pyr+ |
| 10-61 | —CONH—Odc | 3,5-Isoxd | O | O | 3 | 1 | 3-Thi+ |
| 10-62 | —CONH—Hpdc | 3,5-Isoxd | O | O | 3 | 4 | 3-Thi+ |
| 10-63 | —CONH—Hpdc | 2,4-Thd | O | O | 3 | 4 | 3-Thi+ |
| 10-64 | —CONH—Hpdc | 2,4-Thd | O | O | 3 | 5 | 1-Quin+ |
| 10-65 | —CONH—Hpdc | 2,4-Thd | O | O | 3 | 1 | 3-Thi+ |
| 10-66 | —CONH—Hpdc | 2,4-Thd | O | O | 3 | 2 | 1-Quin+ |
| 10-67 | —CONH—Hpdc | 2,4-Oxad | O | O | 3 | 0 | 1-Me-2-Pyr+ |
| 10-68 | —CONH—Hpdc | 2,4-Oxad | O | O | 3 | 3 | 1-Quin+ |
| 10-69 | —CONH—Hpdc | 2,4-Imd | O | O | 3 | 3 | 3-Thi+ |
| 10-70 | —CONH—Hpdc | 2,4-Imd | O | O | 3 | 3 | 1-Me-2-Quin+ |

In the compounds listed above, where the compound is shown as containing a quaternary nitrogen atom, then the compound must also contain an anion to balance the positive charge. Such an anion is not critical and may be chosen from any of the anions exemplified above in relation to Z−.

Of the compounds listed above, the following are preferred: Compounds No. 1-9, 1-10, 1-32, 1-34, 1-35, 1-44, 1-45, 1-46, 1-47, 1-52, 1-53, 1-54, 1-55, 1-56, 1-57, 1-61, 1-63, 1-67, 1-76, 1-77, 1-78, 1-79, 1-80, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 2-5, 2-6, 2-7, 2-14, 2-15, 2-28, 2-29, 2-30, 2-31, 2-32, 3-5, 3-7, 3-14, 3-15, 3-23, 4-13, 4-14, 4-15, 4-21, 5-53, 5-54, 5-83, 5-87, 5-88, 7-4, 9-7, 9-8, 9-9, 9-10, 9-21, 9-33, 9-34, 9-35, 9-36, 9-41, 9-42, 9-43, 9-44, 9-45, 9-46, 9-47, 9-48, 9-50, 9-51, 9-52, 9-53, 9-54, 9-55, 9-56, 9-57, 9-58, 9-60, 9-61, 9-62, 9-63, 9-65, 9-70, 9-71, 9-72, 9-73, 9-75, 9-76, 9-77, 9-78, 9-79, 9-80, 9-82, 9-85, 9-86, 9-87, 9-89, 9-91, 9-92, 9-96, 9-98, 9-100, 9-102, 9-103, 10-7, 10-35, 10-36, 10-37, 10-43, 10-50 and 10-51. More preferred compounds are Compounds No. 1-34, 1-44, 1-45, 1-46, 1-52, 1-53, 1-54, 1-55, 1-56, 1-57, 1-82, 1-84, 1-87, 1-90, 1-91, 1-96, 1-100, 1-101, 1-104, 1-106, 1-108, 1-109, 2-14, 2-15, 2-31, 2-32, 3-14, 3-15, 9-35, 9-36, 9-44, 9-45, 9-46, 9-47, 9-50, 9-51, 9-52, 9-56, 9-58, 9-62, 9-65, 9-70, 9-72, 9-73, 9-77, 9-82, 9-86, 9-92, 9-96 and 9-98.

The most preferred compounds are Compounds No.:

1-34. 3-{6-Ethoxycarbonyl-6-[(3-heptadecylcarbamoyloxytetrahydropyran-2-yl)methoxycarbonylamino]hexyl}thiazolium salts, especially dl-3-{6-ethoxycarbonyl-6-[(trans-3-heptadecylcarbamoyloxytetrahydropyran-2-yl)methoxycarbonylamino]hexyl}thiazolium methanesulfonate 1-53. 3-{5-[(3-Heptadecylcarbamoyloxytetrahydropyran-2-yl)methoxycarbonylamino]pentyl}thiazolium salts, especially dl-3-{5-[(trans-3-heptadecylcarbamoyloxytetrahydropyran-2-yl)methoxycarbonylamino]pentyl}thiazolium bromide 1-57. 1-Ethyl-2-{N-acetyl-N-[3-(N-heptadecylcarbamoyloxy)tetrahydropyran-2-ylmethoxycarbonyl]aminomethyl}pyridinium salts, especially dl-1-ethyl-2-{N-acetyl-N-[trans-3-(N-heptadecylcarbamoyloxy)tetrahydropyran-2-ylmethoxycarbonyl]aminomethyl}pyridinium chloride 1-92. 3-{7-Acetoxy-8-[(3-heptadecylcarbamoyloxytetrahydropyran-2-yl)methoxy]octyl}thiazolium salts 2-31. 1-Ethyl-2-{N-acetyl-N-[3-(N-acetyl-N-heptadecylcarbamoylthio)tetrahydropyran-2-ylmethoxycarbonyl]aminomethyl}pyridinium salts, especially dl-1-ethyl-2-{N-acetyl-N-[cis-3-(N-acetyl-N-heptadecylcarbamoylthio)tetrahydropyran-2-ylmethoxycarbonyl]aminomethyl}pyridinium chloride 2-32. 1-Ethyl-2-{N-[3-(N-acetyl-N-heptadecylcarbamoylthio)tetrahydropyran-2-ylmethoxycarbonyl]aminomethyl}pyridinium salts, especially dl-1-ethyl-2-{N-[cis-3-(N-acetyl-N-heptadecylcarbamoylthio)tetrahydropyran-2-ylmethoxycarbonyl]aminomethyl}pyridinium chloride 9-62. 3-{4-[3-(3-Heptadecylcarbamoyloxytetrahydropyran-2-yl)methoxy-5-isoxazolyl]butyl}thiazolium salts, especially dl-3-{4-[3-(trans-3-heptadecylcarbamoyloxytetrahydropyran-2-yl)methoxy-5-isoxazolyl]butyl}thiazolium methanesulfonate.

Examples of certain preferred compounds of the present invention where one of $R^1$ and $R^2$ is a group of formula (II$f$) are given in the following Tables 21–32, in which compounds of formula (II-1) are as defined in Table 21, compounds of formula (II-2) are as defined in Table 22 and so on.

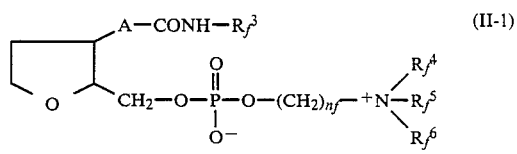
(II-1)

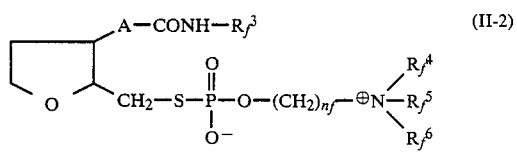
(II-2)

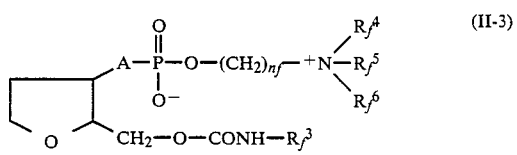
(II-3)

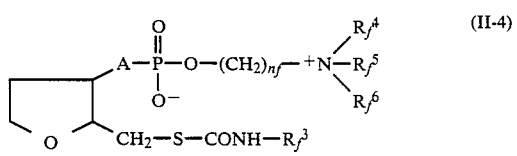
(II-4)

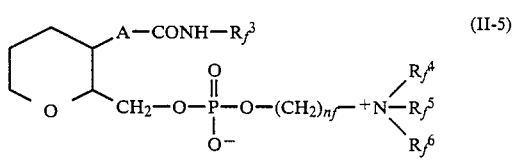
(II-5)

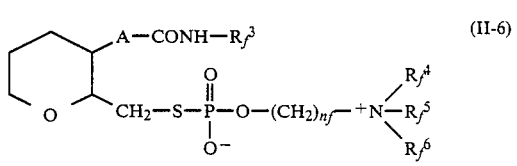
(II-6)

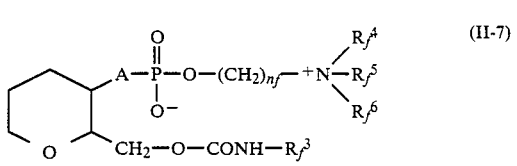
(II-7)

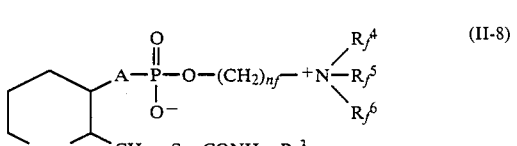
(II-8)

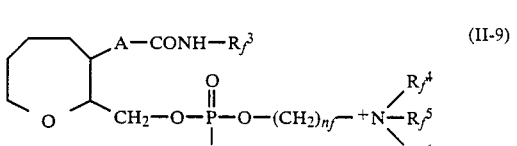
(II-9)

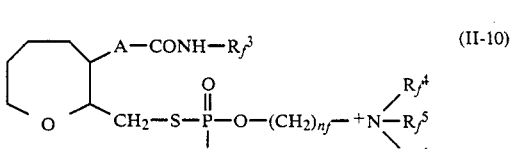
(II-10)

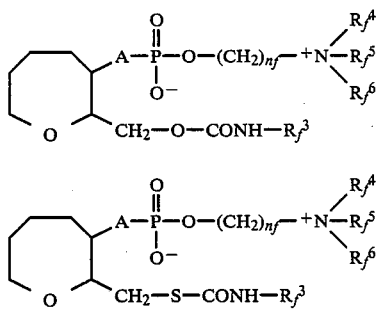

(II-11)

(II-12)

In the following Tables, the abbreviations used have the meanings:

| | |
|---|---|
| Me | methyl |
| Pip+ | piperidinium |
| Pyr+ | pyridinium |
| Thi+ | 1,3-thiazolium |

All alkyl groups are "normal", i.e. straight chain, except where explicitly shown otherwise.

TABLE 21

| Cpd No. | $R_f^3$ | A | $n_f$ | $-N^+R_f^4R_f^5R_f^6$ |
|---|---|---|---|---|
| 1 | $C_{17}H_{35}$ | O | 2 | Thi+ |
| 2 | $C_{16}H_{33}$ | O | 3 | Thi+ |
| 3 | $C_{18}H_{37}$ | O | 2 | Thi+ |
| 4 | $C_{18}H_{37}$ | O | 3 | Thi+ |
| 5 | $C_{17}H_{35}$ | O | 2 | $-N^+H_3$ |
| 6 | $C_{17}H_{35}$ | O | 2 | $-N^+Me_3$ |
| 7 | $C_{18}H_{37}$ | O | 2 | $-N^+Me_3$ |
| 8 | $C_{17}H_{35}$ | O | 3 | 1-Me—Pip+ |
| 9 | $C_{18}H_{37}$ | O | 2 | Pyr+ |
| 10 | $C_{17}H_{35}$ | S | 2 | Thi+ |
| 11 | $C_{18}H_{37}$ | S | 2 | $-N^+Me_3$ |
| 12 | $C_{14}H_{29}CH(Me)-$ | S | 3 | Thi+ |
| 13 | $Me_3C-(CH_2)_{12}-$ | S | 2 | $-N^+H_3$ |
| 14 | $Me_2CH-(CH_2)_{13}-$ | S | 3 | $-N^+Me_3$ |
| 15 | $C_{16}H_{33}$ | S | 2 | 1-Me—Pip+ |
| 16 | $C_{18}H_{37}$ | S | 2 | Pyr+ |
| 17 | $C_{17}H_{35}$ | O | 4 | $-N^+H_3$ |
| 18 | $C_{17}H_{35}$ | O | 5 | 1-Me—Pip+ |
| 19 | $C_{17}H_{35}$ | S | 6 | Thi+ |
| 20 | $C_{14}H_{29}CH(Me)-$ | S | 6 | Thi+ |
| 21 | $Me_3C-(CH_2)_{12}-$ | S | 7 | $-N^+H_3$ |
| 22 | $Me_2CH-(CH_2)_{13}-$ | S | 8 | $-N^+Me_3$ |
| 23 | $C_{16}H_{33}$ | S | 9 | 1-Me—Pip+ |
| 24 | $C_{18}H_{37}$ | S | 10 | Pyr+ |

TABLE 22

| Cpd No. | $R_f^3$ | A | $n_f$ | $-N^+R_f^4R_f^5R_f^6$ |
|---|---|---|---|---|
| 25 | $C_{16}H_{33}$ | O | 2 | Thi+ |
| 26 | $C_{18}H_{37}$ | O | 2 | Thi+ |
| 27 | $C_{16}H_{33}$ | O | 3 | Thi+ |
| 28 | $C_{18}H_{37}$ | O | 3 | Thi+ |
| 29 | $C_{14}H_{29}CH(Me)-$ | O | 2 | Thi+ |
| 30 | $Me_3C-(CH_2)_{12}-$ | O | 2 | $-N^+H_3$ |
| 31 | $Me_2CH-(CH_2)_{13}-$ | O | 2 | $-N^+HMe_2$ |
| 32 | $C_{16}H_{33}$ | S | 2 | $-N^+HMe_2$ |
| 33 | $C_{18}H_{37}$ | S | 3 | $-N^+HMe_2$ |
| 34 | $C_{16}H_{33}$ | S | 2 | $-N^+H_3$ |
| 35 | $C_{18}H_{37}$ | S | 2 | $-N^+Me_3$ |
| 36 | $C_{18}H_{37}$ | O | 4 | Thi+ |
| 37 | $Me_3C-(CH_2)_{12}-$ | O | 6 | $-N^+H_3$ |
| 38 | $Me_2CH-(CH_2)_{13}-$ | O | 8 | $-N^+HMe_2$ |

TABLE 23

| Cpd No. | $R_f^3$ | A | $n_f$ | $-N^+R_f^4R_f^5R_f^6$ |
|---|---|---|---|---|
| 39 | $C_{17}H_{35}$ | O | 2 | Thi+ |
| 40 | $C_{16}H_{33}$ | O | 3 | Thi+ |
| 41 | $C_{18}H_{37}$ | O | 2 | Thi+ |
| 42 | $C_{18}H_{37}$ | O | 3 | Thi+ |
| 43 | $C_{17}H_{35}$ | O | 2 | $-N^+H_3$ |
| 44 | $C_{16}H_{33}$ | O | 3 | $-N^+Me_3$ |
| 45 | $C_{18}H_{37}$ | O | 2 | $-N^+HMe_2$ |
| 46 | $C_{17}H_{35}$ | O | 3 | 1-Me—Pip+ |
| 47 | $C_{18}H_{37}$ | O | 2 | Pyr+ |
| 48 | $C_{17}H_{35}$ | S | 2 | Thi+ |
| 49 | $C_{18}H_{37}$ | S | 3 | Thi+ |
| 50 | $C_{14}H_{29}CH(Me)-$ | S | 3 | Thi+ |
| 51 | $Me_3C-(CH_2)_{12}-$ | S | 2 | $-N^+H_3$ |
| 52 | $Me_2CH-(CH_2)_{13}-$ | S | 3 | $-N^+Me_3$ |
| 53 | $C_{16}H_{33}$ | S | 2 | 1-Me—Pip+ |
| 54 | $C_{18}H_{37}$ | S | 2 | Pyr+ |
| 55 | $C_{18}H_{37}$ | O | 4 | Thi+ |
| 56 | $C_{18}H_{37}$ | O | 5 | Thi+ |
| 57 | $C_{17}H_{35}$ | O | 6 | $-N^+H_3$ |
| 58 | $C_{16}H_{33}$ | O | 7 | $-N^+Me_3$ |
| 59 | $C_{18}H_{37}$ | O | 8 | $-N^+HMe_2$ |
| 60 | $C_{17}H_{35}$ | O | 9 | 1-Me—Pip+ |
| 61 | $C_{18}H_{37}$ | O | 10 | Pyr+ |

TABLE 24

| Cpd No. | $R_f^3$ | A | $n_f$ | $-N^+R_f^4R_f^5R_f^6$ |
|---|---|---|---|---|
| 62 | $C_{16}H_{33}$ | O | 2 | Thi+ |
| 63 | $C_{18}H_{37}$ | O | 2 | Thi+ |
| 64 | $C_{16}H_{33}$ | O | 3 | Thi+ |
| 65 | $C_{18}H_{37}$ | O | 3 | Thi+ |
| 66 | $C_{14}H_{29}CH(Me)-$ | O | 2 | Thi+ |
| 67 | $Me_3C-(CH_2)_{12}-$ | O | 2 | $-N^+H_3$ |
| 68 | $Me_2CH-(CH_2)_{13}-$ | O | 2 | $-N^+HMe_2$ |
| 69 | $C_{16}H_{33}$ | S | 2 | $-N^+HMe_2$ |
| 70 | $C_{18}H_{37}$ | S | 3 | $-N^+HMe_2$ |
| 71 | $C_{16}H_{33}$ | S | 2 | $-N^+H_3$ |
| 72 | $C_{18}H_{37}$ | S | 2 | $-N^+Me_3$ |
| 73 | $C_{14}H_{29}CH(Me)-$ | O | 5 | Thi+ |
| 74 | $Me_3C-(CH_2)_{12}-$ | O | 7 | $-N^+H_3$ |
| 75 | $Me_2CH-(CH_2)_{13}-$ | O | 9 | $-N^+HMe_2$ |

TABLE 25

| Cpd No. | $R_F^3$ | A | $N_F$ | $-N^+R_F^4R_F^5R_F^6$ |
|---|---|---|---|---|
| 76 | $C_{16}H_{33}$ | O | 2 | Thi+ |
| 77 | $C_{16}H_{33}$ | O | 3 | Thi+ |
| 78 | $C_{17}H_{35}$ | O | 2 | Thi+ |
| 79 | $C_{17}H_{35}$ | O | 3 | Thi+ |
| 80 | $C_{18}H_{37}$ | O | 2 | Thi+ |
| 81 | $C_{18}H_{37}$ | O | 3 | Thi+ |
| 82 | $C_{16}H_{33}$ | O | 2 | $-N^+H_3$ |
| 83 | $C_{17}H_{35}$ | O | 2 | $-N^+Me_3$ |
| 84 | $C_{18}H_{37}$ | O | 2 | $-N^+Me_3$ |
| 85 | $C_{18}H_{37}$ | O | 3 | 1-Me-Pip+ |
| 86 | $C_{18}H_{37}$ | O | 2 | Pyr+ |
| 87 | $C_{17}H_{35}$ | S | 2 | Thi+ |
| 88 | $C_{14}H_{29}CH(Me)-$ | S | 3 | Thi+ |
| 89 | $C_{16}H_{33}$ | S | 2 | Thi+ |
| 90 | $Me_3C-(CH_2)_{12}-$ | S | 3 | Thi+ |
| 91 | $Me_2CH-(CH_2)_{13}-$ | S | 2 | Thi+ |
| 92 | $C_{18}H_{37}$ | S | 2 | Thi+ |
| 93 | $C_{18}H_{37}$ | S | 2 | $-N^+Me_3$ |
| 94 | $C_{18}H_{37}$ | S | 2 | $-N^+HMe_2$ |
| 95 | $C_{18}H_{37}$ | S | 2 | 1-Me—Pip+ |
| 96 | $C_{16}H_{33}$ | S | 2 | Pyr+ |
| 97 | $C_{17}H_{35}$ | O | 6 | Thi+ |
| 98 | $C_{17}H_{35}$ | O | 6 | 4-Me—5-(2-OHEt)Thi+ |
| 99 | $C_{17}H_{35}$ | S | 4 | Thi+ |
| 100 | $C_{17}H_{35}$ | S | 5 | Thi+ |
| 101 | $C_{17}H_{35}$ | S | 6 | Thi+ |
| 102 | $C_{17}H_{35}$ | S | 6 | 4-Me—5-(2-OHEt)Thi+ |
| 103 | $C_{17}H_{35}$ | O | 6 | $-N^+Me_3$ |

TABLE 26

| Cpd No. | $R_f^3$ | A | $n_f$ | $-N^+R_f^4R_f^5R_f^6$ |
|---|---|---|---|---|
| 104 | $C_{14}H_{29}CH(Me)-$ | O | 2 | $Thi^+$ |
| 105 | $C_{17}H_{35}$ | O | 2 | $Thi^+$ |
| 106 | $Me_3C-(CH_2)_{12}-$ | O | 2 | $Thi^+$ |
| 107 | $C_{18}H_{37}$ | O | 3 | $Thi^+$ |
| 108 | $Me_2CH-(CH_2)_{13}-$ | O | 2 | $Thi^+$ |
| 109 | $C_{18}H_{37}$ | O | 2 | $-N^+H_3$ |
| 110 | $C_{18}H_{37}$ | O | 2 | $-N^+Me_3$ |
| 111 | $C_{16}H_{33}$ | O | 2 | $-N^+HMe_2$ |
| 112 | $C_{16}H_{33}$ | O | 2 | $1-Me-Pip^+$ |
| 113 | $C_{18}H_{37}$ | O | 2 | $Pyr^+$ |
| 114 | $C_{17}H_{35}$ | S | 2 | $Thi^+$ |
| 115 | $C_{18}H_{37}$ | S | 2 | $Thi^+$ |
| 116 | $C_{17}H_{35}$ | S | 3 | $-N^+Me_3$ |
| 117 | $C_{18}H_{37}$ | O | 4 | $-N^+Me_3$ |
| 118 | $C_{16}H_{33}$ | O | 6 | $-N^+HMe_2$ |
| 119 | $C_{16}H_{33}$ | O | 8 | $1-Me-Pip^+$ |
| 120 | $C_{18}H_{37}$ | O | 10 | $Pyr^+$ |

TABLE 27

| Cpd No. | $R_f^3$ | A | $n_f$ | $-N^+R_f^4R_f^5R_f^6$ |
|---|---|---|---|---|
| 121 | $C_{16}H_{33}$ | O | 2 | $Thi^+$ |
| 122 | $C_{16}H_{33}$ | O | 3 | $Thi^+$ |
| 123 | $C_{17}H_{35}$ | O | 2 | $Thi^+$ |
| 124 | $C_{17}H_{35}$ | O | 3 | $Thi^+$ |
| 125 | $C_{18}H_{37}$ | O | 2 | $Thi^+$ |
| 126 | $C_{18}H_{37}$ | O | 3 | $Thi^+$ |
| 127 | $C_{16}H_{33}$ | O | 2 | $-N^+H_3$ |
| 128 | $C_{16}H_{33}$ | O | 3 | $-N^+Me_3$ |
| 129 | $C_{18}H_{37}$ | O | 2 | $-N^+HMe_2$ |
| 130 | $C_{18}H_{37}$ | O | 3 | $1-Me-Pip^+$ |
| 131 | $C_{18}H_{37}$ | O | 2 | $Pyr^+$ |
| 132 | $C_{16}H_{33}$ | S | 2 | $Thi^+$ |
| 133 | $C_{14}H_{29}CH(Me)-$ | S | 3 | $Thi^+$ |
| 134 | $C_{18}H_{37}$ | S | 2 | $Thi^+$ |
| 135 | $Me_3C-(CH_2)_{12}-$ | S | 3 | $Thi^+$ |
| 136 | $Me_2CH-(CH_2)_{13}-$ | S | 2 | $Thi^+$ |
| 137 | $C_{16}H_{33}$ | S | 2 | $-N^+H_3$ |
| 138 | $C_{16}H_{33}$ | S | 2 | $-N^+Me_3$ |
| 139 | $C_{18}H_{37}$ | S | 2 | $-N^+HMe_2$ |
| 140 | $C_{18}H_{37}$ | S | 2 | $1-Me-Pip^+$ |
| 141 | $C_{16}H_{33}$ | S | 2 | $Pyr^+$ |
| 142 | $C_{18}H_{37}$ | O | 4 | $1-Me-Pip^+$ |
| 143 | $C_{18}H_{37}$ | O | 5 | $Pyr^+$ |
| 144 | $C_{16}H_{33}$ | S | 6 | $-N^+H_3$ |
| 145 | $C_{18}H_{37}$ | S | 7 | $-N^+HMe_2$ |
| 146 | $C_{18}H_{37}$ | S | 8 | $1-Me-Pip^+$ |

TABLE 28

| Cpd No. | $R_f^3$ | A | $n_f$ | $-N^+R_f^4R_f^5R_f^6$ |
|---|---|---|---|---|
| 147 | $C_{14}H_{29}CH(Me)-$ | O | 2 | $Thi^+$ |
| 148 | $C_{17}H_{35}$ | O | 3 | $Thi^+$ |
| 149 | $Me_3C-(CH_2)_{12}-$ | O | 2 | $Thi^+$ |
| 150 | $C_{18}H_{37}$ | O | 3 | $Thi^+$ |
| 151 | $Me_2CH-(CH_2)_{13}-$ | O | 2 | $Thi^+$ |
| 152 | $C_{18}H_{37}$ | O | 2 | $-N^+H_3$ |
| 153 | $C_{18}H_{37}$ | O | 2 | $-N^+Me_3$ |
| 154 | $C_{16}H_{33}$ | O | 2 | $-N^+HMe_2$ |
| 155 | $C_{16}H_{33}$ | O | 2 | $1-Me-Pip^+$ |
| 156 | $C_{18}H_{37}$ | O | 2 | $Pyr^+$ |
| 157 | $C_{17}H_{35}$ | S | 2 | $Thi^+$ |
| 158 | $C_{18}H_{37}$ | S | 3 | $Thi^+$ |
| 159 | $C_{17}H_{35}$ | S | 2 | $-N^+Me_3$ |
| 160 | $C_{14}H_{29}CH(Me)-$ | O | 4 | $Thi^+$ |
| 161 | $Me_3C-(CH_2)_{12}-$ | O | 5 | $Thi^+$ |
| 162 | $Me_2CH-(CH_2)_{13}-$ | O | 6 | $Thi^+$ |
| 163 | $C_{18}H_{37}$ | O | 7 | $-N^+H_3$ |

TABLE 29

| Cpd No. | $R_f^3$ | A | $n_f$ | $-N^+R_f^4R_f^5R_f^6$ |
|---|---|---|---|---|
| 164 | $C_{17}H_{35}$ | O | 2 | $Thi^+$ |
| 165 | $C_{18}H_{37}$ | O | 3 | $Thi^+$ |
| 166 | $C_{17}H_{35}$ | O | 2 | $-N^+Me_3$ |
| 167 | $C_{17}H_{35}$ | S | 2 | $Thi^+$ |
| 168 | $C_{18}H_{37}$ | S | 3 | $Thi^+$ |
| 169 | $C_{17}H_{35}$ | S | 2 | $-N^+HMe_2$ |
| 170 | $C_{17}H_{35}$ | O | 6 | $Thi^+$ |

TABLE 30

| Cpd No. | $R_f^3$ | A | $n_f$ | $-N^+R_f^4R_f^5R_f^6$ |
|---|---|---|---|---|
| 171 | $C_{17}H_{35}$ | O | 2 | $Thi^+$ |
| 172 | $C_{18}H_{37}$ | O | 2 | $-N^+Me_3$ |
| 173 | $C_{17}H_{35}$ | S | 2 | $Thi^+$ |
| 174 | $C_{18}H_{37}$ | S | 2 | $-N^+Me_3$ |

TABLE 31

| Cpd No. | $R_f^3$ | A | $n_f$ | $-N^+R_f^4R_f^5R_f^6$ |
|---|---|---|---|---|
| 175 | $C_{17}H_{35}$ | O | 2 | $Thi^+$ |
| 176 | $C_{18}H_{37}$ | O | 2 | $-N^+Me_3$ |
| 177 | $C_{18}H_{37}$ | S | 2 | $Thi^+$ |
| 178 | $C_{17}H_{35}$ | S | 2 | $-N^+Me_3$ |

TABLE 32

| Cpd No. | $R_f^3$ | A | $n_f$ | $-N^+R_f^4R_f^5R_f^6$ |
|---|---|---|---|---|
| 179 | $C_{17}H_{35}$ | O | 2 | $Thi^+$ |
| 180 | $C_{18}H_{37}$ | O | 2 | $-N^+Me_3$ |
| 181 | $C_{17}H_{35}$ | S | 2 | $Thi^+$ |
| 182 | $C_{18}H_{37}$ | S | 2 | $-N^+Me_3$ |

Of the compounds listed above, preferred compounds are Compounds No. 1, 2, 3, 4, 9, 19, 26, 36, 76, 77, 78, 80, 83, 85, 86, 87, 97, 98, 99, 100, 101, 102, 103, 105, 165, 166, 167 and 170.

Because of the presence of asymmetric carbon atoms at the α- and β-positions (relative to the ether oxygen atom in the ether ring), the compounds of the invention can exist, as explained previously, as four different stereoisomers. Specific preferred compounds are those having the following formulae (a)–(y) and their mirror images:

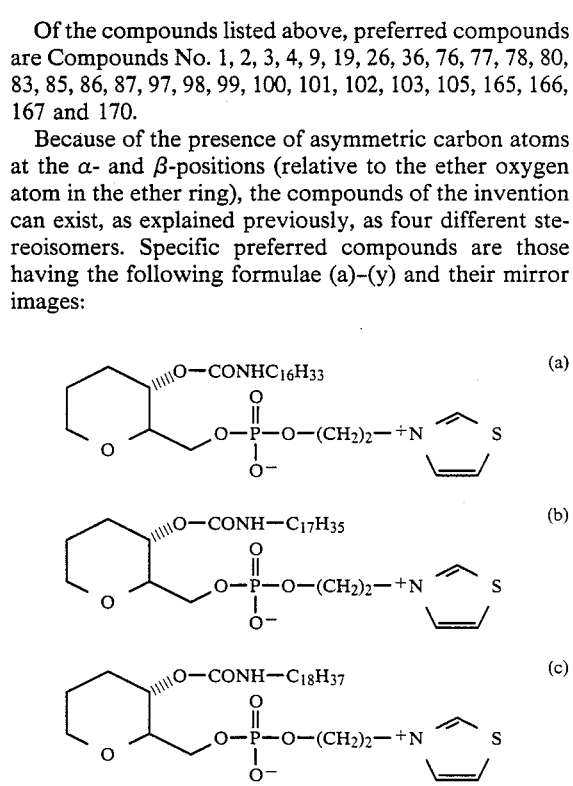

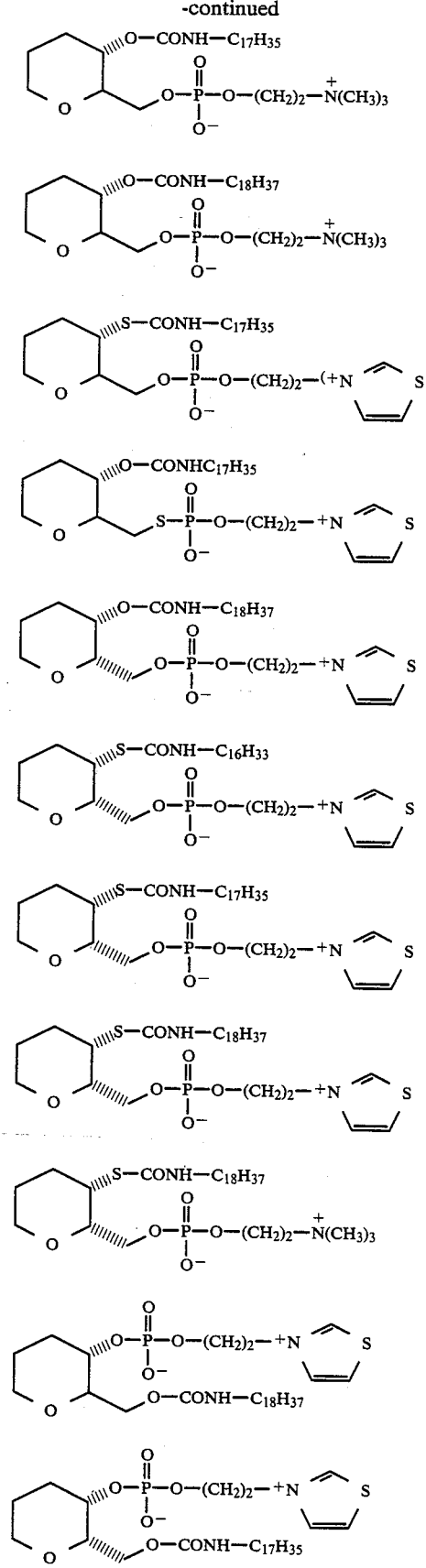

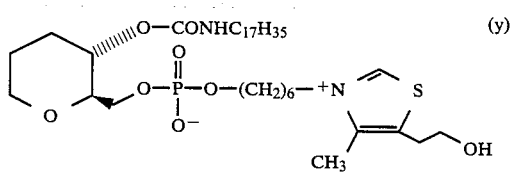 (y)

Of the compounds shown above, compounds (b), (c), (d), (g), (j), (k), (p), (u), (v), (w), (x) and (y) and their mirror images (b'), (c'), (d'), (g'), (j'), (k'), (p'), (u'), (v'), (w'), (x') and (y') are particularly preferred:

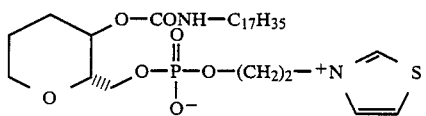 (b')

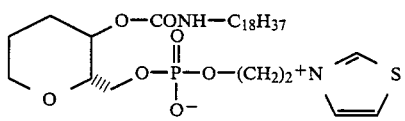 (c')

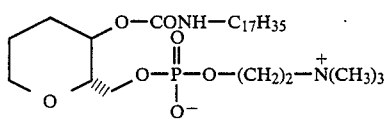 (d')

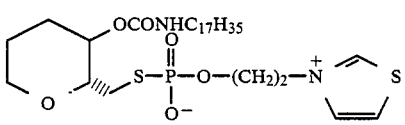 (g')

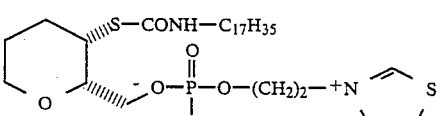 (j)

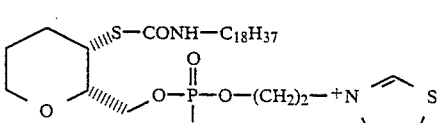 (k)

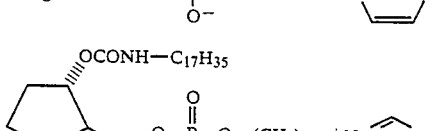 (p)

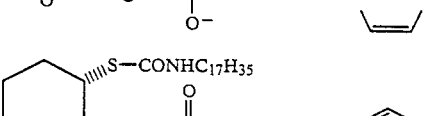 (u)

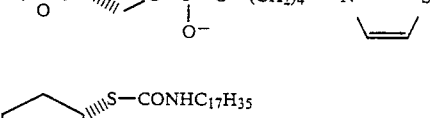 (v)

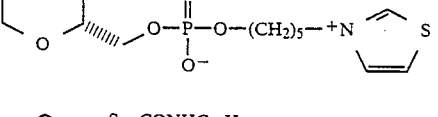 (w)

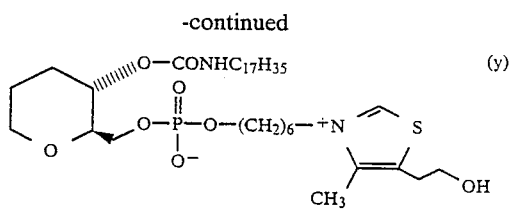 (y)

PREPARATION OF COMPOUNDS OF THE INVENTION

The compounds of the present invention where one of $R^1$ and $R^2$ is a group of formula (III) may be prepared by a variety of processes, for example by any of the following Methods A to K.

Method A

This method is for preparing a compound of general formula (I) in which $R^2$ represents the group of formula (III), i.e. a compound of formula (IX), as shown in the following reaction scheme:

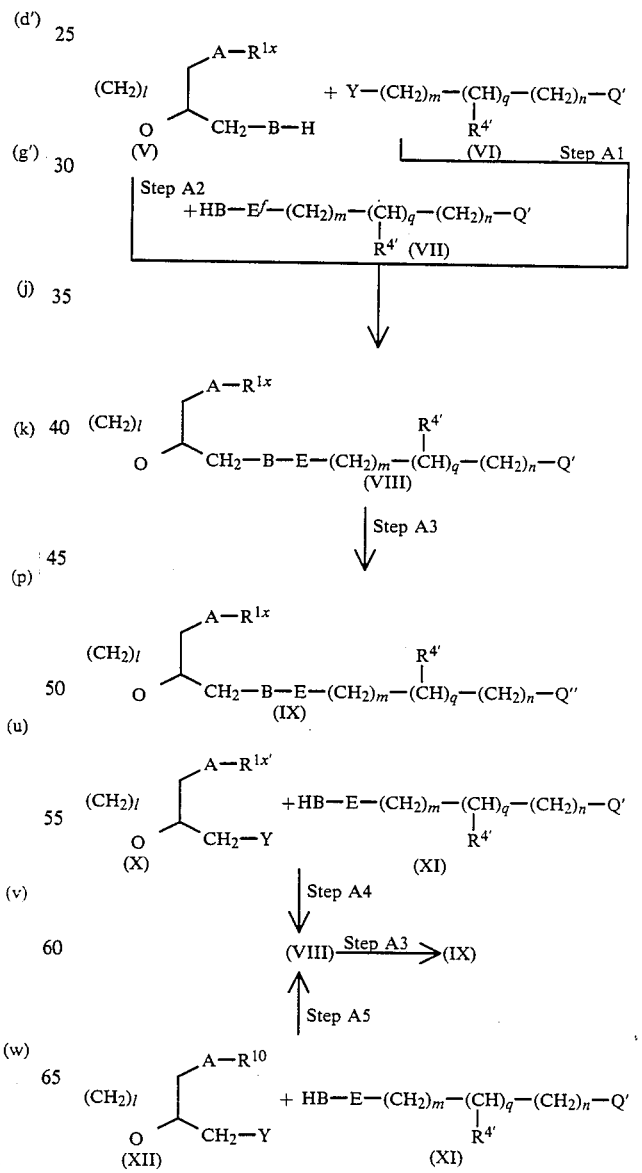

In the above formulae:

A, B, E, l, m, n and q are as defined above.

$R^{1x}$ represents an alkyl group containing from 8 to 22 carbon atoms, an aliphatic carboxylic acyl group containing from 8 to 22 carbon atoms or a group of formula (II):

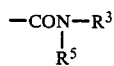
(II)

in which $R^3$ and $R^5$ are as defined above,
i.e. as defined above for $R^1$ or $R^2$.

$R^{1x'}$ represents an alkyl group containing from 8 to 22 carbon atoms.

$R^{4'}$ represents any of the groups defined above for $R^4$, but in which any reactive group is, if necessary, protected. Examples include the $C_1$-$C_6$ alkanoyloxy groups, such as the formyloxy, acetoxy, propionyloxy, butyryloxy, isobutyryloxy, pentanoyloxy, pivaloyloxy, valeryloxy or isovaleryloxy groups, and halogenated derivatives thereof, such as the chloroacetoxy, dichloroacetoxy, trichloroacetoxy or trifluoroacetoxy groups; lower alkoxyalkanoyloxy groups, such as the methoxyacetoxy group; alkenoyloxy groups, such as the (E)-2-methyl-2-butenoyloxy group; aromatic acyloxy groups, for example, arylcarbonyloxy groups, such as the benzoyloxy, α-naphthoyloxy or β-naphthoyloxy groups; halogenated arylcarbonyloxy groups, such as the o-bromobenzoyloxy or p-chlorobenzoyloxy groups; lower alkylated arylcarbonyloxy groups, such as the 2,4,6-trimethylbenzoyloxy or p-toluoyloxy groups; lower alkoxylated arylcarbonyloxy groups, such as the p-anisoyloxy group; nitrated arylcarbonyloxy groups, such as the p-nitrobenzoyloxy or o-nitrobenzoyloxy groups; lower alkoxycarbonylated arylcarbonyloxy groups, such as the o-(methoxycarbonyl)benzoyloxy group; arylated arylcarbonyloxy groups, such as the p-phenylbenzoyloxy group; tetrahydropyranyloxy or tetrahydrothiopyranyloxy groups, such as those exemplified below in relation to $R^{11}$; tetrahydrofuranyloxy or tetrahydrothienyloxy groups, such as the tetrahydrofuran-2-yloxy or tetrahydrothien-2-yloxy groups; silyloxy groups, for example, tri(lower alkyl)silyloxy groups, such as the trimethylsilyloxy, triethylsilyloxy, dimethylisopropylsilyloxy, t-butyldimethylsilyloxy, diisopropylmethylsilyloxy, di-t-butylmethylsilyloxy or triisopropylsilyloxy groups; tri(lower alkyl)silyloxy groups in which 1 to 2 of the alkyl groups are replaced by aryl groups, such as the diphenylmethylsilyloxy, diphenylbutylsilyloxy, diphenylisopropylsilyloxy or diisopropylphenylsilyloxy groups; alkoxymethoxy groups, for example, lower alkoxymethoxy groups, such as the methoxymethoxy, 1,1-dimethyl-1-methoxymethoxy, ethoxymethoxy, propoxymethoxy, isopropoxymethoxy, butoxymethoxy or t-butoxymethoxy groups; lower alkoxylated (lower alkoxy)methoxy groups, such as the 2-methoxyethoxymethoxy group; halogenated (lower alkoxy)methoxy groups, such as the 2,2,2-trichloroethoxymethoxy or bis(2-chloroethoxy)methoxy groups; substituted ethoxy groups, for example, lower alkoxylated ethoxy groups, such as the 1-ethoxyethoxy, 1-methyl-1-methoxyethoxy or 1-(isopropoxy)ethoxy groups; halogenated ethoxy groups, such as the 2,2,2-trichloroethoxy group; arylselenylated lower alkoxy groups substituted with from 1 to 3 aryl groups, such as the phenylselenylmethoxy, 2-phenylselenylethoxy, 3-phenylselenylpropoxy, α-naphthylselenylmethoxy, β-naphthylselenylmethoxy, diphenylselenylmethoxy, triphenylselenylmethoxy, α-naphthyldiphenylselenylmethoxy or 9-anthrylselenylmethoxy groups; lower alkoxy groups substituted with from 1 to 3 aryl groups (which themselves are substituted by substituents such as substituted or unsubstituted lower alkyl, lower alkoxy, nitro, halogen or cyano groups), such as the p-methylbenzyloxy, 2,4,6-trimethylbenzyloxy, 3,4,5-trimethylbenzyloxy, p-methoxybenzyloxy, p-methoxyphenyldiphenylmethoxy, o-nitrobenzyloxy, p-nitrobenzyloxy, p-chlorobenzyloxy, p-bromobenzyloxy, p-cyanobenzyloxy, p-cyanobenzyldiphenylmethoxy, bis(o-nitrophenyl)methoxy or piperonyloxy groups; alkoxycarbonyloxy groups, for example, lower alkoxycarbonyloxy groups, such as the methoxycarbonyloxy, ethoxycarbonyloxy, t-butoxycarbonyloxy or isobutoxycarbonyloxy groups; lower alkoxycarbonyloxy groups (having substituents such as halogen atoms or trialkylsilyl groups), such as the 2,2,2-trichloroethoxycarbonyloxy or 2-trimethylsilylethoxycarbonyloxy groups; alkenyloxycarbonyloxy groups, such as the vinyloxycarbonyloxy or allyloxycarbonyloxy groups; other protected groups of the type commonly used in reactions, for example, aralkyloxycarbonyloxy groups (in which the aryl ring may optionally be substituted with 1 or 2 lower alkoxy or nitro groups), such as the benzyloxycarbonyloxy, p-methoxybenzyloxy-carbonyloxy, 3,4-dimethoxybenzyloxycarbonyloxy, o-nitrobenzyloxycarbonyloxy or p-nitrobenzyloxycarbonyloxy groups; and other protected groups, such as the pivaloyloxymethoxycarbonyloxy group. Of these, we prefer: the aliphatic acyl groups; the aromatic acyloxy groups; the ethoxy group and substituted ethoxy groups, such as the 2-(phenylselenyl)ethoxy group; aralkyloxy groups; tetrahydropyranyloxy groups; aralkyloxy groups; alkoxycarbonyloxy groups; alkenyloxycarbonyloxy groups; and aralkyloxycarbonyloxy groups. The above are examples of protected hydroxy groups which may be represented by $R^{4'}$. Examples of protected thio groups include the thio groups corresponding to the protected hydroxy groups exemplified above. Examples of protected carboxy groups include the ester groups exemplified above in relation to $R^4$.

$R^{10}$ represents a hydroxy-protecting or mercapto-protecting group, e.g. as exemplified in relation to the hydroxy-protecting groups which may be represented by $R^{4'}$.

$E^f$ represents a heterocyclic group containing from 5 to 14, preferably from 5 to 10 and more preferably from 5 to 7, ring atoms, as defined above for E.

$Q'$ represents a group having the formula —O—$R^{11}$ [in which $R^{11}$ represents a hydroxy-protecting group, for example: a tetrahydropyranyl or tetrahydrothiopyranyl group which may be substituted or unsubstituted, such as the tetrahydropyran-2-yl, 3-bromotetrahydropyran-2-yl, 4-methoxytetrahydropyran-4-yl, tetrahydrothiopyran-2-yl or 4-methoxytetrahydrothiopyran-4-yl groups; a lower alkoxymethyl group such as the methoxymethyl, t-butoxymethyl, 2-methoxyethoxymethyl, 2,2,2-trichloroethoxymethyl or bis(2-chloroethoxy)methyl groups; or an aralkyl group such as the benzyl, p-methoxybenzyl, o-nitrobenzyl, p-nitrobenzyl, p-halobenzyl (e.g. p-chlorobenzyl or p-bromobenzyl group), p-cyanobenzyl, diphenylmethyl, triphenylmethyl, α-naphthyldiphenylmethyl, or p-methoxyphenyldiphenylmethyl groups, of which we prefer the tetrahydropyranyl, lower alkoxymethyl and aralkyl groups] or any one of the heterocyclic groups defined above for Q in which, if necessary, any reactive group is protected.

Q" represents a group of formula Y, defined below, or any one of the heterocyclic groups represented by Q, in which Q is as defined above.

Y represents a halogen atom (for example a chlorine, bromine or iodine atom), a lower alkylsulfonyloxy group (for example a methanesulfonyloxy, ethanesulfonyloxy or trifluoromethanesulfonyloxy group), a trihalomethoxy group (for example a trichloromethoxy or tribromomethoxy group) or an arylsulfonyloxy group (for example a benzenesulfonyloxy or p-toluenesulfonyloxy group).

Step A1

In this Step a compound of formula (V) having a terminal hydroxy or mercapto group (—B—H) on the methyl group at the position α to the ethereal oxygen atom is reacted with a compound of formula (VI), to give the compound of formula (VIII). This is a simple alkylation reaction and may be carried out by means well known for this type of reaction. For example, the reaction may be carried out by reacting the compound of formula (V) with the compound of formula (VI) in the presence of a base.

The reaction is preferably effected in the presence of a solvent, the nature of which is not critical, provided that it does not interfere with the reaction. Examples of suitable solvents include: ethers, such as diethyl ether, tetrahydrofuran, or dioxane; aromatic hydrocarbons, such as benzene or toluene; amides, such as dimethylformamide or dimethylacetamide; dimethyl sulfoxide; or hexamethylphosphoric triamide; preferably benzene, dimethylformamide or hexamethylphosphoric triamide.

There is also no particular restriction on the nature of the base to be employed, provided that it does not affect other parts of the compounds involved in the reaction. The base functions as an acid-binding agent and any base capable of fulfilling this function may be employed in the present invention, for example: organic bases, such as triethylamine, 1,5-diazabicyclo[5.4.0]undec-5-ene, pyridine, 2,6-lutidine, dimethylaniline or 4-(N,N-dimethylamino)pyridine; alkali metal hydroxides, such as sodium hydroxide or potassium hydroxide; and alkali metal hydrides, such as sodium hydride or potassium hydride; of these, the alkali metal hydroxides are preferred.

The reaction will take place over a wide range of temperatures and the precise temperature chosen is not particularly critical. We generally find it convenient to conduct the reaction at a temperature from 0° C. to 150° C., more preferably at from 60° C. to 90° C. The time required for the reaction may vary widely, depending on many factors, notably the reaction temperature and the nature of the starting materials, but a period of from 1 hour to 3 days, more preferably from 4 to 16 hours, will normally suffice.

After completion of the reaction, the compound of formula (VIII) can be collected from the reaction mixture by conventional means. For instance, one suitable recovery technique comprises: adding an organic solvent immiscible with water to the reaction mixture; washing with water; and evaporating off the solvent. The desired compound thus obtained can be further purified, if necessary, by such conventional techniques as recrystallization, reprecipitation and the various chromatography techniques, notably column chromatography.

Step A2

In this Step, a compound of formula (V) is reacted with a compound of formula (VII) under the conditions of the Mitsunobu reaction.

Such a reaction may be carried out in the presence of a solvent using a lower dialkyl azodicarboxylate, such as dimethyl azodicarboxylate or diethyl azodicarboxylate, and triphenylphosphine.

There is no particular limitation on the nature of the solvent, provided that it does not interfere with the reaction. Examples of suitable solvents include: ethers, such as diethyl ether or tetrahydrofuran; and aromatic hydrocarbons, such as benzene or toluene.

The reaction will take place over a wide range of temperatures and the precise temperature chosen is not particularly critical. We generally find it convenient to conduct the reaction at a temperature from 0° C. to 100° C. The time required for the reaction may vary widely, depending on many factors, notably the reaction temperature and the nature of the starting materials, but a period of from 15 minute to 2 hours will normally suffice.

After completion of the reaction, the compound of formula (VIII) can be collected from the reaction mixture by conventional means. The desired compound thus obtained can be isolated by various chromatography techniques, notably column chromatography.

Step A3

In Step A3, the desired compound of formula (IX) is prepared by converting the group of formula —O—$R^{11}$, when the compound of formula (VIII) contains this group as Q', into a group of formula Y.

First, the hydroxy-protecting group, $R^{11}$, is removed. The nature of the reaction employed to remove this group will, of course, depend on the nature of the group to be removed. When the hydroxy-protecting group is a tetrahydropyranyl group, a tetrahydrofuranyl group, a substituted ethyl group or a lower alkoxymethyl group, it can be removed by treatment with an acid in a solvent. Examples of suitable acids include acetic acid, p-toluenesulfonic acid, hydrochloric acid or a mixture of acetic acid and sulfuric acid. The reaction is preferably effected in the presence of a solvent, the nature of which is not critical, provided that it does not interfere with the reaction. Examples of suitable solvents include: alcohols, such as methanol or ethanol; ethers, such as tetrahydrofuran or dioxane; and mixtures of one or more of these organic solvents with water.

The reaction will take place over a wide range of temperatures and the precise temperature chosen is not particularly critical. We generally find it convenient to conduct the reaction at a temperature from 0° C. to 100° C., more preferably at from 20° C. to 60° C. The time required for the reaction may vary widely, depending on many factors, notably the reaction temperature and the nature of the starting materials, but a period of from 10 minutes, more commonly from 1 hour, to 24 hours will normally suffice.

When the hydroxy-protecting group is an aralkyl group, it can be removed by contact with a reducing agent. For example, the reduction can be carried out by catalytic reduction at room temperature by using a catalyst, such as palladium on activated carbon, platinum or Raney nickel, in the presence of hydrogen gas. This reaction is preferably effected in the presence of a solvent, the nature of which is not critical, provided that it does not interfere with the reaction. Examples of suitable solvents include: alcohols, such as methanol or ethanol; ethers, such as tetrahydrofuran or dioxane; fatty acids, such as acetic acid; and mixtures of one or more of these organic solvents with water.

The reaction will take place over a wide range of temperatures and the precise temperature chosen is not particularly critical. We generally find it convenient to conduct the reaction at a temperature from 0° C. to about room temperature. The time required for the reaction may vary widely, depending on many factors, notably the reaction temperature and the nature of the starting materials, especially the reducing agent, but a period of from 5 minutes to 12 hours will normally suffice.

Alternatively, the deprotection reaction can be conducted by reacting the protected compound with a metal, such as metallic lithium or sodium, with liquid ammonia or with an alcohol, such as methanol or ethanol, at a relatively low temperature, e.g. from −78° C. to −20° C.

Where the protecting group is an aralkyl group, it can also be removed by using a mixture of aluminum chloride and sodium iodide or an alkylsilyl halide, such as trimethylsilyl iodide. The reaction is preferably carried out in the presence of a solvent, the nature of which is not critical, provided that it does not interfere with the reaction. Examples of preferred solvents include: nitriles such as acetonitrile; halogenated hydrocarbons, particularly halogenated aliphatic hydrocarbons, such as methylene chloride or chloroform; and mixtures of any two or more of the above solvents. The reaction temperature may vary widely, depending upon many factors, notably the nature of the starting materials, but we generally find it convenient to carry out the reaction at a temperature of from 0° C. to 50° C.

When the compound of formula (VIII) contains a mercapto sulfur atom and the hydroxy-protecting group is a benzyl group, this can often best be removed by treatment with aluminum chloride and sodium iodide. When the protecting group is a di- or tri-arylmethyl group, this is preferably removed by treatment with an acid, e.g. trifluoroacetic acid, hydrochloric acid or acetic acid.

Where the hydroxy-protecting group is a silyl group, it can be removed by treatment with a compound producing a fluoride anion, such as tetrabutylammonium fluoride. The reaction is preferably effected in the presence of a solvent, the nature of which is not critical, provided that it does not interfere with the reaction. Examples of suitable solvents include: ethers, such as tetrahydrofuran, or dioxane.

The reaction will take place over a wide range of temperatures and the precise temperature chosen is not particularly critical. We generally find it convenient to conduct the reaction at about room temperature. The time required for the reaction may vary widely, depending on many factors, notably the reaction temperature and the nature of the starting materials, but a period of from 10 to 18 hours will normally suffice.

Where the hydroxy-protecting group is an aliphatic acyl group, an aromatic acyl group or an alkoxycarbonyl group, the protecting group can be removed by treatment with a base. There is no particular restriction on the nature of the base to be employed in this reaction, provided that other parts of the molecule are not affected. Examples of preferred bases include: metal alcoholates, particularly alkali metal alcoholates, such as sodium methoxide; ammonium hydroxide; alkali metal carbonates, such as sodium carbonate or potassium carbonate; alkali metal hydroxides, such as sodium hydroxide or potassium hydroxide; and mixtures of concentrated ammonia and methanol. The reaction is preferably effected in the presence of a solvent, the nature of which is not critical, provided that it has no adverse effect on the reaction, and any solvent conventionally used in hydrolysis reactions may equally be employed here. Suitable examples include such organic solvents as alcohols (such as methanol, ethanol or propanol) and ethers (such as tetrahydrofuran or dioxane), water or a mixture of one or more of the above organic solvents and water. The reaction temperature and the time required for the reaction may vary widely, depending upon the nature of the starting materials and the bases employed and there is no particular restriction. However, in order to avoid adverse reactions, we normally prefer to carry out the reaction at a temperature of from 0° C. to 150° C. and for a period of from 1 hour to 10 hours.

Where the hydroxy-protecting group is an alkenyloxycarbonyl group, it can be removed by treatment with a base in a similar manner to that described above for deprotection when the hydroxy-protecting group is an aliphatic acyl group, an aromatic acyl group or an alkoxycarbonyl group. Where the protecting group is an allyloxycarbonyl group, it can also be removed simply by using palladium and triphenylphosphine or nickel tetracarbonyl, and this reaction has the advantage that there is little if any side reaction.

After completion of the reaction, the desired compound can be isolated from the reaction mixture by conventional means. The product may then, if desired, be further purified by such conventional techniques as recrystallization, preparative thin layer chromatography or column chromatography.

Next, the deprotected hydroxy group is converted to an ester by acylation, for example, by methanesulfonylation, toluenesulfonylation, trifluoromethanesulfonylation or trifluoroacetylation, or it is halogenated.

The ester synthesis is preferably effected in the presence of a solvent, the nature of which is not critical, provided that it does not interfere with the reaction. Examples of suitable solvents include: halogenated hydrocarbons, particularly halogenated aliphatic hydrocarbons, such as chloroform, methylene chloride or dichloroethane; ethers, such as diethyl ether, tetrahydrofuran or dioxanne; and aromatic hydrocarbons, such as benzene or toluene. Of these, methylene chloride or benzene are preferred.

The reaction is preferably effected in the presence of a base, the nature of which is not critical, provided that it does not affect other parts of the compounds. The base functions as an acid-binding agent and any base capable of fulfilling this function may be employed in the present invention, for example: organic bases, such as triethylamine, pyridine, 2,6-lutidine or N,N-dimethylaniline.

The reaction will take place over a wide range of temperatures and the precise temperature chosen is not particularly critical. We generally find it convenient to conduct the reaction at a temperature from 0° C. to 25° C. The time required for the reaction may vary widely, depending on many factors, notably the reaction temperature and the nature of the starting materials, but a period of from 30 minutes to 24 hours will normally suffice.

The nature of the halogenation reaction is not critical, provided that it can replace a hydroxy group by a halogen atom. In general, it is preferably carried out using a carbon tetrahalide and triphenylphosphine, or using a phosphorus trihalide.

The reaction is preferably effected in the presence of a solvent, the nature of which is not critical, provided that it does not interfere with the reaction. Examples of suitable solvents include: halogenated hydrocarbons, particularly halogenated aliphatic hydrocarbons, such as chloroform, methylene chloride or dichloroethane; and nitriles, such as acetonitrile.

The reaction will take place over a wide range of temperatures and the precise temperature chosen is not particularly critical. We generally find it convenient to conduct the reaction at a temperature from −25° C. to room temperature. The time required for the reaction may vary widely, depending on many factors, notably the reaction temperature and the nature of the starting materials, but a period of from 1 to 60 minutes will normally suffice.

The halogen-substituted compound can be also synthesized by reaction of the ester synthesized as described above with an alkali metal halide, such as sodium iodide, sodium bromide or potassium chloride. The reaction is preferably effected in the presence of a solvent, the nature of which is not critical, provided that it does not interfere with the reaction. It is preferably a polar solvent capable of dissolving an alkali metal halide. Examples include: ketones, such as acetone; sulfoxides, such as dimethyl sulfoxide; fatty acid amides, such as dimethylformamide; and phosphorus triamides, such as hexamethylphosphoric triamide. Of these, we prefer dimethylformamide.

The reaction will take place over a wide range of temperatures and the precise temperature chosen is not particularly critical. We generally find it convenient to conduct the reaction at a temperature from 20° C. to 80° C. The time required for the reaction may vary widely, depending on many factors, notably the reaction temperature and the nature of the starting materials, but a period of from 1 to 24 hours will normally suffice.

After completion of the reaction, the desired compound can be isolated from the reaction mixture by conventional means. The product may then, if desired, be further purified by such conventional techniques as recrystallization, preparative thin layer chromatography and column chromatography.

Step A4

This is essentially the same as Step A1, except that, whereas, in Step A1, the group —B—H is on the compound of formula (V) (the cyclic ether) and the group Y is on the compound of fomrula (VI), in Step A4, the group Y is on the compound of formula (X) (the cyclic ether) andthe group —B—H is on the compound of formula (XI). The reaction may be carried out employing the same reagents and reaction conditions as hereinbefore described with reference to Step A1. The resulting compound of formula (VIII) may then be subjected to Step A3, as described above.

Step A5

In this Step, a compound of formula (VIII) is prepared by reacting a compound of formula (XI) having a terminal hydroxy or mercapto group in its molecule with a compound of formula (XII), which functions as an alkylating agent, in a similar manner to that described in Step A1 or A4, to give an ether or thioether compound, followed by removing the hydroxy- or mercapto-protecting group represented by $R^{10}$; the hydroxy or mercapto group of the resulting compound may then be alkylated with a compound of formula $R^{1y}$-Y (in which $R^{1y}$ represents an alkyl group containing from 8 to 22 carbon atoms, and Y is as defined above). Alternatively, it may be acylated by using a reactive derivative of a carboxylic acid having the formula $R^{1z}$-Y (in which Y is as defined above and $R^{1z}$ represents a straight or branched chain aliphatic acyl group containing from 8 to 22 carbon atoms). As a still further alternative, it may be carbamated using a compound of formula $R^3$—N=C=O (in which $R^3$ is as defined above).

The first step of this reaction will take place as described in Step A1 and may be carried out using similar reagents and reaction conditions to those employed in that Step.

The nature of the reaction employed to remove the hydroxy- or mercapto-protecting group $R^{10}$ will, of course, depend on the nature of the group to be removed, but these groups can be removed as described above in relation to the removal of the hydroxy-protecting group $R^{11}$ in Step A3.

Where the resulting deprotected compound is to be alkylated, the reaction may be carried out as described above in relation to the alkylation reaction of Step A1, employing the same reagents and reaction conditions.

Where Y represents a halogen atom, acylation is preferably carried out in a solvent in the presence of a base. Where a solvent is employed, its nature is not critical, provided that it does not interefere with the reaction and that the starting material can dissolve in it, at least to some extent. Preferred examples of such solvents include: halogenated hydrocarbons, particularly halogenated aliphatic hydrocarbons, such as methylene chloride, chloroform or 1,2-dichloroethane; ethers, such as diethyl ether, tetrahydrofuran or dioxane; and aromatic hydrocarbons such as benzene or toluene.

There is likewise no particular limitation on the nature of the base to be employed in the reaction, and any base commonly used for this type of reaction may equally be used here, provided that it has no adverse effect on the reaction and, in particular, that it has no effect on other parts of the molecule. In general, we prefer to use an amine, preferably triethylamine, diethylamine or pyridine.

The reaction will take place over a wide range of temperatures, and the precise temperature chosen is not critical to the invention. However, we generally find it convenient to carry out the reaction at a temperature of from 0° C. to 120° C. The time required for the reaction may vary widely, depending upon many factors, notably the nature of the starting materials, the solvents or the bases and the reaction temperature. However, when the reaction is carried out at a temperature in the range suggested above, a period of from 2 to 24 hours will normally suffice.

Where Y represents a trihalomethoxy group, a lower alkanesulfonyloxy group, a halogenated lower alkanesulfonyloxy group, an arylsulfonyloxy group, an aliphatic acyloxy group or an aromatic acyloxy group, a base is not always required for the reaction, as the reaction occurs spontaneously. Nonetheless, the reaction rate is accelerated in the presence of the base, and, if a base is employed, it is preferably selected from those described above for the case where Y represents a halogen atom.

In this case, too, the reaction is preferably effected in the presence of a solvent, the nature of which is not critical, provided that it has no adverse effect on the reaction. Examples of suitable solvents include: halogenated hydrocarbons, particularly halogenated aliphatic hydrocarbons, such as chloroform, methylene chloride or 1,2-dichloroethane; and ethers, such as diethyl ether, tetrahydrofuran or dioxane. Of these, we prefer methylene chloride or tetrahydrofuran.

The reaction will take place over a wide range of temperatures, and the precise temperature chosen is not critical to the invention. However, we generally find it convenient to carry out the reaction at a temperature of from 0° C. to 50° C., preferably from 0° C. to 20° C. The time required for the reaction may vary widely, depending upon many factors, notably the nature of the starting materials, the solents or the bases (if employed) and the reaction temperature. However, when the reaction is carried out at a temperature in the range suggested above, a period of from 30 minutes to 24 hours will normally suffice.

After completion of the reaction, the desired compound can be recovered from the reaction mixture by conventional means. If required, the compound can be further purified by such conventional purification techniques as recrystallization, preparative thin layer chromatography or column chromatography.

The formation of a carbamate is preferably effected as a two stage reaction, in which first a compound having the formula $R^3$—COOH (in which $R^3$ is as defined above) is reacted with diphenylphosphoryl azide (DPPA) dissolved in an inert solvent, such as chloroform, toluene, benzene, methylene chloride or tetrahydrofuran, to form a compound of formula $R^3$—N=C=O (in which $R^3$ is as defined above). This reaction is preferably carried out in toluene or benzene in the presence of an organic base, such as triethylamine or tributylamine. The cyclic ether compound is then added to the solution of this compound of formula $R^3$—N=C=O, and then the mixture is heated at 60° C. to 150° C. for 2 to 24 hours to afford the desired compound of formula (VIII). We prefer that, immediately after the isocyanate compound is synthesized, the reaction mixture should be washed with a saturated aqueous solution of sodium bicarbonated and water to remove phosphorous compounds followed by distilling off the solvent, drying and dissolving the residue in a solvent (preferably toluene) selected from the above illustrated solvents. The cyclic ether compound should then be added; or a commercial isocyanate is reacted in the same solvent as above.

After completion of the reaction, the desired compound can be recovered from the reaction mixture by conventional means. If required, the compound can be further purified by such conventional purification techniques as recrystallization, preparative thin layer chromatography or column chromatography.

The resulting compound of formula (VIII) may then be subjected to Step A3, as described above.

Method B

In this Method there are prepared compounds of formula (I) in which $R^1$ represents the group of formula (III), i.e. a compound of formula (XV), as shown in the following reaction scheme:

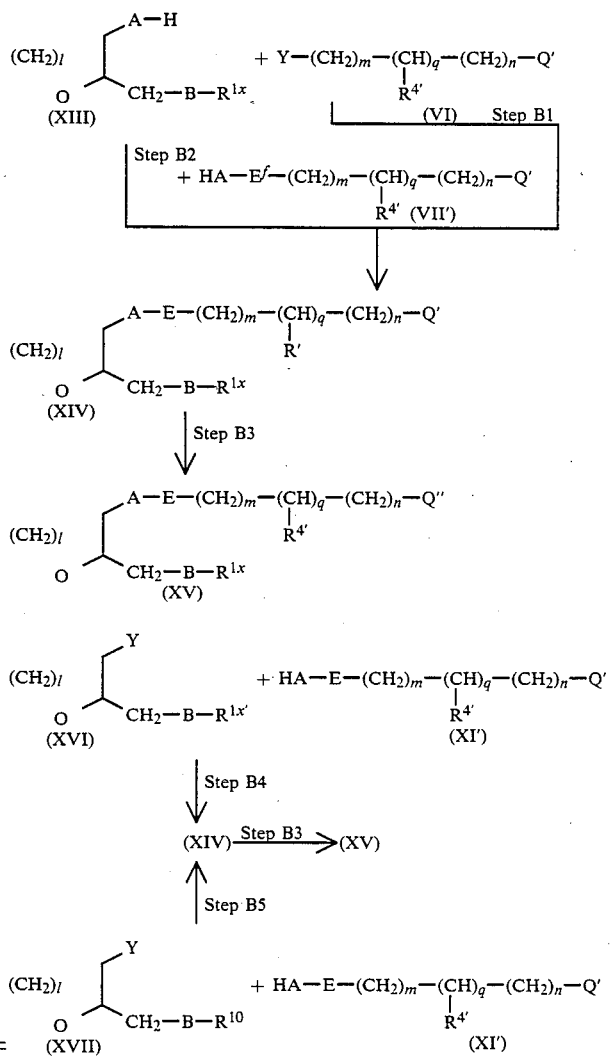

In the above formulae:
A, B, E, l, m, n, q, $R^{1x}$, $R^{1x'}$, $R^{4'}$, $R^{10}$, $E^f$, Q', Q" and Y are as defined above.

These reactions are the same as the reactions involved in the corresponding Steps of Method A, except that, in this case, the group of formula (III) is at the β position to the oxygen atom of the cyclic ether. Each of these Steps may, of course, be carried out in precisely the same way as the corresponding Step of Method A, employing the same reagents and reaction conditions. In Steps B4 and B5, an inversion of the stereochemistry at the β-position takes place.

Method C

This reaction produces compounds of the invention in which the group of formula (III) is on the methyl group at the position α to the oxygen atom of the cyclic ether and E represents a group of formula —C(=O)— or —CO—NR$^6$—, i.e. a compound of formula (XVIII) or (XXI), as shown in the following reaction scheme:

In this Step, a compound of formula (XVIII) is prepared by reacting a compound of formula (V) (see Method A) having a terminal hydroxy or mercapto group with a reactive derivative of an acid (XIX), in the presence or absence of a base.

The reaction is the same as the acylation reaction described in Step A5 of Method A, and may be carried out using the same reagents and reaction conditions.

Step C2

In Step C2, a carbamate or thiocarbamate is prepared by reaction of a compound of formula (V), which has a terminal hydroxy or mercapto group, with an isocyanate compound of formula (XX), followed, if desired, by substitution of the imino group to prepare a com-

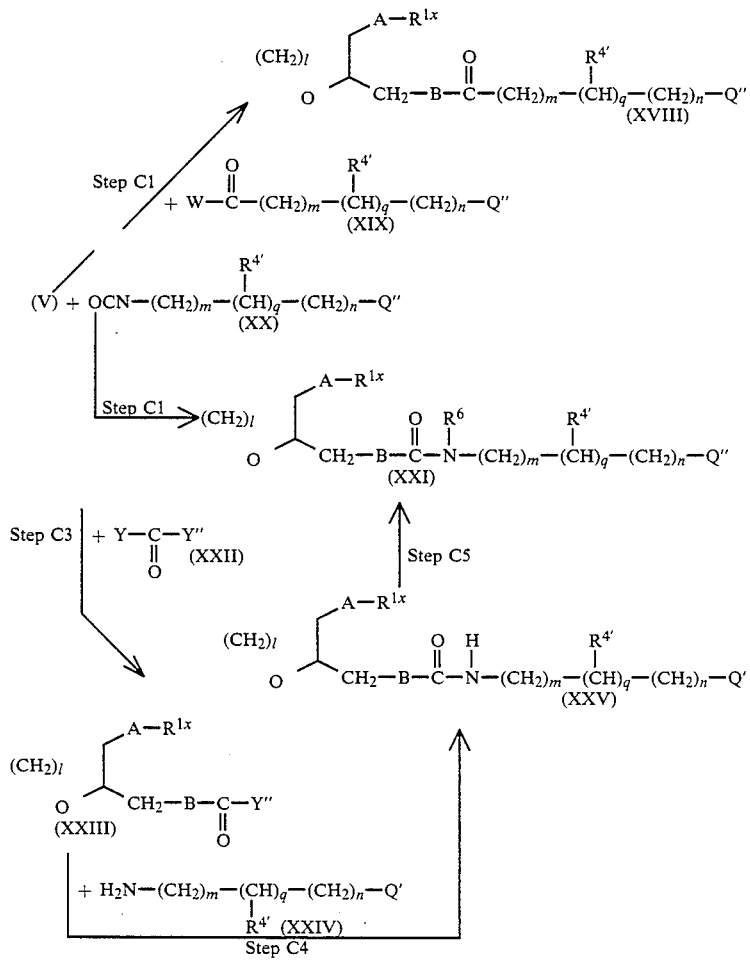

In the above formulae:

A, B, l, m, n, q, R$^{1x}$, R$^{4'}$, R$^6$, Q', Q" and Y are as defined above;

W represents a residue of a reactive carboxylic acid, preferably the same group as those defined as Y, a lower aliphatic acyloxy group or an aromatic acyloxy group (which may be any of those acyloxy groups defined above as protected hydroxy groups to be represented by R$^{4'}$); and Y" represents a leaving group, such as a halogen atom, an aralkyloxy group (e.g. a benzyloxy group) or a trihalomethoxy group (e.g. a trichloromethoxy group).

Step C1 pound of formula (XXI) from the resulting carbamate or thiocarbamate.

The isocyanate compound of formula (XX) can be synthesized without difficulty, for example, by allowing a compound having the formula:

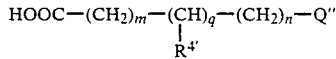

(in which m, q, n, R$^{4'}$ and Q" are as defined above) to react with diphenylphosphoryl azide in an inert solvent, such as chloroform, toluene, benzene, methylene chloride or tetrahydrofuran, preferably toluene or benzene, and in the presence of an organic base, such as triethylamine or tributylamine, preferably at a temperature of from 0° C. to 150° C. The desired compound of formula (XXI) can be prepared directly by adding the compound of formula (V) to a solution of the compound of formula (XX) obtained as described above and then heating for 2 to 24 hours at 60° C. to 150° C. to react further. Preferably, the compound of formula (XX) at the time of its synthesis is washed with a saturated aqueous solution of sodium bicarbonate and with water in order to remove the phosphorus compound, and then, after removal of the solvent, dried, dissolved in any desired one of the solvents mentioned above (preferably toluene) and mixed with the compound of formula (V) to react.

The imino-substitution reaction can be achieved by reaction with, for example, an alkyl halide, a carboxylic acid halide or a carboxylic acid anhydride in the presence of a base.

The reaction is preferably effected in the presence of a solvent, the nature of which is not critical, provided that it does not interfere with the reaction. Examples of suitable solvents include: aromatic hydrocarbons, such as benzene or toluene; and organic amines, such as pyridine.

There is also no particular restriction on the nature of the base to be employed, provided that it does not interfere with other parts of the molecule. It is preferably: an organic base, e.g. an amine, for example, triethylamine, diisopropylethylamine, 4-(N,N-dimethylaminopyridine or pyridine; or an inorganic base, e.g. an alkali metal hydride, for example sodium hydride or potassium hydride.

The reaction will take place over a wide range of temperatures and the precise temperature chosen is not particularly critical. We generally find it convenient to conduct the reaction at a temperature from 20° C. to 120° C. The time required for the reaction may vary widely, depending on many factors, notably the reaction temperature and the nature of the starting materials and base employed, but a period of from 1 to 24 hours will normally suffice.

After completion of the reaction, the desired compound can be isolated from the reaction mixture by conventional means. If required, the compound can be further purified by such conventional purification methods as recrystallization, preparative thin layer chromatography and column chromatography.

Step C3

In this Step, a compound of formula (XXIII) is prepared by reacting a compound of formula (V), which has a terminal hydroxy or mercapto group, with a compound of formula (XXII) in the presence of an organic base.

There is no particular restriction on the nature of the solvent to be employed, provided that it does not interfere with the reaction and that it can dissolve the starting materials at least to some extent. Examples of preferred solvents include: halogenated hydrocarbons, such as methylene chloride or chloroform; aromatic hydrocarbons, such as benzene, toluene or xylene; and ethers, such as tetrahydrofuran or dioxane.

There is also no particular restriction on the nature of the base to be employed, provided that it does not interfere with other parts of the molecule. It is preferably an organic base, e.g. an amine, for example, triethylamine, 1,5-diazabicyclo[5.4.0]undec-5-ene, pyridine, 2,6-lutidine, dimethylaniline or 4-(N,N-dimethylamino)pyridine.

The reaction will take place over a wide range of temperatures and the precise temperature chosen is not particularly critical. We generally find it convenient to conduct the reaction at a temperature from 0° C. to 100° C., preferably from 0° C. to 50° C. The time required for the reaction may vary widely, depending on many factors, notably the reaction temperature and the nature of the starting materials and base employed, but a period of from 30 minutes to 24 hours will normally suffice.

After completion of the reaction, the desired compound can be isolated from the reaction mixture by conventional means. If required, the compound can be further purified by such conventional purification methods as recrystallization, preparative thin layer chromatography and column chromatography.

Alternatively, the compound of formula (XXIII) may be employed as such in the next Step, without isolation.

Step C4

In Step C4, the compound of formula (XXIII) prepared as described in Step C3 is reacted with an amine compound of formula (XXIV) to give a compound of formula (XXV). This reaction is preferably carried out in the presence of a solvent and of a base, and is preferably effected under the conditions described above in Step C3.

Step C5

In this Step, a compound of formula (XXI) is prepared by converting a group of formula $-OR^{11}$ represented by Q' to a group Y and then, if desired, substituting the imino group with a group $R^6$. The first of these reactions may be carried out in a similar manner to that described for Step A3, and the second of these reactions may be carried out in a similar manner to that described for the substituting reaction in Step C2.

Method D

This reaction produces compounds of the invention in which the group of formula (III) is at the position $\beta$ to the oxygen atom of the cyclic ether and E represents a group of formula $-CO-NR^6-$, i.e. a compound of formula (XXVI) or (XXVII), as shown in the following reaction scheme:

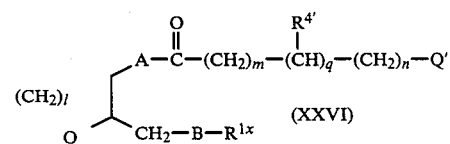

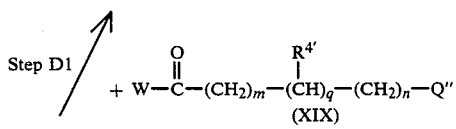

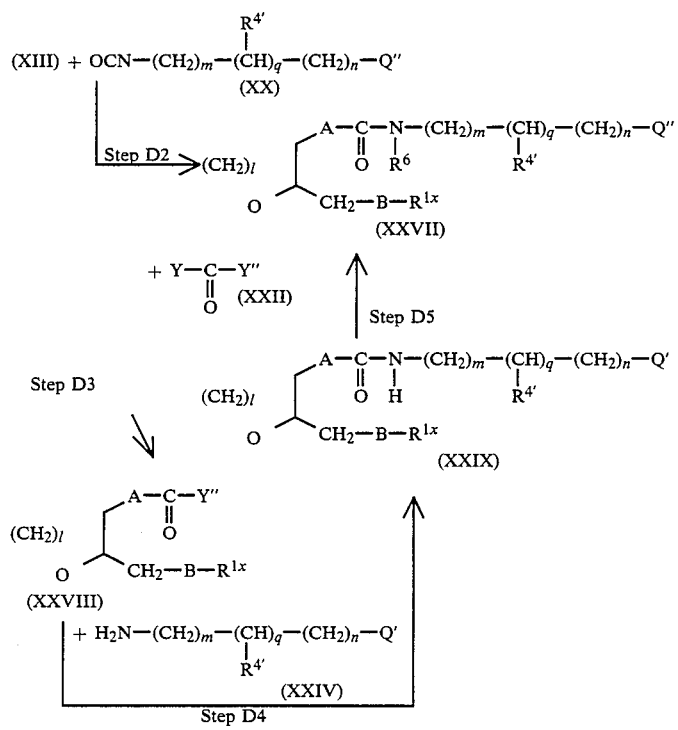

In the above formulae:

A, B, l, m, n, q, $R^{1x}$, $R^{4'}$, $R^6$, $Q'$, $Q''$, W, Y and $Y''$ are as defined above.

These reactions are the same as the reactions involved in the corresponding Steps of Method C, except that, in this case, the group of formula (III) is at the β position to the oxygen atom of the cyclic ether. Each of these Steps may, of course, be carried out in precisely the same way as the corresponding Step of Method C, employing the same reagents and reaction conditions.

Method E

This reaction produces compounds of the invention in which the group of formula (III) is on the methyl group at the position α to the oxygen atom of the cyclic ether and E represents a group of formula —CO—O—, i.e. a compound of formula (XXXII), as shown in the following reaction scheme:

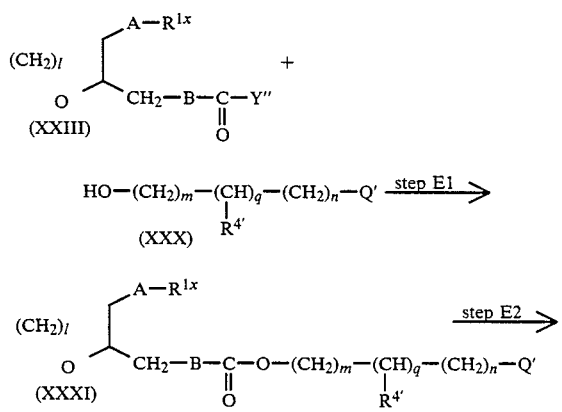

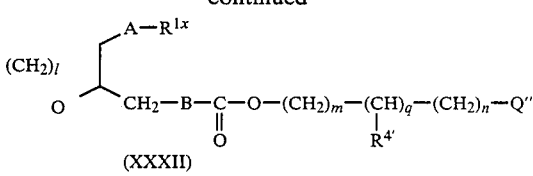

In the above formulae:

A, B, l, m, n, q, $R^{1x}$, $R^{4'}$, $Q'$, $Q''$ and $Y''$ are as defined above.

Step E1

In this Step, a compound of formula (XXIII) is reacted with a hydroxy compound of formula (XXX) to give a compound of formula (XXXI). The reaction is essentially the same as that described in Step C4 of Method C and may be carried out using similar reagents and reaction conditions.

Step E2

In this Step, a compound of formula (XXXII) is prepared by converting a group of formula $-OR^{11}$ represented by Q' to a group Y. This reaction may be carried out in a similar manner to that described for the protecting reaction in Step A3.

Method F

This reaction produces compounds of the invention in which the group of formula (III) is at the position β to the oxygen atom of the cyclic ether and E represents a group of formula —CO—O—, i.e. a compound of formula (XXXIV), as shown in the following reaction scheme:

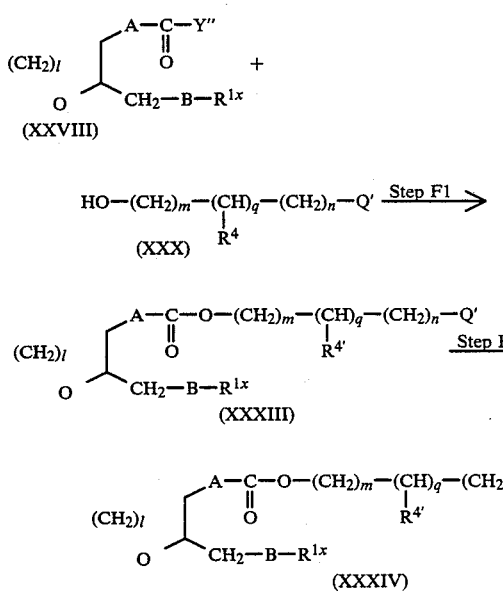

(XXVIII)

HO—(CH₂)$_m$—(CH)$_q$—(CH₂)$_n$—Q'  (XXX)   —Step F1→

R⁴

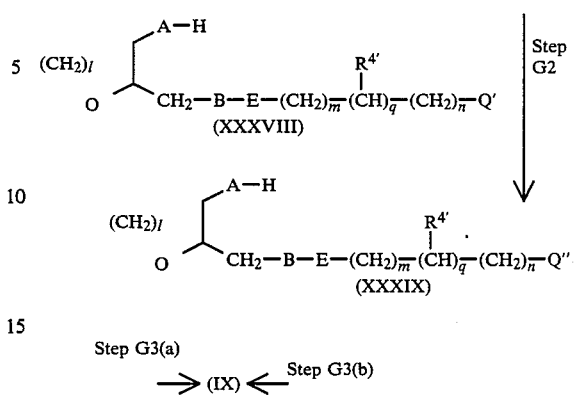

(XXXIII)

(XXXIV)

In the above formulae:

A, B, l, m, n, q, R$^{1x}$, R$^{4'}$, Q', Q'' and Y'' are as defined above.

These reactions are the same as the reactions involved in the corresponding Steps of Method E, except that, in this case, the group of formula (III) is at the β position to the oxygen atom of the cyclic ether. Each of these Steps may, of course, be carried out in precisely the same way as the corresponding Step of Method E, employing the same reagents and reaction conditions.

Method G

This Method provides an alternative way of preparing compounds of formula (IX), as defined in Method A, and is illustrated by the following reaction scheme:

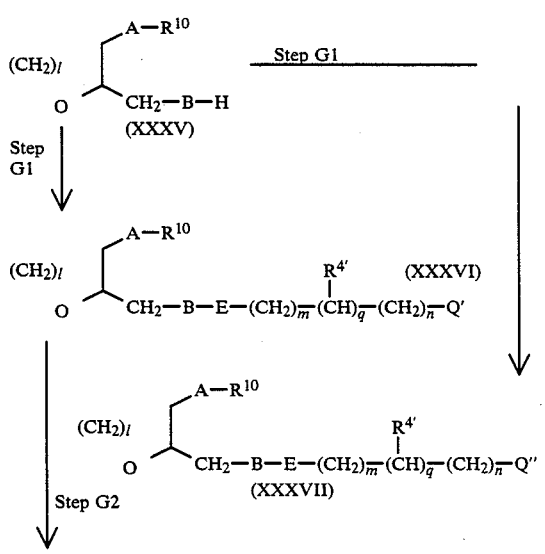

In the above formulae:

A, B, E, l, m, n, q, R¹⁰, R$^{4'}$, Q' and Q'' are as defined above.

Step G1

In this Step, a compound of formula (XXXV) having a protected hydroxy or mercapto group at position 3 and a free hydroxy or mercapto group on the methyl group at position 2 is converted to a compound of formula (XXXVI) and/or a compound of formula (XXXVII) by a sequence of reactions similar to those described in Steps A1–A5, C1–C5, E1 and E2, or any appropriate combination thereof.

Step G2

In this Step, the hydroxy- or mercapto-protecting group R¹⁰ is removed by a reaction similar to those described in Step A3 of Method A, and which may be carried out using the same reagents and reaction conditions.

Step G3

In this Step, a compound of formula (IX) is prepared by either:

(a) in the case of the compound of formula (XXXVIII), converting a group of formula —OR¹¹ represented by Q' to a group Y, by the method described in Step A3, and, before or after this reaction, subjecting the compound to an alkylation, acylation carbamoylation reaction similar to that described in the second part of Step A5, using the same reagents and reaction conditions, or (b) in the case of the compound of formula (XXXIX), only subjecting the compound to an alkylation, acylation carbamoylation reaction similar to that described in the second part of Step A5, using the same reagents and reaction conditions.

Method H

This Method provides an alternative way of preparing compounds of formula (XV), as defined in Method B, and is illustrated by the following reaction scheme:

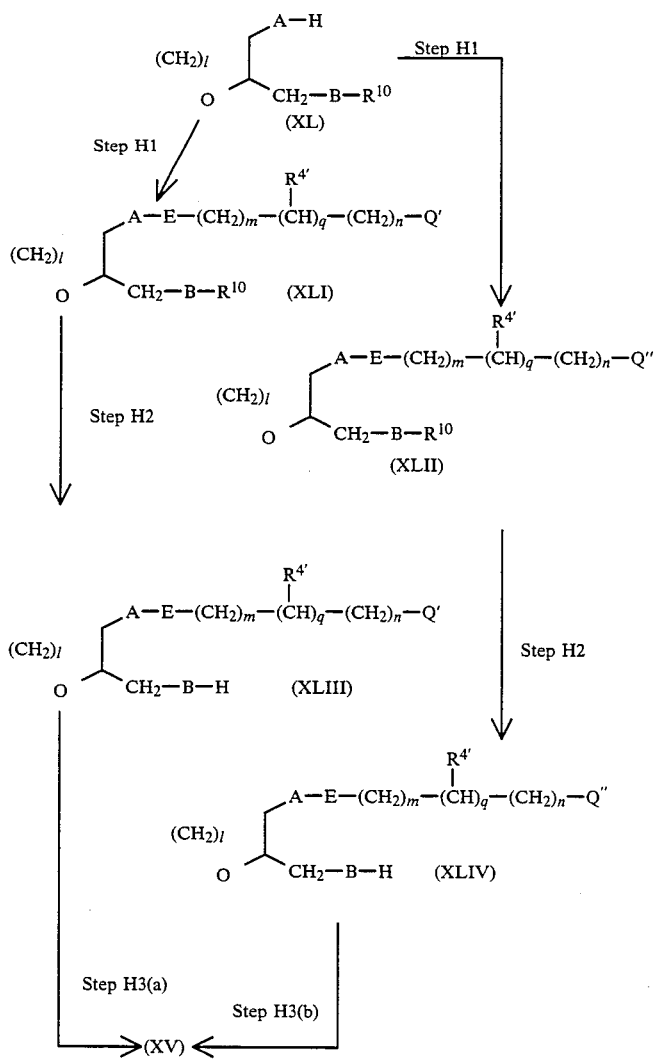

In the above formulae:

A, B, E, l, m, n, q, $R^{10}$, $R^{4'}$, Q' and Q" are as defined above.

These reactions are the same as the reactions involved in the corresponding Steps of Method G, except that, in this case, the group of formula (III) is at the β position to the oxygen atom of the cyclic ether. Each of these Steps may, of course, be carried out in precisely the same way as the corresponding Step of Method G, employing the same reagents and reaction conditions.

Method I

This Method provides an alternative method of preparing compounds of the invention having a group of formula (III) on the methyl group at the 2-position, as illustrated in the following reaction scheme:

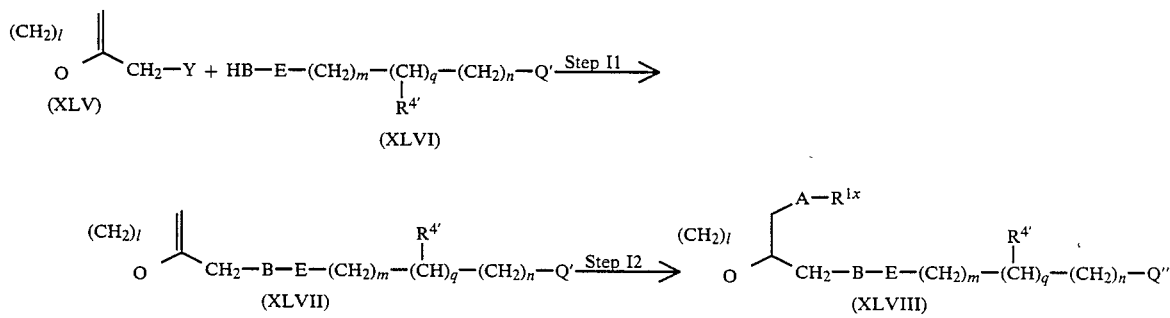

In the above formulae:

A, B, E, l, m, n, q, $R^{1x}$, $R^{4'}$, Y, Q' and Q" are as defined above.

Step I1

In this Step, a compound of formula (XLV) is reacted with a hydroxy or mercapto compound of formula (XLVI) to give a compound of formula (XLVII). This is an alkylation reaction similar to that described in Step A1 and may be carried out using the same reagents and reaction conditions.

Step I2

In this Step, a compound of formula (XLVIII) is prepared from the compound of formula (XLVII) by following essentially the same procedure as described in Japanese Patent Application Kokai No. 267592/86, and then the second half of Step A5.

Method J

This is a process for preparing a compound of the invention where a group of formula (III) is on the methyl group at the 2-position and E represents a direct bond, as illustrated by the following reaction scheme:

$$(CH_2)_l \underset{O}{\overset{A-R^{10}}{\diagdown}} CH_2-B-H \quad (XXXV) \xrightarrow{\text{Step J1}}$$

$$(CH_2)_l \underset{O}{\overset{A-R^{10}}{\diagdown}} CH_2-B-CH_2-CH=CH_2 \quad (XLIX) \xrightarrow{\text{Step J2}}$$

$$(CH_2)_l \underset{O}{\overset{A-R^{10}}{\diagdown}} CH_2-B-CH_2-CH\underset{O}{\overset{}{\diagdown}} CH_2 \quad (L)$$

Step J3 (from XXXV)

$$\xrightarrow{\text{Step J4}} (CH_2)_l \underset{O}{\overset{A-R^{1x}}{\diagdown}} CH_2-B-CH_2-(CH)_q-(CH_2)_n-Q'' \quad \overset{R^{4'}}{|} \quad (LI)$$

In the above formulae:

A, B, l, n, q, $R^{1x}$, $R^{4'}$, $R^{10}$ and Q" are as defined above.

Step J1

In this Step, a compound of formula (XLIX) is prepared by reacting a compound of formula (XXXV) with an active allyl compound, preferably an allyl halide (such as allyl chloride, allyl bromide or allyl iodide) in a solvent and in the presence of a base.

The nature of the solvent employed is not critical, provided that it does not interfere with the reaction. Examples of suitable solvents include: ethers, such as diethyl ether, tetrahydrofuran, or dioxane; aromatic hydrocarbons, such as benzene or toluene; and amides, such as dimethylformamide or dimethylacetamide; of these the amides are preferred.

There is also no particular restriction on the nature of the base to be employed, provided that it does not affect other parts of the compounds involved in the reaction. The base functions as an acid-binding agent and any base capable of fulfilling this function may be employed in the present invention, for example: alkali metal hydrides, such as sodium hydride or potassium hydride; alkali metal hydroxides, such as sodium hydroxide or potassium hydroxide; and organic bases, particularly amines, such as triethylamine, 1,5-diazabicyclo[5.4.-0]undec-5-ene, pyridine, 2,6-lutidine, dimethylaniline or 4-(N,N-dimethylamino)pyridine; of these, the alkali metal hydrides are preferred.

The reaction will take place over a wide range of temperatures and the precise temperature chosen is not particularly critical. We generally find it convenient to conduct the reaction at a temperature from 0° C. to 100° C. The time required for the reaction may vary widely, depending on many factors, notably the reaction temperature and the nature of the starting materials, but a period of from 1 hour to 3 days, more preferably from 1 to 24 hours, will normally suffice.

Step J2

In this Step, an epoxide compound of formula (L) is prepared by oxidation of the double bond in the compound of formula (XLIX) to convert it to an epoxide group.

The reaction is preferably effected in the presence of a solvent, the nature of which is not critical, provided that it does not interfere with the reaction. Examples of suitable solvents include: halogenated hydrocarbons, particularly halogenated aliphatic hydrocarbons, such as chloroform or methylene chloride; and ethers, such as diethyl ether or tetrahydrofuran.

There is no particular limitation on the nature of the oxidising agent used and any such agent conventionally used for this type of reaction may equally be used here. Preferred oxidising agents include: organic peroxides, such as peracetic acid, perbenzoic acid, benzoyl peroxide and m-chloroperbenzoic acid.

The reaction will take place over a wide range of temperatures and the precise temperature chosen is not particularly critical. We generally find it convenient to conduct the reaction at a temperature from −20° C. to +80° C. The time required for the reaction may vary widely, depending on many factors, notably the reaction temperature and the nature of the starting materials, but a period of from 1 hour to 24 hours will normally suffice.

Step J3

In this Step, a compound of formula (L) is prepared directly from a compound of formula (XXXV) by reaction with an epihalohydrin (e.g. an epichlorohydrin, epibromohydrin or epiiodohydrin). The reaction will take place under the conditions described in Step J1.

Step J4

In this Step, the epoxide compound of formula (L) is reacted with a compound of formula M-$(CH_2)_{(n-1)}$-Q' (in which: Q' and n are as defined above; and M represents a metal atom or a multivalent metal atom in association with a suitable anion, for example, an alkali metal atom, such as lithium, sodium or potassium, or a halogenated metal atom, such as a halogenated magnesium atom or a halogenated zinc atom), which can be prepared by conventional means, after which it may be subjected to the reactions described in the latter half of Step A5 and Step A3.

The reaction with the compound of formula M-$(CH_2)_{(n-1)}$-Q' is preferably effected in the presence of a solvent, the nature of which is not critical, provided that it does not interfere with the reaction. Examples of suitable solvents include: aromatic hydrocarbons, such as toluene or benzene; and ethers, such as diethyl ether or tetrahydrofuran; of these, the ethers are preferred.

The reaction will take place over a wide range of temperatures and the precise temperature chosen is not particularly critical. We generally find it convenient to conduct the reaction at a temperature from $-78°$ C. to $+65°$ C. The time required for the reaction may vary widely, depending on many factors, notably the reaction temperature and the nature of the starting materials, but a period of from 15 minutes to 24 hours will normally suffice.

Method K

In this Method, a compound of formula (I) of this invention is prepared by reacting a compound of formula (IX), (XV), (XVIII), (XXI), (XXVI), (XXVII), (XXXII), (XXXIV), (XLVIII) or (LI), which may have been prepared as described above, when Q" represents a group having the formula Y (in which Y is as defined above), with an amine compound of formula (LII) or $Q^1$, and then, if desired, deprotecting the protecting group of $R^5$ and/or $R^6$ and/or deprotecting the protecting group in the group $R^{4'}$, for example as illustrated by the following reaction:

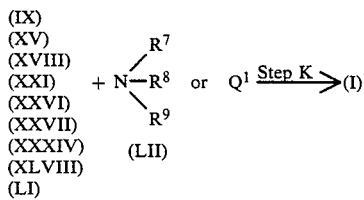

In the above formulae, $R^7$, $R^8$ and $R^9$ are as defined above and $Q^1$ represents a heterocyclic compound corresponding to the definition of Q.

The reaction is preferably effected in the presence of a solvent. There is no particular restriction on the nature of the solvent to be employed, provided that it does not interfere with the reaction and that it can dissolve the starting materials at least to some extent. Examples of preferred solvents include: aromatic hydrocarbons, such as benzene, toluene or xylene; halogenated hydrocarbons, particularly halogenated aliphatic hydrocarbons, such as methylene chloride or chloroform; lower alcohols, such as methanol, ethanol or isopropanol; amides, such as dimethylformamide; ethers, such as diethyl ether, tetrahydrofuran or dioxane; acetonitrile; water; or a mixture of any 2 or more, e.g. 2 to 3, of these solvents, such as a mixture of chloroform, dimethylformamide and isopropanol, e.g. in a volume ratio of about 3:5:5. Of these, a mixture of chloroform, dimethylformamide and isopropanol or an aromatic hydrocarbon are preferred.

The reaction will take place over a wide range of temperatures and the precise temperature chosen is not particularly critical. We generally find it convenient to conduct the reaction at a temperature from 20° C. to 80° C. The time required for the reaction may vary widely, depending on many factors, notably the reaction temperature and the nature of the starting materials and base employed, but a period of from 1 to 48 hours will normally suffice. When gaseous amines are employed, the reaction is preferably carried out in a nitrogen atmosphere and in a sealed reactor (e.g. a sealed tube).

The protecting group or groups may then be removed. Although the nature of the deprotecting reaction will vary depending on the nature of the protected group, it may be performed by known methods as shown below.

When the carboxy protecting group is a lower alkyl group, the protecting group can be removed by treatment with a base. The conditions employed in this reaction are similar to those described when the hydroxy-protecting group is a lower aliphatic acyl group or an aromatic acyl group.

When the carboxy protecting group is an aralkyl group or a halogenated lower alkyl group, the protecting group can be removed by contact with a reducing agent. Preferred examples of the reducing agent include: zinc and acetic acid when the carboxy-protecting group is a halogenated lower alkyl; catalytic reduction using palladium on activated carbon or platinum when the carboxy-protecting group is an aralkyl group; or an alkali metal sulfide such as potassium sulfide or sodium sulfide. The reaction may be carried out in a solvent and there is no particular limitation on the nature of the solvent, provided that it does not participate in the reaction. Preferred examples of such solvents include: alcohols such as methanol or ethanol; ethers such as tetrahydrofuran or dioxane; fatty acids such as acetic acid; and mixtures of one or more of the above organic solvent and water. The reaction is usually carried out at a temperature between 0° C. to room temperature. The time required for the reaction may vary depending on the nature of the starting materials and the reducing agents, nut the reaction is usually carried out for a period of from 5 minutes to 12 hours.

When the carboxy-protecting group is an alkoxymethyl group, the protecting group can be removed by treatment with an acid. Preferred acids include hydrochloric acid or acetic acid-sulfuric acid. There is no particular limitation on the nature of the solvent, provided that it does not interfere with the reaction. Preferred examples of such solvents include: alcohols such as methanol or ethanol; ethers such as tetrahydrofuran or dioxane; and mixtures of any one or more of the above organic solvents and water. The reaction is usually carried out at a temperature in the range of from 0° C. to 50° C. The time required for the reaction may vary depending on the nature of the starting materials and the acid, but the reaction is usually carried out for a period of from 10 minutes to 18 hours.

After completion of the reaction, the desired compound may be recovered from the reaction mixture by conventional means. For example, after insoluble materials have been filtered off. The solvent is distilled off and the residue is purified by such conventional purification methods as recrystallization, preparative thin layer chromatography or column chromatography to give a purified product.

When the imino-protecting group is a lower aliphatic or aromatic acyl group or an alkoxycarbonyl group, the protecting group can be removed by treatment with a base. The reaction conditions are similar to those employed when the hydroxy-protecting group is a lower aliphatic acyl group or an aromatic acyl group.

When the imino-protecting group is an alkenyloxycarbonyl group, the protecting group can be removed by treatment with a base in a similar manner to that described when the hydroxy-protecting group is a lower aliphatic acyl group or an aromatic acyl group.

When the imino-protecting group is an aryloxycarbonyl group, a deprotecting reaction can be simply carried out by using palladium and triphenyl phosphine or nickel tetracarbonyl and few side reactions occur.

The deprotection of the imino-protecting group described above may simultaneously remove a carboxy-protecting group.

After completion of the reaction, the desired compound can be recovered from the reaction mixture by using conventional methods. For example, a purified product can be obtained by such conventional purification methods as recrystallization, preparative thin layer chromatography or column chromatography and the like.

The deprotection of the carboxy-protecting group and the imino-protecting group can be carried out in any desired order.

If desired, the compounds at any appropriate stage may be protected, for example by esterification, in particular by a protecting group capable of being hydrolysed in vivo. This reaction can be performed by using well known methods in this art.

For example, ester compounds protected with a carboxy-protecting group which can be hydrolyzed in vivo can be prepared by reacting the carboxy group with: an aliphatic acyloxymethyl halide, such as acetoxymethyl chloride, propionyloxymethyl bromide or pivaloyloxymethyl chloride; a lower alkoxycarbonyloxyethyl halide, such as 1-methoxycarbonyloxyethyl chloride or 1-ethoxycarbonyloxyethyl iodide; a phthalidyl halide or a (2-oxo-5-methyl-1,3-dioxolen-4-yl)methyl halide, e.g. at from 0° C. to 50° C. There is no particular limitation on the nature of the solvent employed, provided that it does not interfere with the reaction and a preferred solvent is a polar solvent such as dimethylformaimide. The reaction temperature and time vary depending upon the nature of the starting materials, the solvents and the reagents. The reaction is preferably carried out within a temperature range of from 0° C. to 100° C. over a period of from 30 minutes to 10 hours.

After completion of the reaction, the desired compound may be recovered from the reaction mixture by conventional means. For example, one suitable recovery technique comprises: filtering off any insoluble material precipitated from the reaction mixture; and removing the solvent, e.g. by distillation, if necessary under reduced pressure, to give the desired compound. If necessary, this compound may be further purified by such conventional techniques as recrystallisation or the various chromatography techniques, e.g. preparative thin layer chromatography or column chromatography.

When Q' or Q" represents any one of the heterocyclic groups defined for Q, each of the compounds of formula (VIII), (IX), (XIV), (XV), (XVIII), (XXI), (XXV), (XXVI), (XXVII), (XXIX), (XXXI), (XXXII), (XXXIII), (XXXIV), (XLVIII) and (LI) is a compound of the present invention. However, if desired, the protecting groups can be removed and, further if desired, the deprotected groups may be protected again by protecting groups capable of being hydrolysed in vivo in a similar manner to that described in Step K, to prepare the corresponding compounds of formula (I).

PREPARATION OF STARTING MATERIALS

Certain of the starting materials used in the preparation of the compounds of the invention are novel. These may be prepared by methods well known per se, for example as follows:

Method L

In this method are prepared compounds of formulae (V), (X), (XVI), (XVII), (XXXV) and (XL) from the corresponding known compound of formula (LIII), i.e. 3,4-dihydro-2H-pyran, dihydrofuran or 6,7-dihydrooxepine, as shown in the following reaction schemes:

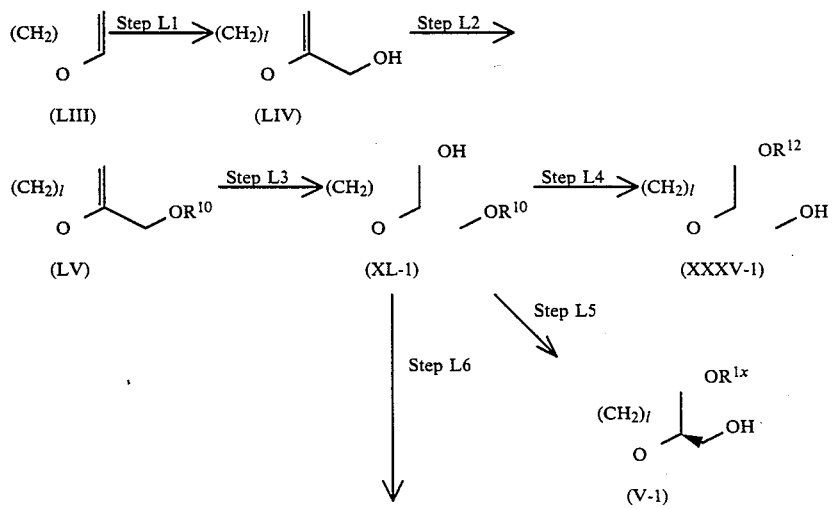

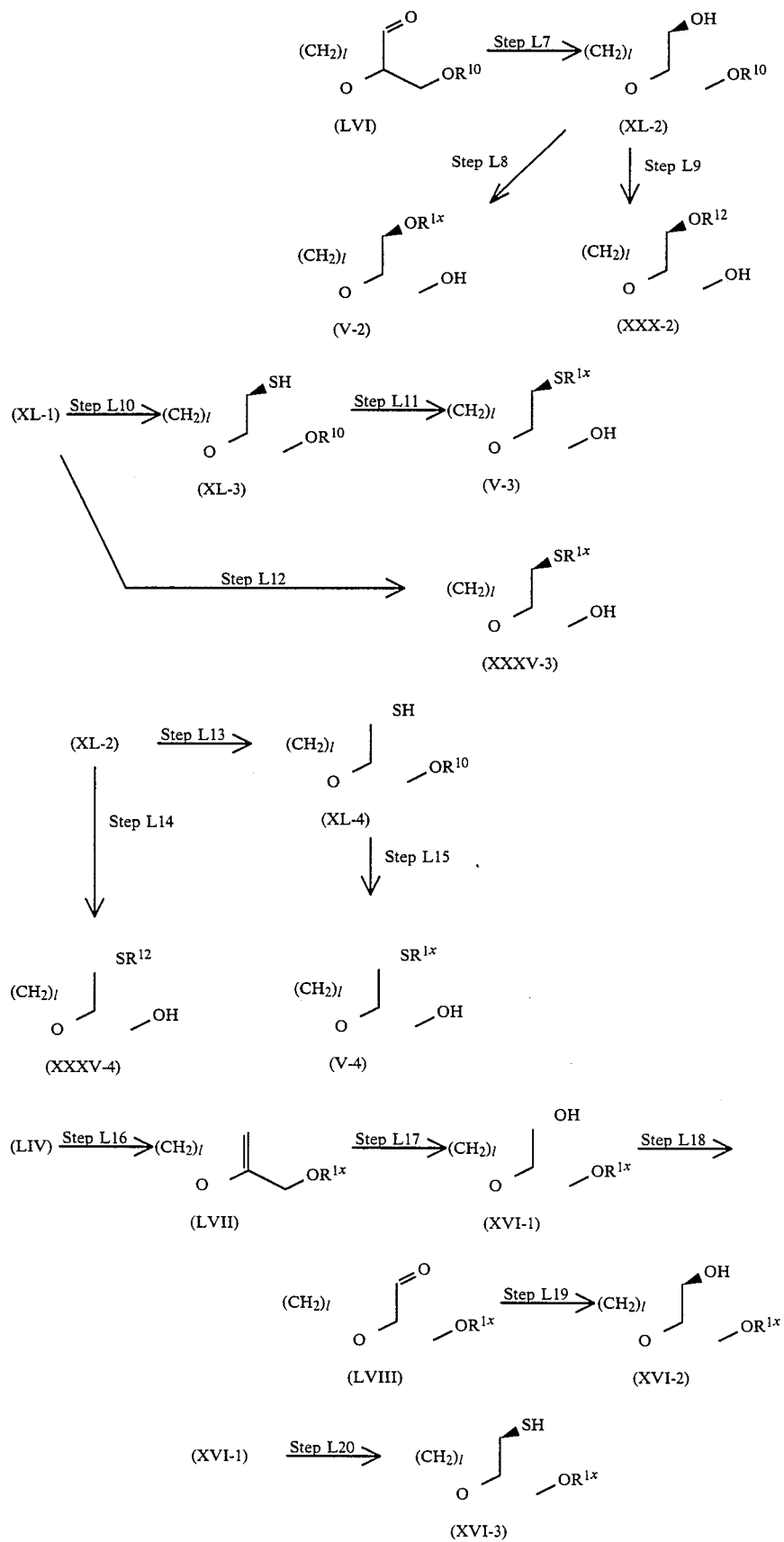

-continued
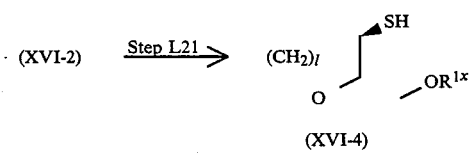
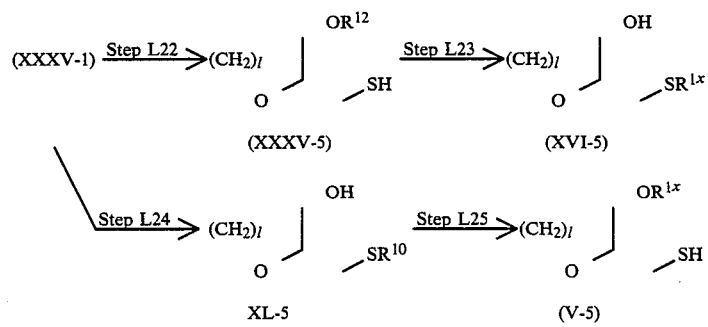
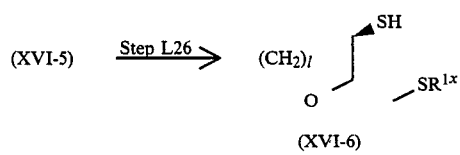
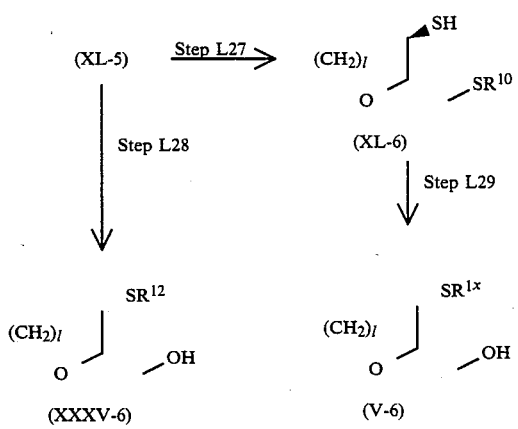
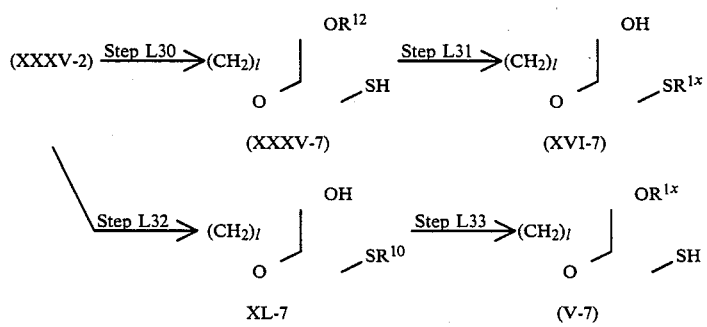
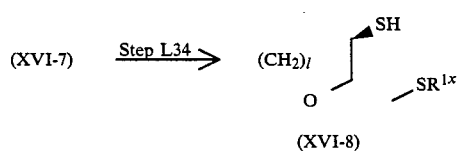

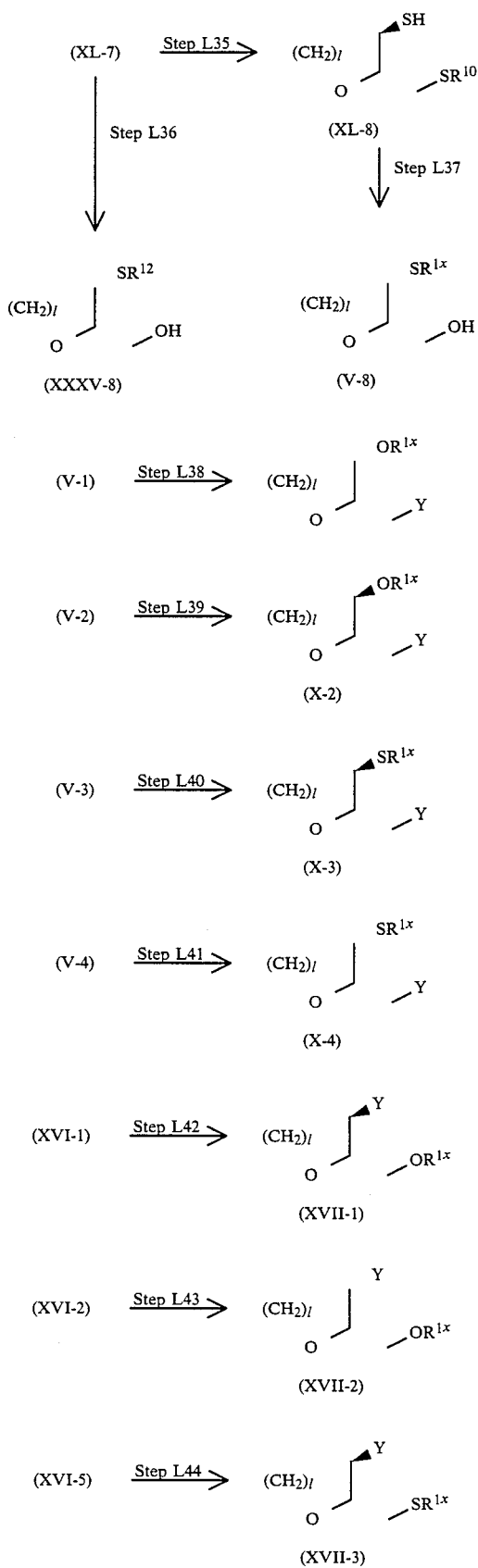

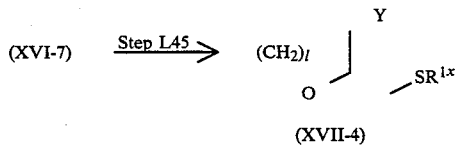

In the above formulae:
l, $R^{1x}$, $R^{10}$ and Y are as defined above; and
$R^{12}$ represents a hydroxy- or mercapto-protecting group, which may be selected from those groups defined above in relation to $R^{10}$, but (since it appears in the same compounds as $R^{10}$) should be removable independently of $R^{10}$.

Since many of the reactions involved in the above reaction schemes are repeated several times, the reactions may be summarised as follows:

Reaction 1:
In this reaction a compound of formula (LIV) is prepared by hydroxymethylation of a compound of formula (LIII). This reaction may be conducted according to the method described by A. Lebouc et al. [Synthesis, 610 (1979)].

Reaction 2:
In this reaction a compound of formula (LV) is prepared by protecting the hydroxy group of the compound of formula (LIV) with a protecting group $R^{10}$, which may be as described above. This reaction may be conducted by conventional methods for protecting a hydroxy group. When the substrate contains a mercapto group instead of a hydroxy group, for example, the mercapto group of a compound of formula (XL-3), this may be protected with a mercapto-protecting group as described above.

Reaction 3:
In this reaction a racemic compound of formula (XL-1) having trans hydroxy groups is prepared by hydroboration of the double bond of a compound of formula (LV), preferably using a borane as the hydroborating agent. The reaction can be carried out asymmetrically and an optically active compound is obtained by using for example, monoisopinocamphenylborane according to Brown's method [J. Org. Chem., 47, 5074 (1982)].

Reaction 4:
This reaction consists of alkylation, acylation or carbamation following the procedure described in the second part of Step A5. A mercapto group of, for example, a compound of formula (XL-3) can be similarly converted instead of the hydroxy group.

Reaction 5:
This reaction consists of deprotecting a protected hydroxy or mercapto group and may be carried out in a similar manner to that described in Step A3.

Reaction 6:
In this reaction a compound of formula (LVI) is prepared by oxidation of a compound of formula (XL-1) with Jones' reagent using chromic acid or pyridinium chlorochromate to convert a hydroxy group to a carbonyl group.

Reaction 7:
This reaction consists in the formation of a pair of hydroxy groups in a cis relationship by stereo-selective reduction of a carbonyl group of a compound of formula (LVI) with L-selectride to give a compound of formula (XL-2).

Reaction 8:
This reaction is for preparing an ester of a compound of formula (XL-3) by acylation of a hydroxy group of a compound of formula (XL-1) following a procedure similar to that described in Step A3, for example, by methanesulfonylation, toluenesulfonylation, trifluoromethanesulfonylation or trifluoroacetylation followed by converting the resulting acyloxy group to a protected thiol group having a sterically inverted configuration using for, example, thioacetic acid.

Reaction 9:
This reaction consists in the preparation of a compound of formula (XXXV-1) by protecting the free hydroxy group of a compound of formula (XL-1) with a protecting group, preferably a tetrahydropyranyl group, differing from the one described in Reaction 1.

Reaction 10:
This reaction consists in the preparation of a compound of formula (X-1) by converting the hydroxy group of a compound of formula (V-1) to a group Y following a procedure similar to that described in Step A3.

The Steps of the above reaction schemes L employing the reactions defined above are tabulated in the following Table 11.

TABLE 11

| Step | Reaction | Step | Reaction | Step | Reaction |
|---|---|---|---|---|---|
| L1 | 1 | L16 | 4 | L31 | 4, 5 |
| L2 | 2 | L17 | 3 | L32 | 8, 5 |
| L3 | 3 | L18 | 6 | L33 | 4, 5 |
| L4 | 9, 5 | L19 | 7 | L34 | 8, 5 |
| L5 | 4, 5 | L20 | 8, 5 | L35 | 8, 5 |
| L6 | 6 | L21 | 8, 5 | L36 | 8, 5 |
| L7 | 7 | L22 | 8, 5 | L37 | 4, 5 |
| L8 | 4, 5 | L23 | 4, 5 | L38 | 10 |
| L9 | 9, 5 | L24 | 8, 5 | L39 | 10 |
| L10 | 8, 5 | L25 | 4, 5 | L40 | 10 |
| L11 | 4, 5 | L26 | 8, 5 | L41 | 10 |
| L12 | 8, 5 | L27 | 4, 5 | L42 | 10 |
| L13 | 8, 5 | L28 | 8, 5 | L43 | 10 |
| L14 | 8, 5 | L29 | 4, 5 | L44 | 10 |
| L15 | 4, 5 | L30 | 8, 5 | L45 | 10 |

Method M

Optically active starting materials can be stereoselectively prepared from an optically active tartaric acid as shown in the following reaction schemes.

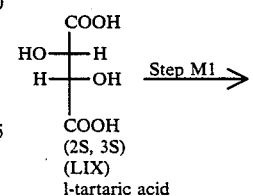

(2S, 3S)
(LIX)
l-tartaric acid

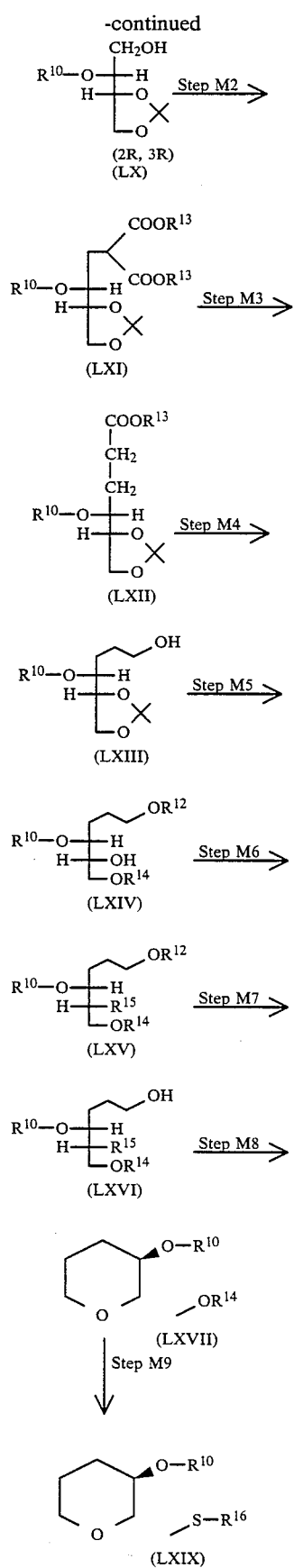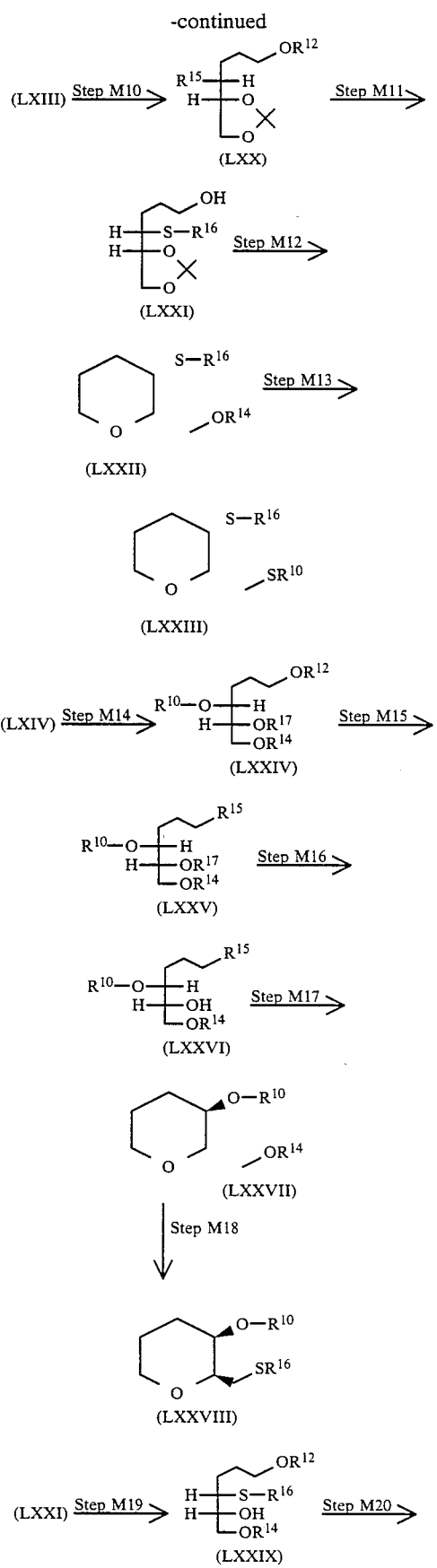

-continued

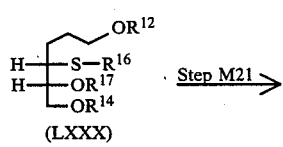
Step M21 →

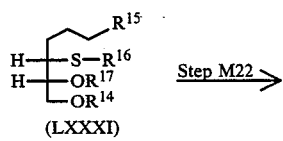
Step M22 →

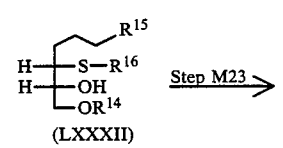
Step M23 →

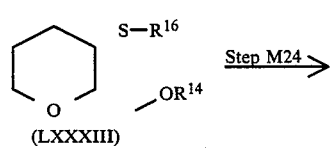
Step M24 →

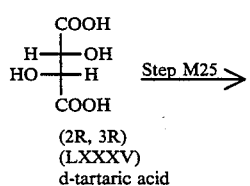

(2R, 3R)
(LXXXV)
d-tartaric acid

Step M25 →

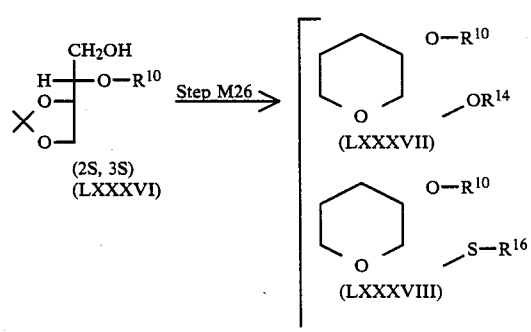
(2S, 3S)
(LXXXVI)
Step M26 →

-continued

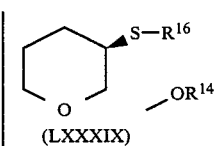
(LXXXIX)

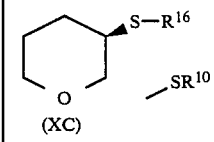
(XC)

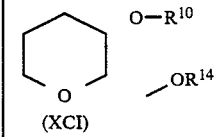
(XCI)

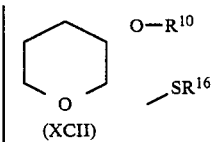
(XCII)

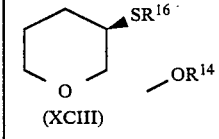
(XCIII)
or

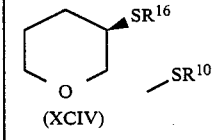
(XCIV)

(LX) Step M27 → 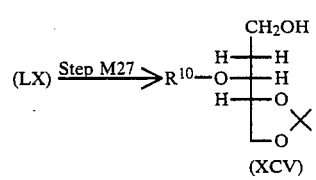
(XCV)

In the above formulae:

$R^{10}$ and $R^{12}$ are as defined above;

$R^{13}$ represents a lower (e.g. $C_1$–$C_4$, more preferably $C_1$ or $C_2$) alkyl group;

$R^{14}$, $R^{16}$ and $R^{17}$ represents hydroxy- or mercapto-protecting groups, like those represented by $R^{10}$ and $R^{12}$, and may be selected from the protecting groups exemplified above for $R^{10}$ and $R^{12}$; preferably, $R^{10}$, $R^{12}$, $R^{14}$, $R^{16}$ and $R^{17}$ are so selected that they can be selectively de-protected, when two or more among them are used in a same molecule; and $R^{15}$ represents a lower alkylsulfonyloxy group or an arylsulfonyloxy group similar to those defined above for Y.

Preferably, $R^{10}$ represents a benzyl group; $R^{12}$ represents a silyl group; $R^{14}$ represents a di- or triarylmethyl group; $R^{16}$ represents a lower aliphatic acyl group; and $R^{17}$ represents a tetrahydropyranyl group.

The starting material is a compound of formula (LIX), which is (2S, 3S) i.e. l-tartaric acid, which is reacted as described by Ohno et al. [Ohno et al., Tetrahedron Lett., 23, 3507 (1982)] in Step M1, to give a (2R, 3R) compound of formula (LX).

In Step M2, a compound of formula (LXI) is prepared by the acylation of the primary hydroxy group of the compound of formula (LX), following a procedure similar to that described in Step A3, followed by substituting the acyloxy group with iodine and reacting it with a di(lower alkyl) malonate.

A compound of formula (LXII) having two more carbon atoms than does the compound of formula (LX) can obtained by decarboxylation of the compound of formula (LXI) for example, by heating it in an aqueous dimethyl sulfoxide solution of sodium chloride (Step M3).

The alcoholic compound (LXIII) can be prepared by reducing the compound of formula (LXII) using a reducing agent such as lithium aluminum hydride in a suitable solvent, e.g. an ether such as those exemplified elsewhere herein (Step M4). After protection of the hydroxy group of the compound with a group of formula $R^{12}$ (preferably a diphenyl-t-butylsilyl group) (Step M5) followed by deprotection of the isopropylidene group, protection of the resulting primary hydroxy group with a group of formula $R^{14}$ (preferably a triphenylmethyl group) and acylation of the resulting secondary hydroxy group in a similar manner to that described in Step A3 give rise to a compound of formula (LXV) (Step M6). An optically active compound (LXVII) can be prepared by deprotecting the hydroxy-protecting group, $R^{12}$, of the compound of formula (LXV) (Step M7) (using a fluoride anion when $R^{12}$ represents a silyl group), followed by cyclization accompanied by inversion of the steric configuration at the 2-position by treatment with a base (e.g. potassium t-butoxide in t-butanol) (Step M8).

In a similar manner to Reaction 8, the compound of formula (LXVII) can be converted to the corresponding mercapto compound (LXIX) with retention of its steric configuration (Step M9).

Alternatively, the compound of formula (LXIII) can be converted to a compound having a protected thiol group with inversion of steric configuration (Steps M10 and M11).

A compound of formula (LXXII) having optical activity can be prepared from a compound of formula (LXXI) following a similar procedure to that described in Steps M5-M8 (Step M12).

A compound of formula (LXXIII) having optical activity can then be prepared from a compound of formula (LXXII) by following a similar procedure to that described in Step M9 (Step M13).

After protection of the secondary hydroxy group of the compound of formula (LXIV) with a group of formula $R^{17}$ (Step M14) and selective deprotection of the protecting group $R^{12}$, a compound of formula (LXXV) can be prepared by acylation of the resulting hydroxy group by a similar method to that described in Step A3 (Step M15).

An optically active compound of formula (LXXVII) can be prepared with retention of steric configuration by deprotecting a hydroxy-protecting group, $R^{17}$, of a secondary hydroxy group of a compound of formula (LXXV) (Step M16) followed by carrying out a similar method to that described in Step M17). Then by following a similar procedure to that described in Step M9, a mercapto compound (LXXVIII) can be prepared (Step M18).

A compound of formula (LXXIX) can be prepared from a compound of formula (LXXI) in a similar manner to that described in Step M5 (Step M19).

A compound of formula (LXXX) can then be prepared from the compound of formula (LXXIX) in a similar manner to that described in Step M14 (Step M20).

A compound of formula (LXXXI) can be prepared from the compound of formula (LXXX) in a similar manner to that described in Step M15 (Step M21).

A compound of formula (LXXXII) can be prepared from the compound of formula (LXXXI) in a similar manner to that described in Step M16 (Step M22).

An optically active compound of formula (LXXXIII) can be prepared from the compound of formula (LXXXII) in a similar manner to that described in Step M17 (Step M23).

An optically active compound of formula (LXXXIV) can be prepared from the compound of formula (LXXXIII) in a similar manner to that described in Step M9 (Step M24).

A (2S, 3S) compound of formula (LXXXVI) can be prepared from d-tartaric acid, which has the formula (LXXXV) and has the (2R, 3R) configuration as a starting material (Step M25), in a manner similar to that described in Step M1.

Optically active compounds of formulae (LXXXVII-XCIV) can be prepared from the compound (LXXXVI) by the similar methods to those described in Steps M2-M24 (Step M26).

On the other hand, starting materials having a 5-membered ring (l=2) for preparing compounds of formula (I) in which l=2 can be prepared by synthesizing a cyano compound using a metal cyanide in place of the malonate in Step M2, followed by an alcohol compound of formula (XCV), which has one more carbon atom than the compound of formula (LX), prepared from this ester by reduction can then be converted to the corresponding optically active compounds using the methods described in Steps M5-M24.

A starting material having a 7-membered ring (l=4) for preparing a compound of formula (I) in which l=4 can be converted to the corresponding optically active compounds and may be prepared from a compound of formula (XCV) as a starting material by using the methods described in Steps M2-M24.

A starting material for use in the invention can be prepared by deprotection of either protecting group of the optically active compound prepared above, followed by alkylation, acylation or carbamation by Reaction 4, as described in Step A5.

The compounds of the present invention where one of $R^1$ and $R^2$ is a group of formula (II$f$) may be prepared as illustrated by the following reaction scheme:

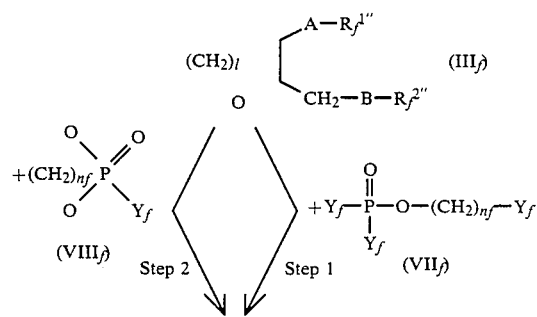

-continued

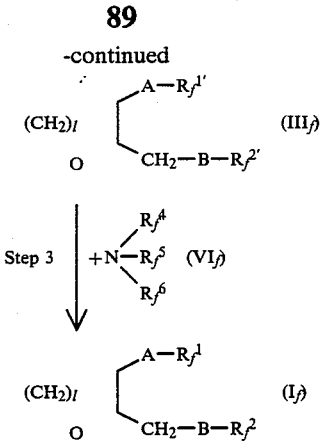

In the above formulae, $R_f^4$, $R_f^5$, $R_f^6$, $R_f^{1'}$, $R_f^{2'}$, A, B, $Y_f$, l and $n_f$ are as defined above. One of $R_f^1$ and $R_f^2$ represents a group of formula —CONH—$R_f^3$ and the other represents said group of formula (II$f$).

One of $R_f^{1''}$ and $R_f^{2''}$ represents a group of formula —CONH—$R_f^3$ (the same as $R_f^1$ or $R_f^2$) and the other represents a hydrogen atom. In the case of the compound of formula (VII$f$), the three halogen atoms represented by $Y_f$ may be the same or different. The nature of the halogen atom represented by $Y_f$ is not particularly critical, since these halogen atoms are eliminated during the reactions of Steps 1 and 2; suitable halogen atoms include the chlorine, bromine and iodine atoms.

Steps 1 and 2 of this reaction scheme are alternatives. In step 1, the hydroxy or mercapto group, —AH or —BH, of the cyclic ether of formula (III$f'$) is reacted with a haloalkyl phosphorodihalidate (preferably phosphorodichloridate) of formula (VII$f$) and the product of this reaction is then treated with water, to give the compound of formula (III$f$) in which $R_f^{1'}$ or $R_f^{2'}$ represents the aforementioned group of formula (IV$f$). Alternatively, in step 2, the compound of formula (III$f'$) is reacted with the cyclic phosphoryl halide, preferably chloride, of formula (VIII$f$) to give the compound of formula (III$f$) in which $R_f^{1'}$ or $R_f^{2'}$ represents the aforementioned group of formula (V$f$).

Both the reaction with the compound (VII$f$) (Step 1) and that with the compound (VIII$f$) (Step 2) are preferably effected in the presence of a solvent, the nature of which is not critical, provided that it does not adversely affect the reaction and that it can dissolve the reagents, at least to some degree. Preferred solvents are: halogenated hydrocarbons, preferably halogenated aliphatic hydrocarbons, such as methylene chloride, chloroform or 1,2-dichloroethane; ethers, such as diethyl ether, tetrahydrofuran or dioxane; and aromatic hydrocarbons, such as benzene or toluene.

Both reactions are preferably also effected in the presence of a base, the nature of which is not particularly critical, provided that it does not adversely affect the reagents. Suitable bases include amines, particularly triethylamine, diethylamine or pyridine.

Both reactions will take place over a wide range of temperatures, and the specific temperature chosen is not particularly critical. In the case of the reaction involving the haloalkyl phosphorodihalidate of formula (VII$f$) the preferred temperature is within the range from 0° to 120° C. In the case of the reaction involving the cyclic phosphoryl halide of formula (VIII$f$), the preferred temperature is within the range of from 20° to 120°

The time required for the reaction will vary, depending upon many factors, including the nature of the reagents, solvent and base employed, as well as the reaction temperature. However, within the reaction temperatures indicated above, both reactions will normally be complete within a period of from 2 to 24 hours.

The treatment with water in Step 1 may be effected at any convenient temperature, e.g. room temperature or the temperature employed for the reaction with the haloalkyl phosphorodihalidate (VII$f$) or any temperature in between. It is conveniently effected simply by adding water to the reaction mixture.

After completion of the reaction, the resulting compound of formula (III$f$) can be isolated from the reaction mixture by conventional means. For example, the solution containing the desired product may be concentrated by evaporating off the solvent under reduced pressure and then the residue purified by such conventional techniques as the chromatography techniques, particularly silica gel column chromatography, or recrystallization.

In Step 3 of the reaction scheme, the ω-haloalkyl phosphate of formula (III$f$) [$R_f^{1'}$ or $R_f^{2'}$ represents the aforementioned group of formula (IV$f$)] or cyclic phosphate of formula (III$f$) [$R_f^{1'}$ or $R_f^{2'}$ represents the aforementioned group of formula (V$f$)] is reacted with the amine of formula (VI$f$) in a suitable solvent to give the desired compound of formula (I$f$), which may be in the form of an inner salt.

There is no particular limitation on the nature of the solvent to be employed, provided that it has no adverse effect upon the reaction and that it can dissolve the reagents, at least to some degree. Suitable solvents include: aromatic hydrocarbons, such as benzene, toluene or xylene; halogenated hydrocarbons, preferably halogenated aliphatic hydrocarbons, such as methylene chloride or chloroform; lower alkanols, such as methanol, ethanol or isopropanol; amides, such as dimethylformamide; ethers, such as diethyl ether, tetrahydrofuran or dioxane; nitriles, such as acetonitrile; and water. A single one of these solvents or a mixture of any two or more, e.g. two or three, thereof may be employed. For example, a suitable mixture might be chloroform, dimethylformamide and isopropanol in an appropriate ratio, e.g. a volume ratio of about 3:5:5.

The temperature at which the reaction is carried out is not particularly critical, although we generally prefer to carry out the reaction at a temperature of from 20° to 80° C. The reaction is preferably effected in a nitrogen atmosphere and may be carried out in a conventional reaction vessel or preferably in a tightly sealed container (e.g. a sealed tube). The time required for the reaction will vary over a wide range, depending upon the reagents and solvent employed and the reaction temperature, but a period of from 1 hour to 6 days will normally suffice.

After completion of the reaction, the product of this reaction, which may be the compound of formula (I$f$) itself (i.e. the inner salt) or may be a salt thereof, may be isolated from the reaction mixture by conventional means. For example, a suitable recovery technique would comprise concentrating the reaction mixture by evaporating off the solvent under reduced pressure and then purifying the residue by conventional techniques, such as the various chromatography techniques and especially silica gel column chromatography.

In the case of the reaction involving the cyclic phosphate of formula (III$f$) [$R_f^{1'}$ or $R_f^{2'}$ represents the aforementioned group of formula (V$f$)] the inner salt of formula (I$f$) will normally be obtained directly. Similarly, in the case of the reaction involving the ω-haloalkyl phosphate of formula (III$f$) [R$_f^{1'}$ or R$_f^{2'}$ represents the aforementioned group of formula (IV$f$)] and where the amine of formula (VI$f$) is pyridine, the inner salt will normally be obtained directly.

However, in other cases involving the ω-haloalkyl phosphate of formula (III$f$) [R$_f^{1'}$ or R$_f^{2'}$ represents the aforementioned group of formula (IV$f$)], the product of Step 3 will normally be a salt of the compound of formula (I$f$), i.e. R$_f^1$ or R$_f^2$ will represent a group of formula (II$f'$). In this case, if the inner salt itself is desired, this may be produced by treating its salt with an ion-exchange resin (for example resin MB-3, produced by Rohm and Haas Co.) or with a silver salt (for example silver carbonate or silver acetate).

If desired, the compound of formula (I$f$) or salt thereof may be converted to a salt of any other ion by known methods.

The cyclic ether compounds of formula (III$f'$) used as starting materials in the above sequence of reactions have previously been described in copending USSN 818,876 and can be prepared from compounds of formula (IX$f$), shown in the following reaction schemes, (specifically, 3,4-dihydro-2H-pyran, dihydrofuran or 6,7-dihydrooxepine); they can be prepared stereoselectively (with respect to the two asymmetric carbon atoms identified above) by any of the reaction schemes shown below:

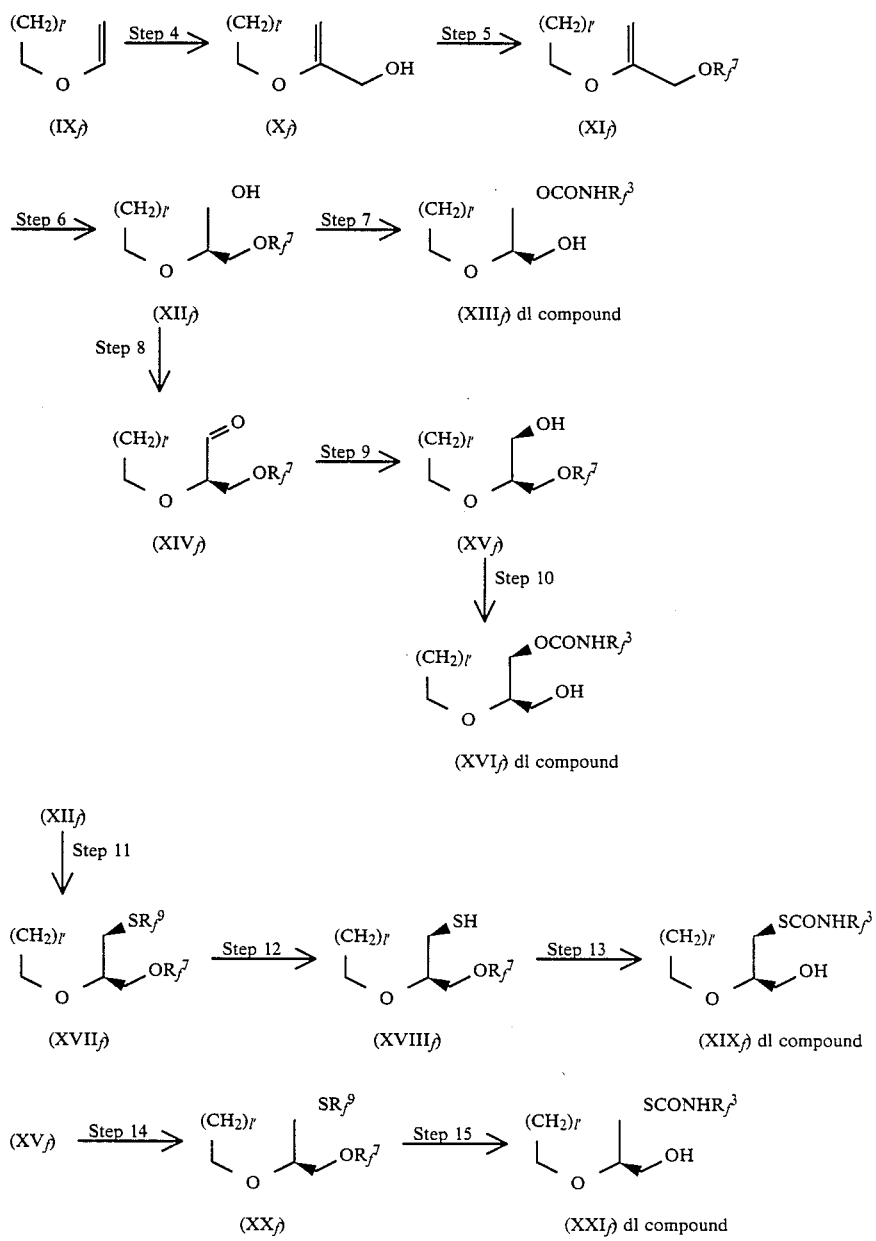

-continued
(XIIf) →Step 16→ 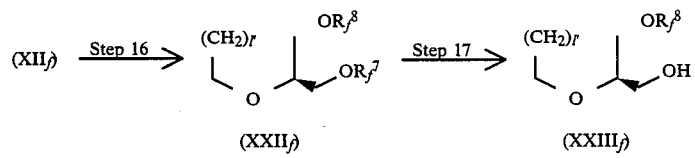 →Step 17→ 
(XXIIf)    (XXIIIf)
→Step 18→ 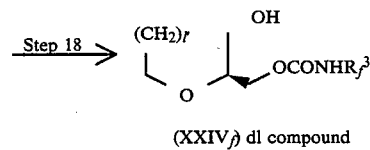
(XXIVf) dl compound
(XVf) →Step 19→ 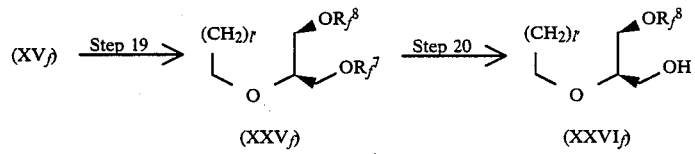 →Step 20→
(XXVf)    (XXVIf)
→Step 21→ 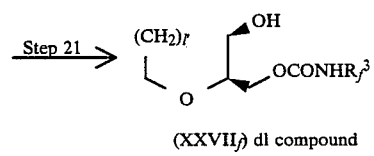
(XXVIIf) dl compound
(XVIIf) →Step 22→ 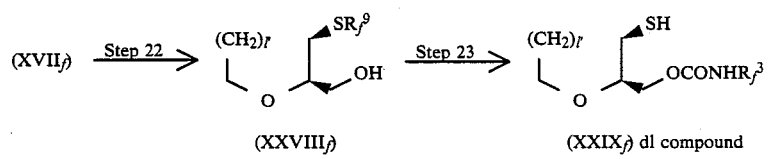 →Step 23→
(XXVIIIf)    (XXIXf) dl compound
(XXf) →Step 24→ 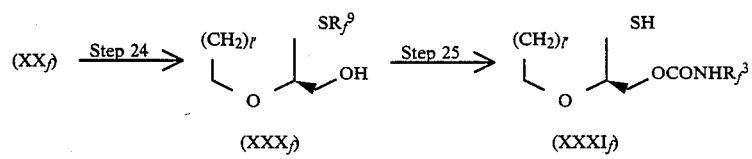 →Step 25→
(XXXf)    (XXXIf)
(XXIIIf) →Step 26→ 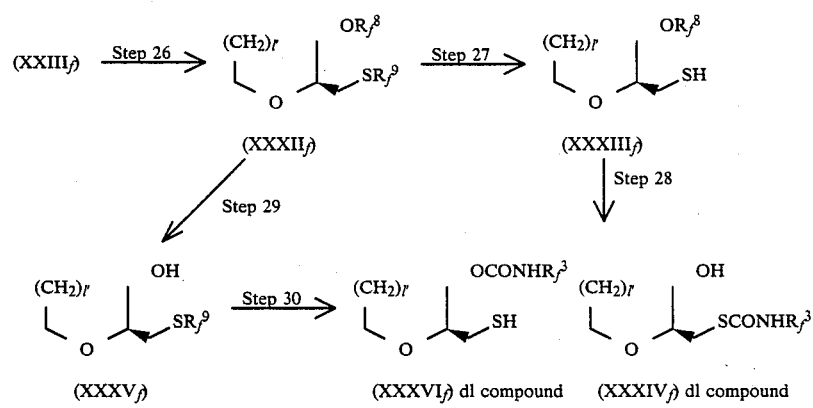 →Step 27→
(XXXIIf)    (XXXIIIf)
↓Step 29    ↓Step 28
(XXXVf) →Step 30→ (XXXVIf) dl compound    (XXXIVf) dl compound
(XXXIVf) →Step 31→ 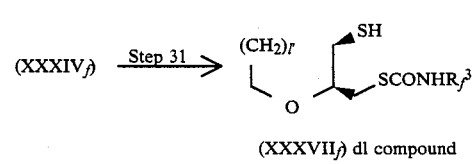
(XXXVIIf) dl compound

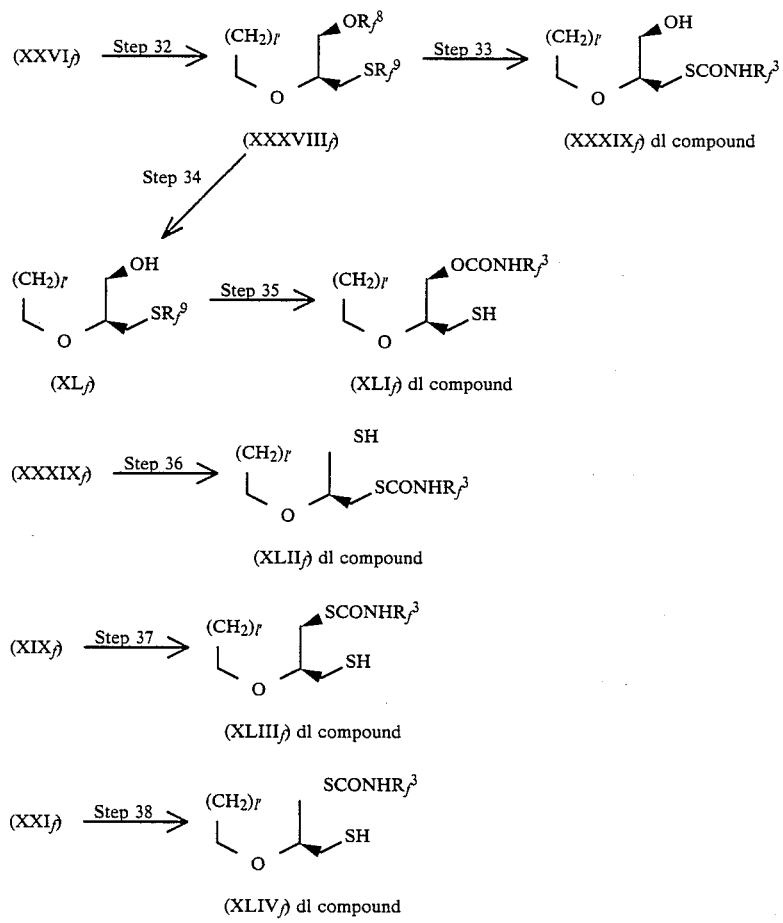

In these formulae, $R_f^3$ is as defined above and $l' = (l-1)$.

$R_f^7$ and $R_f^8$ are both hydroxy-protecting groups, whilst $R_f^9$ represents a mercapto-protecting group. Where $R_f^7$ and $R_f^8$ or $R_f^8$ and $R_f^9$ occur within the same compound, the protecting groups are preferably selected from different classes, so that one protecting group may be removed preferentially, without removing the other.

Examples of classes of hydroxy-protecting groups which may be employed include: di- and tri-arylmethyl groups, for example the diphenylmethyl (=benzhydryl), triphenylmethyl, α-naphthyldiphenylmethyl, p-methoxyphenyldiphenylmethyl and p-(p-bromophenacyloxy)phenyldiphenylmethyl groups; optionally substituted tetrahydropyranyl groups, such as the tetrahydropyran-2-yl, 3-bromotetrahydropyran-2-yl, 4-methoxytetrahydropyran-4-yl, tetrahydrothiopyran-2-yl and 4-methoxytetrahydrothiopyran-2-yl groups; trialkylsilyl groups, in which each alkyl part is preferably $C_1$–$C_4$, for example the trimethylsilyl, triethylsilyl, isopropyldimethylsilyl, t-butyldimethylsilyl, methyldiisopropylsilyl, methyldi-t-butylsilyl and triisopropylsilyl groups; and optionally substituted benzyl groups, for example the benzyl, p-methoxybenzyl, o-nitrobenzyl, p-nitrobenzyl, p-halobenzyl (e.g. p-chlorobenzyl or p-bromobenzyl) and p-cyanobenzyl groups.

Preferred examples of mercapto-protecting groups which may be represented by $R_f^9$ include the aforementioned benzyl groups and di- and tri-arylmethyl groups; also include amongst the preferred mercapto-protecting groups are lower (e.g. $C_2$–$C_5$) aliphatic acyl groups, such as the acetyl group.

We particularly prefer that $R_f^7$ should be one of the aforementioned optionally substituted benzyl groups, $R_f^8$ should be one of the aforementioned optionally substituted tetrahydropyranyl groups and $R_f^9$ should be one of the lower aliphatic acyl groups. More preferably, $R_f^7$ is a benzyl group, $R_f^8$ is a tetrahydropyran-2-yl group and $R_f^9$ is an acetyl group.

Since many of the reactions involved in the above reaction schemes are repeated, they may be summarized as follows:

Reaction 1f

In this reaction, the compound of formula (IXf) is subjected to hydroxymethylation, to prepare the compound of formula (Xf) by the method of A. Lebouc et al. [A. Lebouc et al., Synthesis, 610 (1979)].

Reaction 2f

In this reaction, the hydroxy group of the compound of formula (Xf) may be protected with any one of the appropriate protecting groups mentioned above to prepare the compound of formula (XIf). This reaction may be carried out by conventional means for introduction of protecting groups, preferably benzylation using a benzyl halide.

Reaction 3f

In this reaction, the starting material, for example the compound of formula (XIf), is subjected to a hydroboration reaction to introduce a trans-hydroxy group onto the double bond and give, for example, the compound of formula (XIIƒ). By employing an optically active borane, such as isopinocamphenylborane, in this hydroboration reaction, it is possible to prepare an optically active trans-hydroxy derivative. Otherwise, borane itself, preferably employed as a complex with an organic solvent (e.g. borane-tetrahydrofuran), may conveniently be used.

Reaction 4ƒ

In this reaction, a hydroxy group, for example that of the compound of formula (XIIƒ) or (XVƒ), or a mercapto group, for example that of the compound of formula (XVIIIƒ) or, after deprotection, (XXƒ), is carbamoylated using an alkyl isocyanate in which the alkyl group corresponds to the group $R_f^3$ to be introduced, for example heptadecyl isocyanate. The isocyanate employed may be prepared by reacting a carboxylic acid with diphenylphosphoryl azide and then heating the reaction mixture. The resulting isocyanate may then be reacted, with or without isolation, with the appropriate hydroxy or mercapto compound.

Reaction 5ƒ

In this reaction, a hydroxy-protecting group is removed, for example the hydroxy-protecting group is removed from the compound of formula (XIIƒ) after carbamoylation. The nature of the removal reaction depends upon the particular class of hydroxy-protecting group involved and the nature of such reactions is well-known to those skilled in the art. For example, if the hydroxy-protecting group is one of the aforementioned di- or tri-arylmethyl groups, it may be removed by treatment with an acid such as trifluoroacetic acid, acetic acid or hydrochloric acid. If the hydroxy-protecting group is one of the aforementioned optionally substituted benzyl groups, it may be removed by reduction, preferably catalytic reduction, using palladium-on-carbon as the catalyst. If the hydroxy-protecting group is a trialkylsilyl group, it may be removed by treatment with a compound generating fluoride anions, preferably tetrabutylammonium fluoride. If the hydroxy-protecting group is one of the aforementioned optionally substituted tetrahydropyranyl groups, it may be removed by treatment with an acid, for example acetic acid or p-toluenesulfonic acid.

As is well known, optionally substituted benzyl groups which protect a hydroxy group are usually removed by reduction as described above. However, in the presence of a mercapto or protected mercapto group in the same molecule, the reducing agents used for deprotecting these protected hydroxy groups become rather inactive, adversely affected by the mercapto or protected mercapto group. Consequently, where the compound contains both a mercapto-protecting group (preferably an acyl group, such as an acetyl group) and a hydroxy-protecting group and it is desired to remove the hydroxy-protecting group, then reaction with aluminum chloride and sodium or potassium iodide is employed if the hydroxy-protecting group is one of the optionally substituted benzyl groups, whilst the above-mentioned reaction with an acid is employed if the hydroxy-protecting group is one of the di- or tri-arylmethyl groups.

Reaction 6ƒ

In this reaction, the hydroxy group of the compound of formula (XIIƒ) is oxidized to a carbonyl group by means of Jones' reagent, using chromic acid, or pyridinium chlorochromate, to prepare the compound of formula (XIVƒ).

Reaction 7ƒ

In this reaction, the carbonyl group of the compound of formula (XIVƒ) is reduced stereoselectively, using L-selectride, to form a cis-hydroxy group and give the compound of formula (XVƒ).

Reaction 8ƒ

In this reaction, a hydroxy group, for example a hydroxy group of the compound of formula (XIIƒ), can be acylated to introduce an acyl group, for example a methanesulfonyl, p-toluenesulfonyl, trifluoromethanesulfonyl or trifluoroacetyl group, to form an ester, and then the resulting acyloxy group can be converted to a protected mercapto group whose configuration is inverted, compared to the original hydroxy group, using, for example thioacetic acid. This reaction may be employed in a number of steps in the above reaction schemes.

Reaction 9ƒ

In this reaction a free hydroxy group, of a compound already containing one protected hydroxy group, for example the free hydroxy group of the compound of formula (XIIƒ), may be protected by a different hydroxy-protecting group in order to prepare the compound of formula (XXIIƒ). In this case, the preferred protecting group is one selected from the class of optionally substituted tetrahydropyranyl groups.

Reaction 10ƒ

In this reaction, the mercapto-protecting group $R_f^9$, for example of the compound of formula (XVIIƒ), is removed to give a free mercapto group, for example as in the compound of formula (XVIIIƒ). The mercapto-protecting group, preferably acetyl group, may be removed by treatment with a base, such as methanolic sodium methoxide, aqueous ammonia, aqueous sodium hydroxide or aqueous potassium hydroxide, preferably a 10–30% w/w methanolic solution of sodium methoxide.

The following Table 33 shows the reactions which may be employed for each of the steps of the reaction schemes given above.

TABLE 33

| Step | Reaction used | Step | Reaction used | Step | Reaction used |
|---|---|---|---|---|---|
| 4 | 1ƒ | 17 | 5ƒ | 30 | 4ƒ, 10ƒ |
| 5 | 2ƒ | 18 | 4ƒ, 5ƒ | 31 | 8ƒ, 10ƒ |
| 6 | 3ƒ | 19 | 9ƒ | 32 | 8ƒ |
| 7 | 4ƒ, 5ƒ | 20 | 5ƒ | 33 | 10ƒ, 4ƒ, 5ƒ |
| 8 | 6ƒ | 21 | 4ƒ, 5ƒ | 34 | 5ƒ |
| 9 | 7ƒ | 22 | 5ƒ | 35 | 4ƒ, 10ƒ |
| 10 | 4ƒ, 5ƒ | 23 | 4ƒ, 10ƒ | 36 | 8ƒ, 10ƒ |
| 11 | 8ƒ | 24 | 5ƒ | 37 | 8ƒ, 10ƒ |
| 12 | 10ƒ | 25 | 4ƒ, 10ƒ | 38 | 8ƒ, 10ƒ |
| 13 | 4ƒ, 5ƒ | 26 | 8ƒ | | |
| 14 | 8ƒ | 27 | 10ƒ | | |
| 15 | 10ƒ, 4ƒ, 5ƒ | 28 | 4ƒ, 5ƒ | | |
| 16 | 9ƒ | 29 | 5ƒ | | |

Where it is desired to employ an optically active compound as the starting material of formula (IIIƒ'), this may be prepared, for example, in the case where l is 3 as illustrated by the following reaction scheme:

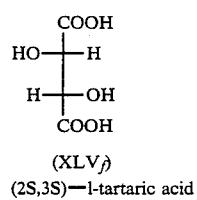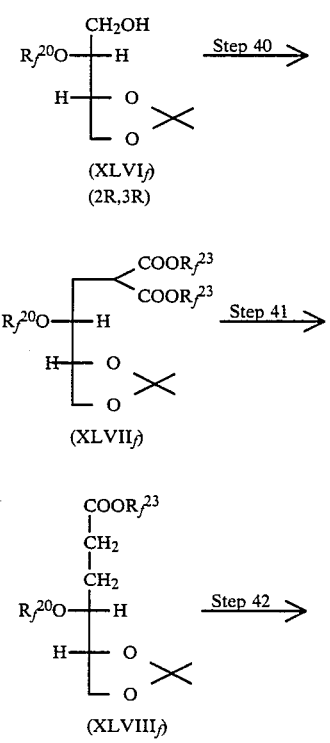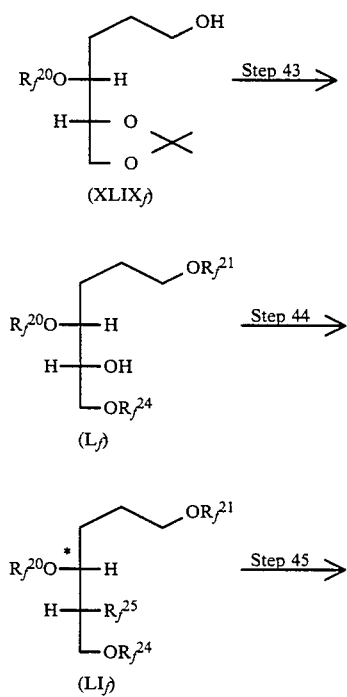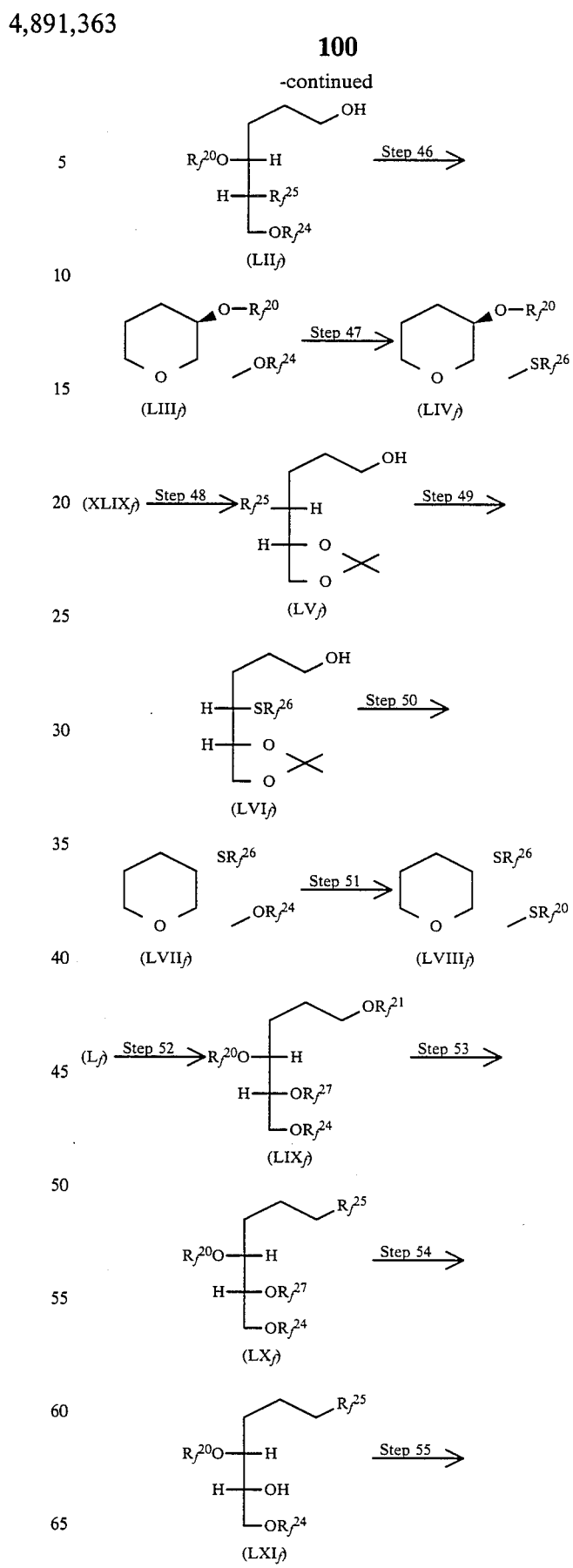

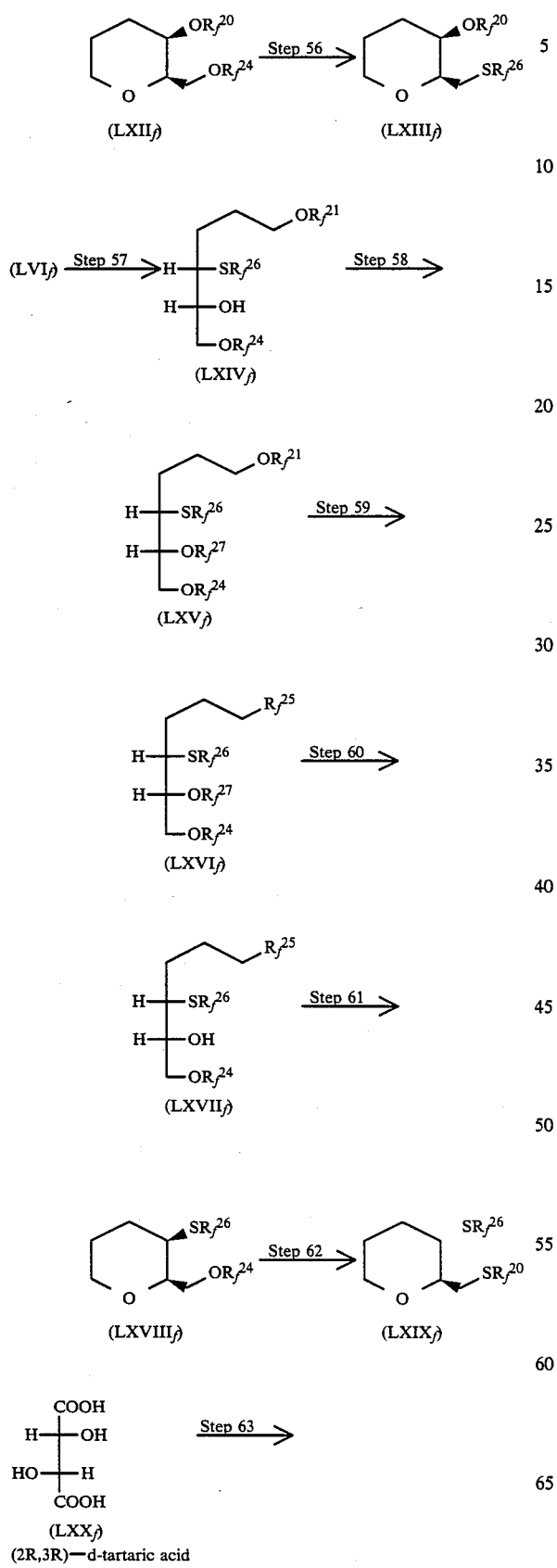

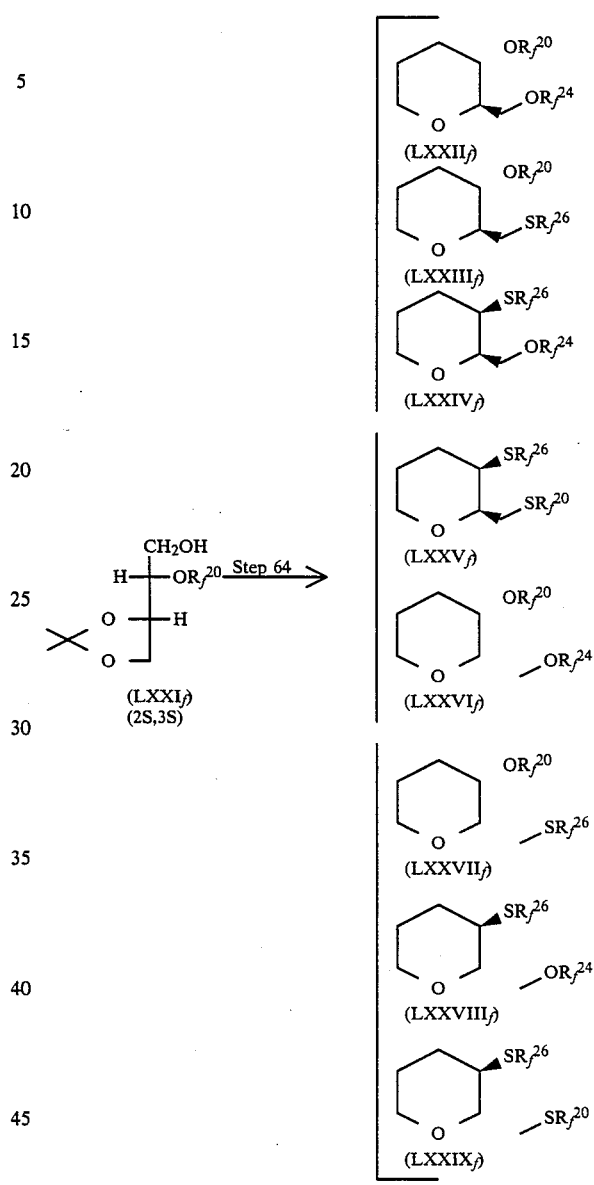

In the above formulae, $R_f^{20}$, $R_f^{21}$, $R_f^{24}$, $R_f^{26}$ and $R_f^{27}$ are the same or different and each represents a hydroxy-protecting group or mercapto-protecting group, examples of which are given above in relation to the groups defined as $R_f^7$, $R_f^8$ and $R_f^9$. Where any molecule contains two or more of the groups $R_f^{20}$, $R_f^{21}$, $R_f^{24}$, $R_f^{26}$ and $R_f^{27}$, it is generally preferred that the two or more groups should be chosen from different classes of protecting group, so that each protecting group can be removed separately without removing the other or others. $R_f^{23}$ represents a lower alkyl group, e.g. a $C_1-C_6$, preferably $C_1-C_4$, alkyl group, such as methyl, ethyl, propyl, isopropyl, butyl, isobutyl, sec-butyl, t-butyl, pentyl or hexyl group, $R_f^{25}$ represents a $C_1-C_6$ alkylsulfonyloxy group or an arylsulfonyloxy group, for example a methanesulfonyloxy, ethanesulfonyloxy, benzenesulfonyloxy, p-toluenesulfonyloxy, naphthalenesulfonyloxy or camphorsulfonyloxy group.

We particularly prefer that the protecting group represented by $R_f^{20}$ should be a benzyl or substituted benzyl group, $R_f^{21}$ should be a substituted silyl group, $R_f^{24}$ should be a di- or tri-arylmethyl group, $R_f^{26}$ should be a lower alkyl group and $R_f^{27}$ should be a tetrahydropyranyl or substituted tetrahydropyranyl group.

The starting material for these reactions can be l- or d-tartaric acid of formula (XLVf) or (LXXf) l-tartaric acid being (2S,3S) and d-tartaric acid being (2R,3R).

In Step 39 of the reaction scheme, the compound of formula (XLVIf) is prepared from l-tartaric acid (XLVf) according to the method described by Ohno et al [Tetrahedron Letters 23, 3507 (1982)].

In Step 40, the remaining primary hydroxy group of this compound of formula (XLVIf) is acylated (for example as described in relation to the first part of Reaction 8), and then the acyloxy group is replaced by an iodine atom and finally the resulting iodide is reacted with a dialkyl malonate in the presence of a base (such as sodium hydride) and a solvent (such as dimethylformamide), in order to give the compound of formula (XLVIIf).

In Step 41, this compound of formula (XLVIIf) is converted to a compound of formula (XLVIIIf) having two more carbon atoms than the original tartaric acid by decarboxylation, by heating the compound in a dimethyl sulfoxide solution of, for example, sodium chloride, in the presence of a trace of water.

In Step 42, the carboxy group of the compound of formula (XLVIIIf) is reduced to a hydroxymethyl group by reduction with a suitable reducing agent, for example lithium aluminum hydride in a solvent, for example an ether.

In Step 43, the resulting compound of formula (XLIXf) is converted to the compound of formula (Lf) by protecting the free primary hydroxy group with a protecting group $R_f^{21}$ (a diphenyl-t-butylsulfonyl group is preferred), removing the isopropylidine group and protecting the primary hydroxy groups thus generated with another hydroxy-protecting group $R_f^{24}$ (the triphenylmethyl group is preferred). In Step 44, the free secondary hydroxy group is then acylated in the same manner as described in Reaction 8 to introduce the sulfonyloxy group $R_f^{25}$.

In Step 45, the hydroxy-protecting group $R_f^{21}$ is removed to give the compound of formula (LIIf). Where $R_f^{21}$ is a substituted silyl group, its removal is preferably effected by means of a compound generating fluoride anions. In Step 46, this compound of formula (LIIf) is cyclized, with inversion at the 2-position, to give the optically active cyclic compound (LIIIf) by treating the compound of formula (LIIf) with a base, for example potassium t-butoxide in t-butanol.

If desired, the corresponding mercapto compound of formula (LIVf) can be prepared, with retention of configuration at the 2-position, by following the procedure hereinbefore described in Reaction 8f.

The compound of formula (LVf) can be prepared from the compound of formula (XLIXf) by protecting the primary hydroxy group with, for example, $R_f^{27}$, removing the protecting group $R_f^{20}$ from the secondary hydroxy group, acylating the secondary hydroxy group thus generated in the same way as described in the first step of Reaction 8f and finally removing the protecting group $R_f^{27}$ from the primary hydroxy group (Step 48). The protected thiol compound of formula (LVIf) can be prepared by reacting the resulting compound (LVf) in the same manner as described in the second step of Reaction 8f. The optically active compound of formula (LVIIf) or its mercapto analog (LVIIIf) can then be prepared by following the procedures described in Steps 43, 44, 45 and 46 (together Step 50) and, if desired, Step 47 (Step 51). The compound of formula (LVIIf) can also be prepared from a compound of formula (LVf) in which the primary hydroxy group is protected (prepared by the third reaction of Step 48) by following the procedures described in Steps 49 and 50.

As a further alternative, in Step 52, the secondary hydroxy group of the compound of formula (Lf) can be protected by a protecting group $R_f^{27}$, to give a compound (LIXf), and then the protecting group $R_f^{21}$ can be selectively removed and the resulting hydroxy group acylated as described in Reaction 8f (Step 53). The resulting compound of formula (LXf) can then be treated by Steps 54, 55 and 56, following the same procedures as described in Steps 45, 46 and 47, to give the compounds of formula (LXIIf) or (LXIIIf).

The compounds (LXVIIIf) and (LXIXf) can be prepared from the compound (LVIf) via Steps 57, 58, 59, 60, 61 and 62, involving the same reactions as described heretofore in Steps 43, 52, 53, 54, 55 and 47, respectively.

Instead of employing l-tartaric acid as the starting material, as illustrated in Steps 63 and 64, d-tartaric acid (LXXf), the (2R,3R) compound can be employed as the starting material to give the corresponding (2S,3S) compound (LXXIf) in Step 63, which corresponds to Step 39 described above, and then, in Step 64, this can be converted to any one of compounds (LXXIIf)–(LXXIXf), following the appropriate ones of Steps 40-62.

The corresponding compounds where l is 2, that is to say optically active 5-membered ring compounds, can be prepared from a compound of formula (LXXXf) and its enantiomer obtained as illustrated in Step 65 by reacting the compound of formula (XLVIf) or (LXXIf) with an alkali metal cyanide, subjecting the resulting compound to alcoholysis to yield the ester and then reducing this ester to the corresponding hydroxy compound (LXXXf) e.g.:

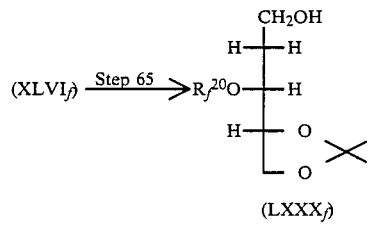

This compound of formula (LXXXf) and its enantiomer may then be subjected to any appropriate combination of Steps 43-62 and 64 to give the corresponding optically active 5-membered ring compounds.

7-Membered ring compounds, in which l is 4, can be prepared by treating the compound of formula (LXXXf) and its enantiomer by any appropriate combination of Steps 40-62 and 64.

After completion of the foregoing reactions, the resulting compounds may be separated from the reaction mixture by conventional means and may, if desired, be further purified by various conventional techniques, for example recrystallization and/or the various chromatography techniques, including column chromatography, thin layer chromatography and liquid chromatography.

The compounds of the present invention have shown excellent PAF antagonistic activity and anti-inflammatory activity, in terms of the duration of the effect and/or bioavailability. They are, accordingly, useful as a new type of anti-shock agent, anti-thrombotic agent, anti-asthmatic agent, anti-allergic agent and anti-inflammatory agent.

The compounds of the invention may be administered orally or parenterally as required and may, if desired, be formulated into appropriate pharmaceutical formulations, depending upon the desired route of administration. For example, for oral administration, the compounds may be formulated as tablets, capsules, granules, powders or syrups. For parenteral administration, they may be formulated as injectible solutions or suspensions or as suppositories. Although the preferred dose will vary, depending upon the nature of the disorder, the symptoms, age condition and body weight of the patient and the route of administration, a preferred dose for an adult human patient would normally be expected to be from 0.1 to 200 mg/kg body weight per day, and this could be administered in a single dose or in divided doses.

The invention is further illustrated by the following non-limiting Examples. Preparation of certain of the starting materials employed in these Examples is illustrated by the subsequent Preparations. The biological activities of certain of the compounds of the invention are then illustrated in the subsequent Experiments. In the Examples and Preparations, values of optical rotation were measured using the sodium D-line, i.e. all are $[\alpha]_D$.

EXAMPLE 1 dl-3-[7-(trans-3-Hexadecyloxytetrahydropyran-2-ylmethoxy)heptyl]thiazolium methanesulfonate (a) A solution of 0.51 ml of methanesulfonyl chloride dissolved in 5 ml of benzene was added dropwise to a solution of 2.067 g of dl-7-(trans-3-hexadecyloxytetrahydropyran-2-ylmethoxy)-1-heptanol (prepared as described in Preparation 55) and 1.83 ml of triethylamine dissolved in 15 ml of benzene, whilst ice-cooling. The reaction mixture was stirred at room temperature for 15 minutes, after which it was washed with water, dried over anhydrous magnesium sulfate and concentrated by evaporation under reduced pressure, to give 2.406 g of crude dl-7-(trans-3-hexadecyloxytetrahydropyran-2-ylmethoxy)heptyl methanesulfonate as a viscous oil.

(b) 1.20 g of the methanesulfonate [prepared as described in step (a) above] and 1.56 ml of thiazole were dissolved in 3 ml of toluene, and the solution was stirrd on an oil bath kept at 70° C. for 5 days. At the end of this time, the mixture was allowed to cool, the solvent was distilled off under reduced pressure, and the residue was subjected to column chromatography through 40 g of silica gel. 0.741 g of the title compound was obtained as a viscous oil from the fractions eluted with a 60:35:5 by volume mixture of methylene chloride, methanol and water.

Nuclear Magnetic Resonance Spectrum (90 MHz, $CDCl_3$) δ ppm: 0.7–2.45 (45H, multiplet); 2.77 (3H, singlet); 2.95–4.05 (10H, multiplet); 4.75 (2H, triplet, J=7.5 Hz); 8.4–8.6 (2H, multiplet); 10.91 (1H, multiplet).

EXAMPLE 2 dl-3-[7-(cis-3-Hexadecyloxytetrahydropyran-2-ylmethyoxy)heptyl]thiazolium methanesulfonate In a similar manner to that described in Example 1(a), 1.42 g of crude dl-7-(cis-3-hexadecyloxytetrahydropyran-2-ylmethoxy)heptyl methanesulfonate was obtained as a viscous oil from 1.215 g of dl-7-(cis-3-hexadecyloxytetrahydropyran-2-ylmethoxy)-1-heptanol (prepared as described in Preparation 58). 0.71 g of the resulting oily product was treated in a similar manner to that described in Example 1(b), to give 0.322 g of the title compound as a viscous oil.

Nuclear Magnetic Resonance Spectrum (90 MHz, $CDCl_3$) δ ppm: 0.75–2.30 (45H, multiplet); 2.77 (3H, singlet); 3.1–3.75 (9H, multiplet); 3.85–4.20 (1H, multiplet); 4.77 (2H, triplet, J=7.5 Hz); 8.4–8.7 (2H, multiplet); 10.97 (1H, multiplet).

Elemental analysis: Calculated for $C_{33}H_{63}NO_6S_2 \cdot H_2O$: C, 60.79%; H, 10.05%; N, 2.15%; S, 9.83%. Found: C, 60.39%; H, 9.94%; N, 2.16%; S, 9.52%.

EXAMPLE 3 dl-3-[5-(trans-3-Hexadecyloxytetrahydropyran-2-ylmethoxycarbonylamino)pentyl]triazolium bromide 1.84 ml of thiazole was added to a solution of 711 mg of dl-trans-3-hexadecyloxytetrahydropyran-2-ylmethyl N-(5-bromopentyl)carbamate (prepared as described in Preparation 47) dissolved in 2 ml of toluene, and the mixture was heated at 80° C. for 86 hours. At the end of this time, the reaction mixture was evaporated to dryness under reduced pressure, and the residue was subjected to column chromatography through 17 g of silica gel. Those fractions eluted with mixtures of methylene chloride and methanol ranging from 19:1 to 17:3 by volume were collected and then subjected to medium pressure liquid chromatography through a Lobar B column. 480 mg of the title compound were obtained as a powder from the fractions eluted with the same solvent mixtures.

Nuclear Magnetic Resonance Spectrum (90 MHz, $CD_3OD$) δ ppm: 0.7–2.4 (41H, multiplet); 2.9–4.5 (10H, multiplet); 4.62 (2H, triplet, J=7 Hz); 8.31 (1H, doublet, J=4 Hz); 8.52 (1H, doublet, J=4 Hz).

Infrared Absorption Spectrum ($CHCl_3$) $\nu_{max}$ cm$^{-1}$: 3470 (—NH) and 1710 (—O—CO—).

EXAMPLE 4 dl-3-[5-(trans-3-Heptadecylcarbamoyloxytetrahydropyran-2-ylmethoxycarbonylamino)pentyl]thiazolium bromide 400 mg of dl-trans-2-[N-(5-bromopentyl)carbamoyloxymethyl]tetrahydropyran-3-yl N-heptadecylcarbamate (prepared as described in Preparation 6) were dissolved in 1 ml of toluene, and then 0.47 ml of thiazole was added to the resulting mixture, after which the mixture was heted at 80° C. for 66 hours. The reaction mixture was then evaporated to dryness under reduced pressure, and the residue was subjected to column chromatography through 10 g of silica gel. 390 mg of the title compound, melting at 54°–56° C., were obtained as a powder from those fractions eluted with mixtures of methylene chloride and methanol ranging from 19:1 to 4:1 by volume.

Nuclear Magnetic Resonance Spectrum (270 MHz, $CD_3OD$) δ ppm: 0.90 (3H, triplet, J=7 Hz); 1.20–1.80

(37H, multiplet); 2.02 (2H, quintet, J=7 Hz); 2.10–2.30 (1H, multiplet); 3.00–3.20 (4H, multiplet); 3.30–3.50 (2H, multiplet); 3.85–3.95 (1H, multiplet); 4.05 (1H, doublet of doublets, J=11 & 6 Hz); 4.17 (1H, doublet of doublets, J=11 & 1 Hz); 4.49 (1H, ddd, J=10, 10 & 5 Hz); 4.61 (2H, triplet, J=7 Hz); 8.30 (1H, doublet, J=4 Hz); 8.50 (1H, doublet, J=4 Hz).

Elemental analysis: Calculated for $C_{33}H_{60}BrN_3O_5S \cdot 1.5H_2O$: C, 55.22%; H, 8.85%; N, 5.85%; S, 4.47%. Found: C, 55.22%; H, 8.56%; N, 5.73%; S, 4.22%.

EXAMPLE 5

3-{5-[(2S, 3R)-3-Heptadecylcarbamoyloxytetrahydropyran-2-yl)methoxycarbonylamino]pentyl}thiazolium bromide Following a procedure similar to that described in Example 4, 553.0 mg of the title compound, melting at 97.0°–99.0° C., were obtained as a white powder starting from 564.0 mg of (2S, 3R)-2-[N-(5-bromopentyl)carbamoyloxymethyl]tetrahydropyran-3-yl N-heptadecylcarbamate (prepared as described in Preparation 31) and 0.66 ml of thiazole.

$[\alpha]^{25}$ −27.3° (c=1.05, methanol).

FAB Mass Spectrum (m/e): 610 (M$^+$ − Br$^-$)

[FAB is Fast Atom Bombardment].

Elemental analysis: Calculated for $C_{33}H_{60}BrN_3O_5S \cdot 1.2H_2O$: C, 55.63%; H, 8.83%; N, 5.90%; S, 4.50%. Found: C, 55.58%; H, 8.62% N, 5.78%; S, 4.36%.

EXAMPLE 6

3-{5-[(3R, 3S)-3-Heptadecylcarbamoyloxytetrahydropyran-2-yl)methoxycarbonylamino]pentyl}thiazolium bromide Following a procedure similar to that described in Example 4, 523.8 mg of the title compound, melting at 97.0°–99.0° C., were obtained as a white powder starting from 540.0 mg of (2R, 3S)-2-[N-(5-bromopentyl)carbamoyloxymethyl]tetrahydropyran-3-yl N-heptadecylcarbamate (prepared as described in Preparation 32) and 0.63 ml of thiazole.

$[\alpha]^{25}$ +27.2° (c=1.05, methanol).

FAB Mass Spectrum (m/e): 610 (M$^+$ − Br$^-$).

Elemental analysis: Calculated for $C_{33}H_{60}BrN_3O_5S \cdot 1.5H_2O$: C, 55.22%; H, 8.85%; N, 5.85%; S, 4.47%. Found: C, 55.18%; H, 8.40%; N, 5.86%; S, 4.32%.

EXAMPLE 7 dl-3-{5-[(cis-3-Heptadecylcarbamoylthiotetrahydropyran-2-yl)methoxycarbonylamino]pentyl}thiazolium bromide 600 mg of dl-[cis-3-(N-heptadecylcarbamoylthio)tetrahydropyran-2-ylmethyl]N-(5-bromopentyl)carbamate (prepared as described in Preparation 42) were dissolved in 1 ml of toluene, and then 0.68 ml of thiazole were added to the resulting mixture. The mixture was then heated on an oil bath kept at 80° C. for 64 hours. At the end of this time, the reaction mixture was evaporated to dryness under reduced pressure, and the residue was subjected to column chromatography through 15 g of silica gel. 595 mg of the title compound were obtained as a white powder, melting at 122°–125° C., from the fractions eluted with mixtures of methylene chloride and methanol ranging from 9:1 to 4:1 by volume.

Nuclear Magnetic Resonance Spectrum (90 MHz, CD$_3$OD) δ ppm: 0.7–2.3 (43H, multiplet); 2.9–4.2 (10H, multiplet); 4.67 (2H, triplet, J=7 Hz); 8.34 (1H, doublet, J=4 Hz); 8.56 (1H, doublet, J=4 Hz).

Infrared Absorption Spectrum (KBr) $v_{max}$ cm$^{-1}$: 3320 (—NH), 1700 (—O—CO—) and 1640 (—S—CO—).

Elemental analysis: Calculated for $C_{33}H_{60}BrN_3O_4S_2 \cdot 1.5H_2O$: C, 54.01%; H, 8.65%; N, 5.73%; S, 8.74%. Found: C, 54.29%; H, 8.21%; N, 5.74%; S, 8.36%.

EXAMPLE 8 dl-3-{5-[(cis-3-Heptadecylcarbamoyloxytetrahydropyran-2-yl)methoxycarbonylamino]pentyl}thiazolium bromide Following a procedure similar to that described in Example 4 but using 550.2 mg of dl-cis-2-[N-(5-bromopentyl)carbamoyloxy]methyltetrahydropyran-3-yl N-heptadecylcarbamate (prepared as described in Preparation 67) and 0.65 ml of thiazole, 526.9 mg of the title compound was obtained as a white powder, melting at 115°–120° C.

Nuclear Magnetic Resonance Spectrum (90 MHz, CD$_3$OD−CDCl$_3$=1:1 by volume) δ ppm: 0.7–2.3 (43H, multiplet); 3.0–3.2 (4H, multiplet); 3.4–3.8 (2H, multiplet); 3.9–4.2 (3H, multiplet); 4.66 (2H, triplet, J=7 Hz); 4.7–4.9 (1H, multiplet); 8.28 (1H, doublet, J=4 Hz); 8.52 (1H, doublet, J=4 Hz).

Infrared Absorption Spectrum (CHCl$_3$) $v_{max}$ cm$^{-1}$: 3460 (—NH—), 1705, 1695 (—O—CO—).

Elemental Analysis: Calculated for $C_{33}H_{60}BrN_3O_5S \cdot 3H_2O$: C, 53.21%; H, 8.12%; Br, 13.48%; N, 5.64%; S, 3.30%. Found: C, 53.31%; H, 7.99%; Br, 13.78%; N, 5.51%; S, 3.59%.

EXAMPLE 9 dl-3-{6-Ethoxycarbonyl-6-[(trans-3-heptadecylcarbamoyloxytetrahydropyran-2-yl)methoxycarbonylamino]hexyl}thiazolium methanesulfonate 0.099 g of methanesulfonyl chloride was added, whilst ice-cooling, to a solution of 0.363 g of ethyl 2-[(dl-trans-3-heptadecylcarbamoyloxytetrahydropyran-2-yl)methoxycarbonylamino]-5-hydroxyheptanoate (prepared as described in Preparation 64) and 0.16 ml of triethylamine in 5 ml of benzene. The mixture was then stirred at room temperature for 15 minutes. At the end of this time, the reaction mixture was washed with water, dried over anhydrous magnesium sulfate and concentrated by evaporation under reduced pressure. The resulting oily residue (0.357 g) and 0.41 ml of thiazole were dissolved in 2.0 ml of toluene, and the mixture was heated for 4 days on an oil bath kept at 90° C., whilst stirring. The solvent was then distilled off under reduced pressure, and the residue was subjected to column chromatography through 30 g of silica gel, eluted with a gradient system of methylene chloride and methanol ranging from 3:1 to 1:1 by volume, to give 0.205 g of the title compound as a white powder, melting at 52°–60° C.

Nuclear Magnetic Resonance Spectrum (270 MHz, CD$_3$OD) δ ppm: 0.90 (3H, triplet, J=7.0 Hz); 1.25 (3H, triplet, J=7.0 Hz); 1.3–1.9 (39H, multiplet); 2.01 (2H, multiplet); 2.20 (1H, multiplet); 2.70 (3H, singlet); 3.06 (2H, triplet, J=6.9 Hz); 3.44 (2H, multiplet); 3.89 (1H, multiplet); 4.0–4.3 (2H, multiplet); 4.16 (2H, quartet, J=7.0 Hz); 4.49 (1H, multiplet); 4.60 (2H, triplet, J=7.5 Hz); 8.29 (1H, doublet, J=3.7 Hz); 8.50 (1H, doublet, J=3.7 Hz).

Elemental Analysis: Calculated for $C_{38}H_{69}N_3O_{10}S_2$: C, 57.61%; H, 8.78%; N, 5.30%. Found: C, 57.57%; H, 8.94%; N, 5.17%.

EXAMPLE 10

S-{dl-cis-2-[N-(2-Pyridylmethyl)carbamcyloxylmethyl-tetrahydropyran-3-yl}N-(heptadecyl)thiocarbamate A solution of 0.778 g of phenyl chlorocarbonate in 8 ml of methylene chloride was added to a solution of 1.424 g of S-[dl-(cis-2-hydroxymethyltetrahydropyran-3-yl)]N-(heptadecyl)thiocarbamate (prepared as described in Preparation 41) and 0.54 ml of pyridine in 20 ml of methylene chloride. The mixture was then stirred at room temperature for 1 hour. At the end of this time, the reaction mixture was poured into water and extracted three times with methylene chloride. The combined extracts were washed, in turn, with 10% w/v aqueous hydrochloric acid, a saturated aqueous solution of sodium bicarbonate and a saturated aquous solution of sodium chloride, and they were then dried over anhydrous magnesium sulfate. The solvent was then removed from the reaction mixture by distillation under reduced pressure, to leave 2.01 g of the crude carbonate, which was dissolved in 28 ml of chloroform. 0.68 ml of 2-(aminomethyl)pyridine was added to the resulting solution, and the mixture was heated under reflux for 44 hours. At the end of this time, the reaction mixture was evaporated to dryness under reduced pressure, and the residue was subjected to column chromatography through 40 g of silica gel. Those fractions eluted with a gradient system of hexane and ethyl acetate ranging from 2:1 to 0:1 by volume were collected and then reprecipitated from a mixture of hexane and methylene chloride to give 1.675 g of the title compound as a white solid, melting at 88°–90° C.

Nuclear Magnetic Resonance Spectrum (90 MHz, $CDCl_3$) δ ppm: 0.7–2.2 (37H, multiplet); 3.1–4.3 (8H, multiplet); 3.26 (2H, quartet); 4.51 (2H, doublet, J=6 Hz); 5.38 (1H, multiplet); 5.82 (1H, multiplet); 7.23, 7.67 and 8.56 (4H, multiplet).

Infrared Absorption Spectrum ($CHCl_3$) $\nu_{max}$ cm$^{-1}$: 3440 (—NH—), 1720 (—O—CO—), 1670 (—S—CO—).

Elemental Analysis: Calculated for $C_{31}H_{53}N_3O_4S$: C, 66.04%; H, 9.47%; N, 7.45% S, 5.69%. Found: C, 66.12%; H, 9.38%; N, 7.53%; S, 5.63%.

EXAMPLE 11

S-{dl-cis-2-[N-Acetyl-N-(2-pyridylmethyl)carbamoyloxy]methyltetrahydropyran-3-yl}N-acetyl-N-(heptadecyl)thiocarbamate A solution of 1.632 g of S-{dl-cis-2-[N-(2-pyridylmethyl)carbamoyloxy]methyltetrahydropyran-3-yl}N-(heptadecyl)thiocarbamate (prepared as described in Example 10), 3.54 g of 4-dimethylaminopyridine and 2.73 ml of acetic anhydride in 32 ml of toluene was heated at 80° C. for 65 hours, whilst stirring. At the end of this time, the reaction mixture was evaporated to dryness under reduced pressure, and the residue was subjected to column chromatography through 40 g of silica gel and then to medium pressure liquid chromatography through a Lobar B column. Those fractions eluted with a 15:5:4 by volume mixture of hexane, methylene chloride and ethyl acetate were collected to give 0.493 g of the title compound as an oil.

Nuclear Magnetic Resonance Spectrum (60 MHz, $CDCl_3$) δ ppm: 0.7–2.2 (37H, multiplet); 2.39 (3H, singlet); 3.58 (3H, singlet); 3.0–4.4 (8H, multiplet); 5.08 (2H, singlet); 7.13, 7.63 and 8.53 (4H, multiplet).

EXAMPLE 12

S-{dl-cis-2-[N-(2-Pyridylmethyl)carbamoyloxymethyl]-tetrahydropyran-3-yl}N-acetyl-N-(heptadecyl)thiocarbamate After the elution of the fraction containing the compound of Example 11, a further elution was carried out using a 1:1:1 by volume mixture of hexane, methylene chloride and ethyl acetate to give an oil. This oil was further purified by column chromatography through a Lobar B column using the same solvent system as above to give 0.379 g of the title compound Nuclear Magnetic Resonance Spectrum (60 MHz, $CDCl_3$) δ ppm: 0.7–2.2 (37H, multiplet); 2.41 (3H, singlet); 3.2–4.6 (10H, multiplet); 5.90 (1H, multiplet); 7.25 (2H, multiplet); 7.67 (1H, multiplet); 8.56 (1H, multiplet).

EXAMPLE 12 dl-1-Ethyl-2-{N-acetyl-N-[cis-3-(N-acetyl-N-heptadecylcarbamoylthio)tetrahydropyran-2-yl]methoxycarbonyl}aminomethylpyridinium chloride A mixture of 0.493 g of S-{dl-cis-2-[N-acetyl-N-(2-pyridylmethyl)carbamoyloxy]methyltetrahydropyran-3-yl} N-acetyl-N-(heptadecyl)thiocarbamate (prepared as described in Example 11) and 10 ml of ethyl iodide was heated under reflux for 91 hours. At the end of this time, the reaction mixture was evaporated to dryness under reduced pressure, and the residue was dissolved in 70% v/v aqueous methanol. The resulting solution was passed through a column packed with 44 ml of an ion exchange resin (IRA-410, Cl$^-$ form, Rohm & Haas), and the column was washed with 70% v/v aqueous methanol. The eluate and the washings were combined and then concentrated by evaporated under reduced pressure, to give a crude chloride. This crude chloride was subjected to column chromatography through 10 g of silica gel and then to medium pressure liquid chromatography through a Lobar B Column.

The fraction eluted with a 9:1 by volume mixture of methylene chloride and methanol was collected to give 0.368 g of the title compound.

Nuclear Magnetic Resonance Spectrum (60 MHz, $CD_3OD$) δ ppm: 0.7–2.2 (40H, multiplet); 1.66 (3H, triplet, J=7 Hz); 2.37 (3H, singlet); 2.61 (3H, singlet); 3.1–4.4 (8H, multiplet); 4.77 (2H, quartet J=7 Hz); 5.40 (2H, singlet); 7.98 (2H, multiplet); 8.53 (1H, multiplet); 9.03 (1H, multiplet).

EXAMPLE 14 dl-trans-2-[N-(2-Pyridylmethyl)carbamoyloxymethyl]-tetrahydropyran-3-yl N-heptadecylcarbamate A solution of 0.795 g of phenyl chlorocarbonate in 8 ml of methylene chloride was added to a solution of 1.400 g of dl-(trans-2-hydroxymethyltetrahydropyran-3-yl) N-heptadecylcarbamate (prepared as described in Preparation 4) and 0.55 ml of pyridine in 20 ml of methylene chloride, and then the mixture was stirred at room temperature for 1 hour. At the end of this time, reaction mixture was poured into water and extracted three times with methylene chloride. The combined extracts were washed, in turn, with 10% w/v aqueous hydrochloric acid, a saturated aqueous solution of sodium bicarbonate and a saturated aqueous solution of sodium chloride and were then dried over anhydrous magnesium sulfate.

The solvent was then distilled off under reduced pressure, to leave 2.04 g of a crude carbonate. The whole of this crude carbonate was dissolved in 28 ml of chloroform, and then 0.70 ml of 2-(aminomethyl)pyridine was added to the solution. The resulting mixture was heated under reflux for 49 hours. At the end of this time, the reaction mixture was evaporated to dryness under reduced pressure, and the residue was subjected to column chromatography through 40 g of silica gel. Those fractions eluted with a gradient system of hexane and ethyl acetate ranging from 1:1 to 0:1 by volume were collected and reprecipitated from a mixture of hexane and methylene chloride, to give 1.663 g of the title compound as a white solid, melting at 78°–80° C.

Nuclear Magnetic Resonance Spectrum (90 MHz, CDCl$_3$) δ ppm: 0.7–2.4 (37H, multiplet); 2.9–3.7 (4H, multiplet); 3.7–4.9 (7H, multiplet); 5.87 (1H, multiplet); 7.22 (2H, multiplet); 7.66 (1H, multiplet); 8.54 (1H, multiplet).

Mass Spectrum (m/e): 547 (M+).

Elemental Analysis: Calculated for C$_{31}$H$_{53}$N$_3$O$_5$: C, 67.97%; H, 9.75%; N, 7.67%. Found: C, 67.94%; H, 9.65%; N, 7.69%.

EXAMPLE 15 dl-trans-2-[N-Acetyl-N-(2-pyridylmethyl)carbamoyloxymethyl]tetrahydropyran-3-yl N-heptadecylcarbamate A solution of 1.613 g of dl-trans-2-[N-(2-pyridylmethyl)carbamoyloxymethyl]tetrahydropyran-3-yl N-heptadecylcarbamate (prepared as described in Example 14), 3.60 g of 4-dimethylaminopyridine and 2.78 ml of acetic anhydride in 32 ml of toluene was heated at 80° C. for 86 hours, whilst stirring. The reaction mixture was then evaporated to dryness under reduced pressure, and the residue was subjected to column chromatography through 40 g of silica gel, and then to medium pressure liquid chromatography through a Lobar B column. The fraction eluted with a 3:2 by volume mixture of hexane and ethyl acetate was collected and then reprecipitated from hexane to give 0.408 g of the title compound as a solid, melting at 79°–81° C. Nuclear Magnetic Resonance Spectrum (60 MHz, CDCl$_3$) δ ppm: 0.7–2.4 (37H, multiplet); 2.62 (3H, singlet); 2.8–3.5 (4H multiplet); 3.7–5.2 (7H, multiplet); 5.11 (2H, singlet); 7.15 (2H, multiplet); 7.65 (1H, multiplet); 8.55 (1H, multiplet).

Elemental Analysis: Calculated for C$_{33}$H$_{55}$N$_3$O$_6$: C, 67.20%; H, 9.40%; N, 7.12%. Found: C, 66.95%; H, 9.67%; N, 7.08%.

EXAMPLE 16 dl-1-Ethyl-2-{N-acetyl-N-[trans-3-(N-heptadecylcarbamoyloxy)tetrahydropyran-2-yl]methoxycarbonyl-}aminomethylpyridinium chloride A mixture of 0.365 g of dl-trans-2-[N-acetyl-N-(2-pyridylmethyl)carbamoyloxymethyl]tetrahydropyran-3-yl N-heptadecylcarbamate (prepared as described in Example 15) and 8 ml of ethyl iodide was heated under reflux for 40 hours. At the end of this time, the reaction mixture was evaporated to dryness under reduced pressure, and the residue was dissolved in 70% v/v aqueous methanol. The solution was passed through a column packed with 35 ml of an ion exchange resin (IRA-410, Cl$^-$ form, Rohm & Haas), and the column was washed with 70% v/v aqueous methanol. The eluate and the washings were combined and then concentrated by evaporation under reduced pressure, to give a crude chloride. This crude chloride was subjected to column chromatography through 10 g of silica gel, and then to medium pressure liquid chromatography through a Lobar B Column. The fraction eluted with a 9:1 by volume mixture of methylene chloride and methanol was collected to give 0.345 g of the title compound.

Nuclear Magnetic Resonance Spectrum (60 MHz, CD$_3$OD)δppm: 0.7–2.3 (40H, multiplet); 1.67 (3H, triplet J=7 Hz); 2.64 (3H, singlet); 2.8–5.1 (11H, multiplet); 4.81 (2H, quartet J=7 Hz); 5.45 (2H, singlet); 8.06 (2H, multiplet); 8.60 (1H, multiplet); 9.10 (1H, multiplet).

EXAMPLE 17 di-1-Ethyl-2-{N-[cis-3-(N-acetyl-N-heptadecylcarbamoylthio)tetrahydropyran-2-yl]methoxycarbonylaminomethyl}pyridinium chloride A mixture of 0.379 g of S-{dl-cis-2-[N-(2-pyridylmethyl)carbamoyloxymethyl]tetrahydropyran-3-yl}N-acetyl-N-(heptadecyl)thiocarbamate (prepared as described in Example 12) and 8 ml of ethyl iodide was heated under reflux for 91 hours. At the end of this time, the reaction mixture was dissolved in 70% v/v aqueous methanol and passed through a column packed with 35 ml of an ion-exchange resin (IRA-410, Cl$^-$ form). The column was washed with 70% v/v aqueous methanol. The eluate and the washings were combined and then concentrated by evaporation under reduced pressure, to give a crude chloride. This crude chloride was subjected to column chromatography through 10 g of silica gel, and then to medium pressure liquid chromatography through a Lobar B column. The fraction eluted with a 9:1 by volume mixture of methylene chloride and methanol was collected to give 0.302 g of the title compound.

Nuclear Magnetic Resonance Spectrum (60 MHz, CD$_3$OD)δppm: 0.7–2.2 (40H, multiplet); 1.63 (3H, triplet, J=7 Hz); 2.38 (3H, singlet); 3.2–5.0 (13H, multiplet); 4.73 (2H, quartet, J=7 Hz.); 8.13 (2H, multiplet); 8.55 (1H, multiplet); 9.05 (1H, multiplet).

EXAMPLE 18 di-3-{4-[3-(trans-3-Heptadecylcarbamoyloxytetrahydropyran-2-ylmethoxy)-5-isoxazolyl]butyl}thiazolium methanesulfonate 0.10 ml of methanesulfonyl chloride was added, whilst ice-cooling, to a solution of 0.470 g of di-trans-2-Z-[5-(4-hydroxybutyl)-3-isoxazolyloxymethyl]tetrahydropyran-3-yl N-heptadecylcarbamate (prepared as described in Preparation 69) and 0.24 ml of triethylamine dissolved in 10 ml of benzene. The mixture was then stirred at room temperature for 15 minutes, after which it was washed with water, dried over anhydrous magnesium sulfate and concentrated by evaporation under reduced pressure. The residue was dissolved in 3 ml of toluene, and 0.60 ml of thiazole was added to the solution. The mixture was then heated on an oil bath kept at 85° C. for 4 days. At the end of this time, the solvent was removed by distillation under reduced pressure, after which the residue was subjected to column chromatography through 30 g of silica gel. 0.349 g of the title compound was obtained, as a white powder, melting at 82°–86° C., from those fractions eluted with mixtures of methylene chloride and methanol ranging from 2:1 to 1:1 by volume.

Nuclear Magnetic Resonance Spectrum (270 MHz, $CD_3OD$)$\delta$ppm: 0.90 (3H, triplet, J=7.0 Hz); 1.2–2.3 (38H, multiplet); 2.69 (3H, singlet); 2.76 (2H, triplet, J=7.3 Hz); 3.04 (2H, triplet, J=7.0 Hz); 3.43 (1H, multiplet); 3.58 (1H, multiplet); 3.93 (1H, doublet, J=11.5 Hz); 4.25 (1H, multiplet); 4.56 (1H, multiplet); 4.62 (2H, triplet, J=7.3 Hz); 5.85 (1H, singlet); 8.29 (1H, doublet, J=4.0 Hz); 8.49 (1H, doublet, J=4.0 Hz).

Elemental Analysis: Calculated for $C_{35}H_{61}N_3O_8S$: C, 58.71%, H, 8.59%; N, 5.87%. Found: C, 58.35%; H, 8.81%; N, 5.71%.

EXAMPLE 19 di-3-{7-Hydroxy-8-[(trans-3-heptadecylcarbamoyloxytetrahydropyran-2-yl)methoxy]octyl}thiazolium p-toluenesulfonate 150 mg of di-trans-2-[2-hydroxy-8-(p-toluenesulfonyloxy)octyloxymethyl]tetrahydropyran-3-yl N-heptadecylcarbamate (prepared as described in Preparation 76) and 0.15 ml of thiazole were dissolved in 1 ml of toluene, and the solution was heated on an oil bath kept at 80° C. for 42 hours. At the end of this time, the solvent was removed by distillation under reduced pressure, after which the residue was subjected to column chromatography through 4 g of silica gel. 56 mg of the title compound were obtained, as a powder melting at 81°–84° C., from the fractions eluted with a 9:1 by volume mixture of methylene chloride and methanol.

Nuclear Magnetic Resonance Spectrum: (60 MHz, $CD_3OD$)$\delta$ppm: 0.7–2.5 (45H, multiplet); 2.35 (3H, singlet); 3.04 (2H, triplet, J=6.5 Hz); 3.3–4.1 (8H, multiplet); 4.58 (2H, doublet, J=7 Hz); 4.3–4.9 (1H, multiplet); 7.22 (2H, doublet, J=8 Hz); 7.73 (2H, doublet, J=8 Hz); 8.27 (1H, doublet, J=4 Hz); 8.60 (1H, doublet, J-4 Hz).

EXAMPLE 20 di-3-{7-Acetoxy-8-[(trans-3-heptadecylcarbamoyloxytetrahydropyran-2-yl)methoxy]octyl}thiazolium p-toluenesulfonate 163 mg of isomer I of di-trans-2-[2-acetoxy-8-p-toluenesulfonyloxyoctyloxymethyl]tetrahydropyran-3-yl N-heptadecylcarbamate (prepared as described in Preparation 77) and 0.15 ml of thiazole were dissolved in 1 ml of toluene, and the mixture was heated on an oil bath kept at 80° C. for 110 hours. At the end of this time, the solvent was removed by distillation under reduced pressure, after which the residue was subjected to column chromatography through 4 g of silica gel. 87 mg of the title compound were obtained, as a resin, from the fractions eluted with mixtures of methylene chloride and methanol ranging from 93:7 to 9:1 by volume.

Nuclear Magnetic Resonance Spectrum: (60 MHz, $CD_3OD$)$\delta$ppm: 0.7–2.3 (47H, multiplet); 2.00 (3H, singlet); 2.33 (3H, singlet); 2.80–4.20 (9H, multiplet); 4.2–4.7 (1H, multiplet); 4.55 (2H, triplet, J=7 Hz); 4.75–5.2 (1H, multiplet); 7.20 (2H, doublet, J=8 Hz); 7.72 (2H, doublet, J=8 Hz); 8.28 (1H, doublet, J=4 Hz); 8.50 (1H, doublet, J=4 Hz);

Elemental Analysis: Calculated for $C_{44}H_{74}N_2O_9S_2 \cdot 0.5H_2O$: C, 62.31%; H, 8.91%; N, 3.30%; S, 7.56%. Found: C, 62.29%; H, 9.08%; N, 2.92%; S, 7.46%.

EXAMPLE 1f dl-[trans-3-(N-Heptadecylcarbamoyloxy)tetrahydropyran-2-yl]methyl 2-thiazolioethyl phosphate (inner salt)

A solution of 2.307 g of 2-bromoethyl phosphorodichloridate in 20 ml of methylene chloride was added dropwise. Whilst ice-cooling, to 40 ml of methylene chloride in which was dissolved 2.630 g of dl-(trans-2-hydroxymethyltetrahydropyran-3-yl) N-heptadecylcarbamate (prepared as described in Preparation 4) and 1.51 ml of triethylamine. The mixture was stirred for 3 hours at room temperature. 5 ml of pyridine and 2.5 ml of water were then added to the reaction mixture. The mixture was stirred for 14 hours at the same temperature and then concentrated by evaporation under reduced pressure to give a residue. Ethyl acetate and water were added to the residue and the aqueous layer was acidified by the addition of a 10% w/v aqueous solution of hydrochloric acid. The organic layer was separated and the aqueous layer was extracted with ethyl acetate. The combined organic layer and extract were washed with water, dried and concentrated by evaporation under reduced pressure. The residue was subjected to column chromatography through 80 g of silica gel. Fractions eluted with methylene chloride were discarded as an impure material. Fractions eluted with mixtures of methylene chloride and methanol ranging from 50:1 to 2:1 by volume were worked up to give 2.998 g of di-[trans-3-(N-heptadecylcarbamoyloxy)tetrahydropyran-2-yl]methyl 2-bromoethyl phosphate as an oil.

Infrared Absorption Spectrum $(CHCl_3)\nu_{max}cm^{-1}$: 3450 (>NH), 3350 (—OH), 1710 (—O—CO—).

1.586 g of the above compound and 1.87 ml of thiazole were dissolved in 2 ml of toluene, and the solution was heated on an oil bath kept at 70° for 6 days, whilst stirring. The solution was cooled and then the solvent was distilled off. The residue was dissolved in 15 ml of a 95:5 by volume mixture of tetrahydrofuran and water. The solution was passed through a column of Amberlite MB-3 resin, and the resulting solution was passed through the same column again. This operation was repeated a total of 6 times, and finally the column was washed with the same solvent. The solution was combined with the washings, and then the solvent was stripped off by evaporation under reduced pressure, and the residue was subjected to column chromatography through 20 g of silica gel, to give 0.422 g of the title compound as a white powder from the fractions eluted with a 32:7:1 by volume mixture of methylene chloride, methanol and water.

Nuclear Magnetic Resonance Spectrum $(CD_3OD)\delta$ppm: 0.8–2.4 (37H, multiplet); 3.05 (2H, multiplet); 3.2–4.9 (10H, multiplet); 8.27 (1H, multiplet); 8.53 (1H, doublet, J=3 Hz); 10.17 (1H, multiplet).

Infrared Absorption Spectrum $(KBr)\nu_{max}cm^{-1}$: 1700 (—O—CO—).

Elemental Analysis: Calculated for $C_{29}H_{53}N_2O_7PS \cdot \frac{1}{2}H_2O$: C, 56.75%; H, 8.87%; N, 4.56%. Found: C, 56.91%; H, 8.80%; N, 4.51%.

EXAMPLE 2f dl-[trans-3-(N-Heptadecylcarbamoyloxy)tetrahydropyran-2-yl]methyl 2-(trimethylammonio)ethyl phosphate (inner salt)

1.402 g of dl-[trans-3-(N-heptadecylcarbamoyloxy)-tetrahydropyran-2-yl]methyl 2-bromoethyl phosphate (prepared as described in Example 1f) was dissolved in a 3:5:5 by volume mixture of chloroform, isopropanol and dimethylformamide, and 7.0 g of gaseous trimethylamine were introduced into the solution. The mixture was heated, under a nitrogen atmosphere, on an oil bath kept at 50° for 6 hours, whilst stirring, and was then cooled, after which 0.483 g of silver carbonate was added The mixture was heated under reflux for 1 hour, and then the solvent was distilled off. Methanol was added to the residue and insolubles were separated by filtration. The solvent was stripped from the resulting solution by evaporation under reduced pressure. The residue was purified by liquid chromatography [using 30 g of silica gel and a Lobar column (size B)], giving 0.930 g of the title compound as a white powder from the fractions eluted with a 32:7:1 by volume mixture of methylene chloride, methanol and water.

Nuclear Magnetic Resonance Spectrum (CD$_3$OD)$\delta$ppm: 0.8–2.4 (37H, multiplet); 3.23 (9H, singlet); 29–4.8 (13H, multiplet).

Infrared Absorption Spectrum (KBr)$\nu_{max}$cm$^{-1}$: 1700 (—O—CO—).

Elemental Analysis: Calculated for C$_{29}$H$_{59}$N$_2$O$_7$P.H$_2$O: C, 58.37%; H, 10.30%; N, 4.69%; P, 5.19%. Found: C, 58.23%; H, 10.23%; N, 4.72%; P, 5.19%.

EXAMPLE 3f dl-[trans-3-(N-Octadecylcarbamoyloxy)tetrahydropyran-2-yl]methyl 2-thiazolioethyl phosphate (inner salt)

0.594 g of dl-(trans-2-hydroxymethyltetrahydropyran-3-yl) N-octadecylcarbamate (prepared as described in Preparation 5) was treated in the same way as described in Example 1f to give 0.284 g of the title compound as a white powder.

Nuclear Magnetic Resonance Spectrum (CD$_3$OD)$\delta$ppm: 0.8–2.5 (39H, multiplet); 2.9–5.1 (13H, multiplet); 8.30 (1H, multiplet); 8.53 (1H, doublet, J=3 Hz); 10.20 (1H, multiplet).

Infrared Absorption Spectrum (KBr)$\nu_{max}$cm$^{-1}$: 1700 (—O—CO—).

Elemental Analysis: Calculated for C$_{30}$H$_{55}$N$_2$O$_7$PS.H$_2$O: C, 56.58%; H, 9.02%; N, 4.40%; P, 4.86%. Found: C, 56.71%; H, 8.65%; N, 4.38%; P, 4.41%.

EXAMPLE 4f dl-[cis-3-(N-Octadecylcarbamoyloxy)tetrahydropyran-2-yl]methyl 2-thiazolioethyl phosphate (inner salt)

0.690 g of dl-(cis-2-hydroxymethyltetrahydropyran-3-yl) N-octadecylcarbamate (prepared as described in Preparation 34) was treated as described in Example 1f, except that the reaction mixture was heated on an oil bath at 80° C. for 64 hours (in place of heating on an oil bath for 6 days at a temperature of 70° C.), to give 0.180 g of the title compound as a white powder.

Nuclear Magnetic Resonance Spectrum (CD$_3$OD)$\delta$ppm: 0.7–2.2 (39H, multiplet); 2.9–4.9 (11H, multiplet); 8.28 (1H, doublet, J=3 Hz); 8.51 (1H, doublet, J=3 Hz); 10.18 (1H, multiplet).

Infrared Absorption Spectrum (KBr)$\nu_{max}$cm$^{-1}$: 1695 (—O—CO—).

Elemental Analysis: Calculated for C$_{30}$H$_{55}$N$_2$O$_7$PS.3/2H$_2$O: C, 55.79%; H, 9.05%; N, 4.34%; P, 4.80%. Found: C, 55.90%; H, 8.65%; N, 4.38%; P, 4.78%.

EXAMPLE 5f dl-[trans-2-(N-Octadecylcarbamoyloxymethyl)tetrahydropyran-3-yl]2-thiazolioethyl phosphate (inner salt)

1.711 g of dl-(trans-3-hydroxytetrahydropyran-2-yl)methyl N-octadecylcarbamate (prepared as described in Preparation 37) was reacted with 2-bromoethyl phosphorodichloridate in a manner similar to that described in Example 1f to afford 1.381 g of dl-[trans-2-(N-octadecylcarbamoyloxymethyl)tetrahydropyran-3-yl] 2-bromoethyl phosphate. 0.888 g of this compound was dissolved in 3 ml of toluene, and the solution was mixed with 1.02 ml of thiazole. The mixture was then heated on an oil bath kept at 80° C. for 60 hours, whilst stirring. The resulting reaction mixture was then worked up as described in Example 1f to give 0.178 g of the title compound as a powder.

Nuclear Magnetic Resonance Spectrum (CD$_3$OD)$\delta$ppm: 0.7–2.4 (39H, multiplet); 2.9–5.0 (13H, multiplet); 8.27 (1H, doublet, J=4 Hz); 8.52 (1H, doublet, J=4 Hz); 10.20 (1H, multiplet).

Elemental Analysis: Calculated for C$_{30}$H$_{55}$N$_2$O$_7$PS.3/2H$_2$O: C, 55.79%; H, 9.05%; N, 4.34%; P, 4.79%. Found: C. 55.60%; H, 9.05%; N, 4.21%; P, 4.31%.

EXAMPLE 6f dl-[cis-3-(N-Octadecylcarbamoylthio)tetrahydropyran-2-yl]methyl 2-thiazolioethyl phosphate (inner salt)

1.300 g of dl-S-(cis-2-hydroxymethyltetrahydropyran-3-yl) N-(octadecyl)thiocarbamate (prepared as described in Preparation 79) was reacted with 2-bromoethyl phosphorodichloridate in a manner similar to that described in Example 1f, to give 1.673 g of dl-[cis-3-(N-octadecylcarbamoylthio)tetrahydropyran-2-yl]methyl 2-bromoethyl phosphate. 1.000 g of this compound was dissolved in 1.0 ml of toluene, and the resulting solution was mixed with 1.12 ml of thiazole. The mixture was heated on an oil bath kept at 80° C. for 109 hours, whilst stirring. It was then worked up as described in Example 1f, to give 0.500 g of the title compound as a powder.

Nuclear Magnetic Resonance Spectrum (CD$_3$OD)$\delta$ppm: 0.7–2.2 (39H, multiplet); 3.0–4.9 (13H, multiplet); 8.30 (1H, multiplet); 8.53 (1H, doublet, J=3 Hz); 10.20 (1H, multiplet).

Elemental Analysis: Calculated for C$_{30}$H$_{55}$N$_2$O$_6$PS$_2$.½H$_2$O; C, 55.96%; H, 8.77%; N, 4.35%; P, 4.81%. Found: C, 55.96%; H, 8.34%; N, 4.33%; P, 4.77%.

EXAMPLE 7f dl-(trans-3-Heptadecylcarbamoyloxytetrahydrofuran-2-yl)methyl 2-thiazolioethyl phosphate (inner salt)

0.421 g of the title compound, as a viscous oil, was prepared from 1.527 g of dl-trans-2-hydroxymethyltetrahydrofuran-3-yl N-heptadecylcarbamate (prepared as described in Preparation 52) by treating it in a manner similar to that described in Example 1f.

Nuclear Magnetic Resonance Spectrum (270 MHz, CD$_3$OD)$\delta$ppm: 0.89 (3H, triplet, J=7.0 Hz); 1.2–1.6

(30H, multiplet); 1.96 (1H, multiplet); 2.20 (1H, multiplet); 3.07 (2H, triplet, J=7.0 Hz); 3.75–4.10 (4H, multiplet); 4.20–4.40 (2H, multiplet); 5.05 (1H, doublet of multiplets, J=6.2 Hz); 8.26 (1H, doublet of doublets, J=3.5 & 2.2 Hz); 8.50 (1H, doublet of doublets, J=3.7 & 1.1 Hz); 10.14 (1H, multiplet).

EXAMPLE 8$f$ dl-[trans-3-(N-Heptadecylcarbamoyloxy)tetrahydropyran-2-yl]methyl 6-thiazoliohexyl phosphate (inner salt)

1.000 g of dl-trans-2-hydroxymethyltetrahydropyran-3-yl N-heptadecylcarbamate (prepared as described in Preparation 4) was reacted with 1.441 g of 6-bromohexyl phosphorodichloridate in a manner similar to that described in Example 1$f$, to give 1.76 g of dl-[trans-3-(N-heptadecylcarbamoyloxy)tetrahydropyran-2-yl]methyl 6-bromohexyl phospate. 0.88 g of this compound was dissolved in 2.0 ml of toluene and 1.72 ml of thiazole were added thereto. The resulting mixture was heated on an oil bath at 80° C. for 86 hours. It was then worked up as described in Example 1$f$, to give 0.344 g of the title compound as a pale yellow powder.

Nuclear Magnetic Resonance Spectrum (CD$_3$OD)δppm: 0.7–2.4 (45H, multiplet); 2.8–4.9 (13H, multiplet); 4.63 (2H, triplet, J=7.5 Hz); 8.30 (1H, doublet, J=4 Hz); 8.54 (1H, doublet, J=4 Hz).

Elemental Analysis: Calculated for C$_{33}$H$_{61}$N$_2$O$_7$PS.-H$_2$O: C, 58.38%; H, 9.35%; N, 4.13%; P, 4.56%; S, 4.72%. Found: C, 58.09%; H, 9.31%; N, 4.15%; P, 4.66%; S, 4.94%.

EXAMPLE 9$f$ dl-[trans-3-(N-Heptadecylcarbamoyloxy)tetrahydropyran-2-yl]methyl 6-[5-(2-hydroxyethyl)-4-methylthiazolio]hexyl phosphate (inner salt)

0.88 g of dl-[trans-3-(N-heptadecylcarbamoyloxy)tetrahydropyran-2-yl]methyl 6-bromohexyl phosphate (prepared as described in the first step of Example 8$f$) was dissolved in 2.0 ml of toluene. The resulting solution was mixed with 2.88 ml of 5-(2-hydroxyethyl)-4-methylthiazole. The mixture was then heated on an oil bath at 80° C. for 90 hours, whilst stirring. It was then worked up as described in Example 1$f$, to give 0.460 g of the title compound as a powder.

EXAMPLE 10$f$ dl-[cis-3-(N-Heptadecylcarbamoylthio)tetrahydropyran-2-yl]methyl 4-thiazoliobutyl phosphate (inner salt)

0.500 g of dl-S-(cis-2-hydroxymethyltetrahydropyran-3-yl) N-(heptadecyl)thiocarbamate (prepared as described in Preparation 41) was reacted with 0.942 g of 4-bromobutyl phosphorodichloridate in a manner similar to that described in Example 1$f$, to give 0.75 g of dl-[cis-3-(N-heptadecylcarbamoylthio)tetrahydropyran-2-yl]methyl 4-bromobutyl phosphate. The whole of this compound was then dissolved in 2.0 ml of toluene, and the resulting solution was mixed with 1.65 ml of thiazole. The mixture was heated on an oil bath kept at 80° C. for 67 hours, whilst stirring, and was then worked up as described in Example 1$f$, to give 0.309 g of the title compound as a pale yellow powder.

Nuclear Magnetic Resonance Spectrum (CD$_3$OD) δ ppm: 0.7–2.4 (4H, multiplet); 2.9–4.2 (11H, multiplet); 4.71 (2H, triplet, J=7.5 Hz); 8.29 (1H, doublet, J=4 Hz); 8.55 (1H, doublet, J=4 Hz).

EXAMPLE 11$f$ dl-[cis-3-(N-Heptadecylcarbamoylthio)tetrahydropyran-2-yl]methyl 5-thiazoliopentyl phosphate (inner salt)

0.500 g of dl-S-(cis-2-hydroxymethyltetrahydropyran-3-yl) N-(heptadecyl)thiocarbamate (prepared as described in Preparation 41) was reacted with 1.322 g of 5-bromopentyl phosphorodichloridate in a manner similar to that described in Example 1$f$, to give 0.85 g of dl-[cis-3-(N-heptadecylcarbamoylthio)tetrahydropyran-2-yl]methyl 5-bromopentyl phosphate. The whole of this compound was dissolved in 2.0 ml of toluene and the resulting solution was mixed with 1.65 ml of thiazole. The mixture was heated on an oil bath at 80° C. for 88 hours, whilst stirring. It was then worked up as described in Example 1$f$, to give 0.340 g of the title compound as a powder.

Nuclear Magnetic Resonance Spectrum (CD$_3$OD) δ ppm: 0.7–2.3 (43H, multiplet); 3.0–4.2 (11H, multiplet); 4.63 (2H, triplet, J=7.5 Hz); 8.29 (1H, doublet, J=4 Hz); 8.54 (1H, doublet, J=4 Hz).

Elemental Analysis: Calculated for C$_{32}$H$_{59}$N$_2$O$_6$PS$_2$.-H$_2$O: C, 56.44%; H, 9.03%; N, 4.11%; P, 4.55%; S, 9.42%. Found: C, 56.48%; H, 9.07%; N, 4.14%; P, 4.75%; S, 9.64%.

EXAMPLE 12$f$ dl-[cis-3-(N-Heptadecylcarbamoylthio)tetrahydropyran-2-yl]methyl 6-thiazoliohexyl phosphate (inner salt)

0.500 g of dl-S-(cis-2-hydroxymethyltetrahydropyran-3-yl) N-(heptadecyl)thiocarbamate (prepared as described in Preparation 41) was reacted with 1.040 g of 6-bromohexyl phosphorodichloridate in a manner similar to that described in Example 1$f$, to give 0.86 g of dl-[cis-3-(N-heptadecylcarbamoylthio)tetrahydropyran-2-yl]methyl 6-bromohexyl phosphate. The whole of this compound was dissolved in 2.0 ml of toluene and the resulting solution was mixed with 1.65 ml of thiazole. The mixture was heated on an oil bath at 80° C. for 87 hours, whilst stirring. It was then worked up as described in Example 1$f$, to give 0.305 g of the title compound as a powder.

Nuclear Magnetic Resonance Spectrum (CD$_3$OD) δ ppm: 0.7–2.4 (45H, multiplet); 3.0–4.2 (11H, multiplet); 4.61 (2H, triplet, J=7.5 Hz); 8.28 (1H, doublet, J=4 Hz); 8.52 (1H, doublet, J=4 Hz).

Elemental Analysis: Calculated for C$_{33}$H$_{61}$N$_2$O$_6$PS$_2$.-H$_2$O: C, 57.03%; H, 9.14%; N, 4.03%; P, 4.46%; S, 9.23%. Found: C, 57.06%; H, 9.18%; N, 3.97%; P, 4.30%; S, 9.59%.

PREPARATION 1

6-Benzyloxymethyl-3,4-dihydro-2H-pyran

A solution of 5.71 g of 6-hydroxymethyl-3,4-dihydro-2H-pyran dissolved in 100 ml of dimethylformamide was added dropwise to a mixture of 2.18 g of sodium hydride (as a 55% w/w dispersion in mineral oil) and dimethylformamide, whilst ice-cooling. The mixture was then stirred at room temperature for 1 hour, after which 6.33 g of benzyl chloride were added to it. The mixture was stirred for 16 hours, after which it was poured into 1 liter of water. The resulting mixture was then extracted twice with ethyl acetate. The combined extracts were washed with water, dried over anhydrous magnesium sulfate and concentrated by evaporation under reduced pressure. The oily residue (13 g) was subjected to column chromatography through 200 g of silica gel. 9.40 g of the title compound were obtained as a colorless oil from those fractions eluted with mixtures of diethyl ether and hexane ranging from 4:100 to 5:100 by volume. It boiled at 125°–130° C. (bath temperature)/1 mmHg (133 Pa).

Nuclear Magnetic Resonance Spectrum (90 MHz, CDCl$_3$) δ ppm: 1.65–2.2 (4H, multiplet); 3.87 (2H, singlet); 4.03 (2H, multiplet); 4.57 (2H, singlet); 4.80 (1H, triplet, J=3.5 Hz); 7.2–7.6 (5H, multiplet).

Elemental analysis: Calculated for $C_{13}H_{16}O_2$: C, 76.44%; H, 7.90%. Found: C, 76.36%; H, 7.90%.

PREPARATION 2 dl-trans-2-Benzyloxymethyltetrahydropyran-3-ol

A 1M solution of borane in 29.3 ml of tetrahydrofuran was added dropwise to a solution of 9.00 g of 6-benzyloxymethyl-3,4-dihydro-2H-pyran (prepared as described in Preparation 1) dissolved in 30 ml of tetrahydrofuran at a temperature, whilst maintaining the temperature in the range from −5° C. to 0° C. The reaction mixture was then stirred at room temperature for 3 hours, after which a 10% w/v aqueous solution of sodium hydroxide was added dropwise. 10.8 ml of 30% v/v aqueous hydrogen peroxide were then added, whilst keeping the temperature in the range from 32° to 40° C. The mixture was then stirred for a further 1 hour at room temperature, after which the organic layer was separated, washed wth water, dried over anhydrous magnesium sulfate and concentrated by evaporation under reduced pressure. The oily residue (10.5 g) was purified by column chromatography through 250 g of silica gel. 8.82 g of the title compound were obtained from those fractions eluted with a 1:20 by volume mixture of ethyl acetate and methylene chloride. It boiled at 130°–135° C. (bath temperature)/1 mmHg (133 Pa).

Nuclear Magnetic Resonance Spectrum (90 MHz, CDCl$_3$) δ ppm: 1.15–2.25 (4H, multiplet); 2.83 (1H, doublet, J=3 Hz); 3.1–3.6 (3H, multiplet); 3.68 (2H, doublet, J=5 Hz); 3.75–4.05 (1H, multiplet); 4.58 (2H, singlet); 7.2–7.5 (5H, multiplet).

Mass Spectrum (m/e): 222 (M+).

Elemental analysis: Calculated for $C_{13}H_{18}O_2$: C, 70.24%; H, 8.16%. Found: C, 70.07%; H, 8.04%.

PREPARATION 3 dl-trans-2-Benzyloxymethyltetrahydropyran-3-yl N-heptadecylcarbamate

A solution of 6.082 g of stearic acid, 3.84 ml of diphenylphosphoryl azide and 2.48 ml of triethylamine dissolved in 200 ml of benzene was heated under reflux for 3 hours. The reaction mixture was then cooled, after which it was washed first with an aqueous solution of sodium bicarbonate and then with a saturated aqueous solution of sodium chloride. It was then dried over anhydrous magnesium sulfate and the solvent was distilled off. The residue was dissolved in 160 ml of benzene, and 1.980 g of dl-trans-2-benzyloxymethyltetrahydropyran-3-ol (prepared as described in Preparation 2) was added to the solution. The mixture was heated under reflux for 38 hours under an atmosphere of nitrogen. At the end of this time, the reaction mixture was washed, in turn, with an aqueous solution of sodium bicarbonate and with water, dried over anhydrous magnesium sulfate and evaporated to dryness under reduced pressure. The residue was subjected to column chromatography through 60 g of silica gel. 3.904 g of the title compound were obtained as a white solid, melting at 61°–63° C., from those fractions eluted with a 6:3:1 by volume mixture of hexane, methylene chloride and diethyl ether.

Infrared Absorption Spectrum (CHCl$_3$) $\nu_{max}$ cm$^{-1}$: 3460 (—NH—) and 1720 (—O—CO—).

Mass Spectrum (m/e): 503 (M+) and 412 (M+—C$_7$H$_7$).

Elemental analysis: Calculated for $C_{31}H_{53}NO_4$: C, 73.91%; H, 10.60%; N, 2.78%. Found: C, 74.27%; H, 10.70%; N, 2.71%.

PREPARATION 4 dl-(trans-2-Hydroxymethyltetrahydropyran-3-yl) N-heptadecylcarbamate 3.800 g of dl-trans-2-benzyloxymethyltetrahydropyran-3-yl N-heptadecylcarbamate (prepared as described in Preparation 3) were dissolved in 120 ml of methanol and allowed to react with hydrogen at room temperature for 8 hours in the presence of 10% w/w palladium on activated carbon in a Paal's apparatus at 4 atmospheres (about 4 bar). The catalyst was then filtered off, and the solvent was removed from the filtrate by distillation under reduced pressure, to give 2.729 g of the title compound as a white solid, melting at 84°–86° C. (after recrystallization from diethyl ether).

Infrared Absorption Spectrum (CHCl$_3$) $\nu_{max}$ cm$^{-1}$: 3570 (—OH), 3450 (—NH) and 1710 (—O—CO—).

Mass Spectrum (m/e): 413 (M+) and 382 (M+—CH$_2$OH).

Elemental analysis: Calculated for $C_{24}H_{47}NO_4$: C, 69.69%; H, 11.45%; N, 3.39%. Found: C, 69.38%; H, 11.35%; N, 3.52%.

PREPARATION 5 dl-(trans-2-Hydroxymethyltetrahydropyran-3-yl) N-octadecylcarbamate

Following a procedure similar to that described in Preparation 3, 5.405 g of nonadecanoic acid were reacted with 1.118 g of dl-trans-2-benzyloxymethyltetrahydropyran-3-ol (prepared as described in Preparation 2). The resulting product was purified by column chromatography through silica gel eluted with a 6:3:1 by volume mixture of hexane, methylene chloride and diethyl ether, to give 1.417 g of dl-(trans-2-benzyloxymethyltetrahydropyran-3-yl) N-octadecylcarbamate as a white solid.

1.395 g of this product was dissolved in 30 ml of tetrahydrofuran, without further purification, and was then hydrogenated at room temperature for 7 hours in the presence of 10% w/w palladium on activated carbon in a Paal's apparatus at 4 atmospheres (about 4 bar). At the end of this time, the catalyst was filtered off and the solvent was stripped from the filtrate by evaporation under reduced pressure, to give 1.128 g of the title compound as a white solid, melting at 84°–86° C. (after recrystallization from diethyl ether).

Nuclear Magnetic Resonance Spectrum (90 MHz, CDCl$_3$) δ ppm: 0.7–2.4 (39H, multiplet); 2.80 (1H, multiplet); 3.0–4.2 (7H, multiplet); 4.5–4.9 (2H, multiplet).

Infrared Absorption Spectrum (CHCl$_3$) $\nu_{max}$ cm$^{-1}$: 3600 (—OH), 3460 (—NH) and 1710 (—O—CO—).

Mass Spectrum (m/e): 427 (M+) and 396 (M+—CH$_2$OH).

Elemental analysis: Calculated for $C_{25}H_{49}NO_4$: C, 70.21%; H, 11.55%; N, 3.28%. Found: C, 69.91%; H, 11.55%; N, 3.19%.

PREPARATION 6 dl-trans-2-[N-(5-Bromopentyl)carbamoyloxymethyl]-tetrahydropyran-3-yl N-heptadecylcarbamate 1.56 ml of diphenylphosphoryl azide and 1.68 ml of triethylamine were added to a solution of 1.41 g of 6-bromohexanoic acid dissolved in 40 ml of benzene. The mixture was then heated under reflux for 3 hours. At the end of this time, the reaction mixture was washed with a saturated aqueous solution of sodium bicarbonate and then with a saturated aqueous solution of sodium chloride. It was then dried over anhydrous magnesium sulfate and concentrated by evaporation under reduced pressure. The residue was dissolved in 20 ml of toluene, and then 1.000 g of dl-(trans-2-hydroxymethyltetrahydropyran-3-yl) N-octadecylcarbamate (prepared as described in Preparation 5) and 1.68 ml of triethylamine were added to the resulting solution. The mixture was then heated on an oil bath kept at 85° C. for 67 hours. At the end of this time, the reaction mixture was concentrated by evaporation under reduced pressure, and the residue was subjected to column chromatography through 30 g of silica gel. Those fractions eluted with mixtures of hexane and ethyl acetate ranging from 4:1 to 3:1 by volume were collected and then subjected to medium pressure liquid chromatography using a Lobar B column. 0.815 g of the title compound was obtained as a white waxy material, melting at 71°–75° C., from those fractions eluted with the same solvent mixtures.

Nuclear Magnetic Resonance Spectrum (90 MHz, CDCl$_3$) δ ppm: 0.7–2.4 (43H, multiplet); 2.6–3.8 (6H, multiplet); 3.38 (2H, triplet, J=7 Hz); 3.8–4.9 (6H, multiplet).

Infrared Absorption Spectrum (CHCl$_3$) ν$_{max}$ cm$^{-1}$: 3450 (—NH) and 1720 (—OCONH—).

Mass Spectrum (m/e): 606, 604 (M$^+$), 525 (M$^+$—Br) and 524 (M$^+$—HBr).

Elemental analysis: Calculated for C$_{30}$H$_{57}$BrN$_2$O$_5$: C, 59.49%; H, 9.49%; N, 4.62%. Found: C, 59.92%; H, 9.44%; N, 4.81%.

PREPARATION 7

(2R, 3S)-3-O-Benzyl-4-iodo-1,2-O,O-isoprpylidenebutane-1,2,3-triol (a) A solution of 21.00 ml of methanesulfonyl chloride in 100 ml of benzene was added dropwise to a solution of 57.00 g of (2R, 3R)-3-O-benzyl-1,2-O,O-isopropylidenethreitol [prepared by the method described by Ohno et al., Chem. Pharm. Bull., 33, 572 (1985)] and 44.10 ml of triethylamine in 1 liter of benzene, whilst ice-cooling. The mixture was stirring at room temperature for 1 hour, after which it was washed with water, dried over anhydrous magnesium sulfate and concentrated by evaporation under reduced pressure, to give 74.80 g of (2R, 3R)-2-benzyloxy-3,4-isopropylidenedioxybutyl methanesulfonate as a colorless oily material.

Nuclear Magnetic Resonance Spectrum (90 MHz, CDCl$_3$) δ ppm: 1.32 (3H, singlet); 1.40 (3H, triplet); 2.92 (3H, singlet); 3.4–4.5 (6H, multiplet) 4.65 (2H, singlet); 7.25 (5H, multiplet).

(b) A mixture of 74.80 g of the methanesulfonate prepared as described in step (a) above, 113.92 g of sodium bicarbonate and 169.39 g of sodium iodide in 1.1 liter of acetone was heated under reflux for 12 hours. At the end of this time, the reaction mixture was cooled, after which it was filtered with the aid of a Celite (trade mark) filter aid to remove insoluble materials. The solvent was stripped from the filtrate, and the residue was diluted with water and then extracted three times with ethyl acetate. The combined extracts were washed with water, dried over anhydrous magnesium sulfate and concentrated by evaporation under reduced pressure. The oily residue was subjected to column chromatography through 600 g of silica gel. 75.64 g of the title compound were obtained, as a colorless oil, from those fractions eluted with a 95:5 by volume mixture of hexane and ethyl acetate. It boiled at 130°–150° C./1 mmHg (133 Pa).

[α]$^{26}$+8.40° (c=1.25, CHCl$_3$).

Nuclear Magnetic Resonance Spectrum (90 MHz, CDCl$_3$) δ ppm: 1.36 (3H, singlet); 1.44 (3H, singlet); 3.16 (1H, doublet of doublets, J=10.5 & 7 Hz); 3.34 (1H, doublet of doublets, J=10.5 & 7 Hz); 3.57 (1H, ddd, J=7, 5 & 5 Hz); 3.78 (1H, doublet of doublets, J=8 & 6.5 Hz); 4.00 (1H, doublet of doublets, J=8 & 6.5 Hz); 4.33 (1H, doublet of triplets, J=6.5 & 5 Hz); 4.74 (2H, AB-quartet, J=12 Hz); 7.40 (5H, multiplet).

Infrared Absorption Spectrum (CHCl$_3$) ν$_{max}$ cm$^{-1}$: 518 (C-I).

Mass Spectrum (m/e): 362 (M$^+$) and 347 (M$^+$—CH$_3$).

Elemental analysis: Calculated for C$_{14}$H$_{19}$O$_3$I: C, 46.22%; H, 5.29%; I, 35.04%. Found: C, 46.47%; H, 5.18%; I, 35.11%.

PREPARATION 8

(2S, 3R)-3-O-Benzyl-4-iodo-1,2-O,O-isopropylidenebutane-1,2,3-triol

Following a procedure similar to that described in Preparation 1, 63.45 g of (2S, 3S)-2-benzyloxy-3,4-isopropylidenedioxybutyl methanesulfonate were prepared from 48.45 g of (2S, 3S)-3-O-benzyl-1,2-O,O-isopropylidenethreitol [prepared by the method of Ohno et al., Chem. Pharm. Bull., 33, 572 (1985)], 37.50 ml of triethylamine and 17.80 ml of methanesulfonyl chloride. Then, following a procedure similar to that described in Preparation 1, 66.87 g of the title compound were obtained by treating this methanesulfonate with 96.80 g of sodium bicarbonate and 143.90 g of sodium iodide.

[α]$^{26}$−8.40° (c=1.00, CHCl$_3$).

PREPARATION 9

Ethyl (4R, 5R)-4-benzyloxy-2-ethoxycarbonyl-5,6-isopropylidenedioxyhexanoate

A solution of 40.00 g of diethyl malonate dissolved in 200 ml of dimethylformamide was added dropwise to a mixture of 12.00 g of sodium hydride (as a 55% w/w dispersion in mineral oil) and 600 ml of dimethylformamide, whilst maintaining the temperature within the range between 5° and 8° C. When the dropwise addition was complete, the mixture was stirred at room temperature for 1 hour, and then a solution of 75.38 g of (2R, 3S)-3-O-benzyl-4-iodo-1,2-O,O-isopropylidenebutane-1,2,3-triol (prepared as described in Preparation 7) dissolved in 300 ml of dimethylformamide was added dropwise whilst maintaining the temperature at 5° to 8° C. The mixture was then stirred at 100° C. for 2 hours, after which the mixture was cooled, poured into 2 liters of water and then extracted three times with ethyl acetate. The combined extracts were washed with water, dried over anhydrous magnesium sulfate and concentrated by evaporation under reduced pressure. The oily residue was subjected to column chromatography through 1 kg of silica gel. 68.92 g of the title compound were obtained, as a colorless oil boiling at 170°–180° C./1 mmHg (133 Pa), from those fractions eluted with a 9:1 by volume mixture of hexane and ethyl acetate.

$[\alpha]^{25}+39.1°$ (c=1.00, CHCl$_3$).

Nuclear Magnetic Resonance Spectrum (90 MHz, CDCl$_3$) δ ppm: 1.22 (3H, triplet, J=7.5 Hz); 1.24 (3H, triplet, J=7.5 Hz); 1.38 (3H, singlet); 1.46 (3H, singlet); 2.01 (2H, triplet, J=6.5 Hz); 3.4–4.4 (5H, multiplet); 4.15 (4H, multiplet); 4.68 (2H, AB-quartet, J=12 Hz); 7.38 (5H, multiplet).

Infrared Absorption Spectrum (CHCl$_3$) $\nu_{max}$ cm$^{-1}$: 1730 (—O—CO—).

Mass Spectrum (m/e): 379 (M$^+$—CH$_3$).

Elemental analysis: Calculated for C$_{21}$H$_{30}$O$_7$: C, 63.94%; H, 7.67%, Found: C, 63.66%; H, 7.49%.

PREPARATION 10

Ethyl (4S, 5S)-4-benzyloxy-2-ethoxycarbonyl-5,6-isopropylidenedioxyhexanoate

Following a procedure similar to that described in Preparation 9, 58.40 g of the title compound were obtained from 35.48 g of diethyl malonate, 10.63 g of sodium hydride (as a 55% w/w dispersion in mineral oil) and 66.87 g of (2S, 3R)-3-O-benzyl-4-iodo-1,2-O,O-isopropylidenebutane-1,2,3-triol (prepared as described in Preparation 8).

$[\alpha]^{26}-39.5°$ (c=1.00, CHCl$_3$).

PREPARATION 11

Ethyl (4R, 5R)-4-benzyloxy-5,6-isopropylidenedioxyhexanoate 68.70 g of ethyl (4R, 5R)-4-benzyloxy-2-ethoxycarbonyl-5,6-isopropylidenedioxyhexanoate (prepared as described in Preparation 9), 12.20 g of sodium chloride and 6.51 ml of water were mixed with 1.1 liter of dimethyl sulfoxide. The mixture was then heated under reflux on an oil bath kept at 210° C. for 2 hours. At the end of this time, the reaction mixture was cooled and then poured into 2.5 liters of water and extracted three times with ethyl acetate. The combined extracts were washed with water, dried over anhydrous magnesium sulfate and concentrated by evaporation under reduced pressure. The resulting oily residue was subjected to column chromatography through 1 kg of silica gel. 41.79 g of the title compound were obtained from those fractions eluted with a 95:5 by volume mixture of hexane and ethyl acetate. It was in the form of a colorless oil boiling at 150°–160° C./1 mmHg (133 Pa).

$[\alpha]^{26}+47.6°$ (c=1.32, methanol).

Nuclear Magnetic Resonance Spectrum (90 MHz, CDCl$_3$) δ ppm: 1.23 (3H, triplet, J=7.5 Hz); 1.38 (3H, singlet); 1.45 (3H, singlet); 1.6–2.0 (2H, multiplet); 2.43 (2H, triplet, J=7.5 Hz); 3.3–3.6 (1H, multiplet); 3.6–4.4 (3H, multiplet); 4.10 (2H, quartet, J=7.5 Hz); 4.69 (2H, AB-quartet, J=12 Hz); 7.38 (5H, singlet).

Infrared Absorption Spectrum (CHCl$_3$) $\nu_{max}$ cm$^{-1}$: 1730 (—O—CO—).

Mass Spectrum (m/e); 322 (M$^+$) and 307 (M$^+$—CH$_3$).

Elemental analysis: Calculated for C$_{18}$H$_{26}$O$_5$: C, 67.06%; H, 8.13%. Found: C, 67.06%; H, 8.13%.

PREPARATION 12

Ethyl (4S, 5S)-4-benzyloxy-5,6-isopropylidenedioxyhexanoate

Following a procedure similar to that described in Preparation 11, 41.79 g of the title compound were obtained from 58.68 g of ethyl (4S, 5S)-4-benzyloxy-2-ethoxycarboyl-5,6-isopropylidenedioxyhexanoate (prepared as described in Preparation 10), 10.43 g of sodium chloride and 5.56 ml of water.

$[\alpha]^{26}-47.4°$ (c=1.30, CHCl$_3$).

PREPARATION 13

(4R, 5R)-4-Benzyloxy-5,6-isopropylidenedioxyhexan-1-ol

A solution of 47.65 g of ethyl (4R, 5R)-4-benzyloxy-5,6-isopropylidenedioxyhexanoate (prepared as described in Preparation 11) dissolved in 250 ml of tetrahydrofuran was added dropwise to a suspension of 6.75 g of lithium hydride in 750 ml of tetrahydrofuran at a temperature maintained within the range between 5° and 8° C. The reaction mixture was then stirred at room temperature for 2 hours, after which 27.00 ml of a 4% w/v aqueous solution of sodium hydroxide was added dropwise to it at a temperature maintained within the range between 4° and 7° C. The suspension was then filtered with the aid of a Celite filter aid, and the filtrate was evaporated to dryness under reduced pressure. The residue was subjected to column chromatography through 800 g of silica gel. 37.34 g of the title compound were obtained, as a colorless oil boiling at 150°–160° C./1 mmHg (133 Pa), from those fractions eluted with a 2:1 by volume mixture of hexane and ethyl acetate.

$[\alpha]^{26}+41.8°$ (c=1.06, CHCl$_3$).

Nuclear Magnetic Resonance Spectrum (90 MHz, CDCl$_3$) δ ppm: 1.36 (3H, triplet); 1.44 (3H, singlet); 1.5–1.8 (4H, multiplet); 1.71 (1H, singlet); 3.4–3.8 (4H, multiplet); 4.02 (1H, doublet of triplets, J=7.5, 6 Hz); 4.25 (1H, doublet of triplets, J=7.5, 6 Hz); 4.71 (2H, AB-quartet, J=12 Hz); 7.38 (5H, multiplet).

Infrared Absorption Spectrum (CHCl$_3$) $\nu_{max}$ cm$^{-1}$: 3450 (—OH).

Mass Spectrum (m/e): 280 (M$^+$) and 265 (M$^+$—CH$_3$).

Elemental analysis: Calculated for C$_{16}$H$_{24}$O$_4$: C, 68.55%; H, 8.63%. Found: C, 68.23%; H, 8.58%.

PREPARATION 14

(4S, 5S)-4-Benzyloxy-5,6-isopropylidenedioxyhexan-1-ol

Following a procedure similar to that described in Preparation 13, 32.15 g of the title compound were obtained, as a colorless oil, from 41.00 g of ethyl (4S, 5S)-4-benzyloxy-5,6-isopropylidenedioxyhexanoate (prepared as described in Preparation 12) and 5.78 g of lithium aluminum hydride.

$[\alpha]^{26}-42.5°$ (c=1.10, CHCl$_3$).

PREPARATION 15

(2R, 3R)-3-Benzyloxy-6-(t-butyldiphenylsilyloxy)-1,2-isopropylidenedioxyhexane

A solution of 20.77 g of t-butyldiphenylsilyl chloride dissolved in 90 ml of dimethylformamide was added dropwise to a solution of 19.27 g of (4R, 5R)-4-benzyloxy-5,6-isopropylidenedioxyhexan-1-ol (prepared as described in Preparation 13) and 10.29 g of imidazole in 300 ml of dimethylformamide, whilst maintaining the temperature in the range from 5° to 7° C. The reaction mixture was then stirred at room temperature for 3 hours, after which it was poured into 2 liters of water and then extracted three times with ethyl acetate. The combined extracts were washed with water, dried over anhydrous magnesium sulfate and then concentrated by evaporation under reduced pressure. The oily residue was subjected to column chromatography through 700 g of silica gel. 32.80 g of the title compound were obtained, as a colorless oil, from those fractions eluted with mixtures of hexane and ethyl acetate ranging from 98:2 to 95:5 by volume.

$[\alpha]^{26}+21.4°$ C. (c=1.11, $CHCl_3$).

Nuclear Magnetic Resonance Spectrum (90 MHz, $CDCl_3$) δ ppm: 1.04 (9H, singlet); 1.37 (3H, singlet); 1.43 (3H, singlet); 1.4–1.8 (4H, multiplet); 3.3–3.8 (4H, multiplet); 4.00 (1H, doublet of triplets, J=7.5 & 6 Hz); 4.20 (1H, doublet of triplets, J=7.5 & 6 Hz); 4.66 (2H, AB-quartet, J=12 Hz); 7.2–7.8 (15H, multiplet).

Infrared Absorption Spectrum ($CHCl_3$) $\nu_{max}$ cm$^{-1}$: 1100 (Si—O).

Mass Spectrum (m/e): 503 (M$^+$—$CH_3$).

Elemental analysis: Calculated for $C_{32}H_{42}O_4Si$: C 74.09%; H, 8.16%. Found: C, 74.20%; H, 8.18%.

PREPARATION 16

(2S, 3S)-3-Benzyloxy-6-(t-butyldiphenylsilyloxy)-1,2-isopropylidenedioxyhexane

Following a procedure similar to that described in Preparation 15, 30.97 g of the title compound were obtained, as a colorless oil, from 18.00 g of (4S, 5S)-4-benzyloxy-5,6-isopropylidenedioxyhexan-1-ol (prepared as described in Preparation 14), 9.62 g of imidazole and 19.41 g of t-butyldiphenylsilyl chloride.

$[\alpha]^{26}-20.8°$ (c=1.25, $CHCl_3$).

PREPARATION 17

(2R, 3R)-3-Benzyloxy-6-(t-butyldiphenylsilyloxy)hexane-1,2-diol 32.49 g of (2R, 3R)-3-benzyloxy-6-(t-butyldiphenylsilyloxy)-1,2-isopropylidenedioxyhexane (prepared as described in Preparation 15) were dissolved in a mixture of 300 ml of acetic acid and 30 ml of water. The resulting solution was stirred at room temperature for 17 hours and then at 50° C. for 2 hours. At the end of this time, the solution was cooled, and the solvent was removed by distillation under reduced pressure. The residue was subjected to column chromatography through 500 g of silica gel. 27.40 g of the title compound were obtained, as a colorless oil, from the fraction eluted with a 1:2 by volume mixture of ethyl acetate and hexane.

$[\alpha]^{26}-20.4°$ (c=1.12, $CHCl_3$).

Nuclear Magnetic Resonance Spectrum (90 MHz, $CDCl_3$) δ ppm: 1.05 (9H, singlet); 1.5–1.9 (4H, multiplet); 1.9–2.3 (1H, multiplet); 2.3–2.65 (1H, multiplet); 3.4–3.9 (6H, multiplet); 4.53 (2H, AB-quartet, J=12 Hz); 7.2–7.8 (15H, multiplet).

Infrared Absorption Spectrum ($CHCl_3$) $\nu_{max}$ cm$^{-1}$: 3590, 3460 (—OH) and 1100 (Si—O).

Mass Spectrum (m/e): 479 (M$^+$+1)

PREPARATION 18

(2S, 3S)-3-Benzyloxy-6-(t-butyldiphenylsilyloxy)hexane-1,2-diol

Following a procedure similar to that described in Preparation 17, 26.15 g of the title compound were obtained, as a colorless oil, from 30.48 g of (2S, 3S)-3-benzyloxy-6-(t-butyldiphenylsilyloxy)-1,2-isopropylidenedioxyhexane (prepared as described in Preparation 16), 300 ml of acetic acid and 30 ml of water.

$[\alpha]^{26}+20.6°$ (C=1.15, $CHCl_3$).

PREPARATION 19

(2R, 3R)-3-Benzyloxy-6-(t-butyldiphenylsilyloxy)-1-triphenylmethoxyhexan-2-ol 18.33 g of triphenylmethyl chloride were added to a solution of 26.22 g of (2R, 3R)-3-benzyloxy-6-(t-butyldiphenylsilyloxy)hexane-1,2-diol (prepared as described in Preparation 17) and 18.40 ml of triethylamine in 500 ml of toluene. The resulting mixture was heated under reflux for 3 hours. At the end of this time, it was cooled and then diluted with water. It was then extracted three times with ethyl acetate. The combined extracts were washed, in turn, with water, with a saturated aqueous solution of sodium bicarbonate and with a saturated aqueous solution of sodium chloride, after which they were dried over anhydrous magnesium sulfate, and the solvent was stripped off by evaporation under reduced pressure. The resulting oily residue was dissolved in 270 ml of tetrahydrofuran, and then 90 ml of a saturated aqueous solution of sodium bicarbonate were added, and the resulting mixture was stirred at room temperature for 1 hour. After this work-up, 40 g of the oily product were subjected to column chromatography through 500 g of silica gel, 37.01 g of the title compound were obtained, as a colorless oil, from those fractions eluted with mixtures of hexane and ethyl acetate ranging from 95:5 to 9:1 by volume.

$[\alpha]^{25}-3.55°$ (c=1.03, $CHCl_3$).

Nuclear Magnetic Resonance Spectrum (90 MHz, $CDCl_3$) δ ppm: 1.05 (9H, singlet); 1.4–1.8 (4H, multiplet); 2.30 (1H, doublet, J=6 Hz); 3.22 (2H, doublet, J=6 Hz); 3.5–3.9 (4H, multiplet); 4.45 (2H, AB-quartet, J=12 Hz); 7.1–7.8 (30H, multiplet).

Infrared Absorption Spectrum ($CHCl_3$) $\nu_{max}$ cm$^{-1}$: 3580 (—OH) and 1100 (O—Si).

Mass Spectrum (m/e): 477 [M$^+$-HC($CH_3$)$_3$].

Elemental analysis: Calculated for $C_{48}H_{52}O_4Si$: C, 79.96%; H, 7.27%. Found: C, 79.71%; H, 7.11%.

PREPARATION 20

(2S, 3S)-3-Benzyloxy-6-(t-butyldiphenylsilyloxy)-1-triphenylmethoxyhexan-2-ol

Following a procedure similar to that described in Preparation 19, 36.50 g of the title compound were obtained, as a colorless oil, from 25.96 g of (2S, 3S)-3-benzyloxy-6-(t-butyldiphenylsilyloxy)hexane-1,2-diol (prepared as described in Preparation 18), 18.20 ml of triethylamine and 18.11 g of triphenylmethyl chloride.

$[\alpha]^{25}+3.56$ (C=1.01, $CHCl_3$).

PREPARATION 21

(2R, 3R)-3-Benzyloxy-6-hydroxy-1-triphenylmethoxy-2-hexyl methanesulfonate (a) 4.75 ml of methanesulfonyl chloride were added dropwise, whilst ice-cooling at 5° C., to a solution of 36.89 g of (2R, 3R)-3-benzyloxy-6-(t-butyldiphenylsilyloxy)-1-triphenylmethoxyhexan-2-ol (prepared as described in Preparation 19) and 8.56 ml of triethylamine dissolved in 500 ml of methylene chloride. The mixture was stirred at room temperature for 1 hour, after which it was poured into water. The organic layer was separated, washed with a saturated aqueous solution of sodium chloride, dried over anhydrous magnesium sulfate and concentrated by evaporation under reduced pressure, to give 40.91 g of (2R, 3R)-3-benzyloxy-6-(t-butyldiphenylsilyloxy)-1-triphenylmethoxy-2-hexyl methaneslfonate as a colorless oil.

Nuclear Magnetic Resonance Spectrum (90 MHz, CDCl$_3$) δ ppm: 1.01 (9H, singlet); 1.3–1.8 (4H, multiplet); 2.96 (3H, singlet); 3.0–3.9(5H, multiplet); 4.50 (2H, singlet); 4.6–4.9 (1H, multiplet); 7.1–7.8 (30H, multiplet).

(b) 61.4 ml of a 1N solution of tetrabutylammonium fluoride in tetrahydrofuran were added dropwise, whilst ice-cooling at 5° C., to a solution of 40.91 g of the methanesulfonate [prepared as described in step (a) above] in 500 ml of tetrahydrofuran, and the mixture was stirred at room temperature for 14 hours. It was then diluted with water, and extracted three times with ethyl acetate. The combined extracts were washed with water, dried over anhydrous magnesium sulfate and concentrated by evaporation under reduced pressure, and the residue was subjected to column chromatography through 700 g of silica gel. 26.45 g of the title compound were obtained, as a colorless oil, from those fractions eluted with mixtures of hexane and ethyl acetate ranging from 4:1–2:1 by volume.

$[\alpha]^{25}$ +21.7° (c=1.22, CHCl$_3$).

Nuclear Magnetic Resonance Spectrum (90 MHz, CDCl$_3$) δ ppm: 1.37 (1H, singlet); 1.4–1.8 (4H, multiplet); 3.00 (3H, singlet); 3.30 (1H, doublet of doublets, J=11 & 6 Hz); 3.4–3.6 (2H, multiplet); 3.60 (1H, doublet of doublets, J=11 & 3 Hz); 3.6–3.9 (1H, multiplet); 4.56 (2H, singlet); 4.82 (1H, ddd, J=6, 6 & 3 Hz); 7.2–7.6 (20H, multiplet).

Infrared Absorption Spectrum (CDCl$_3$) $\nu_{max}$ cm$^{-1}$: 3500 (—OH), 1360 and 1170 (—SO$_2$—).

Mass Spectrum (m/e): 483 (M$^+$—C$_6$H$_5$) and 468 (M$^+$—C$_6$H$_5$CH$_3$).

PREPARATION 22

(2S, 3S)-3-Benzyloxy-6-hydroxy-1-triphenylmethoxy-2-hexyl methanesulfonate

Following a procedure similar to that described in Preparation 21, 25.18 g of the title compound were obtained, as a colorless oil, from 35.60 g of (2S, 3S)-3-benzyloxy-6-(t-butyldiphenylsilyloxy)-1-triphenylmethoxyhexan-2-ol (prepared as described in Preparation 20).

$[\alpha]^{25}$ −21.7° (c=1.23, CHCl$_3$).

PREPARATION 23

(2S, 3R)-3-Benzyloxy-2-triphenylmethoxymethyltetrahydropyran

A solution of 26.08 g of (2R, 3R)-3-benzyloxy-6-hydroxy-1-triphenylmethoxy-2-hexyl methanesulfonate (prepared as described in Preparation 21) dissolved in 290 ml of t-butanol was added dropwise to a solution of 7.01 g of potassium t-butoxide in 250 ml of t-butanol, whilst maintaining the temperaure at 25° C. The mixture was then stirred at 40° C. for 4 hours. At the end of this time, 0.56 ml of acetic acid were added to the mixture, and the solvent was removed by distillation under reduced pressure. The residue was diluted with water, and then extracted three times with ethyl acetate. The combined extracts were washed with a saturated aqueous solution of sodium bicarbonate and with a saturated aqueous solution of sodium chloride, dried over anhydrous magnesium sulfate and concentrated by evaporation under reduced pressure. The residue was then subjected to column chromatography through 430 g of silica gel. 21.04 g of the title compound were obtained from those fractions eluted with a 95:5 by volume mixture of hexane and ethyl acetate, as crystals melting at 86.0°–88.0° C. (after recrystallization from methanol).

$[\alpha]^{25}$ −32.8° (c=1.01, CHCl$_3$).

Nuclear Magnetic Resonance Spectrum (270 MHz, CDCl$_3$) δ ppm: 1.41 (1H, dddd, J=12.3, 10.9, 9.3 & 6.7 Hz); 1.70 (2H, multiplet); 2.26 (1H, ddddd, J=12.3, 4.2, 3.9, 3.9 & 1 Hz); 3.20 (1H, doublet of doublets, J=9.8 & 5.0 Hz); 3.37 (1H, ddd, J=9.3, 5.0 & 2.0 Hz); 3.39 (1H, ddd, J=11.4, 9.3 & 5.3 Hz); 3.48 (1H, doublet of doublets, J=9.8 & 2.0 Hz); 3.49 (1H, ddd, J=10.9, 9.3 & 4.2 Hz); 4.00 (1H, dddd, J=11.4, 2.9, 2.9 & 1 Hz); 4.38 (2H, AB-quartet, J=11.5 Hz); 7.0–7.5 (20H, multiplet).

Infrared Absorption Spectrum (CHCl$_3$) $\nu_{max}$ cm$^{-1}$: 1595, 1490, 1450 (C$_6$H$_5$—), 1090 and 1070 (C—O—C).

Mass Spectrum (m/e): 387 (M$^+$—C$_6$H$_5$) and 373 (M$^+$—C$_7$H$_7$).

Elemental analysis: Calculated for C$_{32}$H$_{32}$O$_3$: C, 82.73%; H, 6.94%. Found: C, 82.56%; H, 6.83%.

PREPARATION 24

(2R, 3S)-3-Benzyloxy-2-triphenylmethoxymethyltetrahydropyran

Following a procedure similar to that described in Preparation 21, 20.12 g of the title compound were obtained, as crystals, melting at 86.5°–88.5° C., from 24.98 g of (2S, 3S)-3-benzyloxy-6-hydroxy-1-triphenylmethoxy-2-hexyl methanesulfonate (prepared as described in Preparation 22) and 6.06 g of potassium t-butoxide.

$[\alpha]^{25}$ +33.0 (c=1.00, CHCl$_3$).

PREPARATION 25

(2S, 3R)-3-Hydroxy-2-triphenylmethoxymethyltetrahydropyran 3.513 g of (2S, 3R)-3-benzyloxy-2-triphenylmethoxymethyltetrahydropyran (prepared as described in Preparation 23) were dissolved in 120 ml of ethanol and hydrogenated at room temperature for 30 hours in the presence of 1.852 g of 10% w/w palladium on activated carbon in a Paal's apparatus at a hydrogen pressure of 4 atmospheres (about 4 bars). The catalyst was filtered off and the filtrate was freed from the solvent by evaporation under reduced pressure. The residue was subjected to column chromatography through 90 g of silica gel, 2.557 g of the title compound were obtained, as a colorless oil, from those fractions eluted with a 7:1 by volume mixture of hexane and ethyl acetate.

$[\alpha]^{25} + 38.2°$ (c=1.07, CHCl$_3$).

Nuclear Magnetic Resonance Spectrum (90 MHz, CDCl$_3$) δ ppm: 1.2–1.8 (3H, multiplet); 1.9–2.3 (1H, multiplet); 3.00 (1H, singlet); 3.1–3.7 (5H, multiplet); 3.75–4.05 (1H, multiplet); 7.2–7.7 (15H, multiplet).

Infrared Absorption Spectrum (CHCl$_3$) $\nu_{max}$ cm$^{-1}$: 3500 (OH), 1600, 1490, 1450 (—Ph) and 1090 (C—O—C).

Mass Spectrum (m/e): 374 (M$^+$) and 297 (M$^+$—C$_6$H$_5$).

PREPARATION 26

(2R, 3S)-3-Hydroxy-2-(triphenylmethoxymethyl)tetrahydropyran

Following a procedure similar to that described in Preparation 25, 2.075 g of the title compound were obtained, as a colorless oil, from 2.835 g of (2R, 3S)-3-benzyloxy-2-triphenylmethoxymethyltetrahydropyran (prepared as described in Preparation 24) in the presence of 1.499 g of 10% w/w palladium on activated carbon.

$[\alpha]^{25} - 38.0°$ (c=1.12, CHCl$_3$).

PREPARATION 27

(2S, 3R)-2-(Triphenylmethoxymethyl)tetrahydropyran-3-yl N-heptadecylcarbamate A solution of 4.782 g of stearic acid, 3.62 ml of diphenylphosphoryl azide and 2.34 ml of triethylamine dissolved in 100 ml of benzene was heated under reflux for 3 hours. At the end of this time, the reaction mixture was cooled and then diluted with ethyl acetate. It was then washed with a saturated aqueous solution of sodium bicarbonate and dried over anhydrous magnesium sulfate. The solvent was then removed by distillation under reduced pressure, and the residue was dissolved in 25 ml of toluene. A solution of 2.34 ml of triethylamine and 2.518 g of (2S, 3R)-3-hydroxy-2-triphenylmethoxymethyltetrahydropyran (prepared as described in Preparation 25) dissolved in 25 ml of toluene was then added to the resulting solution. The mixture was then heated at 100° C. for 90 hours, after which it was allowed to cool and then poured into water saturated with sodium bicarbonate. This was then extracted three times with ethyl acetate. The combined extracts were dried over anhydrous magnesium sulfate and concentrated by evaporation under reduced pressure, to give an oily residue. This was subjected to column chromatography through 120 g of silica gel. 3.131 g of the title compound were obtained, as a colorless oil, from those fractions eluted with a 7:1 by volume mixture of hexane and ethyl acetate.

$[\alpha]^{25} - 28.5°$ (c=1.04, CHCl$_3$).

Nuclear Magnetic Resonance Spectrum (90 MHz, CDCl$_3$) δ ppm: 0.7–2.4 (37H, multiplet); 2.8–3.6 (6H, multiplet); 3.8–4.1 (1H, multiplet); 4.2–4.8 (2H, multiplet); 7.1–7.6 (15H, multiplet).

Infrared Absorption Spectrum (CHCl$_3$) $\nu_{max}$ cm$^{-1}$: 3460 (NH), 1720 and 1510 (—NH—CO).

Mass Spectrum (m/e): 412 (M$^+$—C$_{19}$H$_{15}$), 396 (M$^+$—C$_{19}$H$_{15}$O) and 382 (M$^+$—C$_{21}$H$_{17}$O).

PREPARATION 28

(2R, 3S)-2-(Triphenylmethoxymethyl)tetrahydropyran-3-yl N-heptadecylcarbamate Following a procedure similar to that described in Preparation 11, 2.491 g of the title compound was obtained, as a colorless oil, from 3.553 g of stearic acid, 2.69 ml of diphenylphosphoryl azide and 1.871 g of (2R, 3S)-3-hydroxy-2-(triphenylmethoxymethyl)tetrahydropyran (prepared as described in Preparation 26).

$[\alpha]^{25} + 28.8°$ (c=1.13, CHCl$_3$).

PREPARATION 29

(2S, 3R)-2-Hydroxymethyltetrahydropyran-3-yl N-heptadecylcarbamate 240.0 mg of p-toluenesulfonic acid were added to a solution of 2.753 g of (2S, 3R)-2-(triphenylmethoxymethyl)tetrahydropyran-3-yl N-heptadecylcarbamate (prepared as described in Preparation 27) dissolved in 55 ml of methanol, and the mixture was heated under reflux for 1 hour. At the end of this time, the reaction mixture was cooled, and 352.6 mg of sodium bicarbonate were added. The methanol was then removed by distillation under reduced pressure, and ethyl acetate was added. Insoluble materials were filtered off, and the filtrate was concentrated by evaporation under reduced pressure. The residue was subjected to column chromatography through 55 g of silica gel. 1.476 g of the title compound was obtained from those fractions eluted with mixtures of hexane and ethyl acetate ranging from 2:1 to 1:1 by volume in the form of crystals melting at 92.0°–93.5° C. (after recrystallisation from diethyl ether).

$[\alpha]^{25} - 7.20°$ (c=1.00, CHCl$_3$).

Nuclear Magnetic Resonance Spectrum (90 MHz, CDCl$_3$) δ ppm: 0.7–2.3 (37H, multiplet); 2.6–2.85 (1H, multiplet); 2.9–3.8 (6H, multiplet); 3.8–4.1 (1H, multiplet); 4.4–4.9 (2H, multiplet).

Infrared Absorption Spectrum (CHCl$_3$) $\nu_{max}$ cm$^{-1}$: 3450 (—NH, —OH), 1710 and 1510 (—NH—CO).

Mass Spectrum (m/e): 414 (M$^+$+1) and 382 (M$^+$—CH$_2$OH).

Elemental analysis: Calculated for C$_{24}$H$_{47}$NO$_4$: C, 69.69%; H, 11.45%; N, 3.39%. Found: C, 69.33%; H, 11.40%; N, 3.53%.

PREPARATION 30

(2R, 3S)-2-Hydroxymethyltetrahydropyran-2-yl N-heptadecylcarbamate

Following a procedure similar to that described in Preparation 29), 1.305 g of the title compound was obtained, as crystals melting at 92.5°–93.5° C., from 2.400 g of (2R, 3S)-2-(triphenylmethoxymethyl)tetrahydropyran-3-yl N-heptadecylcarbamate (prepared as described in Preparation 28).

$[\alpha]^{25} + 7.25°$ (c=1.02, CHCl$_3$).

PREPARATION 31

(2S, 3R)-2-[N-(5-Bromopentyl)carbamoyloxymethyl]tetrahydropyran-3-yl N-heptadecylcarbamate Following a procedure similar to that described in Preparation 6, 1.270 g of the title compound was obtained, as a waxy solid melting at 71.0°–72.0° C., from 1.706 g of 5-bromohexanoic acid, 1.88 ml of diphenylphosphoryl azide and 1.206 g of (2S, 3R)-2-hydroxymethyltetrahydropyran-3-yl N-heptadecylcarbamate (prepared as described in Preparation 29).

$[\alpha]^{25} -26.4°$ (c=1.18, CHCl$_3$).

PREPARATION 32

(2R, 3S)-2-[N-(5-Bromopentyl)carbamoyloxymethyl]tetrahydropyran-3-yl N-heptadecylcarbamate Following a procedure similar to that described in Preparation 6), 1.283 g of the title compound was obtained, as a waxy solid melting at 71.5°–72.0° C., from 1.698 g of 5-bromohexanoic acid, 1.88 ml of diphenylphosphoryl azide and 1.200 g of (2R, 3S)-2-hydroxymethyltetrahydropyran-2-yl N-heptadecylcarbamate (prepared as described in Preparation 30).

$[\alpha]^{25} +26.5°$ (c=1.00, CHCl$_3$).

PREPARATION 33 dl-cis-2-Benzyloxymethyltetrahydropyran-3-ol (a) 2.22 g of dl-trans-2-benzyloxymethyltetrahydropyran-3-ol (prepared as described in Preparation 2) were dissolved in 20 ml of acetone, and were then oxidized with 6 ml of Jones' reagent (containing 1.60 g of chromic anhydride), whilst ice-cooling. The reaction mixture was then stirred at room temperature for 1 hour, after which it was poured into water and extracted twice with ethyl acetate. The combined extracts were washed with water, dried and concentrated by evaporation under reduced pressure, to give 2.08 g of a crude oily ketonic compound.

(b) The whole of the ketonic compound prepared as described in step (a) above was dissolved, without further purification, in 10 ml of tetrahydrofuran and was then reduced at a temperature between 0° and 5° C. with 12 ml of a 1M tetrahydrofuran solution of L-selectride. The solution was then stirred for 30 minutes whilst ice-cooling and for 2 hours at room temperature. 6 ml of a 10% w/v aqueous solution of sodium hydroxide were then added dropwise at 5°–15° C., and then 6 ml of 35% v/v aqueous hydrogen peroxide were added dropwise to the mixture at 15°–30° C. The organic layer was then separated, dried over anhydrous magnesium sulfate and concentrated by evaporation under reduced pressure, to give an oily residue. This was purified by column chromatography through 60 g of silica gel. Those fractions eluted with mixtures of hexane and ethyl acetate ranging from 100:15 to 2:1 by volume were worked up, to give 1.135 g of the title compound as a colorless liquid boiling at a bath temperature of 130°–140° C./1 mmHg (about 133 Pa).

Nuclear Magnetic Resonance Spectrum (90 MHz, CDCl$_3$) δ ppm: 1.25–2.30 (4H, multiplet); 2.68 (1H, doublet, J=6 Hz); 3.3–3.7 (4H, multiplet); 3.80 (1H, multiplet); 4.03 (1H, multiplet); 4.59 (2H, singlet); 7.2–7.5 (5H, multiplet).

Mass Spectrum (m/e): 222 (M+).

PREPARATION 34 dl-cis-2-Hydroxymethyltetrahydropyran-3-yl N-octadecylcarbamate 2.627 g of nonadecanoic acid were reacted, in a similar manner to that described in Preparation 3, with 0.815 g of dl-cis-2-benzyloxymethyltetrahydropyran-3-ol (prepared as described in Preparation 33). The resulting crude product was purified by column chromatography through 70 g of silica gel. Those fractions eluted with a 1:5 by volume mixture of ethyl acetate and hexane afforded 1.05 g of dl-cis-2-benzyloxymethyltetrahydropyran-3-yl N-octadecylcarbamate.

The whole of this product was dissolved in 30 ml of methanol, and was then hydrogenated at room temperature for 8 hours in the presence of 0.50 g of a 10% w/w palladium on activated carbon catalyst and hydrogen at an initial pressure of 4 atmospheres (about 4 bars) in a Paar's apparatus. The catalyst was removed by filtration, and then the solvent was distilled off under reduced pressure. The residue was subjected to column chromatography through 20 g of silica gel. Those fractions eluted with mixtures of ethyl acetate and hexane ranging from 1:5 to 1:2 by volume were worked up and then recrystallized from a mixture of diethyl ether and hexane, to give 0.732 g of the title compound as crystals melting at 85°–86° C.

Nuclear Magnetic Resonance Spectrum (90 MHz, CDCl$_3$) δ ppm: 0.7–2.2 (39H, multiplet); 2.9–3.8 (7H, multiplet); 3.9–4.2 (1H, multiplet); 4.65–5.1 (2H, multiplet).

Infrared Absorption Spectrum (CHCl$_3$) $\nu_{max}$ cm$^{-1}$: 3600 (—OH), 3450 (—NH—), 1700 (—O—CO—).

Mass Spectrum (m/e): 427 (M+), 396 (M+—CH$_2$OH).

Elemental Analysis: Calculated for C$_{25}$H$_{49}$NO$_4$: C, 70.21%; H, 11.55%; N, 3.28%. Found: C, 70.27%; H, 11.73%; N, 3.28%.

PREPARATION 35 dl-trans-2-Benzyloxymethyl-3-(tetrahydropyran-2-yloxy)tetrahydropyran 2.22 g of dl-trans-2-benzyloxymethyltetrahydropyran-3-ol (prepared as described in Preparation 2), 2.65 ml of dihydropyran and 0.05 g of pyridinium p-toluenesulfonate were dissolved in 40 ml of methylene chloride, and the mixture was stirred at room temperature for 4 hours. The solvent was then distilled off to give a residue, which was subjected to column chromatography through 80 g of silica gel. Those fractions eluted with mixtures of hexane and diethyl ether ranging from 6:1 to 5:1 by volume were worked up, to afford 2.93 g of the title compound as a colorless oil.

Nuclear Magnetic Resonance Spectrum (90 MHz, CDCl$_3$) δ ppm: 1.1–2.4 (10H, multiplet); 3.15–4.15 (8H, multiplet); 4.57 (2H, AB-quartet, J=12 Hz); 4.78 (1H, multiplet); 7.35 (5H, multiplet).

Mass Spectrum (m/e): 306 (M+).

Elemental Analysis: Calculated for C$_{18}$H$_{26}$O$_4$; C, 70.56%; H, 8.55%. Found: C, 70.65%; H, 8.45%.

PREPARATION 36 dl-trans-3-(Tetrahydropyran-2-yloxy)tetrahydropyran-2-ylmethanol 2.93 g of dl-trans-2-benzyloxymethyl-3-(tetrahydropyran-2-yloxy)tetrahydropyran (prepared as described in Preparation 35) were dissolved in 130 ml of tetrahydrofuran and were then hydrogenated at room temperature for 8 hours in the presence of 1.30 g of a 10% w/w palladium on activated carbon catalyst and of hydrogen at an initial pressure of 4 atmospheres (about 4 bars). The catalyst was removed by filtration, and then the solvent was distilled off. The resulting residue was purified by column chromatography through 50 g of silica gel. Those fractions eluted with mixtures of hexane and diethyl ether ranging from 2:1 to 1:1 by volume were worked up to give 1.87 g of the title compound as a colorless oil.

Nuclear Magnetic Resonance Spectrum (90 MHz, CDCl$_3$) δ ppm: 2.2-2.4 (10H, multiplet); 2.77 (1H, triplet, J=7 Hz); 3.1-4.1 (8H, multiplet); 4.70 (1H, multiplet).

Infrared Absorption Spectrum (CDCl$_3$) $\nu_{max}$ cm$^{-1}$: 3600, 3480 (—OH).

Elemental Analysis: Calculated for C$_{11}$H$_{20}$O$_4$: C, 61.12%; H, 9.33%. Found: C, 60.75%; H, 9.29%.

PREPARATION 37 dl-(trans-3-Hydroxytetrahydropyran-2-yl)methyl N-octadecylcarbamate 6.247 g of nonadecanoic acid were reacted with 1.809 g of dl-trans-3-(tetrahydropyran-2-yloxy)tetrahydropyran-2-ylmethanol (prepared as described in Preparation 36) on an oil bath at 85° C. for 24 hours, in a manner similar to that described in Preparation 3. The reaction mixture was then cooled to room temperature, after which solids were filtered off and the solvent was removed by evaporation under reduced pressure. The residue was purified by column chromatography through 100 g of silica gel. Those fractions eluted with a 1:5:5 by volume mixture of diethyl ether, hexane and methylene chloride were worked up to give 4.20 g of dl-[trans-3-(tetrahydropyran-2-yloxy)tetrahydropyran-2-yl]methyl N-octadecylcarbamate as a solid.

The whole of this compound was dissolved in 30 ml of a 1:2 by volume mixture of tetrahydrofuran and methanol, and then 0.20 g of camphorsulfonic acid was added to the solution. The reaction mixture was then stirred at room temperature for 45 minutes, after which 10 ml of a saturated aqueous solution of sodium bicarbonate was added. The solvent was removed by evaporation under reduced pressure, and diethyl ether was added to the residue. The ethereal layer was separated, washed with water and dried over anhydrous magnesium sulfate. The diethyl ether was then evaporated off under reduced pressure. The residue (3.57 g) was subjected to column chromatography through 70 g of silica gel. Those fractions eluted with a 1:5:5 by volume mixture of diethyl ether, hexane and methylene chloride were worked up and then recrystallized from a mixture of diethyl ether and hexane, to give 3.289 g of the title compound as white crystals melting at 55°-56° C.

Nuclear Magnetic Resonance Spectrum (90 MHz, CDCl$_3$) δ ppm: 0.75-2.30 (39H, multiplet); 3.00-3.60 (5H, multiplet); 3.69 (1H, doublet, J=4 Hz); 3.85-4.20 (2H, multiplet); 4.76 (1H, doublet of doublets, J$_1$=13 Hz, J$_2$=3 Hz); 4.95 (1H, multiplet).

Infrared Absorption Spectrum (CHCl$_3$) $\nu_{max}$ cm$^{-1}$: 3450 (—NH—, —OH), 1700 (—O—CO—).

Mass Spectrum (m/e): 427 (M$^+$), 409 (M$^+$—H$_2$O).

Elemental Analysis:
Calculated for C$_{25}$H$_{49}$NO$_4$: C, 70.21%; H, 11.55%; N, 3.28%. Found: C, 70.31%; H, 11.42%; N, 3.27%.

PREPARATION 38 dl-S-(cis-2-Benzyloxymethyltetrahydropyran-3-yl) thioacetate 1.04 ml of methanesulfonyl chloride were added dropwise, whilst ice-cooling, to a solution of 2.00 g of dl-trans-2-benzyloxymethyltetrahydropyran-3-ol (prepared as described in Preparation 2) and 2.51 ml of triethylamine in 40 ml of benzene. The reaction mixture was then stirred at room temperature for 1 hour, after which it was washed with water and dried over anhydrous magnesium sulfate. The solvent was then evaporated off under reduced pressure, to give a crude methanesulfonate as an oil, which was dissolved, without further purification, in 10 ml of dimethylformamide.

Meanwhile, a solution of 0.77 ml of thioacetic acid in 5 ml of dimethylformamide was added dropwise to a suspension of 0.47 g of sodium hydride (as a 55% w/w dispersion in mineral oil) in 5 ml of dimethylformamide, whilst cooling; the mixture was then stirred at room temperature for 1 hour. At the end of this time, the solution of the crude methanesulfonate prepared as described above was added to this mixture, and the mixture was heated for 16 hours at 80° C. and then for 10 hours at 100° C., whilst stirring. The mixture was then cooled to room temperature, poured into water and then extracted with ethyl acetate. The extract was washed with water and dried over anhydrous magnesium sulfate, and then the solvent was evaporated off under reduced pressure, to give an oily residue. This residue was purified by column chromatography through 50 g of silica gel. Fractions eluted with mixtures of diethyl ether and hexane ranging from 3:97 to 10:90 by volume were worked up, to give 1.448 g of the title compound as an oil.

Nuclear Magnetic Resonance Spectrum (90 MHz, CDCl$_3$) δ ppm: 1.10-2.20 (4H, multiplet); 2.30 (3H, singlet); 3.20-4.20 (6H, multiplet); 4.52 (2H, AB-quartet, J=12 Hz); 7.20-7.50 (5H, multiplet).

Infrared Absorption Spectrum (CHCl$_3$) $\nu_{max}$ cm$^{-1}$: 1685 (—S—CO—).

Mass Spectrum (m/e): 280 (M$^+$).

Elemental Analysis: Calculated for C$_{15}$H$_{20}$O$_3$S: C, 64.26%; H, 7.19%; S, 11.44%. Found: C, 64.19%; H, 6.96%; S, 11.67%.

PREPARATION 39 dl-cis-2-Benzyloxymethyltetrahydropyran-3-thiol 1.04 ml of an approximately 28% w/v methanolic solution of sodium methoxide was added dropwise at −10° C. to 1.422 g of dl-S-(cis-2-benzyloxymethyltetrahydropyran-3-yl) thioacetate (prepared as described in Preparation 38) dissolved in 30 ml of methanol. The reaction mixture was stirred at −10° to 0° C. for 2 hours, and then 0.33 ml of methanesulfonic acid was added. The reaction mixture was then poured into water and extracted with ethyl acetate. The extracts were washed with water, dried over anhydrous magnesium sulfate and concentrated by evaporation under reduced pressure to give an oily residue. The residue was subjected to column chromatography through 30 g of silica gel. Those fractions eluted with mixtures of diethyl ether and hexane ranging from 3:97 to 5:95 by volume were worked up, to give 1.146 g of the title compound as an oil.

Nuclear Magnetic Resonance Spectrum (90 MHz, CDCl$_3$) δ ppm: 1.10-2.40 (4H, multiplet); 1.66 (1H, doublet, J=10 Hz); 2.95-3.25 (1H, multiplet); 3.25-3.85 (4H, multiplet); 3.85-4.20 (1H, multiplet); 4.55 (2H, AB-quartet, J=12 Hz); 7.10-7.50 (5H, multiplet).

Infrared Absorption Spectrum (CHCl$_3$) $\nu_{max}$ cm$^{-1}$: 2580 (—SH).

Mass Spectrum (m/e): 238 (M$^+$).

Elemental Analysis: Calculated for C$_{13}$H$_{18}$O$_2$S: C, 65.51%; H, 7.61%; S, 13.45%. Found: C, 65.62%; H, 7.83%; S, 13.19%.

PREPARATION 40

S-[dl-(cis-2-Benzyloxymethyltetrahydropyran-3-yl)] N-(heptadecyl)thiocarbamate

A similar reaction and treatment procedure to that described in Preparation 3 was repeated, but using 7.75 g of stearic acid in place of the nonadecanoic acid and 2.60 g of dl-cis-2-benzyloxymethyltetrahydropyran-3-thiol (prepared as described in Preparation 39) in place of the dl-trans-2-benzyloxymethyltetrahydropyran-3-ol, to give 5.29 g of the title compound as white crystals melting at 80°–81° C., after recrystallization from a mixture of diethyl ether and hexane.

Nuclear Magnetic Resonance Spectrum (90 MHz, CDCl$_3$) δ ppm: 0.8–2.2 (37H, multiplet); 3.1–4.2 (8H, multiplet); 4.57 (2H, AB-quartet, J$_{AB}$=12 Hz); 5.31 (1H, multiplet); 7.35 (5H, multiplet).

Infrared Absorption Spectrum (CHCl$_3$) $\nu_{max}$ cm$^{-1}$: 3430 (—NH—), 1670 (—SCO—).

Elemental Analysis: Calculated for C$_{31}$H$_{53}$NO$_3$S: C, 71.63%; H, 10.28%; N, 2.69%; S, 6.17%. Found: C, 71.73%; H, 10.19% N, 2.64%; S, 6.43%.

PREPARATION 41

S-[dl-(cis-2-Hydroxymethyltetrahydropyran-3-yl)] N-(heptadecyl)thiocarbamate

A mixture of 200 ml of acetonitrile and 100 ml of methylene chloride was cooled with ice-water. 6.67 g of aluminum chloride and 7.50 g of sodium iodide were added, in turn, to the resulting mixture, followed by a solution of 5.20 g of S-[dl-(cis-2-benzyloxymethyltetrahydropyran-3-yl)] N-(heptadecyl)thiocarbamate (prepared as described in Preparation 40) dissolved in 100 ml of methylene chloride. The mixture was stirred at room temperature for 4 hours. It was then mixed with water and passed through a layer of Celite filter aid to remove insoluble materials. Methylene chloride was added, and the organic layer was separated. The aqueous layer was extracted with methylene chloride. The combined extracts and organic layer were washed, in turn, with an aqueous solution of sodium thiosulfate and with water, dried over anhydrous magnesium sulfate and concentrated by evaporation under reduced pressure. The residue was subjected to column chromatography through 90 g of silica gel. 4.04 g of the title compound were obtained, as white crystals melting at 90°–91° C. (after recrystallisation from hexane), from those fractions eluted with mixtures of hexane, methylene chloride and ethyl acetate ranging from 10:10:1 to 2:2:1 by volume.

Nuclear Magnetic Resonance Spectrum (90 MHz, CDCl$_3$) δ ppm: 0.7–2.3 (38H, multiplet); 3.15–4.15 (8H, multiplet); 5.53 (1H, multiplet).

Infrared Absorption Spectrum (CHCl$_3$) $\nu_{max}$ cm$^{-1}$: 3430 (—NH—, —OH), 1650 (—SCO—).

Elemental Analysis: Calculated for C$_{24}$H$_{47}$NO$_3$S: C, 67.08%; H, 11.02%; N, 3.26%; S, 7.46%. Found: C, 67.04%; H, 10.98%; N, 3.31%; S, 7.63%.

PREPARATION 42 dl-[cis-3-(N-Heptadecylcarbamoylthio)tetrahydropyran-2-yl]methyl N-(5-bromopentyl)carbamate 1.50 ml of diphenylphosphoryl azide and 1.62 ml of triethylamine were added to a solution of 1.36 g of 6-bromohexanoic acid dissolved in 40 ml of benzene. The mixture was then heated under reflux for 3 hours. At the end of this time, it was washed with a saturated aqueous solution of sodium bicarbonate and with a saturated aqueous solution of sodium chloride. It was then dried over anhydrous magnesium sulfate and concentrated by evaporation under reduced pressure. The residue was dissolved in 20 ml of toluene, and 1.000 g of S-[dl-(cis-2-hydroxymethyltetrahydropyran-3-yl)] N-(heptadecyl)thiocarbamate (prepared as described in Preparation 41) was added to the solution so obtained. The resulting mixture was then heated on an oil bath kept at 85° C. for 64 hours. At the end of this time, the reaction mixture was evaporated to dryness under reduced pressure, and the residue was purified by column chromatography through 30 g of silica gel and by medium pressure liquid chromatography using a Lobar B column. 1.279 g of the title compound was obtained, as a waxy solid melting at 73°–75° C., from those fractions eluted with a 4:1 by volume mixture of hexane and ethyl acetate.

Nuclear Magnetic Resonance Spectrum (90 MHz, CDCl$_3$) δ ppm: 0.7–2.2 (43H, multiplet); 2.9–4.3 (10H, multiplet); 3.38 (2H, triplet, J=7 Hz); 4.77 (1H, multiplet); 5.33 (1H, multiplet).

Infrared Absorption Spectrum (CHCl$_3$) $\nu_{max}$ cm$^{-1}$: 3450 (—NH—), 1720 (—O—CO—) and 1675 (—S—CO—).

Mass Spectrum (m/e): 623, 621 (M$^+$ +1) and 541 (M$^+$ —Br).

Elemental analysis: Calculated for C$_{30}$H$_{57}$BrN$_2$O$_4$S: C, 57.95%; H, 9.24%; Br, 12.85%; N, 4.51%; S, 5.61%. Found: C, 57.85%; H, 9.34%; Br, 12.85%; N, 4.52%; S, 5.28%.

PREPARATION 43 dl-trans-2-Benzyloxymethyl-3-hexadecyloxytetrahydropyran

A solution of 2.22 g of dl-trans-2-benzyloxymethyltetrahydropyran-3-ol (prepared as described in Preparation 2) in 10 ml of dimethylformamide was added dropwise, with ice-cooling, to 10 ml of dimethylformamide containing 0.480 g of a 55% w/w suspension of sodium hydride in mineral oil. The reaction mixture was stirred at room temperature for 60 minutes, after which 5.49 g of hexadecyl bromide were added, and the resulting mixture was stirred for a further 4 hours. Finally, the mixture was stirred at 60° C. for 60 minutes and then cooled. It was then poured into 100 ml of water, and extracted twice with ethyl acetate. The combined extracts were washed with water, dried over anhydrous magnesium sulfate and condensed by evaporation under reduced pressure. The resulting oily residue was subjected to column chromatography through 100 g of silica gel. Those fractions eluted with mixtures of diethyl ether and hexane ranging from 1:20 to 1:10 by volume gave 3.82 g of the title compound as a solid having a low melting point, i.e. 28.5°–29.5° C. (after recrystallization from cold methanol).

Nuclear Magnetic Resonance Spectrum (90 MHz, CDCl$_3$) δ ppm: 0.7–2.4 (35H, multiplet); 3.0–4.2 (8H, multiplet); 4.60 (2H, AB-quartet, J=13 Hz); 7.2–7.45 (5H, multiplet).

Mass Spectrum (m/e): 446 (M$^+$).

Elemental Analysis: Calculated for C$_{29}$H$_{50}$O$_3$: C, 77.97%; H, 11.28%. Found: C, 78.06%; H, 11.31%.

PREPARATION 44 dl-trans-3-Hexadecyloxy-2-hydroxymethyltetrahydropyran 1.5 g of 10% w/w palladium on activated carbon was added to a solution of 3.757 g of dl-trans-2-benzyloxymethyl-3-hexadecyloxytetrahydropyran (prepared as described in Preparation 43) in 150 ml of methanol, and the whole was mixed with hydrogen by shaking in a Paar's apparatus at room temperature under a pressure of 4 atmospheres (about 4 bars). After 20 hours, the catalyst was removed by filtration, and the solvent was then removed by distillation to give 2.749 g of the title compound as a solid, melting at 41°–42° C. (after recrystallization from cold hexane).

Infrared Absorption Spectrum (CHCl$_3$) $\nu_{max}$ cm$^{-1}$: 3600, 3470 (—OH).

Mass Spectrum (m/e): 357 (M$^+$+1), 356 (M$^+$).

Elemental Analysis: Calculated for C$_{22}$H$_{44}$O$_3$: C, 74.10%; H, 12.43%. Found: C, 74.12%; H, 12.11%.

PREPARATION 45 dl-cis-2-Benzyloxymethyl-3-hexadecyloxytetrahydropyran

A mixture of 1.037 g of dl-cis-2-benzyloxymethyltetrahydropyran-3-ol (prepared as described in Preparation 33), 1.709 g of hexadecyl bromide, 0.77 g of potassium hydroxide and 15 ml of toluene was heated, with stirring, at 120° C. for 10 hours. At the end of this time, the reaction mixture was cooled and then poured into water. The aqueous layer was extracted twice with diethyl ether. The organic layer and the extracts were combined, washed with water, dried over anhydrous magnesium sulfate and condensed by evaporation under reduced pressure. The resulting oily residue (3.3 g) was subjected to column chromatography through 50 g of silica gel. The fraction eluted with a 1:10 by volume mixture of diethyl ether and hexane gave 1.455 g of the title compound as a colorless oily substance.

Nuclear Magnetic Resonance Spectrum (90 MHz, CDCl$_3$) δ ppm: 0.7–2.3 (35H, multiplet); 3.1–3.8 (5H, multiplet); 3.61 (2H, singlet); 3.85–4.15 (1H, multiplet); 4.55 (2H, AB-quartet, J=13 Hz); 7.2–7.5 (5H, multiplet).

Mass Spectrum (m/e): 447 (M$^+$+1).

Elemental Analysis: Calculated for C$_{29}$H$_{50}$O$_3$: C, 77.97%; H, 11.28%. Found: C, 77.68%; H, 11.16%.

PREPARATION 46 dl-cis-3-Hexadecyloxy-2-hydroxymethyltetrahydropyran 1.409 g of dl-cis-2-benzyloxymethyl-3-hexadecyloxytetrahydropyran (prepared as described in Preparation 45) was dissolved in 100 ml of a 1:1 by volume mixture of methanol and ethanol. 0.70 g of a 10% w/w palladium on activated carbon catalyst was then added to the resulting solution. Catalytic reduction using the same procedure as described in Preparation 44 yielded 1.116 g of a crude substance, which was then subjected to column chromatography through 30 g of silica gel. Those fractions eluted with mixtures of diethyl ether and hexane ranging from 1:20 to 1:5 by volume gave 1.031 g of the title compound, melting at 42°–43° C. (after recrystallisation from cold hexane).

Infrared Absorption Spectrum (CHCl$_3$) $\nu_{max}$ cm$^{-1}$: 3600, 3460(—OH).

Mass Spectrum (m/e): 357 (M$^+$+1), 356 (M$^+$).

Elemental Analysis: Calculated for C$_{22}$H$_{44}$O$_3$: C, 74.10%; H, 12.43%. Found: C, 73.85%; H, 12.13%.

PREPARATION 47 dl-[trans-3-Hexadecyloxytetrahydropyran-2-yl]methyl N-(5-bromopentyl)carbamate 1.09 ml of diphenylphosphoryl azide and 1.17 ml of triethylamine were added to a solution of 985 mg of 6-bromohexanoic acid dissolved in 30 ml of benzene. The mixture was then heated under reflux for 3 hours. At the end of this time, the reaction mixture was washed with a saturated aqueous solution of sodium bicarbonate and with a saturated aqueous solution of sodium chloride, dried over anhydrous magnesium sulfate and concentrated by evaporation under reduced pressure. The residue was dissolved in 12 ml of toluene. 600 mg of dl-(trans-3-hexadecyloxytetrahydropyran-2-yl)methanol (prepared as described in Preparation 44) and 1.17 ml of triethylamine were added to the solution, and the mixture was heated at 85° C. for 15 hours, after which it was evaporated to dryness under reduced pressure. The residue was subjected to column chromatography through 20 g of silica gel. Those fractions eluted with mixtures of hexane and ethyl acetate ranging from 17:3 to 4:1 by volume were collected and then purified by medium pressure liquid chromatography through a Lobar B column. 744 mg of the title compound were isolated, as an oil, from those fractions eluted with mixtures of the above solvent system.

Nuclear Magnetic Resonance Spectrum (90 MHz, CDCl$_3$) δ ppm: 0.7–2.4 (41H, multiplet); 2.9–3.7 (7H, multiplet); 3.38 (2H, triplet, J=7 Hz); 3.96 (1H, multiplet); 4.16 (1H, doublet of doublets, J=12, 5 Hz); 4.40 (1H, doublet of doublets, J=12, 3 Hz); 4.75 (1H, multiplet).

Mass Spectrum (m/e): 550, 548 (M$^+$+1) and 468 (M$^+$—Br).

Elemental analysis: Calculated for C$_{28}$H$_{54}$BrNO$_4$: C, 61.30%; H, 9.92%; Br, 14.56%; N, 2.55%. Found: C, 61.19%; H, 9.79%; Br, 14.24%; N, 2.67%.

PREPARATION 48

4,5-Dihydrofurfuryl alcohol 358 g of a 15.08% w/w solution of butyllithium in hexane were added dropwise to 58.7 g of dihydrofuran in 350 ml of anhydrous tetrahydrofuran over a period of 30 minutes at 5°–10° C., whilst ice-cooling. The reaction mixture was then heated at 50° C. for 2 hours, whilst stirring. At the end of this time, the mixture was cooled to 0° C. in an ice-bath. 25.0 g of paraformaldehyde were added all at once to the reaction mixture, which was then heated for 2 hours at 50° C. The reaction mixture was cooled to room temperature and then washed with 500 ml of ice-water; the aqueous layer was then extracted five times with methylene chloride. The organic layer and the extracts were combined, dried over anhydrous magnesium sulfate and concentrated by evaporation under reduced pressure to give 14 g of a residue. The residue was then distilled under reduced pressure to give 8.97 g of the title compound as a colorless oil boiling at 66°–67° C./7 mmHg (about 933 Pa). The title compound is preferably used as a reagent in the next step (e.g. Preparation 49) immediately after distillation because it dimerizes easily.

Nuclear Magnetic Resonance Spectrum (90 MHz, C$_6$D$_6$) δ ppm: 2.21 (2H, broad triplet, J=9 Hz); 2.98

(1H, broad triplet, J=6 Hz); 3.98 (2H, doublet, J=6 Hz); 4.00 (2H, triplet, J=9 Hz); 4.68 (1H, multiplet).

Mass Spectrum (m/e): 200 (M+×2), 101 (M++1), 100 (M+).

PREPARATION 49

2-Benzyloxymethyl-4,5-dihydrofuran 7.69 g of sodium hydride (as a 55% w/w suspension in mineral oil) were suspended in 150 ml of dimethylformamide, and 17.64 g of 4,5-dihydrofurfuryl alcohol (prepared as described in Preparation 48) in 30 ml of dimethylformamide were added dropwise at 5°–10° C. over 30 minutes, whilst ice-cooling. The mixture was stirred at room temperature for 1 hour, and then 20.93 ml of benzyl bromide were added dropwise thereto at 10°–15° C. over a further 30 minutes, whilst ice-cooling. The reaction mixture was stirred at room temperature for 1 hour, poured into 2 liters of water and extracted twice with ethyl acetate. The extracts were combined, washed with water, dried over anhydrous magnesium sulfate and evaporated to dryness under reduced pressure, to give 17.8 g of an oily residue. This residue was purified by column chromatography through 400 g of silica gel. Those fractions eluted with a 7:100 by volume mixture of hexane and diethyl ether afforded 3.71 g of the title compound as a colorless oil.

Nuclear Magnetic Resonance Spectrum (90 MHz, CDCl$_3$) δ ppm: 2.65 (2H, triplet of multiplets, J=10 Hz); 3.58 (2H, singlet); 4.03 (2H, multiplet); 4.39 (2H, triplet, J=10 Hz); 4.93 (1H, multiplet); 7.35 (5H, multiplet).

Mass Spectrum (m/e): 190 (M+).

PREPARATION 50 dl-trans-2-Benzyloxymethyltetrahydrofuran-3-ol 3.389 g of 2-benzyloxymethyl-4,5-dihydrofuran (prepared as described in Preparation 49) were hydroborated in a similar manner to that described in Preparation 2. 3.93 g of the resulting crude product were purified by column chromatography through 120 g of silica gel. Those fractions eluted with a 1:2 by volume mixture of hexane and ethyl acetate were condensed by evaporation under reduced pressure, to afford 2.012 g of the title compound as a colorless oil.

Nuclear Magnetic Resonance Spectrum (90 MHz, CDCl$_3$) δ ppm: 1.6–2.4 (2H, multiplet); 2.28 (1H, multiplet); 3.43 (1H, doublet of doublets, J$_1$=10 Hz & J$_2$=6 Hz); 3.60 (1H, doublet of doublets, J$_1$=10 Hz & J$_2$=4.5 Hz). 3.75–4.10 (3H, multiplet); 4.27 (1H, multiplet); 4.58 (2H, singlet); 7.30 (5H, singlet).

Mass Spectrum (m/e): 208 (M+).

PREPARATION 51 dl-trans-2-Benzyloxymethyltetrahydrofuran-3-yl N-heptadecylcarbamate 1.967 g of dl-trans-2-benzyloxymethyltetrahydrofuran-3-ol (prepared as described in Preparation 50) were treated in a manner similar to that described in Preparation 3 to give 3.711 g of the title compound as white crystals melting at 54°–56° C., after recrystallization from hexane.

Mass Spectrum (m/e): 489 (M+), 398 (M+—C$_7$H$_7$).

Nuclear Magnetic Resonance Spectrum (270 MHz, CDCl$_3$) δ ppm: 0.8–1.7 (33H, multiplet); 1.90–2.30 (2H, multiplet); 3.15 (2H, doublet of triplets, J$_1$=J$_2$=6.6 Hz); 3.59 (2H, doublet, J=4.4 Hz); 3.88 (1H, multiplet); 4.05 (2H, multiplet); 4.56 (2H, singlet); 4.67 (1H, multiplet); 5.10 (1H, multiplet); 7.32 (5H, multiplet).

Infrared Absorption Spectrum (CHCl$_3$) ν$_{max}$ cm$^{-1}$: 3450 (—NH—), 1720 (—OCONH).

Elemental Analysis: Calculated for C$_{30}$H$_{51}$NO$_4$: C, 73.57%; H, 10.50%; N, 2.86%. Found: C, 73.09%; H, 10.33%; N, 2.87%.

PREPARATION 52 dl-trans-2-Hydroxymethyltetrahydrofuran-3-yl N-heptadecylcarbamate 1.142 g of dl-trans-2-benzyloxymethyltetrahydrofuran-3-yl N-heptadecylcarbamate (prepared as described in Preparation 51) were subjected to debenzylation in a similar manner to that described in Preparation 4, to give 0.841 g of the title compound as white crystals melting at 77°–78° C., after recrystallization from a mixture of diethyl ether and hexane.

Nuclear Magnetic Resonance Spectrum (270 MHz, CDCl$_3$) δ ppm: 0.8–1.7 (33H, multiplet); 1.95–2.25 (2H, multiplet); 2.41 (1H, triplet, J=6.2 Hz); 3.16 (2H, doublet or triplets, J$_1$=J$_2$=6.6 Hz); 3.70 (2H, multiplet); 3.80–4.10 (3H, multiplet); 4.72 (1H, multiplet); 5.01 (1H, multiplet).

Infrared Absorption Spectrum (CHCl$_3$) ν$_{max}$ cm$^{-1}$: 3600 (—OH), 3450 (—NH—), 1710 (—OCONH—).

Elemental Analysis: Calculated for C$_{23}$H$_{45}$NO$_4$: C, 69.13%; H, 11.35%; N, 3.50%. Found: C, 68.98%; H, 11.22%; N, 3.70%.

Mass Spectrum (m/e): 400 (M++1), 399 (M+), 368 (M+—OCH$_3$).

PREPARATION 53

6-[7-(Tetrahydropyran-2-yloxy)heptyloxymethyl]-3,4-dihydro-2H-pyran (a) A solution of 2.32 ml of methanesulfonyl chloride dissolved in 10 ml of benzene was added dropwise, whilst ice-cooling, to a solution of 4.32 g of 7-(tetrahydropyran-2-yloxy)-1-heptanol and 5.56 ml of triethylamine dissolved in 80 ml of benzene. The mixture was stirred at room temperature for 1 hour, after which it was washed with water, dried over anhydrous magnesium sulfate and concentrated by evaporation under reduced pressure, to give 5.86 g of 7-(tetrahydropyran-2-yloxy)heptyl methanesulfonate, as an oil.

(b) A solution of 2.28 g of 6-hydroxymethyl-3,4-dihydro-2H-pyran in 5 ml of dimethylformamide was added dropwise to a suspension of 0.87 g of sodium hydride (as a 55% w/w dispersion in mineral oil) in 20 ml of dimethylformamide. The mixture was stirred at room temperature for 1 hour, after which a solution of the whole of the methanesulfonate prepared as described in step (a) above dissolved in 5 ml of dimethylformamide was added dropwise to it. The mixture was then stirred on an oil bath kept at 70° C. for 1 hour, after which it was poured into 200 ml of water and then extracted twice with diethyl ether. The combined extracts were washed with water, dried over anhydrous magnesium sulfate and concentrated by evaporation under reduced pressure. The oily residue (6.47 g) was subjected to column chromatography through 180 g of silica gel. 5.26 g of the title compound were obtained, as a colorless oil, from those fractions eluted with mixtures of hexane and diethyl ether ranging from 1:10 to 1:5 by volume.

Nuclear Magnetic Resonance Spectrum (90 MHz, CDCl$_3$) δ ppm: 1.1–2.2 (20H, multiplet); 3.25–4.15 (10H, multiplet); 4.60 (1H, multiplet); 4.80 (1H, multiplet).

Mass Spectrum (m/e): 312 (M$^+$) and 225 (M$^+$—C$_5$H$_9$O).

Elemental analysis Calculated for C$_{18}$H$_{32}$O$_4$: C, 69.19%; H, 10.33%. Found: C, 69.16%; H, 10.22%.

PREPARATION 54 dl-trans-2-[7-(Tetrahydropyran-2-yloxy)heptyloxymethyl]tetrahydropyran-3-ol 5.26 g of 6-[7-(tetrahydropyran-2-yloxy)heptyloxymethyl]-3,4-dihydro-2H-pyran (prepared as described in Preparation 53) were hydroborated by following a procedure similar to that described in Preparation 2. The crude product (5.64 g) was subjected to column chromatography through 100 g of silica gel. 4.17 g of the title compound were obtained, as a colorless oil, from those fractions eluted with a 2:1 by volume mixture of hexane and ethyl acetate.

Nuclear Magnetic Resonance Spectrum (90 MHz, CDCl$_3$) δ ppm: 1.1–2.3 (20H, multiplet); 3.10 (1H, doublet, J=2.5 Hz); 3.15–4.10 (12H, multiplet); 4.60 (1H, multiplet).

Mass Spectrum (m/e); 329 (M$^+$—1).

Elemental analysis: Calculated for C$_{18}$H$_{34}$O$_5$: C, 65.42%; H, 10.37%. Found: C, 65.05%; H, 10.07%.

PREPARATION 55 dl-7-(trans-3-Hexadecyloxytetrahydropyran-2-yl)methoxy-1-heptanol

A solution of 1.652 g of dl-trans-2-[7-(tetrahydropyran-2-yloxy)heptyloxymethyl]tetrahydropyran-3-ol (prepared as described in Preparation 54) in 5 ml of dimethylformamide was added dropwise at room temperature to a suspension of 0.24 g of sodium hydride (as a 55% w/w dispersion in mineral oil) in 5 ml of dimethylformamide. The reaction mixture was stirred at room temperature for 30 minutes, after which it was heated on an oil bath kept at 60° C. for a further 30 minutes. At the end of this time, 1.83 g of hexadecyl bromide were added at room temperature, after which the mixture was heated on an oil bath kept at 60° C. for 30 minutes, whilst stirring. The mixture was then cooled, and 0.24 g of sodium hydride (as a 55% w/w dispersion in mineral oil) was added to it at room temperature. The mixture was then heated on an oil bath kept at 60° C. for 30 minutes. The reaction mixture was allowed to cool to room temperature and a further 1.83 g of hexadecyl bromide was added to it. The reaction mixture was then heated on an oil bath kept at 60° C. for 30 minutes, whilst stirring, after which it was cooled and poured into water and then extracted three times with methylene chloride. The combined extracts were dried over anhydrous magnesium sulfate and concentrated by evaporation under reduced pressure. 40 ml of methanol and 0.5 ml of concentrated hydrochloric acid were added to a solution of the oil residue (5.74 g) dissolved in 15 ml of tetrahydrofuran, and the mixture was stirred at room temperature for 30 minutes. The solvent was then removed by distillation under reduced pressure, and the residue was diluted with water and then extracted twice with diethyl ether. The combined extracts were washed with a saturated aqueous solution of sodium bicarbonate and with a saturated aqueous solution of sodium chloride, dried over anhydrous magnesium sulfate and concentrated by evaporation under reduced pressure. The oily residue (5.14 g) was subjected to column chromatography through 90 g of silica gel. 2.123 g of the title compound were obtained, as a viscous oil, from those fractions eluted with a 2:1 by volume mixture of hexane and ethyl acetate.

Nuclear Magnetic Resonance Spectrum (90 MHz, CDCl$_3$) δ ppm: 0.75–2.5 (44H, multiplet); 2.1–2.4 (1H, multiplet); 3.00–3.80 (12H, multiplet); 3.80–4.10 (1H, multiplet).

Mass Spectrum (m/e): 471 (M$^+$ +1).

Elemental analysis: Calculated for C$_{29}$H$_{58}$O$_4$: C, 73.99%; H, 12.42%. Found: C, 73.69%; H, 12.30%.

PREPARATION 56 dl-2-[7-(Tetrahydropyran-2-yloxy)heptyloxymethyl]tetrahydropyran-3-one

A solution of 2.387 g of dl-trans-2-[7-(tetrahydropyran-2-yloxy)heptyloxymethyl]tetrahydropyran-3-ol (prepared as described in Preparation 54) in 10 ml of methylene chloride was added all at once to a mixture of 2.33 g of pyridine chlorochromate, 1.78 g of sodium acetate and 10 ml of methylene chloride. The mixture was then stirred at room temperature for 3 hours, after which it was mixed with 30 ml of diethyl ether, and the solution was passed through a chromatography column containing 50 g of silica gel. The column was then washed with diethyl ether and the eluate was combined with the washings and then concentrated by evaporation under reduced pressure. The oily residue (2.24 g) was subjected to column chromatography through 60 g of silica gel. 1.786 g of the title compound was obtained, as an oil, from those fractions eluted with mixtures of hexane and ethyl acetate ranging from 3:1 to 2:1 by volume.

Infrared Absorption Spectrum (CHCl$_3$) $\nu_{max}$ cm$^{-1}$: 1730.

Mass Spectrum (m/e): 244 (M$^+$—C$_5$H$_8$O) and 227 (M$^+$—C$_5$H$_9$O$_2$).

PREPARATION 57 dl-cis-2-[7-(Tetrahydropyran-2-yloxy)heptyloxymethyl]tetrahydropyran-3-ol

Following a procedure similar to that described in Preparation 33(b), 1.718 g of dl-2-[7-(tetrahydropyran-2-yloxy)heptyloxymethyl]tetrahydropyran-3-one (prepared as described in Preparation 56) was reduced to give 1.320 g of the title compound as a colorless oil.

Nuclear Magnetic Resonance Spectrum (90 MHz, CDCl$_3$) δ ppm: 1.15–2.40 (20H, multiplet); 2.95 (1H, doublet, J=4 Hz); 3.25–4.25 (10H, multiplet); 4.60 (1H, multiplet).

Mass Spectrum: 330 (M$^+$) and 329 (M$^+$—1).

Elemental analysis: Calculated for C$_{18}$H$_{34}$O$_5$: C, 65.42%; H, 10.37%. Found: C, 65.22%; H, 10.44%.

PREPARATION 58 dl-7-(cis-3-Hexadecyloxytetrahydropyran-2-ylmethoxy)-1-heptanol 1.150 g of dl-cis-2-[7-(tetrahydropyran-2-yloxy)heptyloxymethyl]tetrahydropyran-3-ol (prepared as described in Preparation 57) were treated in a similar manner to that described in Preparation 55 to afford 1.282 g of the title compound as a viscous oil.

Nuclear Magnetic Resonance Spectrum (90 MHz, CDCl$_3$) δppm: 0.7–2.35 (45H, multiplet); 2.16 (1H, multiplet); 3.10–3.85 (11H, multiplet); 3.90–4.20 (1H, multiplet).

Mass Spectrum (m/e): 470 (M+) and 411 (M+—C$_3$H$_7$O).

Elemental analysis: Calculated for C$_{29}$H$_{58}$O$_4$: C, 73.99%; H, 12.42%. Found: C, 73.72%; H, 12.31%.

PREPARATION 59

5-(2-Methoxyethoxy)methoxy-1-pentanol

A solution of 50.00 g of 1,5-pentanediol dissolved in 100 ml of dimethylformamide was added dropwise to a mixture of 23.00 g of sodium hydride (as a 55% w/w dispersion in mineral oil) in 300 ml of dimethylformamide, whilst ice-cooling at 5° to 7° C. The mixture was stirred at room temperature for 1 hour, after which 65.79 g of 2-methoxyethoxymethyl chloride dissolved in 100 ml of dimethylformamide were added dropwise, whilst ice-cooling at 5° to 7° C. The mixture was stirred at room temperature for 3 hours, after which it was poured into 2.5 liters of water and then extracted five times with methylene chloride. The combined extracts were washed with water, dried over anhydrous magnesium sulfate and concentrated by evaporation under reduced pressure. The residue was subjected to column chromatography through 850 g of silica gel, and 48.40 g of the title compound were obtained, as a colorless oil, from those fractions eluted with mixtures of methylene chloride and methanol ranging from 98:2 to 95:5 by volume.

Nuclear Magnetic Resonance Spectrum (90 MHz, CDCl$_3$) δ ppm: 1.3–1.8 (7H, multiplet); 3.39 (3H, singlet); 3.4–3.8 (8H, multiplet); 4.72 (2H, singlet).

Infrared Absorption Spectrum (CHCl$_3$) ν$_{max}$ cm$^{-1}$: 3480 (—OH) and 1050 (C—O—C).

Mass Spectrum (m/e): 193 (M++1) and 117 [M+—C$_3$H$_7$O$_2$].

Elemental analysis: Calculated for C$_9$H$_{20}$O$_4$: C, 56.23%; H, 10.49%. Found: C, 55.95%; H, 10.28%.

PREPARATION 60

1-Bromo-5-(2-methoxyethoxy)methoxypentane 79.32 g of triphenylphosphine were added, whilst ice-cooling (at 5° to 8° C.), to a solution of 48.40 g of 5-(2-methoxyethoxy)methoxy-1-pentanol (prepared as described in Preparation 59) and 100.19 g of carbon tetrabromide dissolved in 500 ml of methylene chloride. The mixture was stirred at room temperature for 1 hour, after which the solvent was removed by evaporation under reduced pressure. Diethyl ether was then added to the resulting residue. The insoluble materials were filtered off, and the filtrate was concentrated by evaporation under reduced pressure. The residue was subjected to column chromatography through 850 g of silica gel, and 57.87 g of the title compound were obtained, as a colorless oil, from those fractions eluted with a 1:9 by volume mixture of ethyl acetate and hexane.

Nuclear Magnetic Resonance Spectrum (90 MHz, CDCl$_3$) δ ppm: 1.4–1.8 (4H, multiplet); 1.90 (2H, quintet, J=6.5 Hz); 3.40 (3H, singlet); 3.4–3.8 (8H, multiplet); 4.72 (2H, singlet).

Infrared Absorption Spectrum (CHCl$_3$) ν$_{max}$ cm$^{-1}$: 1045 (C—O—C) and 565 (—Br).

Mass Spectrum (m/e): 225, 223 (M+—OCH$_3$), 181 and 179 (M+—OCH$_2$CH$_2$OCH$_3$).

Elemental analysis: Calculated for C$_{19}$H$_{19}$BrO$_3$: C, 42.37%; H, 7.51%; Br, 31.32%. Found: C, 42.39%; H, 7.31%; Br, 31.13%.

PREPARATION 61

Diethyl 2-[5-(2-methoxyethoxy)methoxypentyl]malonate

A solution of 37.80 of diethyl malonate dissolved in 20 ml of absolute ethanol was added dropwise to a solution of sodium ethoxide prepared by gradually adding 3.00 g of metallic sodium to 30 ml of absolute ethanol. To the mixture was added a solution of 30.01 g of 1-bromo-5-(2-methoxyethoxy)methoxypentane (prepared as described in Preparation 60) dissolved in 10 ml of absolute ethanol. The mixture was heated under reflux for 21 hours, after which it was allowed to cool, and then the solvent was distilled off. The residue was mixed with water, and the mixture was extracted three times with ethyl acetate. The combined extracts were washed with water, dried over anhydrous magnesium sulfate and concentrated by evaporation under reduced pressure. The residue was subjected to column chromatography through 850 g of silica gel, and 32.78 g of the title compound were obtained, as a colorless oil, from those fractions eluted with a 4:1 by volume mixture of hexane and ethyl acetate.

Nuclear Magnetic Resonance Spectrum (90 MHz, CDCl$_3$) δ ppm: 1.26 (6H, triplet, J=7.0 Hz); 1.3–2.1 (8H, multiplet); 3.2–3.8 (7H, multiplet); 3.40 (3H, singlet); 4.20 (4H, quartet, J=7.0 Hz); 4.71 (2H, singlet).

Infrared Absorption Spectrum (CHCl$_3$) ν$_{max}$ cm$^{-1}$: 1725 (—CO—) and 1040 (—C—O—C).

Mass Spectrum (m/e): 275 (M+—C$_3$H$_7$O) and 259 (M+—C$_3$H$_7$O$_2$).

Elemental analysis: Calculated for C$_{16}$H$_{30}$O$_7$: C, 57.47%; H, 9.04%. Found: C, 57.56%; H, 8.98%.

PREPARATION 62

Ethyl hydrogen 2-[5-(2-methoxyethoxy)methoxypentyl]malonate 1.5 ml of an aqueous solution containing 0.203 g of potassium hydroxide was added, whilst ice-cooling, to a solution of 1.029 g of diethyl 2-[5-(2-methoxyethoxy)-methoxypentyl]malonate (prepared as described in Preparation 61) dissolved in 1.5 ml of ethanol. The reaction mixture was stirred at room temperature for 5 hours, after which it was washed with diethyl ether. The aqueous layer was adjusted to a pH value of 2 by adding 10% w/v aqueous hydrochloric acid, and it was then extracted four times with methylene chloride. The combined extracts were dried over anhydrous magnesium sulfate and concentrated by evaporation under reduced pressure. The oily residue (0.94 g) was subjected to column chromatography through 20 g of silica gel, and 0.764 g of the title compound was obtained, as a colorless oil, from those fractions eluted with mixtures of hexane and ethyl acetate ranging from 2:1 to 1:1 by volume.

Nuclear Magnetic Resonance Spectrum (90 MHz, CDCl$_3$) δ ppm: 1.28 (3H, triplet, J=7 Hz); 1.15–2.10 (8H, multiplet); 3.25–3.80 (7H, multiplet); 3.42 (3H, singlet); 4.24 (2H, quartet, J=7 Hz); 4.73 (2H, singlet).

Elemental analysis: Calculated for C$_{14}$H$_{26}$O$_7$: C, 54.88%; H, 8.55%. Found: C, 54.70%; H, 8.45%.

PREPARATION 63

Ethyl 2-[(dl-trans-3-heptadecylcarbamoyloxytetrahydropyran-2-yl)methoxycarbonylamino]-5-[(2-methoxyethoxy)methoxy]heptanoate A mixture of 0.731 g of ethyl hydrogen 2-[5-(2-methoxyethoxy)methoxypentyl]malonate (prepared as described in Preparation 62), 0.51 ml of diphenylphosphoryl azide and 0.50 ml of triethylamine dissolved in 15 ml of benzene was heated under reflux for 4 hours. At the end of this time, the reaction mixture was cooled; it was then washed, in turn, with a saturated aqueous solution of sodium bicarbonate and with water, dried over anhydrous magnesium sulfate and concentrated by evaporation under reduced pressure. The oily residue (0.748 g) was dissolved in 15 ml of toluene, and 0.329 g of dl-(trans-2-hydroxymethyltetrahydropyran-3-yl) N-heptadecylcarbamate (prepared as described in Preparation 4) and 0.50 ml of triethylamine were added to the solution, which was then heated on an oil bath kept at 90° C. for 24 hours, whilst stirring. The solvent was then removed by distillation under reduced pressure, and the residue was subjected to column chromatography through 30 g of silica gel. 0.596 g of the title compound was obtained, as a waxy material, from those fractions eluted with mixtures of hexane and ethyl acetate ranging from 2:1 to 1:1 by volume.

Nuclear Magnetic Resonance Spectrum (90 MHz, CDCl$_3$) δ ppm: 0.8–2.5 (48H, multiplet); 3.17 (2H, doublet of triplets, J$_1$=J$_2$=7 Hz); 3.43 (3H, singlet); 3.35–4.95 (14H, multiplet); 4.23 (2H, quartet, J=7 Hz); 4.73 (2H, singlet); 5.37 (1H, multiplet).

Mass Spectrum (m/e): 641 (M$^+$—C$_3$H$_7$O$_2$) and 627 (M$^+$—C$_4$H$_9$O$_2$).

PREPARATION 64

Ethyl 2-[(dl-trans-3-heptadecylcarbamoyloxytetrahydropyran-2-yl)methoxycarbonylamino]-5-hydroxyheptanoate 0.2 ml of acetyl chloride was added, whilst ice-cooling, to a solution of 0.584 g of ethyl 2-[(dl-trans-3-heptadecylcarbamoyloxytetrahydropyran-2-yl)methoxycarbonylamino]-5-[(2-methoxyethoxy)methoxy]heptanoate (prepared as described in Preparation 63) in 10 ml of ethanol. The mixture was then stirred at room temperature for 4.5 hours, after which it was diluted with 50 ml of ethyl acetate and then washed with a saturated aqueous solution of sodium bicarbonate and with water. The reaction mixture was then dried, and the solvent was removed by distillation under reduced pressure. The waxy residue (0.479 g) was subjected to column chromatography through 20 g of silica gel. 0.405 g of the title compound was obtained, as a waxy solid melting at 43°–46° C., from those fractions eluted with mixtures of hexane and ethyl acetate ranging from 1:1 to 2:1 by volume.

Nuclear Magnetic Resonance Spectrum (90 MHz, CD$_3$OD) δ ppm: 0.8–2.40 (48H, multiplet); 3.08 (2H, triplet, J=7 Hz); 3.2–4.7 (7H, multiplet); 3.55 (2H, triplet, J=6 Hz); 4.17 (2H, quartet, J=7 Hz).

Infrared Absorption Spectrum (CHCl$_3$) ν$_{max}$ cm$^{-1}$: 3500 (—OH), 3450 (—NH) and 1720 (—O—CO—).

PREPARATION 65 dl-cis-2-Benzyloxymethyltetrahydropyran-3-yl N-heptadecylcarbamate

Following a procedure similar to that described in Preparation 3, but using 2.758 g of stearic acid, 2.09 ml of diphenylphosphoryl azide and 0.862 g of dl-cis-2-benzyloxymethyltetrahydropyran-3-ol (prepared as described in Preparation 33), 1.407 g of the title compound was obtained as crystals. These crystals melted at 63.0°–65.0° C. after recrystallisation from a mixture of diethyl ether and hexane.

Nuclear Magnetic Resonance Spectrum (90 MHz, CDCl$_3$) δ ppm: 0.7–2.4 (37H multiplet); 3.0–3.8 (6H, multiplet); 3.9–4.2 (1H, multiplet); 4.55 (2H, AB-quartet, J=12 Hz); 4.5–5.0 (2H, multiplet); 7.2–7.4 (5H, multiplet).

Infrared Absorption Spectrum (CHCl$_3$) ν$_{max}$ cm$^{-1}$: 3460 (—NH—), 1715 (—O—CO—).

Mass Spectrum (m/e): 504 (M$^+$+1), 396 (M$^+$—OC$_7$H$_7$), 382 (M$^+$—CH$_2$OC$_7$H$_7$).

Elemental analysis: Calculated for C$_{31}$H$_{53}$NO$_4$: C, 73.91%; H, 10.60%; N, 2.78%. Found: C, 73.76%; H, 10.72%; N, 2.79%.

PREPARATION 66 dl-cis-2-Hydroxymethyltetrahydropyran-3-yl N-heptadecylcarbamate

Following a procedure similar to that described in Preparation 4, but using a solution of 1.300 g of dl-cis-2-benzyloxymethyltetrahydropyran-3-yl N-heptadecylcarbamate (prepared as described in Preparation 65) in 30 ml of ethanol and 0.819 g of 10% w/w palladium on activated carbon, 0.977 g of the title compound was obtained as crystals. These crystals melted at 81.0°–82.0° C. after recrystallisation from diethyl ether.

Nuclear Magnetic Resonance Spectrum (90 MHz, CDCl$_3$) δ ppm: 0.7–2.3 (37H, multiplet); 2.9–3.1 (1H, multiplet); 3.0–3.7 (6H, multiplet); 3.9–4.2 (1H, multiplet); 4.7–5.1 (2H, multiplet).

Infrared Absorption Spectrum (CHCl$_3$) ν$_{max}$ cm$^{-1}$: 3600 (—OH), 3460 (—NH—), 1700 (—O—CO—).

Mass Spectrum (m/e): 413 (M$^+$), 382 (M$^+$—CH$_2$OH).

PREPARATION 67 dl-cis-2-[N-(5-Bromopentyl)carbamoyloxymethyl]tetrahydropyran-3-yl N-heptadecylcarbamate Following a procedure similar to that described in Preparation 6, but using 1.245 g of 5-bromohexanoic acid, 1.37 ml of diphenylphosphoryl azide and 0.880 g of dl-cis-2-hydroxymethyltetrahydropyran-3-yl N-heptadecylcarbamate (prepared as described in Preparation 66), 0.933 g of the title compound was obtained as a waxy solid.

The compound melted at 95.0°–96.0° C. after recrystallisation from diethyl ether.

Nuclear Magnetic Resonance Spectrum (90 MHz, CDCl$_3$) δ ppm: 0.7–2.3 (43H, multiplet; 3.0–3.8 (6H, multiplet); 3.38 (2H, triplet, J=7 Hz); 4.00 (1H, multiplet); 4.13 (2H, doublet, J=7 Hz); 4.6–5.1 (3H, multiplet).

Infrared Absorption Spectrum (CHCl$_3$) ν$_{max}$ cm$^{-1}$: 3460 (—NH—), 1720 (—O—CO—).

Mass Spectrum (m/e): 606, 604 (M$^+$), 524 (M$^+$—HBr).

Elemental analysis: Calculated for $C_{30}H_{57}BrN_2O_5$: C, 59.49%; H, 9.49%; Br, 13.19%; N, 4.62%. Found: C, 59.61%; H, 9.58%; Br, 13.14%; N, 4.74%.

Preparation 68

3-Hydroxy-5-[4-(2-tetrahydropyranyl)oxybutyl]isoxazole 13.95 ml of a 15% by weight solution of butyllithium in hexane were added dropwise, at $-25°$ to $-15°$ C., to a solution of 3.08 ml of diisopropylamine in 100 ml of tetrahydrofuran. The mixture was stirred at $-20°$ C. for 15 minutes, after which a solution of 0.990 g of 3-hydroxy-5-methylisoxazole in 10 ml of tetrahydrofuran was added to the mixture at $-20°$ to $-10°$ C. over a period of 10 minutes. The mixture was then stirred at $-10°$ C. for 30 minutes, after which it was cooled to $-50°$ C., and then 3.35 g of 1-bromo-3-(2-tetrahydropyranyl)oxypropane were added to it all at once. The mixture was then stirred at $15°$–$20°$ C. for 2 hours, after which it was mixed with 1.20 ml of acetic acid. It was then poured into water. The organic layer was separated and the aqueous layer was adjusted to a pH value of 3 by adding 10% w/v aqueous hydrochloric acid followed by extraction twice with diethyl ether. The combined organic layer and extracts were washed with water, dried over anhydrous magnesium sulfate and concentrated by evaporation under reduced pressure, to give a residue, which was subjected to column chromatography through 60 g of silica gel. 1.720 g of the title compound was obtained, as a colorless oil, from the fractions eluted with mixtures of ethyl acetate and hexane ranging from 1:2 to 1:1 by volume.

Nuclear Magnetic Resonance Spectrum: (90 MHz, $CDCl_3$) δ ppm: 9.91 (1H, singlet); 5.68 (1H, singlet); 4.58 (1H, singlet); 3.2–4.1 (4H, multiplet); 1.3–2.1 (10H, multiplet).

Mass Spectrum (m/e): 241 (M+), 186, 157 and 140.

PREPARATION 69 dl-trans-2-[5-(4-Hydroxybutyl)-3-isoxazolyloxymethyl]-tetrahydropyran-3-yl N-heptadecylcarbamate A solution of 0.321 g of dimethyl azodicarboxylate in 2 ml of tetrahydrofuran was added to a solution of 0.827 g of dl-(trans-2-hydroxymethyltetrahydropyran-3-yl) N-heptadecylcarbamate (prepared as described in Preparation 4), 0.482 g of 3-hydroxy-5-[4-(2-tetrahydropyranyl)oxybutyl]isoxazole (prepared as described in Preparation 68) and 0.577 g of triphenylphosphine in 14 ml of tetrahydrofuran, and the mixture was stirred at room temperature for 4.5 hours. At the end of this time, the solvent was removed by distillation under reduced pressure, after which the residue was subjected to column chromatography through 30 g of silica gel. The fractions eluted with a 1:1 by volume mixture of diethyl ether and hexane were collected to give 1.3 g of an oily material, which was dissolved in 10 ml of methanol. 0.05 g of camphorsulfonic acid was added to the resulting solution, and the mixture was stirred at room temperature for 16 hours. At the end of this time, the solvent was removed by distillation under reduced pressure, after which water was added to the residue, and the resulting mixture was extracted with methylene chloride. The extract was dried over anhydrous magnesium sulfate and concentrated by evaporation under reduced pressure, to give 1.19 g of a solid residue, which was subjected to column chromatography through 40 g of silica gel. 0.555 g of the title compound was obtained from the fractions eluted with a 1:1 by volume mixture of hexane and ethyl acetate. It melted at 86°–87° C. (after recrystallisation from a mixture of methylene chloride and diethyl ether).

Nuclear Magnetic Resonance Spectrum (90 MHz, $CDCl_3$) δ ppm: 0.75–2.50 (42H, multiplet); 2.65 (2H, triplet, J=6.5 Hz); 3.12 (2H, triplet of doublets, $J_1$=6.5 Hz, $J_2$=6 Hz); 3.3–4.9 (9H, multiplet); 5.67 (1H, singlet).

Infrared Absorption Spectrum ($CHCl_3$) $\nu_{max}$ cm$^{-1}$: 3600 (—OH), 3450 (—NH—) and 1720 (—OCONH—).

Mass Spectrum (m/e): 552 (M+).

Elemental Analysis: Calculated for $C_{31}H_{56}N_2O_6$: C, 67.35%; H, 10.21%; N, 5.06%. Found: C, 67.57%; H, 10.42%; N, 4.83%.

PREPARATION 70

2-Hydroxy-8-(tetrahydropyran-2-yloxy)octanenitrile (a) A solution of 20.37 g of 7-(tetrahydropyran-2-yloxy)-1-heptanol in 200 ml of methylene chloride was added, whilst ice-cooling, to a mixture of 40.60 g of pyridinium chlorochromate, 3.86 g of sodium acetate and 200 ml of methylene chloride. The resulting mixture was stirred at 0° C. for 1 hour and then at room temperature for 3 hours, after which was diluted with 1.5 liter of diethyl ether and passed through a column containing 250 g of silica gel. The eluate was concentrated by evaporation under reduced pressure, and the residue was subjected to column chromatography through 400 g of silica gel. 14.11 g of 7-(tetrahydropyran-2-yloxy)heptanal were obtained, as a colorless oil, from those fractions eluted with mixtures of hexane and ethyl acetate ranging from 40:1 to 9:1 by volume.

Nuclear Magnetic Resonance Spectrum (60 MHz, $CDCl_3$) δ ppm: 1.1–2.1 (14H, multiplet); 2.42 (2H, multiplet); 3.1–4.1 (4H, multiplet); 4.56 (1H, multiplet); 9.83 (1H, triplet, J=2 Hz).

(b) 14.11 g of the aldehyde prepared as described in step (a) above and 12.86 g of potassium cyanide were dissolved in 300 ml of a 1:1 by volume mixture of dioxane and water, and then 32.9 ml of 6N aqueous hydrochloric acid were added dropwise over a period of 10 minutes, whilst ice-cooling. When the dropwise addition was complete, the reaction mixture was stirred for 1 hour at 0° C., after which it was poured into 600 ml of water and then extracted twice with ethyl acetate. The combined extracts were washed with water, dried over anhydrous magnesium sulfate and concentrated by evaporation under reduced pressure. The residue was subjected to column chromatography through 300 g of silica gel. 11.90 g of the title compound were obtained, as a colorless oil, from those fractions eluted with mixtures of hexane and ethyl acetate ranging from 1:9 to 1:4 by volume.

Nuclear Magnetic Resonance Spectrum (60 MHz, $CDCl_3$) δ ppm: 1.2–2.2 (16H, multiplet); 3.1–4.2 (5H, multiplet); 4.40 (1H, multiplet); 4.58 (1H, multiplet).

Infrared Absorption Spectrum ($CHCl_3$) $\nu_{max}$ cm$^{-1}$: 3600, 3360 and 2250.

PREPARATION 71

Methyl 2,8-dihydroxyoctanoate 7.73 g of 2-hydroxy-8-(tetrahydropyran-2-yloxy)octanenitrile (prepared as described in Preparation 70) were dissolved in a mixture of 80 ml of diethyl ether and 80 ml of methanol, and the solution was saturated with hydrogen chloride, whilst ice-cooling. The reaction mixture was stirred at room temperature for 3 hours, and then 160 ml of water was added to the mixture over a period of 10 minutes, whilst ice-cooling. It was then stirred at room temperature for 1 hour, after which it was diluted with water and then extracted six times with ethyl acetate. The combined extracts were washed with water, dried over anhydrous magnesium sulfate and concentrated by evaporation under reduced pressure. The residue was subjected to column chromatography through 120 g of silica gel. 3.75 g of the title compound were obtained, as a colorless oil, from those fractions eluted with mixtures of hexane and ethyl acetate ranging from 4:1 to 2:1 by volume.

Nuclear Magnetic Resonance Spectrum (90 MHz, CDCl$_3$) δ ppm: 1.2–2.0 (10H, multiplet); 1.67 (1H, multiplet); 2.85 (1H, multiplet); 3.63 (2H, triplet, J=7 Hz); 4.70 (1H, multiplet).

Infrared Absorption Spectrum (CHCl$_3$) $\nu_{max}$ cm$^{-1}$: 3550 and 1735

Mass Spectrum (m/e): 191 (M$^+$+1), 131 and 113.

Elemental Analysis: Calculated for C$_9$H$_{18}$O$_4$: C, 56.82%; H, 9.54%. Found: C, 56.46%; H, 9.45%.

PREPARATION 72

2,8-Bis(tetrahydropyran-2-yloxy)-1-octanol 2.71 g of methyl 2,8-dihydroxyoctanoate (prepared as described in Preparation 71), 3.90 ml of 3,4-dihydro-2H-pyran and 0.072 g of pyridinine p-toluenesulfonate were dissolved in 50 ml of methylene chloride, and the resulting solution was stirred at room temperature for 15 hours. At the end of this time, the solvent was removed by evaporation under reduced pressure, and the residue was dissolved in 30 ml of tetrahydrofuran. The solution was added dropwise to a mixtur of 1.081 g of lithium aluminum hydride and 30 ml of tetrahydrofuran over a period of 10 minutes, whilst ice-cooling. When the dropwise addition was complete, the mixture was stirred at room temperature for 1 hour, and then 4.3 ml of a 4% w/v aqueous solution of sodium hydroxide was added dropwise to it, whist ice-cooling. The reaction mixture was filtered by passing it through a layer of a Celite filter aid, and insoluble materials were washed with 100 ml of tetrahydrofuran. The filtrate and the washings were combined and concentrated by evaporation under reduced pressure, and the residue was subjected to column chromatography through 100 g of silica gel. 4.51 g of the title compound were obtained, as a colorless oil, from those fractions eluted with mixtures of hexane and ethyl acetate ranging from 1:4 to 2:3 by volume.

Nuclear Magnetic Resonance Spectrum (90 MHz, CDCl$_3$): 1.1–2.1 (22H, multiplet); 2.18 (1H, triplet, J=6 Hz); 3.15–4.30 (9H, multiplet); 4.35–4.85 (2H, multiplet).

Mass Spectrum (m/e): 331, 330 (M$^+$+1) and 329.

Elemental Analysis: Calculated for C$_{18}$H$_{34}$O$_5$: C, 65.42%; H, 10.37%. Found: C, 65.04%; H, 10.08%.

PREPARATION 73

6-[2,8-Bis(tetrahydropyran-2-yloxy)octyloxymethyl]-3,4-dihydro-2H-pyran (a) A solution of 2.174 g of 6-hydroxymethyl-3,4-dihydro-2H-pyran and 5.31 ml of triethylamine in 45 ml of benzene was cooled in an ice bath, and then 2.21 ml of methanesulfonyl chloride was added to the solution. The reaction mixture was stirred at room temperature for 1 hour, after which it was washed with water, dried over anhydrous magnesium sulfate and concentrated by evaporation under reduced pressure, to give 3.22 g of an oily residue.

(b) A solution of 1.049 g of 2,8-bis(tetrahydropyran-2-yloxy)-1-octanol (prepared as described in Preparation 72) in 10 ml of dimethylformamide was added, whilst ice-cooling, to a mixture of 0.152 g of sodium hydride (as a 55% dispersion in mineral oil) and 10 ml of dimethylformamide. The mixture was then stirred at room temperature for 1 hour. At the end of this time, a solution of the residue prepared as described in step (a) above dissolved in 15 ml of dimethylformamide was added to the mixture, which was then stirred at room temperature for 19 hours. It was then poured into 350 ml of water and extracted twice with ethyl acetate. The combined extracts were washed with water, dried over anhydrous magnesium sulfate and concentrated by evaporation under reduced pressure. The residue was subjected to column chromatography through 60 g of silica gel. 0.934 g of the title compound was obtained, as a colorless oil, from the fractions eluted with a 9:1 by volume mixture of hexane and ethyl acetate.

Nuclear Magnetic Resonance Spectrum (60 MHz, CDCl$_3$) δ ppm: 1.0–2.3 (26H, multiplet); 3.1–4.2 (11H, multiplet); 4.35–4.95 (3H, multiplet).

0.295 g of the starting material, 2,8-bis(tetrahydropyran-2-yloxy)-1-octanol (the compound of Preparation 72), was removed from the fractions eluted with mixtures of hexane and ethyl acetate ranging from 1:4 to 1:1 by volume.

PREPARATION 74 dl-trans-2-[2,8-Bis(tetrahydropyran-2-yloxy)octyloxymethyl]tetrahydropyran-3-ol 1.46 ml of a 1M borane-tetrahydrofuran complex was added dropwise, whist ice-cooling, to a solution of 0.934 g of 6-[2,8-bis(tetrahydropyran-2-yloxy)octyloxymethyl]-3,4-dihydro-2H-pyran (prepared as described in Preparation 73) in 3 ml of tetrahydrofuran. The mixture was then stirred at room temperature for 4.5 hours. At the end of this time, 0.80 ml of a 10% w/v aqueous solution of sodium hydroxide and 0.60 ml of a 30% v/v aqueous solution of hydrogen peroxide were added, in turn, to the mixture at 30° to 40° C., and then the mixture was stirred at room temperature for a further 1 hour. The reaction mixture was then diluted with 50 ml of water and extracted twice with ethyl acetate. The combined extracts were washed with water, dried over anhydrous magnesium sulfate and concentrated by evaporation under reduced pressure, to give a residue, which was purified by column chromatography through 20 g of silica gel and by medium pressure liquid chromatography using a Lobar B column. 0.615 g of the title compound was obtained, as a colorless oil, from the fractions euted with a 7:3 by volume mixture of hexane and ethyl acetate.

Nuclear Magnetic Resonance Spectrum (90 MHz, CDCl$_3$) δ ppm: 1.1–2.5 (27H, multiplet); 2.8–4.2 (10H, multiplet); 4.5–5.0 (2H, multiplet).

Mass Spectrum (m/e): 445, 444 (M$^+$) and 443.

PREPARATION 75 dl-trans-2-(2,8-Dihydroxyoctyloxymethyl)tetrahydropyran-3-yl N-heptadecylcarbamate A solution of 0.94 g of stearic acid, 0.71 ml of diphenylphosphoryl azide and 0.46 ml of triethylamine in 20 ml of benzene was heated under reflux for 3 hours.

At the end of this time, the mixture was cooled and washed with 20 ml of a saturated aqueous solution of sodium bicarbonate and with water. The solvent was removed by distillation under reduced pressure, and 0.90 g of the residue and 0.586 g of dl-trans-2-[2,8-bis(-tetrahydropyran-2-yloxy)octyloxymethyl]tetrahydropyran-3-ol (prepared as described in Preparation 74) were dissolved in 15 ml of toluene. 0.46 ml of triethylamine were added to the resulting mixture, which was then heated under reflux on an oil bath kept at 100° C. for 88 hours. At the end of this time, the solvent was removed by distillation under reduced pressure, and the residue thus obtained was subjected to column chromatography through 20 g of silica gel. 0.695 g of an oily product was obtained by collecting the fractions eluted with mixtures of hexane and ethyl acetate ranging from 3:17 to 1:4 by volume and concentrating it by evaporation under reduced pressure. This oily product was dissolved in 15 ml of methanol, and 55 mg of p-toluenesulfonic acid were added to the resulting solution. The mixture was then heated under reflux for 1 hour and cooled. 121 mg of sodium bicarbonate were added, and then the solvent was removed by distillation under reduced pressure. The residue was mixed with ethyl acetate and insoluble materials were filtered off. The filtrate was concentrated by evaporation under reduced pressure, to give a residue. This residue was subjected to column chromatography through 12 g of silica gel. 0.481 g of the title compound was obtained from the fractions eluted with mixtures of hexane and ethyl acetate ranging from 2:3 to 1:4 by volume. It melted at 67°-68° C. (after recrystallisation from a mixture of diethyl ether and hexane).

Nuclear Magnetic Resonance Spectrum (90 MHz, $CDCl_3$) δ ppm: 0.7-2.3 (47H, multiplet); 2.13 (2H, multiplet); 2.9-4.2 (12H, multiplet); 4.4-5.0 (2H, multiplet).

Infrared Absorption Spectrum ($CHCl_3$) $\nu_{max}$ cm$^{-1}$: 3450 and 1710.

Mass Spectrum (m/e): 557 (M+) and 456.

Elemental Analysis: Calculated for $C_{32}H_{63}NO_6$: C, 68.90%; H, 11.38%; N, 2.51%. Found: C, 68.45%; H, 11.75%; N, 2.69%.

PREPARATION 76 dl-trans-2-[2-Hydroxy-8-(p-toluenesulfonyloxy)octyloxymethyl]tetrahydropyran-3-yl N-heptadecylcarbamate 0.458 g of dl-trans-2-[(2,8-dihydroxyoctyloxy)methyl]tetrahydropyran-3-yl N-heptadecylcarbamate (prepared as described in Preparation 75), 0.27 ml of triethylamine and 5 mg of 4-dimethylaminopyridine were dissolved in 10 ml of methylene chloride. 0.188 g of p-toluenesulfonyl chloride were added to the mixture, whilst ice-cooling, after which the mixture was stirred at room temperature for 14 hours. At the end of this time, the reaction mixture was washed with water, dried over anhydrous magnesium sulfate and concentrated by evaporation under reduced pressure. The residue was purified by column chromatography through 12 g of silica gel and by medium pressure liquid chromatography through a Lobar B column. 0.492 g of the title compound was obtained, as a white wax, from the fractions eluted with mixtures of hexane and ethyl acetate ranging from 3:2 to 1:1 by volume.

Nuclear Magnetic Resonance Spectrum (90 MHz, $CDCl_3$) δ ppm: 0.8-2.3 (47H, multiplet); 2.45 (3H, singlet); 2.50 (1H, multiplet); 3.0-4.9 (8H, multiplet); 4.03 (2H, triplet, J=7 Hz); 4.4-5.0 (2H, multiplet); 7.37 (2H, doublet, J=9 Hz); 7.81 (2H, doublet, J=9 Hz).

Mass Spectrum (m/e): 712 M+ +1) and 540.

Elemental Analysis: Calculated for $C_{39}H_{69}NO_8S$: C, 65.79%; H. 9.77%; N, 1.97%; S, 4.50%. Found: C, 65.76%; H. 9.87%; N, 1.97%; S, 4.50%.

PREPARATION 77 dl-trans-2-[2-Acetoxy-8-p-toluenesulfonyloxyoctyloxymethyl]tetrahydropyran-3-yl N-heptadecylcarbamate 0.04 ml of acetyl chloride was added dropwise, whilst ice-cooling, to a solution of 0.311 g of dl-trans-2-[2-hydroxy-8-(p-toluenesulfonyloxy)octyloxymethyl]tetrahydropyran-3-yl N-hetpadecylcarbamate (prepared as described in Preparation 76) and 0.09 ml of triethylamine in 6 ml of benzene. The mixture was then stirred at room temperature for 3 hours, after which it was washed with water, dried over anhydrous magnesium sulfate and concentrated by evaporation under reduced pressure. The residue was subjected to column chromatography through 10 g of silica gel followed by medium pressure liquid chromatography through a Lobar B column. 163 mg of one isomer of the title compound (designated as Isomer I) were obtained, as a waxy material, from those fractions eluted with a 3:1 by volume mixture of hexane and ethyl acetate. It had an Rf value of 0.59 on thin layer chromatography on silica gel using a 1:1 by volume mixture of hexane and ethyl acetate as the developing solvent.

Nuclear Magnetic Resonance Spectrum (60 MHz, $CDCl_3$) δ ppm: 0.7-2.6 (47H, multiplet); 2.05 (3H, singlet); 2.46 (3H, singlet); 2.8-4.0 (9H, multiplet); 4.00 (2H, triplet, J=6 Hz); 4.2-5.2 (3H, multiplet). 7.36 (2H, doublet, J=9 Hz); 7.82 (2H, doublet, J=9 Hz).

Infrared Absorption Spectrum ($CHCl_3$) $\nu_{max}$ cm$^{-1}$: 3460 and 1720

72 mg of another isomer (designated as Isomer II) were isolated, as an oil, from those fractions eluted with a 2:1 by volume mixture of hexane and ethyl acetate. It had an Rf value of 0.45 on thin layer chromatography under the same conditions as described above.

Nuclear Magnetic Resonance Spectrum (60 MHz, $CDCl_3$) δ ppm: 0.7-2.6 (47H, multiplet); 2.27 (3H, singlet); 2.45 (3H, singlet); 2.8-4.0 (9H, multiplet); 4.00 (2H, triplet, J=6 Hz); 4.2-5.3 (3H, multiplet); 7.37 (2H, doublet, J=8 Hz); 7.82 (2H, doublet, J=8 Hz).

Infrared Absorption Spectrum ($CHCl_3$) $\nu_{max}$ cm$^{-1}$: 3460, 1720 and 1710.

PREPARATION 78

S-[dl-(cis-2-Benzyloxymethyltetrahydropyran-3-yl)]N-(octadecyl)thiocarbamate 3.38 g of nonadecanoic acid were allowed to react with 1.124 g of dl-cis-2-benzyloxymethyltetrahydropyran-3-thiol (prepared as described in Preparation 39) in a similar manner to that described in Preparation 3 to give a crude product. This product was purified by column chromatography through 80 g of silica gel. Those fractions eluted with mixtures of diethyl ether and hexane ranging from 1:5 to 1:2 by volume were worked up, to give 2.283 g of the title compound as white crystals melting at 85°-86° C. (after recrystallisation from a mixture of hexane and diethyl ether).

Nuclear Magnetic Resonance Spectrum (90 MHz, $CDCl_3$) δ ppm:

0.8–2.2 (39H, multiplet); 3.1–4.2 (8H, multiplet); 4.57 (2H, AB-quartet, $J_{AB}=12$ Hz); 5.33 (1H, multiplet); 7.35 (5H, multiplet).

Infrared Absorption Spectrum (CHCl$_3$) $\nu_{max}$ cm$^{-1}$: 3450 (—NH—), 1675 (—S—CO—).

Elemental Analysis: Calculated for $C_{32}H_{55}NO_3S$: C, 71.99%; H, 10.38%; N, 2.62%; S, 6.01%. Found: C, 71.87%; H, 10.30%; N, 2.67%; S, 6.17%.

PREPARATION 79

S-[dl-(cis-2-Hydroxymethyltetrahydropyran-3-yl)]N-(octadecyl)thiocarbamate 2.32 g of aluminum chloride and 2.61 g of sodium iodide were added succesively to a mixture of 70 ml of acetonitrile and 35 ml of methylene chloride, whilst ice-cooling. A methylene chloride solution containing 1.859 g of S-[dl-(cis-2-benzyloxymethyltetrahydropyran3-yl)]N-(octadecyl)thiocarbamate (prepared as described in Preparation 78) was then added, and the reaction mixture was stirred at room temperature for 7 hours. It was then diluted with water and purified by filtration with a Celite filter aid. The filtrate was mixed with methylene chloride. The methylene chloride layer was separated and the aqueous layer was extracted with methylene chloride. The combined extract and methylene chloride layer were washed successively with an aqueous solution of sodium thiosulfate and then with water, dried over anhydrous magnesium sulfate and concentrated by evaporation under reduced pressure. The residue was purified by column chromatography through 45 g of silica gel. Those fractions eluted with mixtures of ethyl acetate and hexane ranging from 1:5 to 1:2 by volume were worked up, to give 1.200 g of the title compound as white crystals, melting at 93°–94° C. (after recrystallisation from diethyl ether).

Nuclear Magnetic Resonance Spectrum (90 MHz, CDCl$_3$) δ ppm: 0.7–2.3 (40H, multiplet); 3.15–4.15 (8H, multiplet); 5.53 (1H, multiplet).

Infrared Absorption Spectrum (CHCl$_3$) $\nu_{max}$ cm$^{-1}$: 3450 (—NH—, —OH), 1650 (—S—CO—).

Elemental Analysis: Calculated for $C_{25}H_{49}NO_3S$: C, 67.67%; H, 11.13%; N, 3.16%; S, 7.23%. Found: C, 67.65%; H, 11.24%, N, 2.96%; S, 7.51%.

PREPARATION 80

2-Hydroxymethyl-7-(2-methoxyethoxy)methoxy-1-heptanol

A solution of 10.29 g of diethyl 2-[5-(2-methoxyethoxy)methoxypentyl]malonate (prepared as described in Preparation 61) dissolved in 100 ml of tetrahydrofuran was added dropwise to 2.40 g of lithium aluminum hydride dispersed in 100 ml of tetrahydrofuran, whilst ice-cooling (at 5° to 7° C.). The mixture was then stirred at room temperature for 3 hours, and then 9.60 ml of a 4% w/v aqueous solution of sodium hydroxide were added dropwise whilst maintaining the temperature at from 5° to 9° C. The mixture was stirred for 30 minutes at room temperature, after which it was filtered with a Celite filter aid, and the filtrate was concentrated by evaporation under reduced pressure. The residue was subjected to column chromatography through 105 g of silica gel, and 6.94 g of the title compound were obtained, as a colorless oil, from those fractions eluted with mixtures of methylene chloride and methanol ranging from 98:2 to 95:5 by volume.

Nuclear Magnetic Resonance Spectrum (90 MHz, CDCl$_3$) δ ppm: 1.2–2.0 (9H, multiplet); 2.52 (2H, multiplet); 3.40 (3H, singlet); 3.5–4.0 (10H, multiplet); 4.71 (2H, singlet).

Infrared Absorption Spectrum (CHCl$_3$) $\nu_{max}$ cm$^{-1}$: 3420 (OH) and 1040 (C—O—C—).

Mass Spectrum (m/e): 251 (M$^+$+1).

Elemental analysis: Calculated for $C_{12}H_{26}O_5$: C, 57.57%; H, 10.47%. Found: C, 57.46%; H, 10.22%.

PREPARATION 81

(2RS)-2-Benzyloxymethyl-7-(2-methoxyethoxy)methoxy-1-heptanol

A solution of 3.06 g of 2-hydroxymethyl-7-(2-methoxyethoxy)methoxy-1-heptanol (prepared as described in Preparation 80) dissolved in 20 ml of dimethylformamide was added dropwise to 587 mg of sodium hydride (as a 55% w/w dispersion in mineral oil) dispersed in 40 ml of dimethylformamide, whilst ice-cooling (at 5° to 7° C.). The mixture was then stirred at room temperature for 1 hour, after which 1.60 ml of benzyl bromide were added dropwise, whilst ice-cooling (at 5° to 7° C.) The reaction mixture was stirred at room temperature for 2 hours, after which it was poured into 300 ml of water and then extracted five times with ethyl acetate. The combined extracts were washed with water, dried over anhydrous magnesium sulfate and concentrated by evaporation under reduced pressure. The resulting oily residue was subjected to column chromatography through 60 g of silica gel, and 2.37 g of the title compound were obtained, as a colorless oil, from the fractions eluted with mixtures of hexane and ethyl acetate ranging from 2:1 to 1:1 by volume.

Nuclear Magnetic Resonance Spectrum (90 MHz, CDCl$_3$) δ ppm: 1.2–2.0 (9H, multiplet); 2.47 (1H, triplet J=6 Hz); 3.39 (3H, singlet); 3.4–3.8 (10H, multiplet); 4.52 (2H, singlet); 4.71 (2H, singlet); 7.26 (5H, singlet).

Infrared Absorption Spectrum (CHCl$_3$) $\nu_{max}$ cm$^{-1}$: 3500 (—OH) and 1040 (C—O—C—).

Mass Spectrum (m/e): 341 (M$^+$+1).

Elemental analysis: Calculated for $C_{19}H_{32}O_5$: C, 67.03%; H, 9.47%. Found: C, 66.88%; H, 9.39%.

EXPERIMENT 1

Inhibition of PAF-induced hypotension

The test animals employed were rats of the Wistar-Imamichi strain, each weighing between 350 and 450 g. Under Inactin anesthesia (90 mg/kg administered intraperitoneally) the left femoral artery and vein of each test animal were cannulated to enable the arterial blood pressure to be monitored continuously and for drug administration, respectively. At intervals of about 5 minutes, each animal was given by intravenous injection 10 ng/kg of synthetic 1-$C_{16:0}$ PAF until a steady hypotensive response was achieved. At this time, the drug to be tested was administered by intravenous injection in doses increasing cumulatively by a factor of 3. Within 1 minute of this injection, a further 10 ng/kg of the 1-$C_{16:0}$ PAF was administered. The hypotensive response to PAF was inhibited by the test drug in a dose-related manner.

The PAF was administered in the form of a solution in physiological saline containing 0.25% w/v bovine serum albumin. The test drugs were dissolved in physiological saline containing 20% v/v ethanol.

The 50% inhibitory dose (ID$_{50}$) was calculated from the dose-response curve constructed for the inhibition of PAF-induced hypotension.

This test was carried out using compounds of the invention, as well as the prior art compound CV-3988, disclosed in U.S. Pat. No. 4,408,052 and represented by the foregoing formula (B). The results are shown in the following Tables 12 and 34.

EXPERIMENT 2

Inhibition of PAF-induced platelet aggregation in vitro

Blood was drawn from a rabbit and immediately mixed with one ninth of its volume of a 3.8% w/v aqueous solution of sodium citrate. A platelet-rich plasma (PRP) was obtained as a supernatant by centrifugation of the blood at 150×g for 15 minutes at room temperature. The precipitated fraction was centrifuged for a further 15 minutes at 1000×g to obtain a platelet-poor plasma (PPP) as a supernatant. Appropriate proportions of this PRP and PPP were mixed to obtain a plasma having a platelet count of $6\times 10^5/\mu l$.

Platelet aggregation was determined by the method of Born et al. [G. V. R. Born et al., J. Physiol., 62, 67–68 (1962)] where an increase in light transmission is measured by an aggregometer. 25 µl of a saline solution containing the compound to be tested at an appropriate concentration was added to 250 µl of the above plasma. One minute thereafter, 25 µl of a saline solution of synthetic $C_{16:0}$ PAF (at a concentration sufficient to give a final concentration of $1\times 10^{-8} - 3\times 10^{-8}M$) was added and aggregation was observed for 5 minutes. The aggregation resulting from the addition of PAF alone, without the prior addition of the test compound, was taken as 100%.

The $IC_{50}$ values (i.e. concentrations to inhibit aggregation by 50%) were calculated from dose-response curves and are shown in Tables 12 and 34.

TABLE 12

| Test compound | Inhibition of Hypotension $ID_{50}$ (mg/kg) | Inhibition of Platelet aggregation $IC_{50}$ (M) |
|---|---|---|
| Cpd. of Ex. 1 | 0.17 | $1.1 \times 10^{-6}$ |
| Cpd. of Ex. 2 | 0.13 | $2.4 \times 10^{-6}$ |
| Cpd. of Ex. 3 | 0.11 | $9.7 \times 10^{-7}$ |
| Cpd. of Ex. 4 | 0.027 | $2.0 \times 10^{-7}$ |
| Cpd. of Ex. 7 | 0.17 | $4.2 \times 10^{-6}$ |
| Cpd. of Ex. 9 | 0.018 | $4.1 \times 10^{-7}$ |
| Cpd. of Ex. 13 | 0.030 | $3.9 \times 10^{-7}$ |
| Cpd. of Ex. 16 | 0.0074 | $1.5 \times 10^{-7}$ |
| Cpd. of Ex. 17 | 0.21 | $2.9 \times 10^{-6}$ |
| Cpd. of Ex. 18 | 0.08 | $4.4 \times 10^{-6}$ |
| Cpd. of Ex. 19 | 0.21 | $9.0 \times 10^{-7}$ |
| Cpd. of Ex. 20 | 0.06 | $2.7 \times 10^{-7}$ |
| CV - 3988 | 0.42 | $8.7 \times 10^{-6}$ |

TABLE 34

| Test compound | Inhibition of Hypotension $ID_{50}$ (mg/kg) | Inhibition of Platelet aggregation $IC_{50}$ (M) |
|---|---|---|
| Cpd. of Ex. 1f | 0.57 | $1.5 \times 10^{-6}$ |
| Cpd. of Ex. 3f | 0.46 | $4.3 \times 10^{-6}$ |
| Cpd. of Ex. 4f | 0.09 | $8.4 \times 10^{-5}$ |
| Cpd. of Ex. 6f | 0.08 | $1.8 \times 10^{-6}$ |
| CV - 3988 | 0.42 | $9.8 \times 10^{-6}$ |

EXPERIMENT 3

Reversal of endotoxin-induced hypotension (Anti-endotoxin shock)

The test animals used were male rats of the Sprague-Dawley strain with a body weight of 250–350 g. They were anesthetized by the intraperitoneal administration of 60 mg/kg of pentobarbital sodium. The mean arterial blood pressure was recorded via a cannula inserted into the femoral artery, whilst endotoxin and the test compounds were administered through a cannula inserted into the femoral vein.

Endotoxin (5 mg/kg) was administered to each rat. When the maximum reduction in blood pressure was observed (after about 4 minutes), the test compound was administered.

The anti-endotoxin shock activity of the test compound at each dose was calculated from:

$$[(C-B)/(A-B)] \times 100\%$$

where:
A = blood pressure just before injection of endotoxin;
B = blood pressure 4 minutes after injection of endotoxin; and
C = blood pressure 1 minute after injection of test compound.

The experiment was repeated for each test compound at several doses and $ED_{50}$ values were calculated from the dose-response curves. The results are shown in Table 35.

Endotoxin (Lipopolysaccharide W E. coli 0127: B8) and the test compounds were dissolved in physiological saline just before use.

TABLE 35

| Test Compound | $ED_{50}$ (mg/kg, i.v.) |
|---|---|
| Cpd. of Ex. 1f | 0.14 |
| Cpd. of Ex. 6f | 0.058 |
| CV-3988 | 0.24 |

EXPERIMENT 4

Anti-inflammatory effect

This test was carried out by the carrageenin edema method [C. A. Winter, E. A. Risley, G. W. Ness, J. Pharmacol. Exp. Therap., 141, 369 (1963)] using rats of the Wistar strain and employing the compound of Example 2f at a dose of 50 mg/kg per os. The inhibition rate was 65.9%.

We claim:
1. A compound of formula (I):

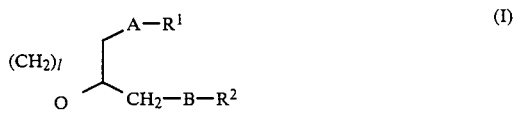

in which:
l is an integer of from 2 to 4;
A and B are independently selected from the group consisting of oxygen atoms and sulfur atoms;
one of $R^1$ and $R^2$ represents a group of formula (II):

in which
$R^3$ is $R_f^3$ wherein $R_f^3$ represents an alkyl group containing from 10 to 22 carbon atoms, and
$R^5$ represents a hydrogen atom,
and the other of $R^1$ and $R^2$ represents a group of (IIf):

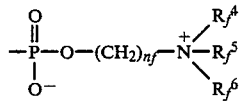

wherein $n_f$ is an integer of from 2 to 10;

$R_f^4$, $R_f^5$ and $R_f^6$ are independently selected from the group consisting of hydrogen atoms and $C_1$-$C_6$ alkyl groups, or $R_f^4$ and $R_f^5$ or $R_f^4$, $R_f^5$ and $R_f^6$, together with the nitrogen atom to which they are attached, form a heterocyclic ring which may be aromatic or partly or wholly saturated;

said heterocyclic groups in formula (II$f$) having from 3 to 10 ring atoms, of which from 1 to 4 atoms are hetero-atoms selected from the group consisting of nitrogen, oxygen and sulfur atoms, at least one of these being a nitrogen atom, and said heterocyclic group being unsubstituted or having at least one substituent selected from the group consisting of substituents (c):

substituents (c):

$C_1$-$C_6$ alkyl groups, $C_1$-$C_5$ hydroxyalkyl groups, $C_1$-$C_6$ alkoxy groups, carbamoyl groups, mono- and di-alkylcarbamoyl groups in which the or each alkyl part is $C_1$-$C_5$ and halogen atoms; or a pharmaceutically acceptable salt or ester thereof.

2. A compound as claimed in claim 1, wherein said compound has the formula (I) as shown in claim 1 in which $R^1$ represents a group of formula (II$f$).

3. A compound as claimed in claim 1, wherein $n_f$ is 2 or 3.

4. A compound as claimed in claim 1, wherein l is 2 or 3.

5. A compound as claimed in claim 1, wherein $n_f$ is an integer from 2 to 6.

6. A compound as claimed in claim 1, wherein $R_f^4$, $R_f^5$ and $R_f^6$ are independently selected from the group consisting of hydrogen atoms and $C_1$-$C_6$ alkyl groups.

7. A compound as claimed in claim 1, wherein $R_f^4$ and $R_f^5$, together with the nitrogen atom to which they are attached, represent a non-aromatic heterocyclic group having from 5 to 7 ring atoms, and $R_f^6$ represents a hydrogen atom or a $C_1$-$C_6$ alkyl group.

8. A compound as claimed in claim 1, wherein $R_f^4$, $R_f^5$ and $R_f^6$, together with the nitrogen atom to which they are attached, represent an aromatic heterocyclic group having from 5 to 10 ring atoms, said heterocyclic group bein unsubstituted or having at least one substituent selected from the group consisting of $C_1$-$C_4$ alkyl groups, $C_1$-$C_5$ alkoxy groups, $C_1$-$C_5$ hydroxyalkyl groups, carbamoyl groups and halogen atoms.

9. A compound as claimed in claim 1, wherein $R^1$ represents said group of formula —CONHR$_f^3$ and $R^2$ represents said group of formula (II$f$).

10. A compound as claimed in claim 1, wherein $R_f^3$ represents an alkyl group having from 16 to 18 carbon atoms.

11. A compound as claimed in claim 1, wherein:
$R^1$ represents said group of formula —CONHR$_f^3$;
$R^2$ represents said group of formula (II$f$);
$R_f^4$, $R_f^5$ and $R_f^6$ are independently selected from the group consisting of hydrogen atoms and $C_1$-$C_6$ alkyl groups;
$n_f$ is an integer from 2 to 6; and
l is 2 or 3.

12. A compound as claimed in claim 1, wherein:
$R^1$ represents said group of formula —CONHR$_f^3$;
$R^2$ represents said group of formula (II$f$);
$R_f^4$ and $R_f^5$, together with the nitrogen atom to which they are attached, represent a non-aromatic heterocyclic group having from 5 to 7 ring atoms, and $R_f^6$ represents a hydrogen atom or a $C_1$-$C_6$ alkyl group;
$n_f$ is an integer from 2 to 6; and
l is 2 or 3.

13. A compound as claimed in claim 1, wherein:
$R^1$ represents said group of formula —CONHR$_f^3$;
$R^2$ represents said group of formula (II$f$);
$R_f^4$, $R_f^5$ and $R_f^6$, together with the nitrogen atom to which they are attached, represent an aromatic heterocyclic group having from 5 to 10 ring atoms, said group being unsubstituted or having at least one substituent selected from the group consisting of $C_1$-$C_5$ alkyl groups, $C_1$-$C_5$ alkoxy groups, $C_1$-$C_5$ hydroxyalkyl groups, carbamoyl groups and halogen atoms;
$n_f$ is an integer from 2 to 6; and
l is 2 or 3.

14. A compound as claimed in claim 1, wherein:
$R^1$ represents a group of formula —CONHR$_f^3$, where $R_f^3$ represents a $C_{16}$-$C_{18}$ alkyl group;
$R^2$ represents said group of formula (II$f$);
$R_f^4$, $R_f^5$ and $R_f^6$ are independently selected from the group consisting of $C_1$-$C_6$ alkyl groups;
$n_f$ is an integer from 2 to 6; and
l is 2 or 3.

15. A compound as claimed in claim 1, wherein:
$R^1$ represents a group of formula —CONHR$_f^3$, where $R_f^3$ represents a $C_{16}$-$C_{18}$ alkyl group;
$R^2$ represents said group of formula (II$f$);
$R_f^4$ and $R_f^5$, together with the nitrogen atom to which they are attached, represent a non-aromatic heterocyclic group having from 5 to 7 ring atoms, and $R_f^6$ represents a hydrogen atom or a $C_1$-$C_6$ alkyl group;
$n_f$ is an integer from 2 to 6; and
l is 2 or 3.

16. A compound as claimed in claim 1, wherein:
$R^1$ represents a group of formula —CONHR$_f^3$, where $R_f^3$ represents a $C_{16}$-$C_{18}$ alkyl group;
$R^2$ represents said group of formula (II$f$);
$R_f^4$, $R_f^5$ and $R_f^6$, together with the nitrogen atom to which they are attached, represent an aromatic heterocyclic group having from 5 to 7 ring atoms, said group being unsubstituted or having at least one substituent selected from the group consisting of $C_1$-$C_5$ alkyl groups and $C_1$-$C_5$ hydroxyalkyl groups;
$n_f$ is an integer from 2 to 6; and
l is 2 or 3.

17. A compound as claimed in claim 1, wherein:
$R^1$ represents a group of formula —CONHR$_f^3$, where $R_f^3$ represents a $C_{16}$-$C_{18}$ alkyl group;
$R^2$ represents said group of formula (II$f$);
$R_f^4$ and $R_f^5$, together with the nitrogen atom to which they are attached, represent a piperidino or 1-pyrrolidinyl group, and $R_f^6$ represents a hydrogen atom or a $C_1$-$C_6$ alkyl group;

$n_f$ is an integer from 2 to 6; and
l is 2 or 3.

18. A compound as claimed in claim 1, wherein:
R¹ represents a group of formula —CONHR$_f^3$, where R$_f^3$ represents a $C_{16}$-$C_{18}$ alkyl group;
R² represents said group of formula (II$f$);
R$_f^4$, R$_f^5$ and R$_f^6$, together with the nitrogen atom to which they are attached, represent a 1-pyridyl or 1-thiazolyl group which is unsubstituted or has at least one substituent selected from the group consisting of $C_1$-$C_5$ alkyl groups and $C_1$-$C_5$ hydroxyalkyl groups;
$n_f$ is an integer from 2 to 6; and
l is 2 or 3.

19. A compound as claimed in claim 1, selected from the group consisting of the compound of formula:

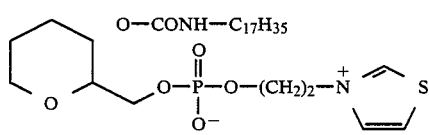
(b)

its mirror image and pharmaceutically acceptable salts of said compound and of its mirror image.

20. A compound as claimed in claim 1, selected from the group consisting of the compound of formula:

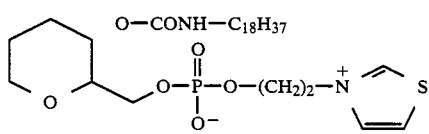
(c)

its mirror image and pharmaceutically acceptable salts of said compound and of its mirror image.

21. A compound as claimed in claim 1, selected from the group consisting of the compound of formula:

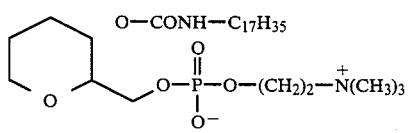
(d)

its mirror image and pharmaceutically acceptable salts of said compound and of its mirror image.

22. A compound as claimed in claim 1, selected from the group consisting of the compound of formula:

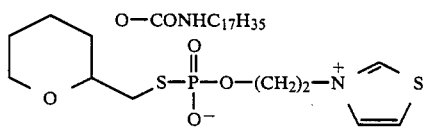
(g)

its mirror image and pharmaceutically acceptable salts of said compound and of its mirror image.

23. A compound as claimed in claim 1, selected from the group consisting of the compound of formula:

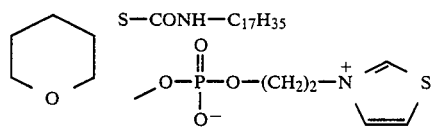
(j)

its mirror image and pharmaceutically acceptable salts of said compound and of its mirror image.

24. A compound as claimed in claim 1, selected from the group consisting of the compound of formula:

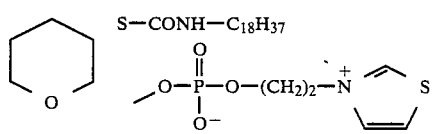
(k)

its mirror image and pharmaceutically acceptable salts of said compound and of its mirror image.

25. A compound as claimed in claim 1, selected from the group consisting of the compound of formula:

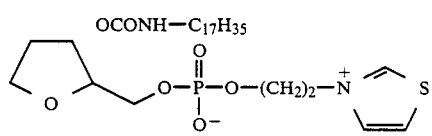
(p)

its mirror image and pharmaceutically acceptable salts of said compound and of its mirror image.

26. A compound as claimed in claim 1, selected from the group consisting of the compound of formula:

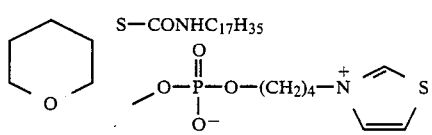
(u)

its mirror image and pharmaceutically acceptable salts of said compound and of its mirror image.

27. A compound as claimed in claim 1, selected from the group consisting of the compound of formula:

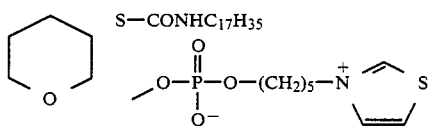
(v)

its mirror image and pharmaceutically acceptable salts of said compound and of its mirror image.

28. A compound as claimed in claim 1, selected from the group consisting of the compound of formula:

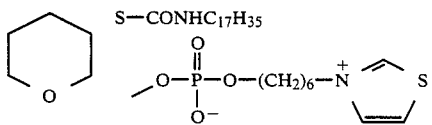
(w)

its mirror image and pharmaceutically acceptable salts of said compound and of its mirror image.

29. A compound as claimed in claim 1, selected from the group consisting of the compound of formula:

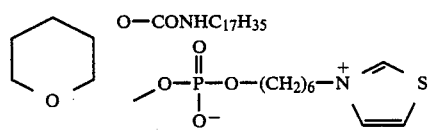

its mirror image and pharmaceutically acceptable salts of said compound and of its mirror image.

30. A compound as claimed in claim 1, selected from the group consisting of the compound of formula:

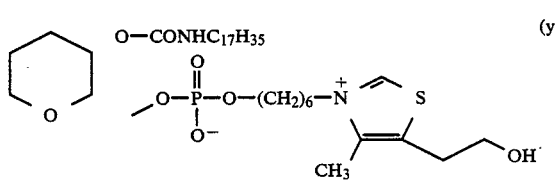

its mirror image and pharmaceutically acceptable salts of said compound and of its mirror image.

31. A pharmaceutical composition for the treatment of inflammation or shock, comprising an effective amount of a PAF antagonist in combination with a pharmaceutically acceptable carrier or diluent, wherein the PAF antagonist is selected from the group consisting of compounds of claim 1.

32. A composition as claimed in claim 31, wherein said compound has the formula (I) as shown in claim 31 in which $R^1$ represents a group of formula $(II_f)$.

33. A pharmaceutical composition as claimed in claim 31, wherein:
   $R^1$ represents said group of formula $—CONHR_f^3$;
   $R^2$ represents said group of formula $(II_f)$;
   $R_f^4$, $R_f^5$ and $R_f^6$ are independently selected from the group consisting of hydrogen atoms and $C_1$-$C_6$ alkyl groups;
   $n_f$ is an integer from 2 to 6; and
   $l$ is 2 or 3.

34. A pharmaceutical composition as claimed in claim 31, wherein:
   $R^1$ represents said group of formula $—CONHR_f^3$;
   $R^2$ represents said group of formula $(II_f)$:
   $R_f^4$ and $R_f^5$, together with the nitrogen atom to which they are attached, represent a non-aromatic heterocyclic group having from 5 to 7 ring atoms, and $R_f^6$ represents a hydrogen atom or a $C_1$-$C_6$ alkyl group;
   $n_f$ is an integer from 2 to 6; and
   $l$ is 2 or 3.

35. A pharmaceutical composition as claimed in claim 31, wherein:
   $R^1$ represents said group of formula $—CONHR_f^3$;
   $R^2$ represents said group of formula $(II_f)$;
   $R_f^4$, $R_f^5$ and $R_f^6$, together with the nitrogen atom to which they are attached, represent an aromatic heterocyclic group having from 5 to 10 ring atoms, said group being unsubstituted or having at least one substituent selected from the group consisting of $C_1$-$C_5$ alkyl groups. $C_1$-$C_5$ alkoxy groups, $C_1$-$C_5$ hydroxyalkyl groups, carbamoyl groups and halogen atoms;
   $n_f$ is an integer from 2 to 6; and
   $l$ is 2 or 3.

36. A pharmaceutical composition as claimed in claim 31, wherein:
   $R^1$ represents a group of formula $—CONHR_f^3$, where $R_f^3$ represents a $C_{16}$-$C_{18}$ alkyl group;
   $R^2$ represents said group of formula $(II_f)$;
   $R_f^4$, $R_f^5$ and $R_f^6$ are independently selected from the group consisting of $C_1$-$C_6$ alkyl groups;
   $n_f$ is an integer from 2 to 6; and
   $l$ is 2 or 3.

37. A pharmaceutical composition as claimed in claim 31, wherein:
   $R^1$ represents a group of formula $—CONHR_f^3$, where $R_f^3$ represents a $C_{16}$-$C_{18}$ alkyl group;
   $R^2$ represents said group of formula $(II_f)$;
   $R_f^4$ and $R_f^5$, together with the nitrogen atom to which they are attached, represent a non-aromatic heterocyclic group having from 5 to 7 ring atoms, and $R_f^6$ represents a hydrogen atom or a $C_1$-$C_6$ alkyl group;
   $n_f$ is an integer from 2 to 6; and
   $l$ is 2 or 3.

38. A pharmaceutical composition as claimed in claim 31, wherein:
   $R^1$ represents a group of formula $—CONHR_f^3$, where $R_f^3$ represents a $C_{16}$-$C_{18}$ alkyl group;
   $R^2$ represents said group of formula $(II_f)$;
   $R_f^4$, $R_f^5$ and $R_f^6$, together with the nitrogen atom to which they are attached, represent an aromatic heterocyclic group having from 5 to 7 ring atoms, said group being unsubstituted or having at least one substituent selected from the group consisting of $C_1$-$C_5$ alkyl groups and $C_1$-$C_5$ hydroxyalkyl groups;
   $n_f$ is an integer from 2 to 6; and
   $l$ is 2 or 3.

39. A pharmaceutical composition as claimed in claim 31, wherein:
   $R^1$ represents a group of formula $—CONHR_f^3$, where $R_f^3$ represents a $C_{16}$-$C_{18}$ alkyl group;
   $R^2$ represents said group of formula $(II_f)$;
   $R_f^4$ and $R_f^5$, together with the nitrogen atom to which they are attached, represent a piperidino or 1-pyrrolidinyl group, and $R_f^6$ represents a hydrogen atom or a $C_1$-$C_6$ alkyl group;
   $n_f$ is an integer from 2 to 6; and
   $l$ is 2 or 3.

40. A pharmaceutical composition as claimed in claim 31, wherein:
   $R^1$ represents a group of formula $—CONHR_f^3$, where $R_f^3$ represents a $C_{16}$-$C_{18}$ alkyl group;
   $R^2$ represents said group of formula $(II_f)$;
   $R_f^4$, $R_f^5$ and $R_f^6$, together with the nitrogen atom to which they are attached, represent a 1-pyridyl or 1-thiazolyl group which is unsubstituted or has at least one substituent selected from the group consisting of $C_1$-$C_5$ alkyl groups and $C_1$-$C_5$ hydroxyalkyl groups;
   $n_f$ is an integer from 2 to 6; and
   $l$ is 2 or 3.

41. A method for the treatment of prophylaxis of asthma, inflammation or shock comprising administering an amount of a PAF antagonist to an animal sufficient to effect treatment or prophylaxis of inflammation or shock, wherein said PAF antagonist is selected from the group consisting of compounds of claim 1.

42. A method as claimed in claim 41, wherein said compound has the formula (I) as shown in claim 41 in which $R^1$ represents a group of formula $(II_f)$.

43. A method as claimed in claim 41, wherein:
$R^1$ represents said group of formula —CONHR$_f^3$;
$R^2$ represents said group of formula (II$_f$);
$R_f^4$, $R_f^5$ and $R_f^6$ are independently selected from the group consisting of hydrogen atoms and $C_1$–$C_6$ alkyl groups;
$n_f$ is an integer from 2 to 6; and
l is 2 or 3.

44. A method as claimed in claim 41, wherein:
$R^1$ represents said group of formula —CONHR$_f^3$;
$R^2$ represents said group of formula (II$_f$);
$R_f^4$ and $R_f^5$, together with the nitrogen atom to which they are attached, represent a non-aromatic heterocyclic group having from 5 to 7 ring atoms, and $R_f^6$ represents a hydrogen atom or a $C_1$–$C_6$ alkyl group;
$n_f$ is an integer from 2 to 6; and
l is 2 or 3.

45. A method as claimed in claim 41, wherein:
$R^1$ represents said group of formula —CONHR$_f^3$;
$R^2$ represents said group of formula (II$_f$);
$R_f^4$, $R_f^5$ and $R_f^6$, together with the nitrogen atom to which they are attached, represent an aromatic heterocyclic group having from 5 to 10 ring atoms, said group being unsubstituted or having at least one substituent selected from the group consisting of $C_1$–$C_5$ alkyl groups, $C_1$–$C_5$ alkoxy groups, $C_1$–$C_5$ hydroxyalkyl groups, carbamoyl groups and halogen atoms;
$n_f$ is an integer from 2 to 6; and
l is 2 or 3.

46. A method as claimed in claim 41, wherein:
$R^1$ represents a group of formula —CONHR$_f^3$, where $R_f^3$ represents a $C_{16}$–$C_{18}$ alkyl group;
$R^2$ represents said group of formula (II$_f$);
$R_f^4$, $R_f^5$ and $R_f^6$ are independently selected from the group consisting of $C_1$–$C_6$ alkyl group
$n_f$ is an integer from 2 to 6; and
l is 2 or 3.

47. A method as claimed in claim 41, wherein:
$R^1$ represents a group of formula —CONHR$_f^3$, where $R_f^3$ represents a $C_{16}$–$C_{18}$ alkyl group;
$R^2$ represents said group of formula (II$_f$);
$R_f^4$ and $R_f^5$, together with the nitrogen atom to which they are attached, represent a non-aromatic heterocyclic group having from 5 to 7 ring atoms, and $R_f^6$ represents a hydrogen atom or a $C_1$–$C_6$ alkyl group;
$n_f$ is an integer from 2 to 6; and
l is 2 or 3.

48. A method as claimed in claim 41, wherein:
$R^1$ represents a group of formula —CONHR$_f^3$, where $R_f^3$ represents a $C_{16}$–$C_{18}$ alkyl group;
$R^2$ represents said group of formula (II$_f$);
$R_f^4$, $R_f^5$ and $R_f^6$, together with the nitrogen atom to which they are attached, represent an aromatic heterocyclic group having from 5 to 7 ring atoms, said group being unsubstituted or having at least one substituent selected from the group consisting of $C_1$–$C_5$ alkyl groups and $C_1$–$C_5$ hydroxyalkyl groups;
$n_f$ is an integer from 2 to 6; and
l is 2 or 3.

49. A method as claimed in claim 41, wherein:
$R^1$ represents a group of formula —CONHR$_f^3$, where $R_f^3$ represents a $C_{16}$–$C_{18}$ alkyl group;
$R^2$ represents said group of formula (II$_f$)
$R_f^4$ and $R_f^5$, together with the nitrogen atom to which they are attached, represent a piperidino or 1-pyrrolidinyl group, and $R_f^6$ represents a hydrogen atom or a $C_1$–$C_6$ alkyl group;
$n_f$ is an integer from 2 to 6; and
l is 2 or 3.

50. A method as claimed in claim 41, wherein:
$R^1$ represents a group of formula —CONHR$_f^3$, where $R_f^3$ represents a $C_{16}$–$C_{18}$ alkyl group;
$R^2$ represents said group of formula (II$_f$);
$R_f^4$, $R_f^5$ and $R_f^6$, together with the nitrogen atom to which they are attached, represent a 1-pyridyl or 1-thiazolyl group which is unsubstituted or has at least one substituent selected form the group consisting of $C_1$–$C_5$ alkyl groups and $C_1$–$C_5$ hydroxyalkyl groups;
$n_f$ is an integer from 2 to 6; and
l is 2 or 3.

51. A method as claimed in claim 41 wherein said compound has the formula

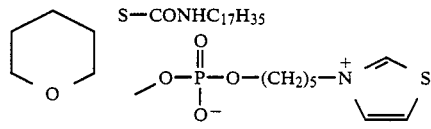

* * * * *